(12) United States Patent
Gajiwala et al.

(10) Patent No.: US 11,964,978 B2
(45) Date of Patent: Apr. 23, 2024

(54) MODULATORS OF STING (STIMULATOR OF INTERFERON GENES)

(71) Applicant: PFIZER INC., New York, NY (US)

(72) Inventors: Ketan Satish Gajiwala, San Diego, CA (US); Chan Woo Huh, East Lyme, CT (US); Mehran Jalaie, San Diego, CA (US); Ryan Lloyd Patman, San Diego, CA (US); Eugene Yuanjin Rui, San Diego, CA (US); Jianmin Sun, East Lyme, CT (US); Martin James Wythes, Solana Beach, CA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 17/693,197

(22) Filed: Mar. 11, 2022

(65) Prior Publication Data
US 2022/0306641 A1    Sep. 29, 2022

Related U.S. Application Data

(60) Provisional application No. 63/165,459, filed on Mar. 24, 2021, provisional application No. 63/162,640, filed on Mar. 18, 2021.

(51) Int. Cl.
| | | |
|---|---|---|
| C07D 487/04 | (2006.01) | |
| A61K 31/437 | (2006.01) | |
| A61K 31/519 | (2006.01) | |
| A61P 35/00 | (2006.01) | |
| C07D 471/04 | (2006.01) | |

(52) U.S. Cl.
CPC ......... *C07D 487/04* (2013.01); *C07D 471/04* (2013.01)

(58) Field of Classification Search
CPC ..... C07D 487/04; C07D 471/04; A61P 35/00; A61K 31/437; A61K 31/519
USPC ........................................................ 514/262
See application file for complete search history.

(56) References Cited

U.S. PATENT DOCUMENTS

| | | | |
|---|---|---|---|
| 8,337,850 B2 | 12/2012 | Ahrens et al. | |
| 10,155,037 B2 | 12/2018 | Abdiche et al. | |
| 2013/0078240 A1 | 3/2013 | Ahrens et al. | |
| 2019/0284216 A1* | 9/2019 | Wythes | C07F 9/65744 |
| 2020/0040009 A1* | 2/2020 | Wu | A61P 31/00 |

FOREIGN PATENT DOCUMENTS

| | | | | |
|---|---|---|---|---|
| WO | 91/11172 A1 | 8/1991 | | |
| WO | 94/02518 A1 | 2/1994 | | |
| WO | 98/55148 A1 | 12/1998 | | |
| WO | 2010/132999 A1 | 11/2010 | | |
| WO | 2016/092419 A1 | 6/2016 | | |
| WO | 2017/130076 A1 | 8/2017 | | |
| WO | 2017/175156 A1 | 10/2017 | | |
| WO | WO-2017175156 A1 * | 10/2017 | ......... | A61K 31/4184 |
| WO | 2018/234808 A1 | 12/2018 | | |
| WO | WO-2018234808 A1 * | 12/2018 | ........... | A61K 31/517 |
| WO | 2020/181050 A1 | 9/2020 | | |
| WO | WO-2020181050 A1 * | 9/2020 | ........... | A61K 31/437 |
| WO | 2020/232375 A1 | 11/2020 | | |
| WO | WO-2020232375 A1 * | 11/2020 | ........... | A61K 31/473 |
| WO | 2021/059136 A1 | 4/2021 | | |

OTHER PUBLICATIONS

Bala et al., "PLGA Nanoparticles in Drug Delivery: The State of the Art", Critical Reviews in Therapeutic Drug Carrier Systems, 2004, 21(5), 387-422.
Barber, Glen N., "STING: infection, inflammation and cancer", Nature Reviews Immunology, 2015, 15, 760-770.
Basu, S., et al., "The discovery of potent small molecule cyclic urea activators of STING", European Journal of Medicinal Chemistry, 2022, Article 114087, vol. 229.
Berger, G., et al., "Pharmacological Modulation of the STING Pathway for Cancer Immunotherapy," Trends in Molecular Medicine, 2019, 412-427, vol. 25, No. 5.
Bundesmann, et al., "Amidation of esters assisted by Mg(OCH3)2 or CaCl2", Tetrahedron Letters, 2010, 51, 3879-3882.
Burdette, "STING and the innate immune response to nucleic acids in the cystol", Nature Immunology, 2013, 14(1), 19-26.
Chen, "Activation of STAT6 by STING Is Critical for Antiviral Innate Immunity", Cell, 2011, 147, 436-446.

(Continued)

*Primary Examiner* — Jared Barsky
*Assistant Examiner* — Liyuan Mou
(74) *Attorney, Agent, or Firm* — Alexey Kuznetsov; Bryan C. Zielinski

(57) ABSTRACT

Provided herein are compounds of the general formula (I):

(I)

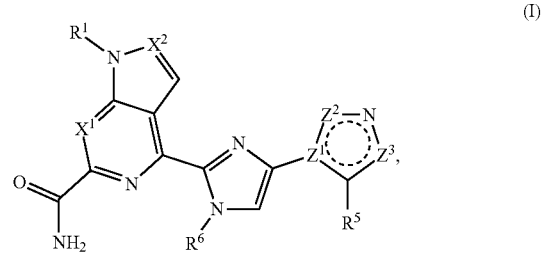

and pharmaceutically acceptable salts thereof, processes for the preparation of these compounds, compositions containing these compounds, and the uses of these compounds.

4 Claims, No Drawings

(56) References Cited

OTHER PUBLICATIONS

Cheng, "Relationship Between the Inhibition Constant (k1) and the Concentration of Inhibitor Which Causes 50 Per Cent Inhibition (I50) of an Enzymatic Reaction*", Biochemical Pharmacology, 1973, 22, 3099-3108.
Cherney, E., et al., "Discovery of Non-Nucleotide Small-Molecule STING Agonists via Chemotype Hybridization," Journal of Medicinal Chemistry, 2022, 3518-3538, vol. 65, No. 4.
Cheuk, "Role of 4-1BB:4-1BB ligand in cancer immunotherapy", Cancer Gene Therapy, 2004, 11, 215-226.
Chin, E., et al., "Antitumor activity of a systemic STING-activating non-nucleotide cGAMP mimetic," Science, 2020, 993-999, vol. 369, No. 6506.
Chmielewski, S., et al., "Development of selective small molecule STING agonists suitable for systemic administration," American Association for Cancer Research, Virtual Annual Meeting II, Jun. 22-24, 2020, Abstract No. 5845, Poster No. 4532A.
Corrales, et al., "Direct Activation of STING in the Tumor Microenvironment Leads to Potent and Systemic Tumor Regression and Immunity", Cell Reports, 2015, pp. 1018-1030, 11.
Dong, "B7-H1, a third member of the B7 family, co-stimulates T-cell proliferation and interleukin-10 secretion", Nature Medicine, 1999, 5(12), 1365-1369.
Freeman, "Engagement of the PD-1 Immunoinhibitory Receptor by a Novel B7 Family Member Leads to Negative Regulation of Lymphocyte Activation", Journal Experimental Medicine, 2000, 192(7), 1027-1034.
Fuertes, et al., "Host type I IFN signals are required for antitumor CD8+ T cell responses through CD8alpha+ dendritic cells", The Journal of Experimental Medicine, 2011, pp. 2005-2016, 208(10).
Haleblian, John K., "Characterization of Habits and Crystalline Modification of Solids and Their Pharmaceutical Applications", 1975, 64(8), 1269-1288.
Harding, et al., "Mitotic progression following DNA damage enables pattern recognition within micronuclei", Nature, 2017, pp. 466-480, 548.
Hughes, "Nanostructure-mediated drug delivery", Nanomedicine: Nanotechnology, Biology, and Medicine, 2005, 1, 22-30.
International Search Report for International Appln. No. PCT/IB2022/052300 completed Jun. 9, 2022.
Iwai, "Involvement of PD-L1 on tumor cells in the escape from host immune system and tumor immunotherapy by PD-L1 blockade", PNAS, 2002, 99(19), 12293-12297.
Joo et al., "C—H Bonds as Ubiquitous Functionality: Preparation of Multiple Regioisomers of Arylated 1,2,4-Triazoles via C—H Arylation", The Journal of Organic Chemistry, 2013, 78, 738-743.
Lian, Yiqian et al., "STING Activation and its Application in Immuno-Oncology", Current Topics in Medicinal Chemistry, 2019, 19(24), 2205-2227.
Libanova, "Cyclic di-nucleotides: new era for small molecules as adjuvants", Microbial Biotechnology, 2012, 5(2), 168-176.
Liu, "Systematic identification of type I and type II interferon-induced antiviral factors", PNAS, 2012, 109(11), 4239-4244.
McCune, "Active Specific Immunotherapy With Tumor Cells and Corynebcterium Parvum A Phase I Study", 1979, 43, 1619-1623.
Pan, B., et al., "An orally available non-nucleotide STING agonist with antitumor activity," Science, 2020, Article eaba6098, vol. 369, No. 6506.
Pryde, D., et al., "The discovery of potent small molecule activators of human STING," European Journal of Medicinal Chemistry, 2021, Article 112869, vol. 209.
Ramanjulu, J., et al., "Design of amidobenzimidazole STING receptor agonists with systemic activity", Nature, 2018, 439-454, vol. 564, No. 7736.
Rogacki, M., et al., "Development of improved small molecule STING agonists suitable for systemic administration," Society for Immunotherapy of Cancer, Nov. 9-14, 2020, Virtual, Abstract ID: 601.
Rogacki, M., et al., "New generation of STING agonists: development and characterization of a novel series of systemic immunomodulators with improved potency," American Association for Cancer Research, Virtual Annual Meeting, Apr. 10-15, 2021 and May 17-21, 2021, Abstract No. 1280.
Rogacki, M., et al., "Characterization of RVU-27065, a novel small-molecule STING agonist suitable for systemic administration," Society for Immunotherapy of Cancer, Nov. 10-14, 2021, Washington, D.C., Poster No. 764.
Stocks et al., "Efficient and Regiospecific One-Pot Synthesis of Substituted 1,2,4-Triazoles", Organic Letters, 2004, 6(17), 2969-2971.
Sivick, et al., "Magnitude of Therapeutics STING Activation Determines CD8+ T Cell-Mediated Anti-tumor Immunity", Cell Reports, 2018, pp. 3074-3085, 25.
Sivick, et al., "Magnitude of Therapeutics STING Activation Determines CD8+ T Cell-Mediated Anti-tumor Immunity", Cell Reports Correction, 2018, pp. 3074-3085, e1-e5, 25.
Vanpouille-Box, "DNA exonuclease Trex1 regulates radiotherapy-induced tumor immunogenicity", Nature Communications, 2017, pp. 1-15.
Viller, N., et al., "TTI-10001, A Next Generation Small Molecule STING Agonist, Demonstrates Potent Anti-Tumor Activity in Mice Following Intravenous or Oral Administration", , Society for Immunotherapy of Cancer, Nov. 6-10, 2019, National Harbor, MD, Poster No. 668.
Wang, Z., et al., "Preclinical Characterization of a Novel Non-Cyclic Dinucleotide Small Molecule STING Agonist with Potent Anti-Tumor Activity in Mice," , American Association for Cancer Research, 2019 Annual Meeting, Mar. 29-Apr. 3, 2019, Atlanta, GA, Abstract No. 3854.
Woo, et al, "STING-Dependent Cytosolic DNA Sensing Mediates Innate Immune Recognition of Immunogenic Tumors", Immunity, 2014, pp. 830-842, 41.
Written Opinion of the International Searching Authority for International Appln. No. PCT/IB2022/052300 completed on Jun. 9, 2022.

* cited by examiner

MODULATORS OF STING (STIMULATOR OF INTERFERON GENES)

CROSS-REFERENCE TO RELATED APPLICATIONS

This patent application claims the benefit of priority to U.S. Provisional Patent Application Ser. No. 63/162,640, filed Mar. 18, 2021, and U.S. Provisional Patent Application Ser. No. 63/165,459, filed Mar. 24, 2021, the contents of which are hereby incorporated by reference in their entireties.

FIELD OF THE INVENTION

The present invention relates to compounds of formulae (A), (I), (II), (III), (III-A), (IV), (V), (VI), (VII), (VIII), or (IX) and their pharmaceutically acceptable salts, to pharmaceutical compositions comprising such compounds or salts thereof, and to the compounds for use as a medicament. The compounds, salts and compositions of the present invention are useful for treating or ameliorating diseases or conditions such as inflammatory diseases and conditions, allergic disease, autoimmune diseases, infectious diseases, abnormal cell growth including cancer, and as vaccine adjuvants.

BACKGROUND

The innate immune system is the first line of defense which is initiated by pattern recognition receptors (PRRs) upon detection of ligands from pathogens as well as damage associated molecular patterns. A growing number of these receptors have been identified, which include sensors of double stranded DNA and unique nucleic acids called cyclic dinucleotides (CDNs). Activation of PRRs leads to up regulation of genes involved in the inflammatory response, including type 1 interferons (also known as IFNs or INFs), proinflammatory cytokines and chemokines which suppress pathogen replication and facilitate adaptive immunity.

The adaptor protein STING, also known as TMEM173, has been identified as a central signalling molecule in the innate immune sensing pathway in response to cytosolic nucleic acids. STING is critical for responses to cytosolic DNA from pathogens or of host origin. Activation of STING by CDNs, generated in response to cytosolic DNA, results in up-regulation of IRF3 and NFκB pathways leading to induction of interferon beta (INF-β) and other cytokines. G. N. Barber, "Sting: infection, inflammation and cancer," *Nat. Rev. Immun.*, 2015, 15, pp 760.

CDNs were first identified as bacterial messengers responsible for controlling numerous responses in prokaryotic cells. Bacterial CDNs, such as c-di-GMP are symmetrical molecules characterized by two 3',5' phosphodiester linkages. Direct activation of STING by bacterial CDNs has recently been confirmed through X-ray crystallography (Burdette D. L. and Vance R. E., *Nature Immunology*, 2013: 14 19-26). Bacterial CDNs have consequently attracted interest as potential vaccine adjuvants (Libanova R. et al, *Microbial Biotechnology* 2012: 5, 168-176). More recently, the response to cytosolic DNA has been shown to involve generation of endogenous CDNs by an enzyme called cyclic guanine adenine synthase (cGAS), producing a novel mammalian CDN signalling molecule identified as cyclic guanine adenine monophosphate (cGAMP), which binds to and activates STING. Interaction of cGAMP with STING has also been demonstrated by X-ray crystallography. Unlike bacterial CDNs, cGAMP is an unsymmetrical molecule characterised by its mixed 2',5' and 3',5' phosphodiester linkages. Like bacterial CDNs, cGAMP activates STING leading to induction of type 1 interferons (type 1 INFs). The role of type 1 INFs in response to invading pathogens is well established. Recombinant interferon alpha (IFNα) was the first approved biological therapeutic and has become an important therapy in viral infections and in cancer. INFs are also known to be potent modulators of the immune response, acting on cells of the immune system.

Administration of a small molecule compound which could stimulate the innate immune response, including the activation of type 1 INF and other cytokines, could become an important strategy for the treatment and prevention of human diseases including viral infections and cancer. This type of immunomodulatory strategy has the potential to identify compounds which may be useful to treat diseases and conditions such as inflammatory diseases and conditions, allergic disease, autoimmune diseases, infectious diseases, abnormal cell growth including cancer, and as vaccine adjuvants.

Given its role in regulating various biological processes, STING continues to be an attractive target for modulation with small molecules. There remains a need to identify further compounds which bind to STING. There remains a need to identify further compounds which activate STING. There remains a need to identify further compounds which have adequate cell permeability. Further there remains a need for compounds which bind to and/or activate STING and which may be useful as therapeutic agents.

Human bioavailability of a therapeutic agent, including, for example, human oral bioavailability of a therapeutic agent, is determined by factors such as the therapeutic agent's absorption, distribution, metabolism, and excretion properties. There remains a need to identify compounds which bind to STING and/or which activate STING and which are bioavailable. There remains a need to identify compounds which bind to STING and/or which activate STING and which are orally bioavailable. As such, there remains a need to identify compounds which bind to STING and/or which activate STING and which have appropriate properties such as, but not limited to, solubility, permeability, absorption, pharmacokinetics, and the like.

SUMMARY

The present invention provides, in part, novel compounds and pharmaceutically acceptable salts thereof. Such compounds may bind to STING, activate STING and/or induce type 1 INFs and/or other cytokines and/or co-stimulatory factors upon incubation with human dendritic cells (DCs), thereby being useful for treating or ameliorating diseases or conditions such as inflammatory diseases and conditions, allergic disease, autoimmune diseases, infectious diseases, abnormal cell growth including cancer, and as vaccine adjuvants.

Also provided are pharmaceutical compositions and medicaments comprising the compounds or salts of the invention, alone or in combination with other therapeutic agents or palliative agents. The present invention also provides, in part, methods for preparing the novel compounds, salts and compositions thereof, and methods of using the foregoing.

In one aspect, the invention provides a compound of formula (I):

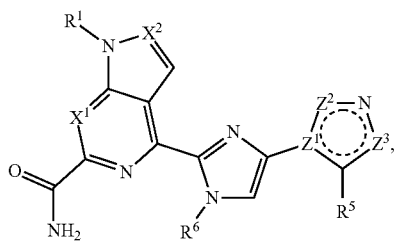

(I)

or a pharmaceutically acceptable salt thereof, wherein
○ represents two conjugated double bonds in a five-membered heteroaryl ring;
$X^1$ is selected from the group consisting of CH and N;
$X^2$ is selected from the group consisting of CH and N;
$R^1$ is selected from the group consisting of $C_1$-$C_4$alkyl, cyclopropyl, cyclobutyl, $C_1$-$C_2$alkylene-(cyclopropyl), and $C_1$-$C_2$alkylene-(cyclobutyl), which $C_1$-$C_4$alkyl, cyclopropyl, cyclobutyl, $C_1$-$C_2$alkylene-(cyclopropyl), or $C_1$-$C_2$alkylene-(cyclobutyl) is optionally substituted by one, two or three substituents each independently selected from the group consisting of halo, hydroxy, and —$OC_1$-$C_4$alkyl;
$Z^1$, $Z^2$ and $Z^3$ are selected such that:
  $Z^1$ is C, $Z^2$ is $NR^2$, and $Z^3$ is $CR^4$; or
  $Z^1$ is N, $Z^2$ is $CR^3$, and $Z^3$ is $CR^4$; or
  $Z^1$ is C, $Z^2$ is $CR^3$, and $Z^3$ is $NR^2$;
$R^2$ is selected from the group consisting of $C_1$-$C_4$alkyl, cyclopropyl, cyclobutyl, oxetanyl, $C_1$-$C_2$alkylene-(cyclopropyl), $C_1$-$C_2$alkylene-(cyclobutyl), and $C_1$-$C_2$alkylene-(oxetanyl), which $C_1$-$C_4$alkyl, cyclopropyl, cyclobutyl, oxetanyl, $C_1$-$C_2$alkylene-(cyclopropyl), $C_1$-$C_2$alkylene-(cyclobutyl), or $C_1$-$C_2$alkylene-(oxetanyl) is optionally substituted by one, two, three, four, five or six substituents each independently selected from the group consisting of halo, hydroxy, —CN and —$OC_1$-$C_4$alkyl;
$R^3$ is selected from the group consisting of halo, hydroxy, —CN, —$OC_1$-$C_4$alkyl, $C_1$-$C_4$alkyl, cyclopropyl, cyclobutyl, oxetanyl, $C_1$-$C_2$alkylene-(cyclopropyl), $C_1$-$C_2$alkylene-(cyclobutyl), and $C_1$-$C_2$alkylene-(oxetanyl), which —$OC_1$-$C_4$alkyl, $C_1$-$C_4$alkyl, cyclopropyl, cyclobutyl, oxetanyl, $C_1$-$C_2$alkylene-(cyclopropyl), $C_1$-$C_2$alkylene-(cyclobutyl), or $C_1$-$C_2$alkylene-(oxetanyl) is optionally substituted by one, two, three, four, five or six substituents each independently selected from the group consisting of halo, hydroxy, —CN and —$OC_1$-$C_4$alkyl;
$R^4$ is selected from the group consisting of H, halo, hydroxy, $C_1$-$C_4$alkyl, and —$OC_1$-$C_4$alkyl, which $C_1$-$C_4$alkyl, or —$OC_1$-$C_4$alkyl is optionally substituted by one, two or three substituents each independently selected from the group consisting of halo and hydroxy; $R^5$ is selected from the group consisting of H, halo, hydroxy, —CN, $C_1$-$C_4$alkyl, and —$OC_1$-$C_4$alkyl, which $C_1$-$C_4$alkyl, or —$OC_1$-$C_4$alkyl is optionally substituted by one, two or three substituents each independently selected from the group consisting of halo and hydroxy; and
$R^6$ is selected from the group consisting of $C_1$-$C_4$alkyl, cyclopropyl, cyclobutyl, oxetanyl, $C_1$-$C_2$alkylene-(cyclopropyl), $C_1$-$C_2$alkylene-(cyclobutyl), and $C_1$-$C_2$alkylene-(oxetanyl), which $C_1$-$C_4$alkyl, cyclopropyl, cyclobutyl, oxetanyl, $C_1$-$C_2$alkylene-(cyclopropyl), $C_1$-$C_2$alkylene-(cyclobutyl), or $C_1$-$C_2$alkylene-(oxetanyl) is optionally substituted by one, two or three substituents each independently selected from the group consisting of halo, hydroxy, —CN and —$OC_1$-$C_4$alkyl.

In another aspect, the invention provides a pharmaceutical composition comprising a compound of any one of the formulae described herein, or a pharmaceutically acceptable salt thereof, and a pharmaceutically acceptable carrier or excipient.

In another aspect, the invention provides a compound of any one of the formulae described herein, or a pharmaceutically acceptable salt thereof, for use as a medicament.

In another aspect, the invention provides therapeutic methods and uses comprising administering a compound of any one of the formulae described herein, or a pharmaceutically acceptable salt thereof.

Also embodied in the invention is a method for the treatment of abnormal cell growth in a mammal, the method comprising administering to the mammal a therapeutically effective amount of a compound of any one of the formulae described herein, or a pharmaceutically acceptable salt thereof.

Further still, embodiments of the invention include those where there is provided a method of upregulating the activity of STING in a mammal, comprising the step of administering to said mammal an effective amount of a compound or salt as described herein; and/or a method of increasing interferon-beta levels in a mammal, comprising the step of administering to said mammal an effective amount of a compound or salt as described herein. In one embodiment the mammal is a human. In such embodiments, the mammal is a human in need of treatment.

Yet further embodiments of the invention include those where there is provided a method of activating STING in a mammal, comprising the step of administering to said mammal an effective amount of a compound or salt described herein. Also provided is a method of stimulating the innate immune response in a mammal, comprising the step of administering to said mammal an effective amount of a compound or salt described herein. In one embodiment the mammal is a human. In such embodiments, the mammal is a human in need of treatment.

DETAILED DESCRIPTION

Unless otherwise stated, the following terms used in the specification and claims have the meanings discussed below. Variables defined in this section, such as R, X, n, and the like, are for reference within this section only, and are not meant to have the same meaning as may be used outside of this definitions section. Further, many of the groups defined herein can be optionally substituted. The listing in this definitions section of typical substituents is exemplary and is not intended to limit the substituents defined elsewhere within this specification and claims.

As used herein, the singular form "a", "an" and "the" include plural references unless indicated otherwise. For example, "a" substituent includes one or more substituents.

"Alkoxy" refers to —O-alkyl where alkyl, unless otherwise defined, is preferably $C_1$-$C_8$, $C_1$-$C_7$, $C_1$-$C_6$, $C_1$-$C_5$, $C_1$-$C_4$, $C_1$-$C_3$, $C_1$-$C_2$ or $C_1$ alkyl, and maybe expressed, for example, as —$OC_1$-$C_4$alkyl.

"Alkyl" refers to a saturated, monovalent, aliphatic hydrocarbon radical including straight chain and branched chain groups of, unless otherwise defined, 1 to 20 carbon atoms ("$C_1$-$C_{20}$alkyl"), preferably 1 to 12 carbon atoms ("$C_1$-$C_{12}$alkyl"), more preferably 1 to 8 carbon atoms ("$C_1$-$C_8$alkyl"), or 1 to 6 carbon atoms ("$C_1$-$C_6$alkyl"), or 1 to 4 carbon atoms ("$C_1$-$C_4$alkyl"). Examples of alkyl groups include methyl, ethyl, n-propyl, iso-propyl (also known as 2-propyl), n-butyl, iso-butyl, tert-butyl, pentyl, neopentyl, and the like. Alkyl may be substituted or unsubstituted. In particular, unless otherwise specified, typical substituent groups include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, oxo, thioxo, amino and —NR$^x$R$^y$, where R$^x$ and R$^y$ are for example hydrogen, alkyl, cycloalkyl, aryl, carbonyl, acetyl, sulfonyl, trifluoromethanesulfonyl and, combined, a five- or six-member heteroalicyclic ring. "Haloalkyl" refers to an alkyl having one or more halo substituents. In some embodiments, haloalkyl has 1, 2, 3, 4, 5, or 6 halo substituents. In some embodiments, haloalkyl has 1, 2, or 3 halo substituents. In some embodiments, haloalkyl is fluoroalkyl.

"Alkylene" refers to a di-valent hydrocarbyl group having the specified number of carbon atoms which can link two other groups together. In some embodiments, alkylene is —(CH$_2$)$_n$— wherein n is 1-8. In some embodiments, n is 1-4. In some embodiments, n is 1-2. Wherein specified, an alkylene may also be substituted by other groups. Typical substituent groups include the same groups that are described herein as suitable for alkyl. The open valences of an alkylene need not be at opposite ends of the chain. Where an alkylene group is described as optionally substituted, the substituents include those typically present on alkyl groups as described herein. For example, "C$_1$-C$_2$alkylene" refers to —CH$_2$—, —CH$_2$CH$_2$—, or —CH(CH$_3$)—, which alkylene may be substituted or unsubstituted as defined herein.

"Amino" refers to the —NH$_2$ group.

"Cyano" refers to the —C≡N group. Cyano may be expressed as —CN.

The term "cycloalkyl", or "carbocyclic" as used interchangeably herein, refers to a non-aromatic, monocyclic, fused or bridged bicyclic or tricyclic carbocyclic ring group containing, in certain embodiments, from three to ten carbon atoms. As used herein, a cycloalkyl group may optionally contain one or two double bonds. The term "cycloalkyl" also includes spirocyclic carbocyclic groups, including multi-ring systems joined by a single atom. The terms "C$_3$-C$_{10}$ cycloalkyl", "C$_3$-C$_7$ cycloalkyl", "C$_3$-C$_6$ cycloalkyl", "C$_3$-C$_5$ cycloalkyl", "C$_3$-C$_4$ cycloalkyl", and "C$_5$-C$_7$ cycloalkyl" contain from three to ten, from three to seven, from three to six, from three to five, from three to four, and from five to seven carbon atoms, respectively. Cycloalkyl groups include, but are not limited to, cyclopropyl, cyclobutyl, cyclopentyl, cyclohexyl, cycloheptyl, cyclopentenyl, cyclohexenyl, octahydropentalenyl, octahydro-1H-indenyl, bicyclo[2.2.1]heptanyl, bicyclo[3.2.1]octanyl, bicyclo[5.2.0]nonanyl, adamantanyl, cyclohexadienyl, adamantanyl, cycloheptanyl, cycloheptatrienyl, and the like. A cycloalkyl group may be substituted or unsubstituted. Typical substituent groups include the same groups that are described herein as suitable for alkyl.

"Halogen" or the prefix "halo" refers to fluoro, chloro, bromo and iodo. In some embodiments, halogen or halo refers to fluoro or chloro. In some embodiments, halogen or halo refers to fluoro.

The term "heterocyclyl", "heterocyclic" or "heteroalicyclic" may be used interchangeably herein to refer to a non-aromatic, monocyclic, saturated or partially unsaturated, fused or bridged bicyclic or tricyclic, or spirocyclic ring group containing, in certain embodiments, a total of three to ten ring atoms, three to seven ring atoms, or four to six ring atoms, in which one, one to two, one to three, or one to four ring atoms are heteroatoms. Said heteroatoms are independently selected from nitrogen, oxygen, and sulfur, and wherein the sulfur atom may be optionally oxidized with one or two oxygen atoms, the remaining ring atoms being carbon, with the proviso that such ring systems may not contain two adjacent oxygen atoms or two adjacent sulfur atoms. The heterocycle ring may also be substituted by an oxo (=O) group at any available carbon atom. The rings may also have one or more double bonds. Heterocyclic rings may be fused to one or more other heterocyclic or carbocyclic rings, which fused rings maybe saturated, partially unsaturated or aromatic. Furthermore, such groups may be bonded to the remainder of the compounds of embodiments disclosed herein through either a carbon atom or a heteroatom, if possible. Examples of heterocycle groups include, but are not limited to:

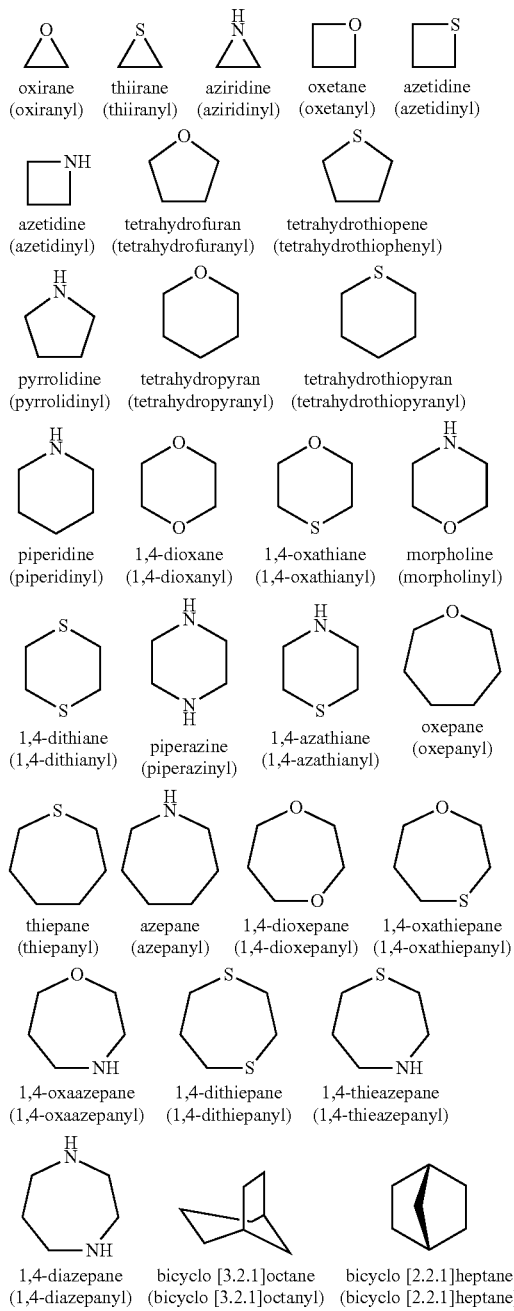

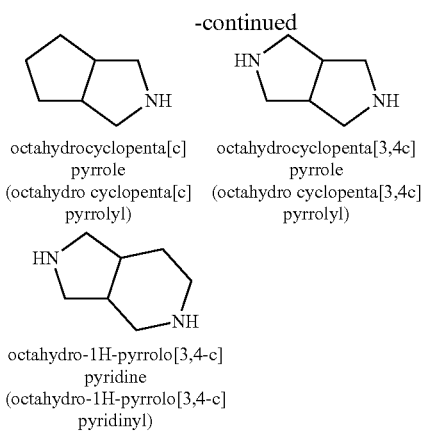

octahydrocyclopenta[c]pyrrole
(octahydro cyclopenta[c]pyrrolyl)

octahydrocyclopenta[3,4c]pyrrole
(octahydro cyclopenta[3,4c]pyrrolyl)

octahydro-1H-pyrrolo[3,4-c]pyridine
(octahydro-1H-pyrrolo[3,4-c]pyridinyl)

The heterocyclyl group may be optionally substituted. Typical substituent groups include those described herein as suitable for alkyl, aryl or heteroaryl. In addition, ring N atoms may be optionally substituted by groups suitable for an amine, for example alkyl, acyl, carbamoyl, sulfonyl substituents.

"Hydroxy" or "hydroxyl" refers to the —OH group.

"Oxo" refers to the =O group.

"Thioxo" refers to the =S group.

"Aryl" or "aromatic" refers to an optionally substituted monocyclic, biaryl or fused bicyclic or polycyclic ring system, having the well-known characteristics of aromaticity, wherein at least one ring contains a completely conjugated pi-electron system. Typically, aryl groups contain 6 to 20 carbon atoms ("$C_6$-$C_{20}$ aryl") as ring members, preferably 6 to 14 carbon atoms ("$C_6$-$C_{14}$ aryl") or more preferably 6 to 12 carbon atoms ("$C_6$-$C_{12}$ aryl"). Fused aryl groups may include an aryl ring (e.g., a phenyl ring) fused to another aryl ring, or fused to a saturated or partially unsaturated carbocyclic or heterocyclic ring. The point of attachment to the base molecule on such fused aryl ring systems may be a C atom of the aromatic portion or a C or N atom of the non-aromatic portion of the ring system. Examples, without limitation, of aryl groups include phenyl, biphenyl, naphthyl, anthracenyl, phenanthrenyl, indanyl, indenyl, and tetrahydronaphthyl. The aryl group may be unsubstituted or substituted as further described herein.

Similarly, "heteroaryl" or "heteroaromatic" refer to monocyclic, heterobiaryl or fused bicyclic or polycyclic ring systems having the well-known characteristics of aromaticity that contain the specified number of ring atoms and include at least one heteroatom selected from N, O and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Examples of unsubstituted heteroaryl groups often include, but are not limited to, pyrrole, furan, thiophene, pyrazole, imidazole, isoxazole, oxazole, isothiazole, thiazole, triazole, oxadiazole, thiadiazole, tetrazole, pyridine, pyridazine, pyrimidine, pyrazine, benzofuran, benzothiophene, indole, benzimidazole, indazole, quinoline, isoquinoline, purine, triazine, naphthyridine and carbazole. In some embodiments, 5- or 6-membered heteroaryl groups are selected from the group consisting of pyrrolyl, furanyl, thiophenyl, pyrazolyl, imidazolyl, isoxazolyl, oxazolyl, isothiazolyl, thiazolyl, triazolyl, pyridinyl, pyrimidinyl, pyrazinyl and pyridazinyl rings. The heteroaryl group may be unsubstituted or substituted as further described herein.

Illustrative examples of monocyclic heteroaryl groups include, but are not limited to:

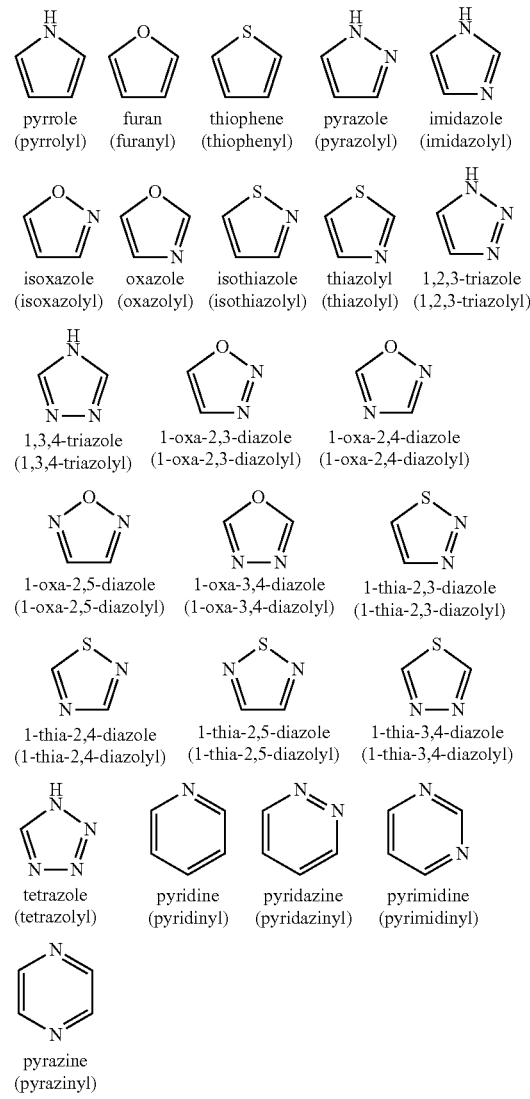

Illustrative examples of fused ring heteroaryl groups include, but are not limited to:

benzimidazole (benzimidazolyl)
indzaole (indzaolyl)
benzotriazole (benzotriazolyl)

pyrrolo[2,3-b]pyridine (pyrrolo[2,3-b]pyridinyl)
pyrrolo[2,3-c]pyridine (pyrrolo[2,3-c]pyridinyl)

pyrrolo[3,2-c]pyridine (pyrrolo[3,2-c]pyridinyl)
pyrrolo[3,2-b]pyridine (pyrrolo[3,2-b]pyridinyl)

pyrrolo[4,5-b]pyridine (pyrrolo[4,5-b]pyridinyl)
pyrrolo[4,5-c]pyridine (pyrrolo[4,5-c]pyridinyl)

pyrazolo[4,3-d]pyridine (pyrazolo[4,3-d]pyidinyl)
pyrazolo[4,3-c]pyridine (pyrazolo[4,3-c]pyidinyl)

pyrazolo[3,4-c]pyridine (pyrazolo[3,4-c]pyidinyl)
pyrazolo[3,4-b]pyridine (pyrazolo[3,4-b]pyidinyl)

isoindole (isoindolyl)
indazole (indazolyl)
pyrine (purinyl)

indolizine (indolininyl)
imidazo[1,2-a]pyridine] (imidazo[1,2-a]pyridinyl)

imidazo[1,5-a]pyridine] (imidazo[1,5-a]pyridinyl)
pyrazolo[1,5-a]pyridine] (pyrazolo[1,5-a]pyridinyl)

pyrrpolo[1,2-b]pyridazine (pyrrolo[1,2-b]pyridazinyl)
imidazo[1,2-c]pyrimidine (imidazo[1,2-c]pyrimidinyl)

quinoline (quinolinyl)
isoquinoline (isoquinolinyl)
cinnoline (cinnolinyl)

quinazoline (azaquinazoline)
quinoxaline (quinoxalinyl)
phthalazine (pthalazinyl)

1,6-naphthyridine (1,6-naphthyridinyl)
1,7-naphthyridine (1,7-naphthyridinyl)
1,8-naphthyridine (1,8-naphthyridinyl)

1,5-naphthyridine (1,5-naphthyridinyl)
2,6-naphthyridine (2,6-naphthyridinyl)
2,7-naphthyridine (2,7-naphthyridinyl)

pyrido[3,2-d]pyrimidine (pyrido[3,2-d]pyrimidinyl)
pyrido[4,3-d]pyrimidine (pyrido[4,3-d]pyrimidinyl)

pyrido[3,4-d]pyrimidine (pyrido[3,4-d]pyrimidinyl)
pyrido[2,3-d]pyrimidine (pyrido[2,3-d]pyrimidinyl)

pyrido[2,3-b]pyrazine (pyrido[2,3-b]pyrazinyl)
pyrido[3,4-b]pyrazine (pyrido[3,4-b]pyrazinyl)

pyrimido[5,4-d]pyrimidine (pyrimido[5,4-d]pyrimidinyl)
pyrazino[2,3-b]pyrazine (pyrazino[2,3-b]pyrazinyl)

pyrimido[4,5-d]pyrimidine pyrimido[4,5-d]pyriminyl

Aryl and heteroaryl moieties described herein as optionally substituted by may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintained in the case of aryl and heteroaryl rings. Optionally substituted aryl, heteroaryl or heterocyclyl groups typically contain from 1 to 5 optional substituents, in some embodiments 1 to 4 optional substituents, in some embodiments 1 to 3 optional substituents, and in some other embodiments 1 to 2 optional substituents. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, oxo, thioxo, and amino.

"Optional" or "optionally" means that the subsequently described event or circumstance may but need not occur, and that the description includes instances where the event or circumstance occurs and instances in which it does not.

The terms "optionally substituted" and "substituted or unsubstituted" may be used interchangeably to indicate that the particular group being described may not have non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described, to the extent that such substitution makes chemical sense. Where an optional substituent is attached via a double bond, such as an oxo (=O) substituents, the group occupies two available valences so the total number of other substituents that may be included is reduced by two. In the case where optional substituents are selected independently from a list of alternatives, the selected groups may be the same or different. For example, "heterocycle group optionally substituted with an alkyl group" means that the alkyl may but need not be present, and the description includes situations where the heterocycle group is substituted with an alkyl group and situations where the heterocycle group is not substituted with the alkyl group. In some embodiments, the particular group is substituted with 1-6 non-hydrogen substituents. In some embodiments, the particular group is substituted with 1-4 non-hydrogen substituents. In some embodiments, the particular group is substituted with 1-2 non-hydrogen substituents. In some embodiments, optional substituents are independently selected from D, halogen, —CN, —NH$_2$, —OH, =O, —NH(CH$_3$), —N(CH$_3$)$_2$, —NH(cyclopropyl), —CH$_3$, —CH$_2$CH$_3$, —CF$_3$, —OCH$_3$, and —OCF$_3$.

In one aspect, the invention provides a compound of formula (A):

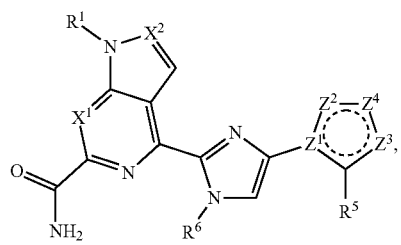

(A)

or a pharmaceutically acceptable salt thereof, wherein
○ represents two conjugated double bonds in a five-membered heteroaryl ring;
$X^1$ is selected from the group consisting of CH and N;
$X^2$ is selected from the group consisting of CH and N;
$R^1$ is selected from the group consisting of C$_1$-C$_6$alkyl, cyclopropyl, cyclobutyl, C$_1$-C$_2$alkylene-(cyclopropyl), and C$_1$-C$_2$alkylene-(cyclobutyl), which C$_1$-C$_6$alkyl, cyclopropyl, cyclobutyl, C$_1$-C$_2$alkylene-(cyclopropyl), or C$_1$-C$_2$alkylene-(cyclobutyl) is optionally substituted by one, two or three substituents each independently selected from the group consisting of halo, hydroxy, and —OC$_1$-C$_6$alkyl;

$Z^1$, $Z^2$ and $Z^3$ are selected such that:
    $Z^1$ is C, $Z^2$ is NR$^2$, and $Z^3$ is CR$^4$; or
    $Z^1$ is N, $Z^2$ is CR$^3$, and $Z^3$ is CR$^4$; or
    $Z^1$ is C, $Z^2$ is CR$^3$, and $Z^3$ is NR$^2$.
$Z^4$ is N or NR$^7$;
$R^2$ is selected from the group consisting of C$_1$-C$_6$alkyl, cyclopropyl, cyclobutyl, oxetanyl, C$_1$-C$_2$alkylene-(cyclopropyl), C$_1$-C$_2$alkylene-(cyclobutyl), and C$_1$-C$_2$alkylene-(oxetanyl), which C$_1$-C$_6$alkyl, cyclopropyl, cyclobutyl, oxetanyl, C$_1$-C$_2$alkylene-(cyclopropyl), C$_1$-C$_2$alkylene-(cyclobutyl), or C$_1$-C$_2$alkylene-(oxetanyl) is optionally substituted by one, two, three, four, five or six substituents each independently selected from the group consisting of halo, hydroxy, oxo, amino, —CN, —OC$_1$-C$_6$alkyl, and —OC$_1$-C$_6$haloalkyl;

$R^3$ is selected from the group consisting of H, halo, hydroxy, —CN, —OC$_1$-C$_6$alkyl, C$_1$-C$_6$alkyl, cyclopropyl, cyclobutyl, oxetanyl, C$_1$-C$_2$alkylene-(cyclopropyl), C$_1$-C$_2$alkylene-(cyclobutyl), and C$_1$-C$_2$alkylene-(oxetanyl), which —OC$_1$-C$_6$alkyl, C$_1$-C$_6$alkyl, cyclopropyl, cyclobutyl, oxetanyl, C$_1$-C$_2$alkylene-(cyclopropyl), C$_1$-C$_2$alkylene-(cyclobutyl), or C$_1$-C$_2$alkylene-(oxetanyl) is optionally substituted by one, two, three, four, five or six substituents each independently selected from the group consisting of halo, hydroxy, —CN and —OC$_1$-C$_6$alkyl;

$R^4$ is selected from the group consisting of H, halo, hydroxy, C$_1$-C$_6$alkyl, and —OC$_1$-C$_6$alkyl, which C$_1$-C$_6$alkyl or —OC$_1$-C$_6$alkyl is optionally substituted by one, two or three substituents each independently selected from the group consisting of halo and hydroxy;

$R^5$ is selected from the group consisting of H, halo, hydroxy, —CN, C$_1$-C$_6$alkyl, and —OC$_1$-C$_6$alkyl, which C$_1$-C$_6$alkyl, or —OC$_1$-C$_6$alkyl is optionally substituted by one, two or three substituents each independently selected from the group consisting of halo and hydroxy;

$R^6$ is selected from the group consisting of C$_1$-C$_6$alkyl, cyclopropyl, cyclobutyl, oxetanyl, C$_1$-C$_2$alkylene-(cyclopropyl), C$_1$-C$_2$alkylene-(cyclobutyl), and C$_1$-C$_2$alkylene-(oxetanyl), which C$_1$-C$_6$alkyl, cyclopropyl, cyclobutyl, oxetanyl, C$_1$-C$_2$alkylene-(cyclopropyl), C$_1$-C$_2$alkylene-(cyclobutyl), or C$_1$-C$_2$alkylene-(oxetanyl) is optionally substituted by one, two or three substituents each independently selected from the group consisting of halo, hydroxy, phenyl, —CN and —OC$_1$-C$_6$alkyl; and $R^7$ is H or C$_1$-C$_6$alkyl, which C$_1$-C$_6$alkyl is optionally substituted by one, two or three substituents each independently selected from the group consisting of halo, hydroxy, and —OC$_1$-C$_6$alkyl.

In some embodiments, $Z^4$ is N. In some embodiments, $Z^4$ is NR$^7$. In some embodiments, $R^7$ is H. In some embodiments, $R^7$ is C$_1$-C$_4$alkyl. In some embodiments, $R^7$ is —CH$_3$. In some embodiments, $R^7$ is —CH$_2$CH$_3$. In some embodiments, $R^7$ is —CH$_2$F. In some embodiments, $R^7$ is —CH$_2$CF$_3$.

In another aspect, the invention provides a compound of formula (I):

(I)

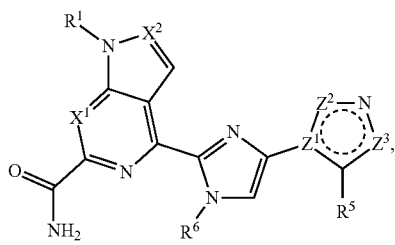

or a pharmaceutically acceptable salt thereof, wherein
◯ represents two conjugated double bonds in a five-membered heteroaryl ring;
$X^1$ is selected from the group consisting of CH and N;
$X^2$ is selected from the group consisting of CH and N;
$R^1$ is selected from the group consisting of $C_1$-$C_4$alkyl, cyclopropyl, cyclobutyl, $C_1$-$C_2$alkylene-(cyclopropyl), and $C_1$-$C_2$alkylene-(cyclobutyl), which $C_1$-$C_4$alkyl, cyclopropyl, cyclobutyl, $C_1$-$C_2$alkylene-(cyclopropyl), or $C_1$-$C_2$alkylene-(cyclobutyl) is optionally substituted by one, two or three substituents each independently selected from the group consisting of halo, hydroxy, and —O$C_1$-$C_4$alkyl;
$Z^1$, $Z^2$ and $Z^3$ are selected such that:
    $Z^1$ is C, $Z^2$ is $NR^2$, and $Z^3$ is $CR^4$; or
    $Z^1$ is N, $Z^2$ is $CR^3$, and $Z^3$ is $CR^4$; or
    $Z^1$ is C, $Z^2$ is $CR^3$, and $Z^3$ is $NR^2$;
$R^2$ is selected from the group consisting of $C_1$-$C_4$alkyl, cyclopropyl, cyclobutyl, oxetanyl, $C_1$-$C_2$alkylene-(cyclopropyl), $C_1$-$C_2$alkylene-(cyclobutyl), and $C_1$-$C_2$alkylene-(oxetanyl), which $C_1$-$C_4$alkyl, cyclopropyl, cyclobutyl, oxetanyl, $C_1$-$C_2$alkylene-(cyclopropyl), $C_1$-$C_2$alkylene-(cyclobutyl), or $C_1$-$C_2$alkylene-(oxetanyl) is optionally substituted by one, two, three, four, five or six substituents each independently selected from the group consisting of halo, hydroxy, —CN and —O$C_1$-$C_4$alkyl;
$R^3$ is selected from the group consisting of halo, hydroxy, —CN, —O$C_1$-$C_4$alkyl, $C_1$-$C_4$alkyl, cyclopropyl, cyclobutyl, oxetanyl, $C_1$-$C_2$alkylene-(cyclopropyl), $C_1$-$C_2$alkylene-(cyclobutyl), and $C_1$-$C_2$alkylene-(oxetanyl), which —O$C_1$-$C_4$alkyl, $C_1$-$C_4$alkyl, cyclopropyl, cyclobutyl, oxetanyl, $C_1$-$C_2$alkylene-(cyclopropyl), $C_1$-$C_2$alkylene-(cyclobutyl), or $C_1$-$C_2$alkylene-(oxetanyl) is optionally substituted by one, two, three, four, five or six substituents each independently selected from the group consisting of halo, hydroxy, —CN and —O$C_1$-$C_4$alkyl;
$R^4$ is selected from the group consisting of H, halo, hydroxy, $C_1$-$C_4$alkyl, and —O$C_1$-$C_4$alkyl, which $C_1$-$C_4$alkyl, or —O$C_1$-$C_4$alkyl is optionally substituted by one, two or three substituents each independently selected from the group consisting of halo and hydroxy;
$R^5$ is selected from the group consisting of H, halo, hydroxy, —CN, $C_1$-$C_4$alkyl, and —O$C_1$-$C_4$alkyl, which $C_1$-$C_4$alkyl, or —O$C_1$-$C_4$alkyl is optionally substituted by one, two or three substituents each independently selected from the group consisting of halo and hydroxy; and
$R^6$ is selected from the group consisting of $C_1$-$C_4$alkyl, cyclopropyl, cyclobutyl, oxetanyl, $C_1$-$C_2$alkylene-(cyclopropyl), $C_1$-$C_2$alkylene-(cyclobutyl), and $C_1$-$C_2$alkylene-(oxetanyl), which $C_1$-$C_4$alkyl, cyclopropyl, cyclobutyl, oxetanyl, $C_1$-$C_2$alkylene-(cyclopropyl), $C_1$-$C_2$alkylene-(cyclobutyl), or $C_1$-$C_2$alkylene-(oxetanyl) is optionally substituted by one, two or three substituents each independently selected from the group consisting of halo, hydroxy, —CN and —O$C_1$-$C_4$alkyl.

In one embodiment, the invention provides a compound of formula (II):

(II)

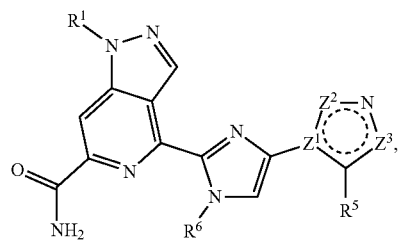

or a pharmaceutically acceptable salt thereof, wherein
◯ represents two conjugated double bonds in a five-membered heteroaryl ring; and
wherein $R^1$; $Z^1$; $Z^2$; $Z^3$; $R^2$; $R^3$; $R^4$; $R^5$; and $R^6$ are defined as for formula (I).

In one embodiment, the invention provides a compound of formula (III):

(III)

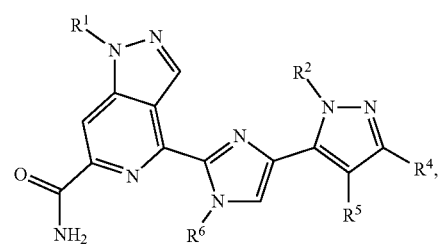

or a pharmaceutically acceptable salt thereof, wherein $R^1$; $R^2$; $R^4$; $R^5$; and $R^6$ are defined as for formula (I).

In one embodiment, the invention provides a compound of formula (IV):

(IV)

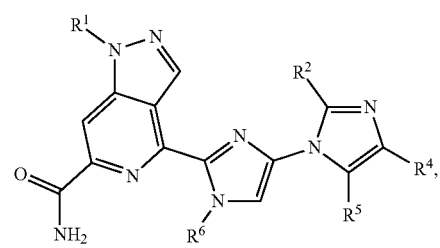

or a pharmaceutically acceptable salt thereof, wherein $R^1$; $R^3$; $R^4$; $R^5$; and $R^6$ are defined as for formula (I).

In one embodiment, the invention provides a compound of formula (V):

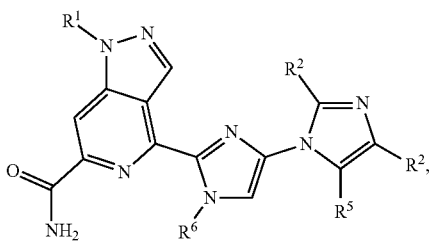

(V)

or a pharmaceutically acceptable salt thereof, wherein $R^1$; $R^2$; $R^3$; $R^5$; and $R^6$ are defined as for formula (I).

In one embodiment, the invention provides a compound of formula (VI):

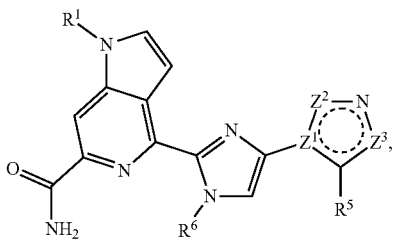

(VI)

or a pharmaceutically acceptable salt thereof, wherein
○ represents two conjugated double bonds in a five-membered heteroaryl ring; and
wherein $R^1$; $Z^1$; $Z^2$; $Z^3$; $R^2$; $R^3$; $R^4$; $R^5$; and $R^6$ are defined as for formula (I).

In one embodiment, the invention provides a compound of formula (VII):

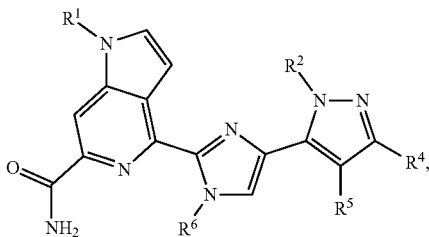

(VII)

or a pharmaceutically acceptable salt thereof, wherein $R^1$; $R^2$; $R^4$; $R^5$; and $R^6$ are defined as for formula (I).

In one embodiment, the invention provides a compound of formula (VIII):

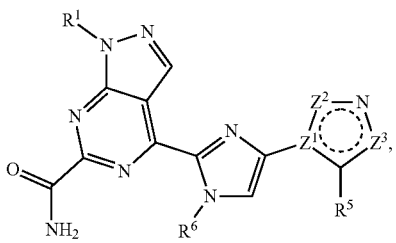

(VIII)

or a pharmaceutically acceptable salt thereof, wherein
○ represents two conjugated double bonds in a five-membered heteroaryl ring; and wherein $R^1$; $Z^1$; $Z^2$; $Z^3$; $R^2$; $R^3$; $R^4$; $R^5$; and $R^6$ are defined as for formula (I).

In one embodiment, the invention provides a compound of formula (IX):

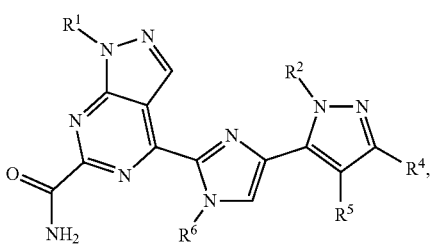

(IX)

or a pharmaceutically acceptable salt thereof, wherein $R^1$; $R^2$; $R^4$; $R^5$; and $R^6$ are defined as for formula (I).

In one embodiment of compounds of the invention, including those of formulae (A), (I), (II), (III), (IV), (V), (VI), (VII), (VIII), and (IX) or a pharmaceutically acceptable salt thereof, $R^1$ is $C_1$-$C_4$alkyl, for example —$CH_3$ or —$CH_2CH_3$. In one embodiment of compounds of the invention, including those of formulae (A), (I), (II), (III), (IV), (V), (VI), (VII), (VIII), and (IX) or a pharmaceutically acceptable salt thereof, $R^1$ is selected from the group consisting of —$CH_3$ and —$CH_2CH_3$. In some embodiments, $R^1$ is —$CH_3$. In some embodiments, $R^1$ is —$CH_2CH_3$.

In one embodiment of compounds of the invention, including those of formulae (A), (I), (II), (III), (IV), (V), (VI), (VII), (VIII), and (IX) or a pharmaceutically acceptable salt thereof, $R^2$ is selected from the group consisting of $C_1$-$C_4$alkyl and $C_1$-$C_2$alkylene-(cyclopropyl), which $C_1$-$C_4$alkyl or $C_1$-$C_2$alkylene-(cyclopropyl) is optionally substituted by one, two, three, four, five or six substituents each independently selected from the group consisting of halo, hydroxy, —CN and —$OC_1$-$C_4$alkyl. In one embodiment of compounds of the invention, including those of formulae (A), (I), (II), (III), (IV), (V), (VI), (VII), (VIII), and (IX) or a pharmaceutically acceptable salt thereof, $R^2$ is $C_1$-$C_4$alkyl, for example —$CH_3$, —$CH_2CH_3$, or —$(CH_2)_2CH_3$, which $C_1$-$C_4$alkyl is optionally substituted by one, two, three, four, five or six substituents each independently selected from the group consisting of halo, hydroxy, —CN and —$OC_1$-$C_4$alkyl to form, for example, —$CH_2CF_3$, —$(CH_2)_2CF_3$, —$(CH_2)_2OH$, —$(CH_2)_2OCH_3$, or —$(CH_2)_3OCH_3$. In one embodiment of compounds of the invention, including those of formulae (A), (I), (II), (III), (IV), (V), (VI), (VII), (VIII), and (IX) or a pharmaceutically acceptable salt thereof, $R^2$ is $C_1$-$C_2$alkylene-(cyclopropyl), for example —$CH_2$(cyclopropyl), which $C_1$-$C_2$alkylene-(cyclopropyl) is optionally substituted by one, two, three, four, five or six substituents each independently selected from the group consisting of halo, hydroxy, —CN and —$OC_1$-$C_4$alkyl. In one embodiment of compounds of the invention, including those of formulae (A), (I), (II), (III), (IV), (V), (VI), (VII), (VIII), and (IX) or a pharmaceutically acceptable salt thereof, $R^2$ is selected from the group consisting of —$CH_3$, —$CH_2CH_3$, —$(CH_2)_2CH_3$, —$CH_2CF_3$, —$(CH_2)_2CF_3$, —$(CH_2)_3OH$, —$(CH_2)_2OCH_3$, —$(CH_2)_3OCH_3$ and —CH$_2$(cyclopropyl). In some embodiments, R$^2$ is —CH$_3$. In some embodiments, R$^2$ is —CH$_2$CH$_3$. In some embodiments, R$^2$ is —(CH$_2$)$_2$CH$_3$. In some embodiments, R$^2$ is —CH$_2$CF$_3$. In some embodiments, R$^2$ is —(CH$_2$)$_2$CF$_3$. In some embodiments, R$^2$ is —(CH$_2$)$_3$OH. In some embodiments, R$^2$ is —(CH$_2$)$_2$OCH$_3$. In some embodiments, R$^2$ is —(CH$_2$)$_3$OCH$_3$. In some embodiments, R$^2$ is —CH$_2$(cyclopropyl).

In one embodiment of compounds of the invention, including those of formulae (A), (I), (II), (III), (IV), (V), (VI), (VII), (VIII), and (IX) or a pharmaceutically acceptable salt thereof, R$^3$ is C$_1$-C$_4$alkyl, for example —CH$_2$CH$_3$, which C$_1$-C$_4$alkyl is optionally substituted by one, two, three, four, five or six substituents each independently selected from the group consisting of halo, hydroxy, —CN and —OC$_1$-C$_4$alkyl.

In one embodiment of compounds of the invention, including those of formulae (A), (I), (II), (III), (IV), (V), (VI), (VII), (VIII), and (IX) or a pharmaceutically acceptable salt thereof, R$^4$ is selected from the group consisting of H and C$_1$-C$_4$alkyl, for example —CH$_3$, which C$_1$-C$_4$alkyl is optionally substituted by one, two or three substituents each independently selected from the group consisting of halo and hydroxy. In one embodiment of compounds of the invention, including those of formulae (A), (I), (II), (III), (IV), (V), (VI), (VII), (VIII), and (IX) or a pharmaceutically acceptable salt thereof, R$^4$ is selected from the group consisting of H and —CH$_3$. In some embodiments, R$^4$ is H. In some embodiments, R$^4$ is —CH$_3$.

In one embodiment of compounds of the invention, including those of formulae (A), (I), (II), (III), (IV), (V), (VI), (VII), (VIII), and (IX) or a pharmaceutically acceptable salt thereof, R$^5$ is selected from the group consisting of H, halo, for example fluoro or chloro, and hydroxy. In one embodiment of compounds of the invention, including those of formulae (A), (I), (II), (III), (IV), (V), (VI), (VII), (VIII), and (IX) or a pharmaceutically acceptable salt thereof, R$^5$ is selected from the group consisting of H, chloro and hydroxy. In some embodiments, R$^5$ is H. In some embodiments, R$^5$ is chloro. In some embodiments, R$^5$ is hydroxy.

In one embodiment of compounds of the invention, including those of formulae (A), (I), (II), (III), (IV), (V), (VI), (VII), (VIII), and (IX) or a pharmaceutically acceptable salt thereof, R$^6$ is selected from the group consisting of C$_1$-C$_4$alkyl, for example —CH$_3$, —CH$_2$CH$_3$, or —CH(CH$_3$)$_2$, and cyclopropyl, which C$_1$-C$_4$alkyl or cyclopropyl is optionally substituted by one, two or three substituents each independently selected from the group consisting of halo, for example fluoro to form, for example, —CH$_2$CHF$_2$, hydroxy, —CN and —OC$_1$-C$_4$alkyl. In one embodiment of compounds of the invention, including those of formulae (A), (I), (II), (III), (IV), (V), (VI), (VII), (VIII), and (IX) or a pharmaceutically acceptable salt thereof, R$^6$ is selected from the group consisting of —CH$_3$, —CH$_2$CH$_3$, —CH$_2$CHF$_2$, —CH(CH$_3$)$_2$, and cyclopropyl. In some embodiments, R$^6$ is —CH$_3$. In some embodiments, R$^6$ is —CH$_2$CH$_3$. In some embodiments, R$^6$ is —CH$_2$CHF$_2$. In some embodiments, R$^6$ is —CH(CH$_3$)$_2$. In some embodiments, R$^6$ is cyclopropyl.

In another aspect, the invention provides a compound of formula (III-A):

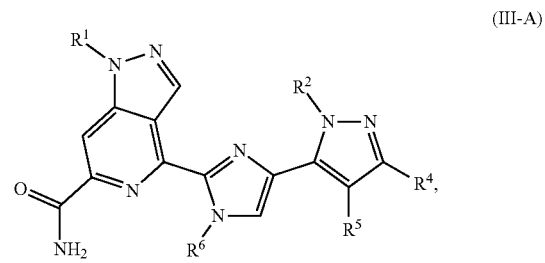

(III-A)

or a pharmaceutically acceptable salt thereof, wherein

R$^1$ is C$_1$-C$_4$alkyl or C$_1$-C$_4$fluoroalkyl;

R$^2$ is C$_1$-C$_4$alkyl or (C$_1$-C$_4$alkylene)-OC$_1$-C$_4$alkyl, which C$_1$-C$_4$alkyl or (C$_1$-C$_4$alkylene)-OC$_1$-C$_4$alkyl is optionally substituted by one, two, or three substituents each independently selected from the group consisting of halo, oxo, and hydroxy;

R$^4$ is C$_1$-C$_4$alkyl;

R$^5$ is H; and

R$^6$ is C$_1$-C$_4$alkyl.

In some embodiments of a compound of formula (III-A), R$^1$ is C$_1$-C$_4$alkyl. In some embodiments, R$^1$ is C$_1$-C$_2$alkyl. In some embodiments, R$^1$ is C$_1$-C$_4$fluoroalkyl. In some embodiments, R$^1$ is C$_1$-C$_2$fluoroalkyl. In some embodiments, R$^1$ is —CH$_3$, —CH$_2$CH$_3$, —CH$_2$F, —CHF$_2$, —CF$_3$, —CHFCH$_3$, —CF$_2$CH$_3$, —CH$_2$CH$_2$F, —CH$_2$CHF$_2$, or —CH$_2$CF$_3$. In some embodiments, R$^1$ is —CH$_3$, —CH$_2$CH$_3$, or —CH$_2$F. In some embodiments, R$^1$ is —CH$_3$. In some embodiments, R$^1$ is —CH$_2$CH$_3$. In some embodiments, R$^1$ is —CH$_2$F. In some embodiments, R$^2$ is C$_1$-C$_4$alkyl. In some embodiments, R$^2$ is C$_1$-C$_2$alkyl. In some embodiments, R$^2$ is (C$_1$-C$_4$alkylene)-OC$_1$-C$_2$alkyl. In some embodiments, R$^2$ is —CH$_3$, —CH$_2$CH$_3$, —(CH$_2$)$_2$OCH$_3$, —(CH$_2$)$_3$OCH$_3$, —(CH$_2$)$_2$OCH$_2$CH$_3$, or —(CH$_2$)$_3$OCH$_2$CH$_3$. In some embodiments, R$^2$ is —CH$_3$, —CH$_2$CH$_3$, —(CH$_2$)$_2$OCH$_3$, or —(CH$_2$)$_3$OCH$_3$. In some embodiments, R$^2$ is —CH$_3$. In some embodiments, R$^2$ is —CH$_2$CH$_3$. In some embodiments, R$^2$ is —(CH$_2$)$_2$OCH$_3$. In some embodiments, R$^2$ is —(CH$_2$)$_3$OCH$_3$. In some embodiments, R$^4$ is C$_1$-C$_3$alkyl. In some embodiments, R$^4$ is C$_1$-C$_2$alkyl. In some embodiments, R$^4$ is —CH$_3$, —CH$_2$CH$_3$, —CH$_2$CH$_2$CH$_3$, or —CH(CH$_3$)$_2$. In some embodiments, R$^4$ is —CH$_3$ or —CH$_2$CH$_3$. In some embodiments, R$^4$ is —CH$_3$. In some embodiments, R$^4$ is —CH$_2$CH$_3$. In some embodiments, R$^6$ is C$_1$-C$_3$alkyl. In some embodiments, R$^6$ is C$_1$-C$_2$alkyl. In some embodiments, R$^6$ is —CH$_3$, —CH$_2$CH$_3$, —CH$_2$CH$_2$CH$_3$, or —CH(CH$_3$)$_2$. In some embodiments, R$^6$ is —CH$_3$ or —CH$_2$CH$_3$. In some embodiments, R$^6$ is —CH$_3$. In some embodiments, R$^6$ is —CH$_2$CH$_3$.

Further embodiments of the invention include a compound selected from:

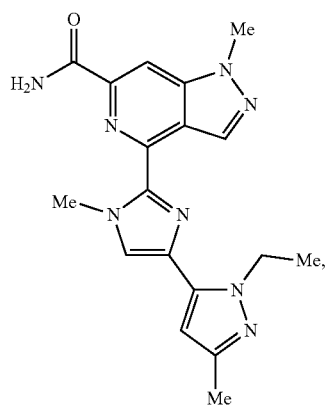
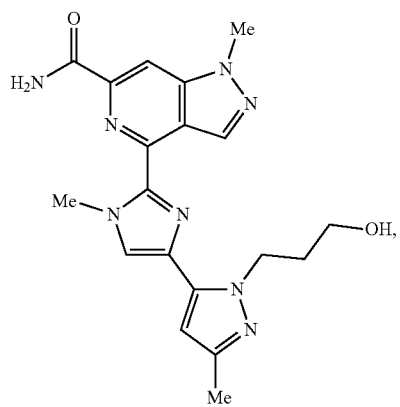
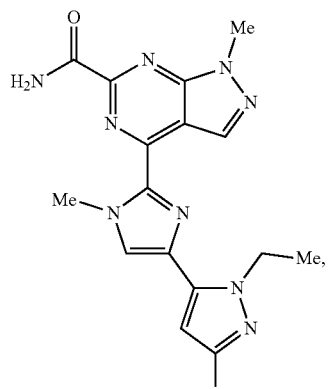
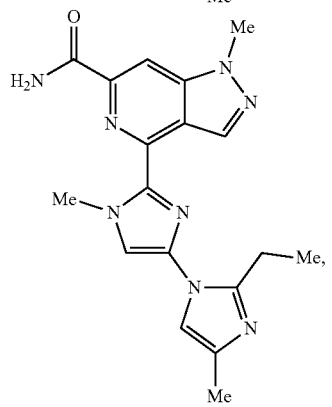
-continued
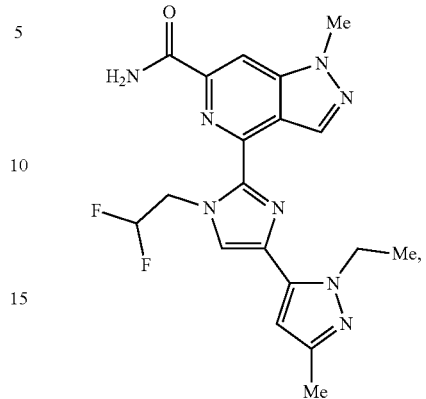
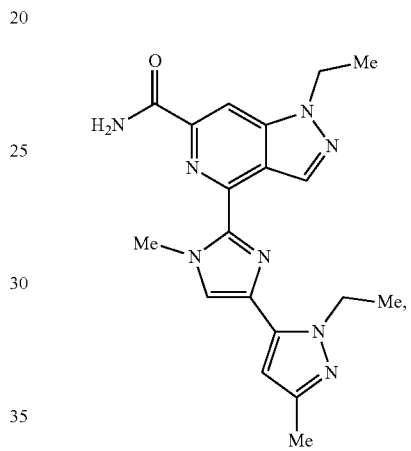
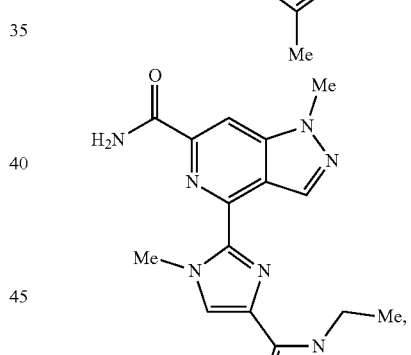
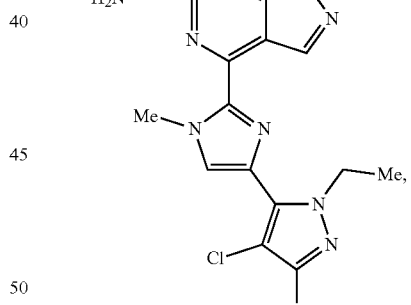
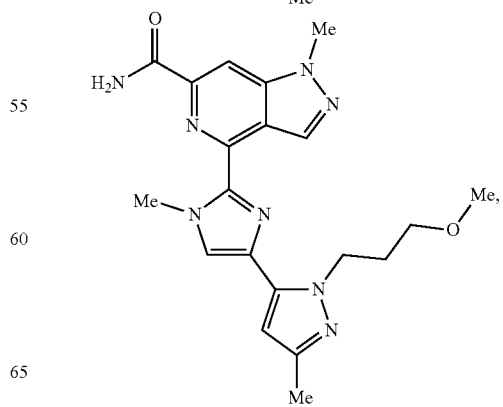

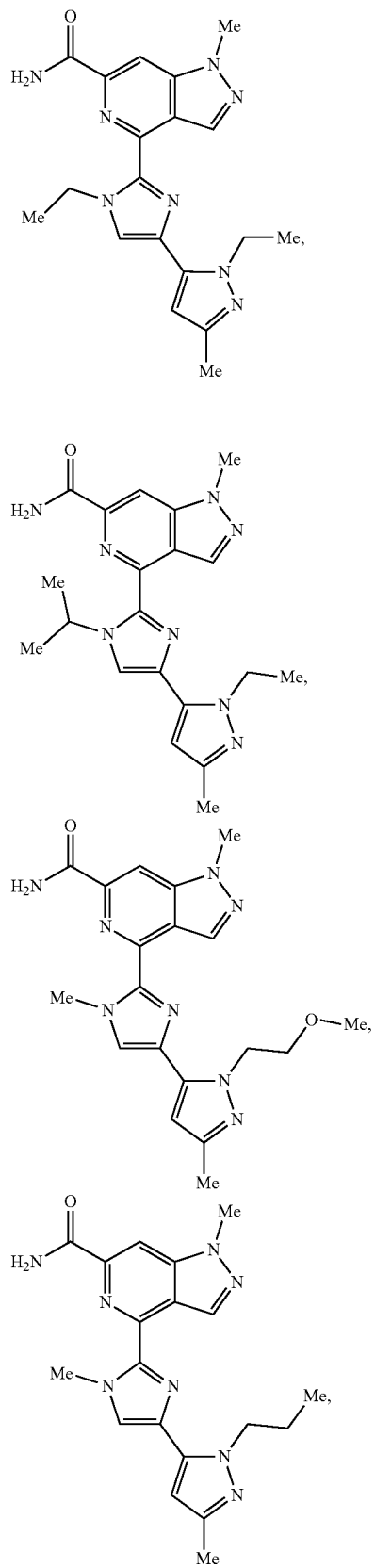
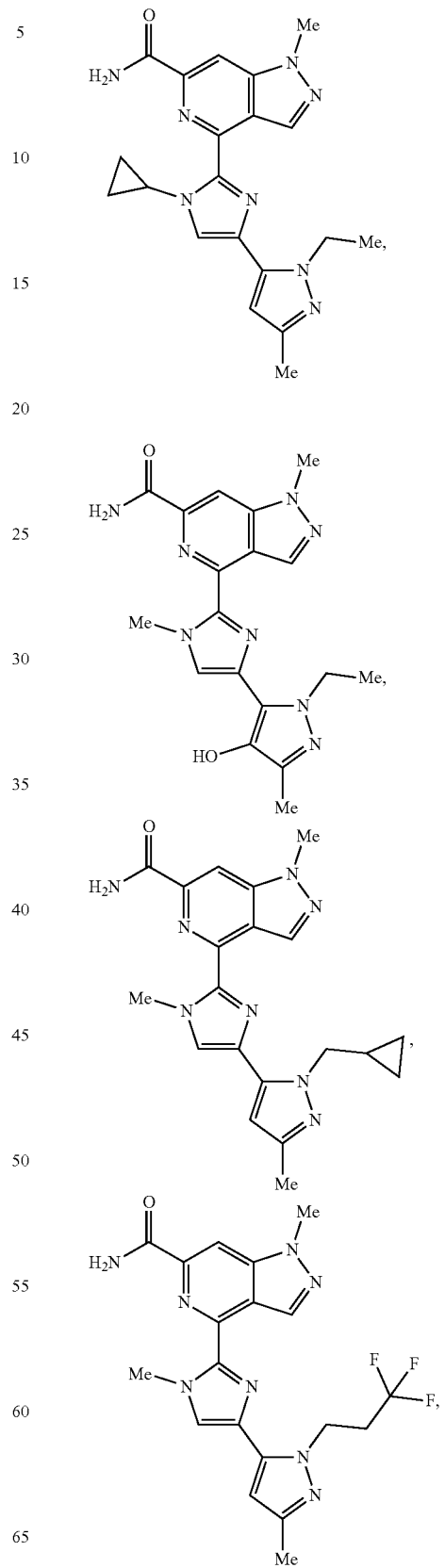

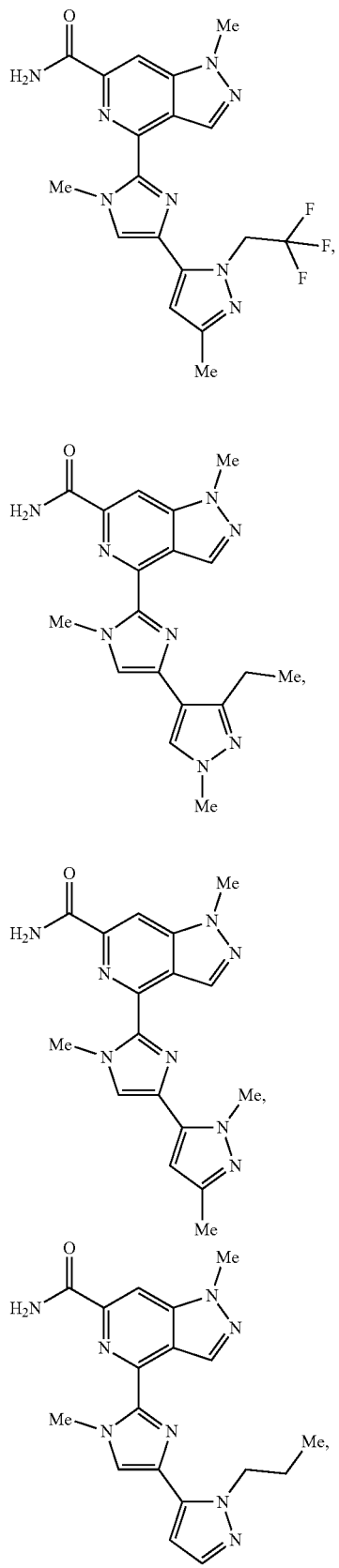
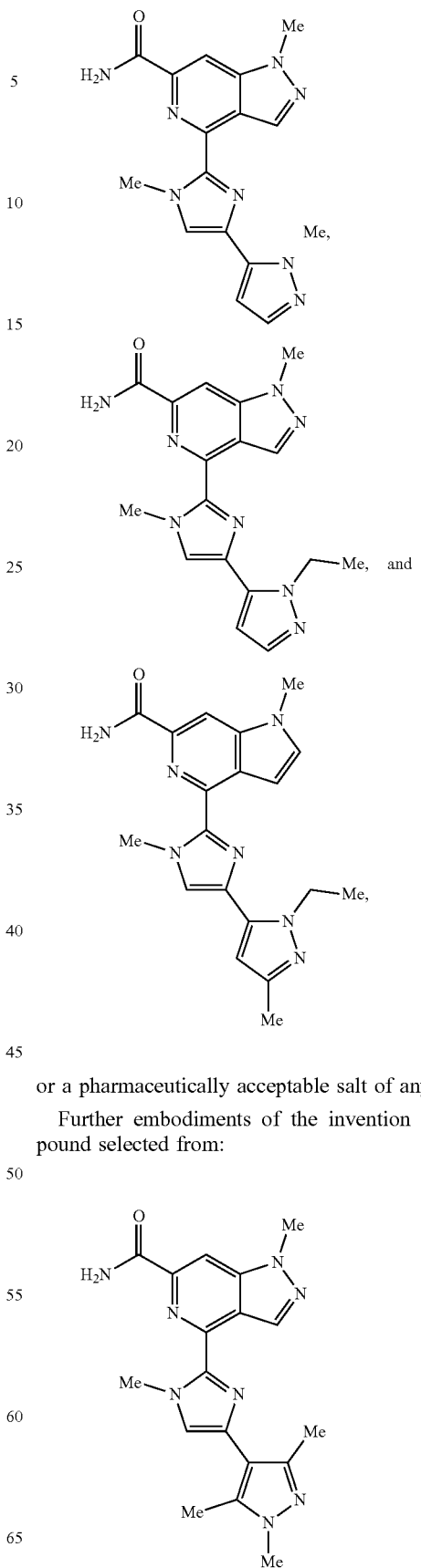
or a pharmaceutically acceptable salt of any thereof.
Further embodiments of the invention include a compound selected from:

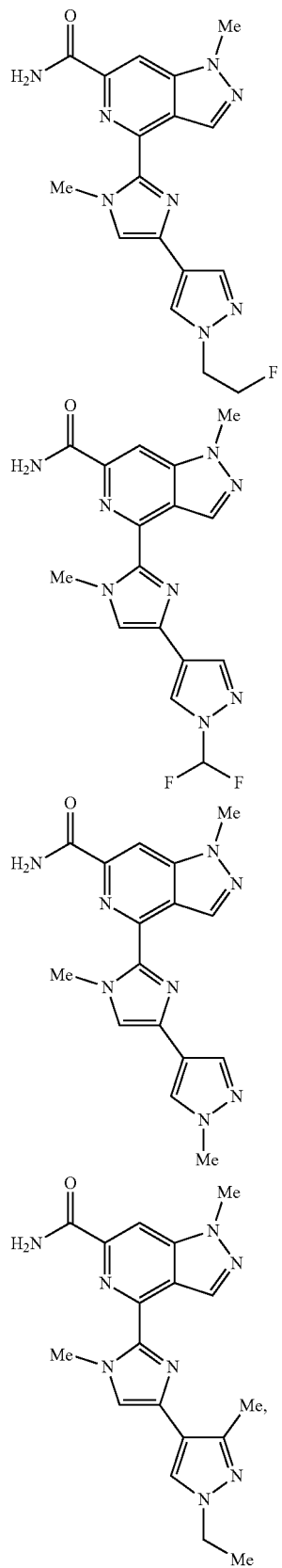
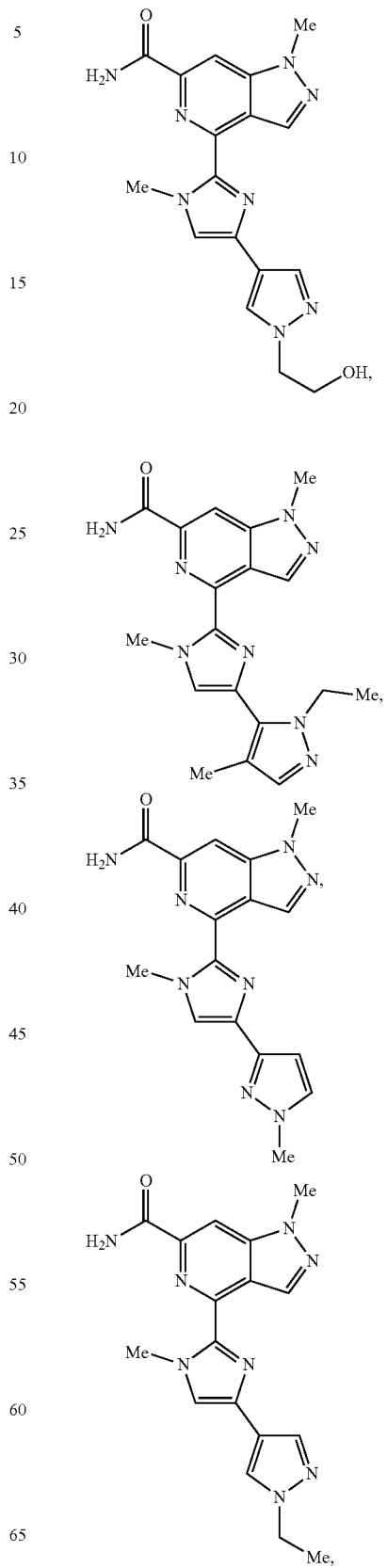

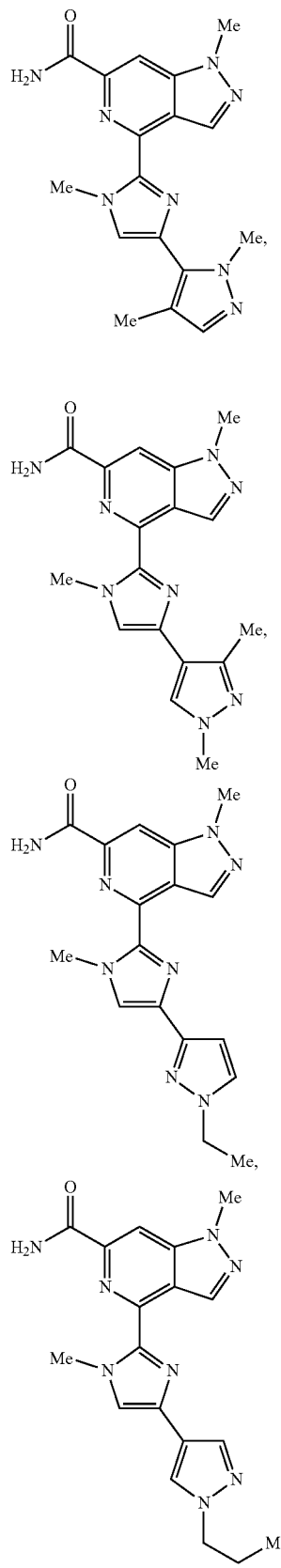
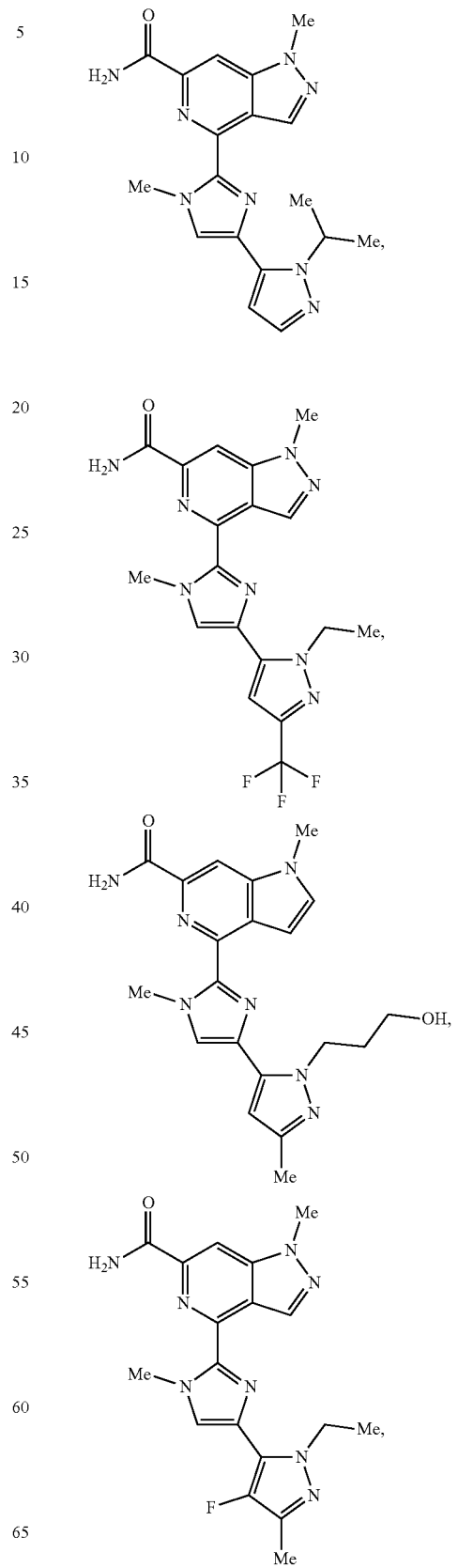

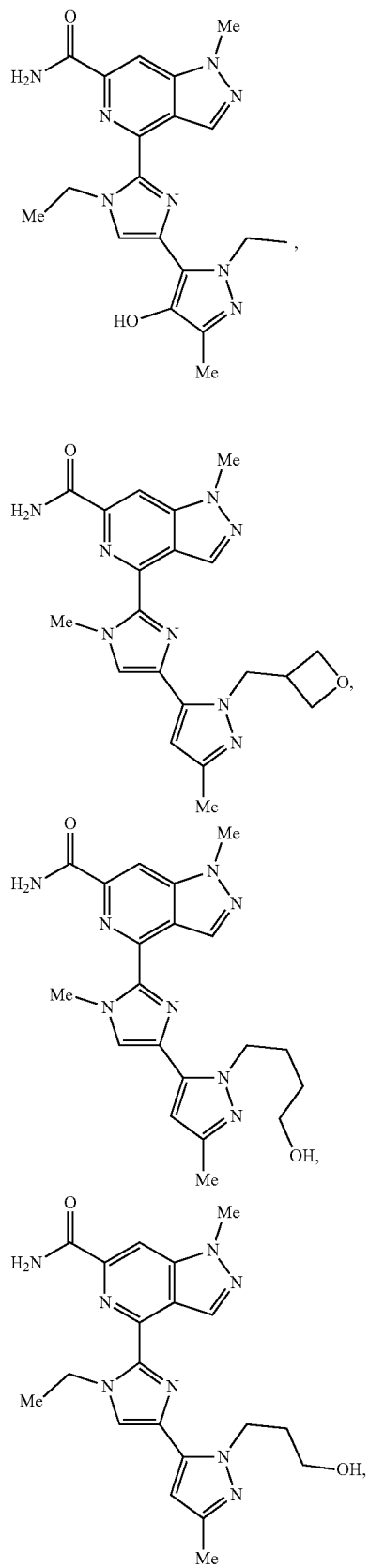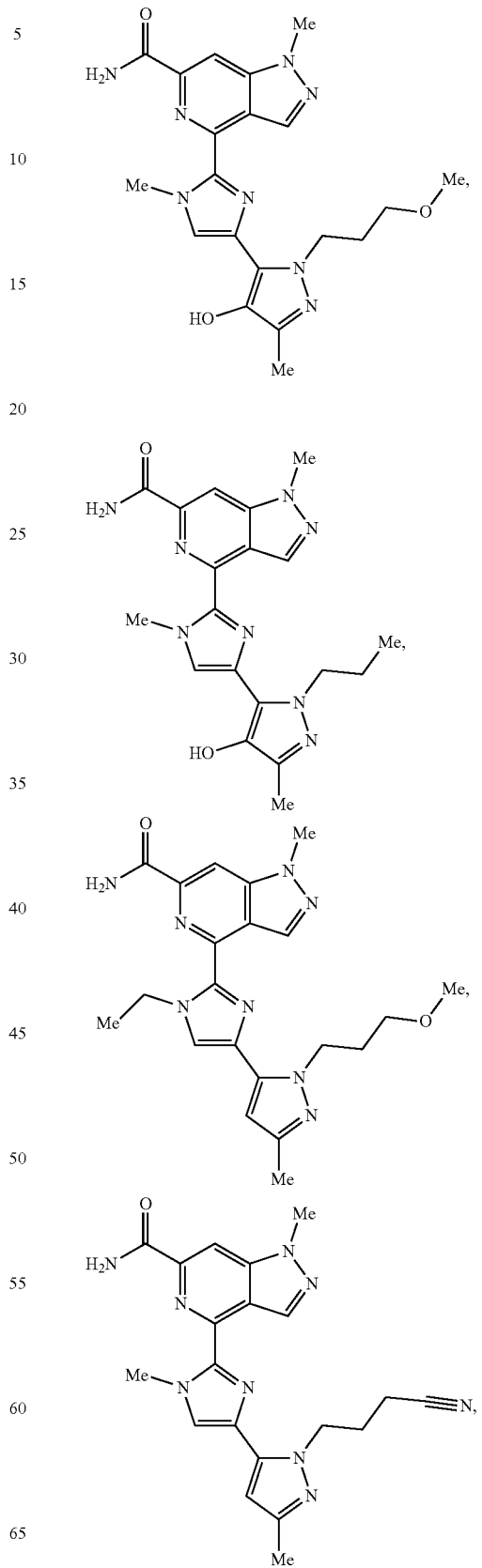

31
-continued
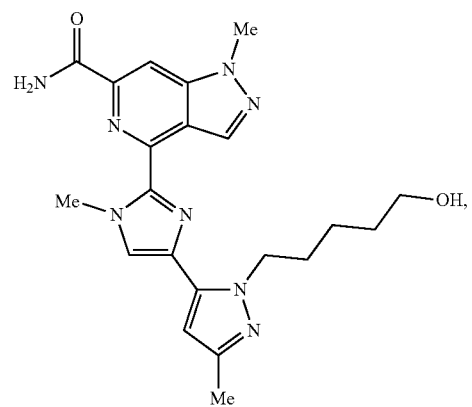
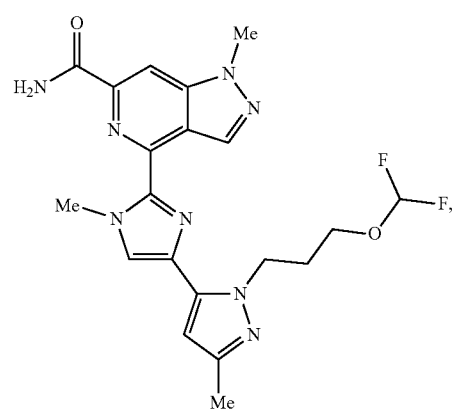
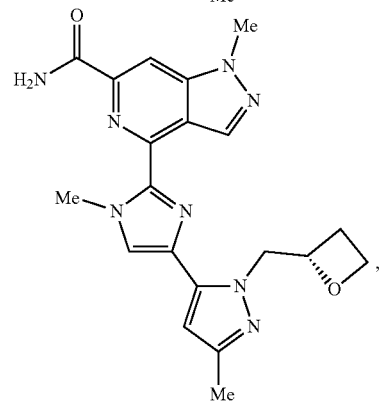
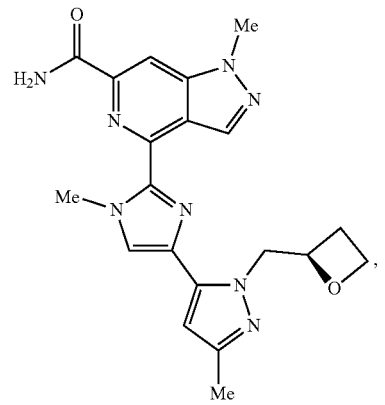
32
-continued
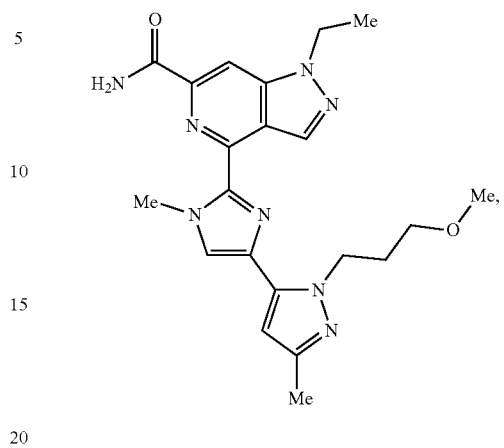
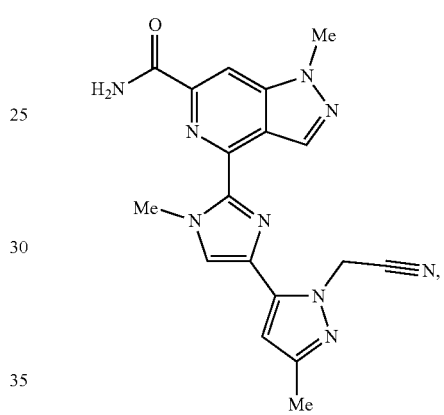
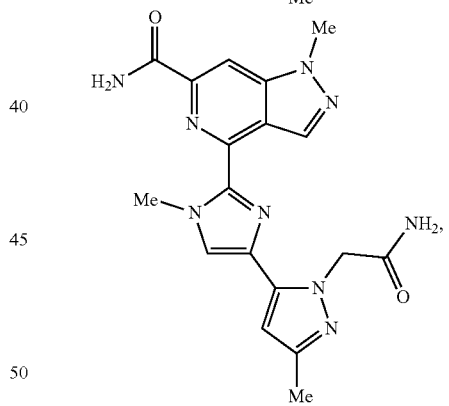
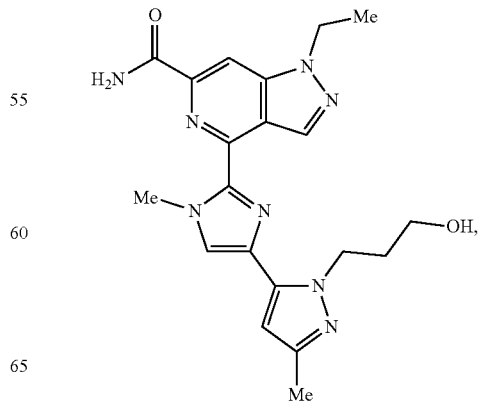

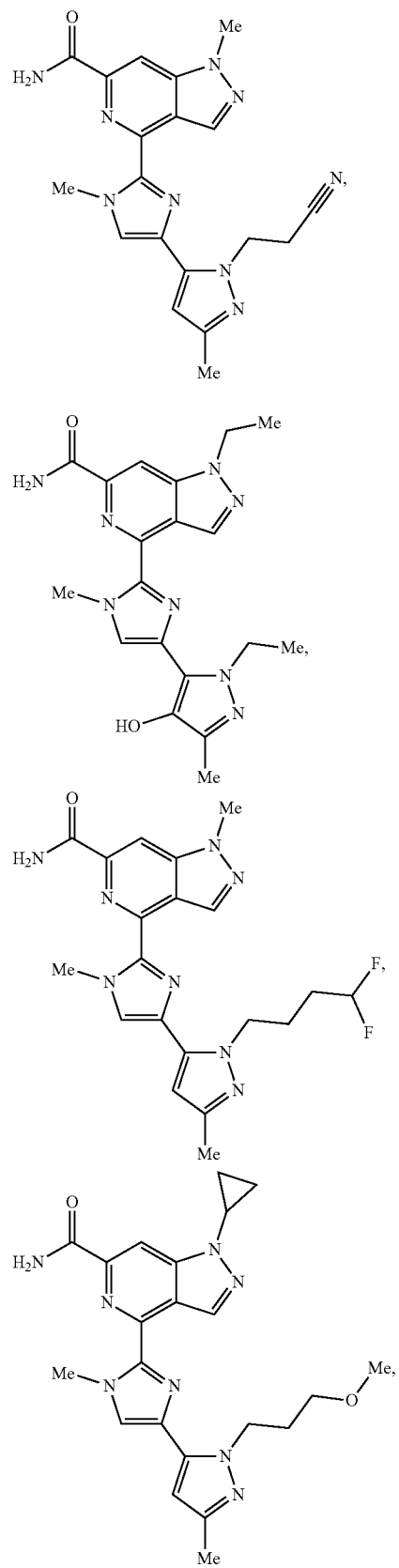
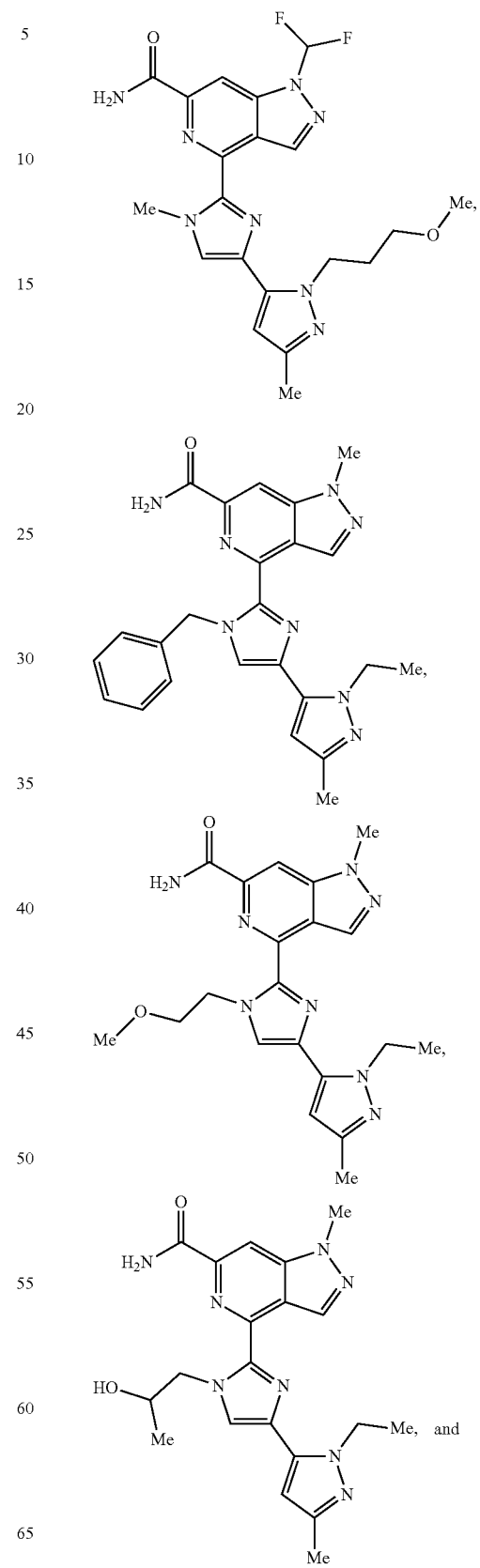

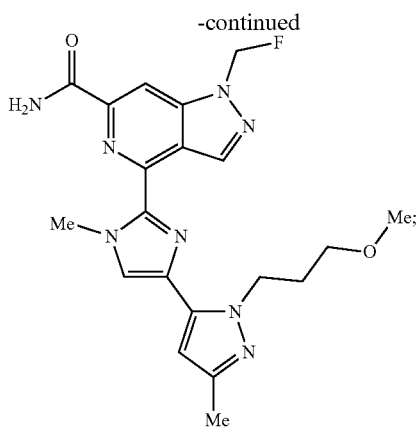

or a pharmaceutically acceptable salt of any thereof.

General schemes for synthesizing the compounds of the invention can be found in the Examples section herein.

Unless indicated otherwise, all references herein to the compounds of the invention include references to salts, solvates, hydrates and complexes thereof, and to solvates, hydrates and complexes of salts thereof, including tautomers, polymorphs, stereoisomers, and isotopically labeled versions thereof.

As used herein, the term "pharmaceutically acceptable salt", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode and valerate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Those compounds of the invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In some embodiments, stoichiometric quantities of reagents are employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at room temperature of between about 0° C. and about 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry may exist. The term 'solvate' is used herein to describe a molecular complex comprising the compound of the invention and one or more pharmaceutically acceptable solvent molecules, for example, ethanol. When the solvent is water the term 'hydrate' may optionally be used interchangeable with the term 'solvate'. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the compounds of the invention.

Derivatives of compounds of the invention which may have little or no pharmacological activity themselves but can, when administered to a subject or patient, be converted into the compounds of the invention, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the compounds of the invention with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs include:

(i) where the compound contains a carboxylic acid functionality —(COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl; and (iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate and the like.

Further examples of replacement groups in accordance with the foregoing examples and examples of other prodrug types may be found in the aforementioned references.

Finally, certain compounds of the invention may themselves act as prodrugs of other of the compounds of the invention.

Compounds of the invention containing one or more asymmetric carbon and/or phosphorous atoms can exist as two or more stereoisomers. The carbon-carbon bonds of the compounds of the invention may be depicted herein using a solid line, a solid wedge, or a dotted wedge. The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric atom. Where the compounds according to this invention have at least one chiral center, they may accordingly exist as enantiomers. Where the compounds possess two or more chiral centers, they may additionally exist as diastereomers.

Compounds of the invention that have chiral centers may exist as stereoisomers, such as racemates, enantiomers, or diastereomers.

Included within the scope of the invention are all stereoisomers, geometric isomers and tautomeric forms of the compounds of the invention, including compounds exhibiting more than one type of isomerism, and mixtures of one or more thereof. Stereoisomers of the compounds of the formulae herein may include cis and trans (or Z/E) isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs). Also included are acid addition or base salts wherein the counterion is optically active, for example, D-lactate or L-lysine, or racemic, for example, DL-tartrate or DL-arginine.

When a racemate crystallizes, crystals of two different types may be possible. The first type is the racemic compounds (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included with in the scope of compounds of the invention. Tautomers exist as mixtures of a tautomeric set in solution.

In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecules and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers may be possible. Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or supercritical fluid chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereomers converted to the corresponding pure enantiomer(s) by means well known to one skilled in the art.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, which are identical to those recited in one of the formulae provided, but for the fact that one or more atoms are replaced by an atom having an atomic mass or mass number different from the atomic mass or mass number usually found in nature.

Isotopically-labeled compounds of the invention may generally be prepared by conventional techniques known to those skilled in the art or by processes analogous to those described herein, using an appropriate isotopically-labeled reagent in place of the non-labeled reagent otherwise employed.

Examples of isotopes suitable for inclusion in the compounds of the invention include isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^{3}$H, and carbon-14, $^{14}$C, are particularly useful for this purpose in view of their ease of incorporation and ready means of detection. Substitution with heavier isotopes such as deuterium, $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Pharmaceutical Compositions and Routes of Administration

In one embodiment, the present invention relates to pharmaceutical compositions comprising a compound of the invention, or a pharmaceutically acceptable salt thereof, and a pharmaceutically acceptable carrier or excipient.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols. The choice of excipient will to a large extent depend on factors such as the particular mode of administration, the effect of the excipient on solubility and stability, and the nature of the dosage form.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The pharmaceutically acceptable carrier may comprise any conventional pharmaceutical carrier or excipient. The choice of carrier and/or excipient will to a large extent depend on factors such as the particular mode of administration, the effect of the excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

In one aspect, the invention provides a pharmaceutical composition comprising a compound of the invention, including those of formulae (A), (I), (II), (III), (III-A), (IV), (V), (VI), (VII), (VIII), and (IX), or a pharmaceutically acceptable salt thereof, and a pharmaceutically acceptable carrier or excipient. In some embodiments, the pharmaceutical composition comprises two or more pharmaceutically acceptable carriers and/or excipients. Optionally, such compositions may comprise a compound or salt as described herein which is a component of an antibody-drug conjugate; and/or may comprise a compound as described herein which is a component of a particle-based delivery system.

In one embodiment, compounds of the invention, including those of formulae (A), (I), (II), (III), (III-A), (IV), (V), (VI), (VII), (VIII), or (IX), or a pharmaceutically acceptable salt thereof, may be administered orally. Oral administration may involve swallowing, so that the compound enters the gastrointestinal tract, or buccal or sublingual administration may be employed by which the compound enters the blood stream directly from the mouth. Thus, the pharmaceutical composition may, for example, be in a form suitable for oral administration as a tablet, capsule, pill, powder, sustained release formulation, solution or suspension.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, the active agent may make up from 1 wt % to 80 wt % of the dosage form, more typically from 5 wt % to 60 wt % of the dosage form. In addition to the active agent, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant may comprise from 1 wt % to 25 wt % and in some embodiments from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt % and in some embodiments from 0.5 wt % to 3 wt % of the tablet.

Other conventional ingredients include anti-oxidants, colorants, flavoring agents, preservatives and taste-masking agents.

Exemplary tablets may contain up to about 80 wt % active agent, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles may be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intravesical (e.g., bladder), subcutaneous and intratumoral. Suitable devices for parenteral administration include needle (including micro needle) injectors, needle-free injectors and infusion techniques. Suitable formulations for parenteral administration include, but are not limited to, a sterile solution, suspension or emulsion.

In one embodiment compounds of the invention, including those of formulae (A), (I), (II), (III), (III-A), (IV), (V), (VI), (VII), (VIII), or (IX), or a pharmaceutically acceptable salt thereof, may be administered intravenously.

In one embodiment, compounds of the invention, including those of formulae (A), (I), (II), (III), (III-A), (IV), (V), (VI), (VII), (VIII), or (IX), or a pharmaceutically acceptable salt thereof, may be administered intravesically.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may potentially be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted- and programmed-release. Thus, compounds of the invention may potentially be formulated as a solid, semi-solid, or thixotropic liquid for administration as an implanted depot providing modified release of the active compound. Examples of such formulations include drug-coated stents and PGLA microspheres.

Exemplary parenteral administration forms include solutions or suspensions of an active compound in a sterile aqueous solution, for example, aqueous propylene glycol or dextrose solutions. Such dosage forms may be suitably buffered, if desired.

The compounds of the invention may also potentially be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted- and programmed-release.

Compounds of the invention may also potentially be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer may contain a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the compound may be micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-co-glycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired amount of the compound of the invention. The overall daily dose may be administered in a single dose or, more usually, as divided doses throughout the day.

Compounds of the invention may potentially be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Compounds of the invention may also potentially be administered directly to the eye or ear, typically in the form of drops of a micronized suspension or solution in isotonic, pH-adjusted, sterile saline. Other formulations suitable for ocular and aural administration may include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted-, or programmed-release.

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, may be useful for different dosage forms and administration routes. Both inclusion and non-inclusion complexes may potentially be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Nanoparticles also represent drug delivery systems suitable for most administration routes. Over the years, a variety of natural and synthetic polymers have been explored for the preparation of nanoparticles, of which Poly(lactic acid) (PLA), Poly(glycolic acid) (PGA), and their copolymers (PLGA) have been extensively investigated because of their biocompatibility and biodegradability. Nanoparticles and other nanocarriers act as potential carries for several classes of drugs such as anticancer agents, antihypertensive agents, immunomodulators, and hormones; and macromolecules such as nucleic acids, proteins, peptides, and antibodies. See, e.g., Crit. Rev. Ther. Drug Carrier Syst. 21:387-422, 2004; Nanomedicine: Nanotechnology, Biology and Medicine 1:22-30, 2005.

The compounds and compositions of the present invention may be administered as a component of an antibody-drug conjugate or other targeted delivery modality.

The pharmaceutical composition may be in unit dosage forms suitable for single administration of precise amounts.

Therapeutic Methods and Uses

The invention further provides therapeutic methods and uses comprising a compound of the invention, including those of formulae (A), (I), (II), (III), (III-A), (IV), (V), (VI), (VII), (VIII), or (IX), or a pharmaceutically acceptable salt thereof, alone or in combination with one or more therapeutic agents or palliative agents.

As used herein, the terms "treat", "treating" and "treatment" refer to a method of alleviating or abrogating a cellular disorder and/or its attendant symptoms. With regard particularly to cancer, these terms simply mean that the life expectancy of an individual affected with a cancer will be increased or that one or more of the symptoms of the disease will be reduced.

"In vitro" refers to procedures performed in an artificial environment such as, e.g., without limitation, in a test tube or culture medium.

"In vivo" refers to procedures performed within a living organism such as, without limitation, a mouse, rat, rabbit and/or human.

"Organism" refers to any living entity comprised of at least one cell. A living organism can be as simple as, for example, a single eukaryotic cell or as complex as a mammal, including a human being.

As used herein, the term "subject" refers to a human or animal subject. In certain preferred embodiments the subject is a human.

As used herein, the term "patient" refers to a "subject" in need of therapy. In certain preferred embodiments the patient is a human.

The terms "abnormal cell growth" and "hyperproliferative disorders" are used interchangeably. "Abnormal cell growth", unless otherwise indicated, refers to cell growth that is independent of normal regulatory mechanisms (e.g., loss of contact inhibition). Abnormal cell growth may be benign (non-cancerous), or malignant (cancerous).

As used here "cancer" refers to any malignant and/or invasive growth or tumor caused by abnormal cell growth. As used herein "cancer" refers to solid tumors named for the type of cells that form them initially, cancer of blood, bone marrow or the lymphatic systems. Examples of solid tumors include, but are not limited to, sarcomas and carcinomas. Examples of cancers of the blood includes, but are not limited to, leukemias, lymphomas and myelomas. The term "cancer" includes, but is not to limited to, a primary cancer that originates at a specific site in the body, a metastatic cancer that has spread from the place in which it started to other parts of the body, a recurrence from the original primary cancer after remissions, and a second primary cancer that is a new primary cancer in a person with a history of previous cancer of different type from latter one. In particular, the compounds of the invention may be useful in the prevention and treatment of a variety of human hyperproliferative disorders, such a malignant or benign abnormal cell growth.

The stimulator of interferon genes (STING) protein functions as both a cytosolic DNA sensor and an adaptor protein in Type 1 interferon signaling. The terms "STING" and "stimulator of interferon genes" refer to any form of the STING protein, as well as variants, isoforms, and species homologs that retain at least a part of the activity of STING. Unless indicated differently, such as by specific reference to human STING, STING includes all mammalian species of native sequence STING, e.g. human, monkey, and mouse.

As used herein, the term "STING activator" or "STING agonist" refers to a compound which, upon binding, (1) stimulates or activates STING and inducing downstream signal transduction characterized by activation of the molecules associated with STING function; (2) enhances, increases, promotes, induces, or prolongs an activity, function, or presence of STING, or (3) enhances, increases, promotes, or induces the expression of STING. Such actions include, but are not limited to, direct phosphorylation of STING, IRF3 and/or NF-κB and could also include STAT6. STING pathway activation results in, for example, increased production of type 1 interferons (mainly IFN-α and IFN-β) and expression of interferon-stimulated genes (Chen H, et al. "Activation of STAT6 by STING is Critical for Antiviral Innate Immunity". Cell, 2011, vol 14: 433-446; and Liu S-Y., et al. "Systematic identification of type I and type II interferon-induced antiviral factors". Proc. Natl. Acad. Sci. 2012: vol 109 4239-4244).

As used herein, the term "STING-modulated" refers to a condition affected by STING directly or via the STING pathway, including, but not limited to, inflammatory diseases and conditions, allergic disease, autoimmune diseases, infectious diseases, abnormal cell growth including cancer, and as vaccine adjuvants.

In one embodiment, the compounds of the invention, including those of formulae (A), (I), (II), (III), (III-A), (IV), (V), (VI), (VII), (VIII), and (IX), or pharmaceutically acceptable salts thereof, bind to STING.

In one embodiment, the compounds of the invention, including those of formulae (A), (I), (II), (III), (III-A), (IV), (V), (VI), (VII), (VIII), and (IX), or pharmaceutically acceptable salts thereof, activate STING including, for example as determined by modulation of interferon-β induction, phosphorylation of IRF3, and the like.

In one aspect, the invention provides a compound of the invention, including those of formulae (A), (I), (II), (III), (III-A), (IV), (V), (VI), (VII), (VIII), and (IX), or a pharmaceutically acceptable salt thereof, for use as a medicament.

In one aspect, the invention provides therapeutic methods and uses comprising administering a compound of the invention, including those of formulae (A), (I), (II), (III), (III-A), (IV), (V), (VI), (VII), (VIII), and (IX), or a pharmaceutically acceptable salt thereof.

In one aspect, the invention is a method for the treatment of inflammatory diseases and conditions, allergic diseases, autoimmune diseases, infectious diseases, and abnormal cell growth in a mammal, the method comprising administering to the mammal a therapeutically effective amount of a compound of the invention, including those of formulae (A), (I), (II), (III), (III-A), (IV), (V), (VI), (VII), (VIII), and (IX), or a pharmaceutically acceptable salt thereof. This method may optionally employ a compound or salt as described herein as a component of an antibody-drug conjugate, or as a component of a particle-based delivery system. One embodiment of the invention is a method for the treatment of inflammatory diseases and conditions in a mammal. One embodiment of the invention is a method for the treatment of allergic diseases in a mammal. One embodiment of the invention is a method for the treatment of autoimmune disease in a mammal. One embodiment of the invention is a method for the treatment of infectious diseases in a mammal. In one embodiment, the mammal is a human. In such embodiments, the mammal is a human in need of treatment.

In one aspect, the invention is a method for the treatment of abnormal cell growth in a mammal, the method comprising administering to the mammal a therapeutically effective amount of a compound of the invention, including those of formulae (A), (I), (II), (III), (III-A), (IV), (V), (VI), (VII), (VIII), and (IX), or a pharmaceutically acceptable salt thereof.

In another aspect, the invention provides a method for the treatment of abnormal cell growth in a mammal, comprising administering to the mammal an amount of a compound of the invention, including those of formulae (A), (I), (II), (III), (III-A), (IV), (V), (VI), (VII), (VIII), and (IX), or a pharmaceutically acceptable salt thereof, that is effective in treating abnormal cell growth.

In such embodiments the abnormal cell growth may be cancer. If the abnormal cell growth is cancer, the cancer to be treated may be lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. In one embodiment, the cancer is cancer of the bladder. In one embodiment, the cancer of the bladder is urothelial carcinoma. In one embodiment, the cancer of the bladder is non-muscle invasive bladder cancer (NMIBC). In one embodiment the cancer of the bladder is muscle invasive bladder cancer (MIBC). In one embodiment, the cancer of the bladder is non-metastatic urothelial carcinoma. In one embodiment, the cancer of the bladder is metastatic urothelial carcinoma. In one embodiment, the cancer of the bladder is non-urothelial carcinoma. In one embodiment the mammal is a human. In such embodiments, the mammal is a human in need of treatment.

In still another embodiment, the invention provides a method of inhibiting cancer cell proliferation in a subject, comprising administration to the subject a compound of the invention, or a pharmaceutically acceptable salt thereof, in an amount effective to inhibit cancer cell proliferation.

These methods of the invention described herein may optionally employ a compound or salt as described herein as a component of an antibody-drug conjugate, or as a component of a particle-based delivery system.

Also embodied in the invention is a compound of the invention, including those of formulae (A), (I), (II), (III), (III-A), (IV), (V), (VI), (VII), (VIII), and (IX), or a pharmaceutically acceptable salt thereof, for use in the treatment of abnormal cell growth in a mammal. In such embodiments the abnormal cell growth may be cancer. In such embodiments, the mammal is a human. In such embodiments, the mammal is a human in need of treatment.

Also embodied in the invention is the use of a compound of the invention, including those of formulae (A), (I), (II), (III), (III-A), (IV), (V), (VI), (VII), (VIII), and (IX), or a pharmaceutically acceptable salt thereof, for the preparation of a medicament useful in the treatment of abnormal cell growth in a mammal. In such embodiments the abnormal cell growth may be cancer. In such embodiments, the mammal is a human. In such embodiments, the mammal is a human in need of treatment.

Further still, embodiments of the invention include those where there is provided a method of upregulating the activity of STING in a mammal, comprising the step of administering to said mammal an effective amount of a compound or salt as described herein; and/or a method of increasing interferon-beta levels in a mammal, comprising the step of administering to said mammal an effective amount of a compound or salt as described herein. In one embodiment the mammal is a human. In such embodiments, the mammal is a human in need of treatment.

Yet further embodiments of the invention include those where there is provided a method of activating STING in a mammal, comprising the step of administering to said mammal an effective amount of a compound or salt described herein. Also provided is a method of stimulating the innate immune response in a mammal, comprising the step of administering to said mammal an effective amount of a compound or salt described herein. In one embodiment the mammal is a human. In such embodiments, the mammal is a human in need of treatment.

Dosing Regimens

The amount of the active compound administered will be dependent on the subject being treated, the severity of the disorder or condition, the rate of administration, the disposition of the compound and the discretion of the prescribing physician.

Dosage regimens may be adjusted to provide the optimum desired response. For example, a single bolus may be administered, several divided doses may be administered over time, or the dose may be proportionally reduced or increased as indicated by the exigencies of the therapeutic situation. "Dosage unit form" as used herein, refers to physically discrete units suited as unitary dosages for the mammalian subjects to be treated, each unit containing a predetermined quantity of active compound calculated to produce the desired therapeutic effect in association with the required pharmaceutical carrier.

The skilled artisan would appreciate, based upon the disclosure provided herein, that the dose and dosing regimen is adjusted in accordance with methods well known in the therapeutic arts. That is, the maximum tolerable dose may be readily established, and the effective amount providing a detectable therapeutic benefit to a patient may also be determined, as can the temporal requirements for administering each agent to provide a detectable therapeutic benefit to the patient.

It is to be noted that dosage values may vary with the type and severity of the condition to be alleviated and may include single or multiple doses. It is to be further understood that for any particular subject, specific dosage regimens should be adjusted over time according to the individual need and the professional judgement of the person administering or supervising the administration of the compositions, and that dosage ranges set forth herein are exemplary only and are not intended to limit the scope or practice of the claimed inventions. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well known in the relevant art and would be understood to be encompassed by the skilled artisan once provided with the teachings disclosed herein.

One possible dosage is in the range of about 0.001 to about 100 mg per kg body weight, administered daily, every other day, every third day, every fourth day, every fifth day, every sixth day, weekly, every other week, every three weeks, monthly, or on other dosing schedules. In some instances, dosage levels below the lower limit of the aforesaid range may be more than adequate, while in other cases still larger doses may be used without causing any harmful side effect, with such larger doses typically divided into several smaller doses for administration throughout the day.

In one embodiment, the compositions described herein are administered to a subject, either alone or in combination with a pharmaceutically acceptable excipient, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression.

Combination Therapies

As used herein, the term "combination therapy, refers to the administration of a compound of the invention, including those of formulae (A), (I), (II), (III), (III-A), (IV), (V), (VI), (VII), (VIII), and (IX), or a pharmaceutically acceptable salt thereof, together with an at least one additional therapeutic agent (e.g., an anti-cancer agent) or therapy, either sequentially or simultaneously.

In one embodiment, the additional therapeutic agent or therapy is administered to a mammal (e.g., a human) prior to administration of the compound of the invention. In another embodiment, the additional therapeutic agent or therapy is administered to a mammal (e.g., a human) after administration of the compound of the invention. In another embodiment, the additional therapeutic agent or therapy is administered to a mammal (e.g., a human) simultaneously with the administration of the compound of the invention.

In one embodiment the additional therapeutic agent is selected from the group consisting of an interferon, a CTLA-4 pathway antagonist, an anti-4-1 BB antibody, an anti-PD-1 antibody, and an anti-PD-L1 antibody.

The invention also relates to a pharmaceutical composition for the treatment of abnormal cell growth, including cancer, in a mammal, including a human, which comprises an amount of a compound of the invention, as defined above, in combination with one or more (preferably one, two or three) additional therapeutic agents, and a pharmaceutically acceptable carrier, wherein the amounts of the active agent and the additional therapeutic agents when taken as a whole is therapeutically effective for treating said abnormal cell growth.

The compounds of the invention, and compositions thereof, may be administered as an initial treatment, or for treatment of cancers that are unresponsive to conventional therapies. In addition, the compounds of the invention, and compositions thereof, may be used in combination with other therapies (e.g., surgical excision, radiation, additional anti-cancer drugs etc.) to thereby elicit additive or potentiate therapeutic effects and/or reduce cytotoxicity of some anti-cancer agents. The compounds of the invention, and compositions thereof, may be co-administered or co-formulated with additional agents, or formulated for consecutive administration with additional agents in any order. For combination therapies, the compounds are administered within any time frame suitable for performance of the intended therapy. Thus, the single agents may be administered substantially simultaneously (i.e., as a single formulation or within minutes or hours) or consecutively in any order. For example, single agent treatments may be administered within about 1 year of each other, such as within about 10, 8, 6, 4, or 2 months, or within 4, 3, 2 or 1 week(s), or within about 5, 4, 3, 2 or 1 day(s).

In some embodiments, the methods described herein further comprise administering to the subject an amount of an anti-cancer therapeutic agent or a palliative agent, in particular standard of care agents appropriate for the particular cancer, which amounts may be together effective in treating or ameliorating said abnormal cell growth.

In one embodiment, the additional therapeutic agents is one or more of a palliative agent.

In one embodiment, the additional therapeutic agents is one or more of an anti-cancer therapeutic agent. In some embodiments, the one or more anti-cancer therapeutic agents is selected from anti-tumor agents, anti-angiogenesis agents, signal transduction inhibitors, and anti-proliferative agents, which amounts are together effective in treating said abnormal cell growth.

In one aspect of the invention, the methods described herein further include a step of treating a subject with an additional form of therapy. In one aspect the additional form of therapy is an additional anti-cancer therapy including, but not limited to, chemotherapy, radiation, surgery, hormone therapy, and/or additional immunotherapy.

In certain embodiments, the compounds of the invention, and compositions thereof, are administered in conjunction with one or more additional compositions including vaccines intended to stimulate an immune response to one or more predetermined antigens or adjuvants.

The compounds of the invention and compositions thereof may be used in combination with other therapeutic agents including, but not limited to, therapeutic antibodies, antibody drug conjugates (ADCs), immunomodulating agents, cytotoxic agents, and cytostatic agents. A cytotoxic effect refers to the depletion, elimination and/or the killing of a target cells (i.e., tumor cells). A cytotoxic agent refers to an agent that has a cytotoxic and/or cytostatic effect on a cell. A cytostatic effect refers to the inhibition of cell proliferation. A cytostatic agent refers to an agent that has a cytostatic effect on a cell, thereby inhibiting the growth and/or expansion of a specific subset of cells (i.e., tumor cells). An immunomodulating agent refers to an agent that stimulates the immune response though the production of cytokines and/or antibodies and/or modulating T cell function thereby inhibiting or reducing the growth of a subset of cells (i.e., tumor cells) either directly or indirectly by allowing another agent to be more efficacious. The compounds of the invention, and one or more other therapeutic agents may be administered as part of the same or separate dosage forms, via the same or different routes of administration and on the same or different administration schedules according to standard pharmaceutical practice known to the person of ordinary skill in the art.

The compounds of the invention and compositions thereof may also be used in combination with other therapeutic agents including, but not limited to, B7 costimulatory molecule, interleukin-2, interferon, interferon-7, GM-CSF, CTLA-4 antagonist, PD-1 pathway antagonist, anti 41 BB antibody, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, oil or hydrocarbon emulsions, adjuvants, lipids, interbilayer crosslinked multilamellar vesicles, biodegradeable poly(D, L-lactic-co-glycolic acid) [PLGA]-based or poly anhydride-based nanoparticles or microparticles, and nanoporous particle-supported lipid bilayers such as liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRs), retinoic acid inducible gene-based (RIG)-I-like receptors (RLRs), C-type lectin receptors (CLRs), pathogen associated molecular patterns ("PAMPs"), chemotherapeutic agent, and the like. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and in addition retinoic acid-inducible gene I (RIG-1) agonists such as poly 1:C, used separately or in combination with the described compositions are also potential adjuvants. Other representative examples of adjuvants include the synthetic adjuvant QS-21 comprising a homogeneous saponin purified from the bark of *Quillaja saponaria* and *Colynebacterium parvum* (McCune et al., *Cancer*, 1979; 43:1619). It will be understood that the adjuvant is subject to optimization. In other words, the skilled artisan can engage in routine experimentation to determine the best adjuvant to use.

In one embodiment the other therapeutic agent is an interferon. The term "interferon" or "IFN" or "INF", each of which may be used interchangeably, refers to any member of the family of highly homologous species-species proteins that inhibit viral replication and cellular proliferation and modulate immune response. For example, human interferons are groups into three classes: Type I, which includes interferon-alpha, interferon-beta, and interferon-omega; Type II which includes interferon-gamma, and Type III which includes interferon-lambda. Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons may include pegylated interferons and glycosylated interferons. Examples of interferons also include, but are not limited to, interferon-alpha-2a, interferon-alpha-2b, interferon-alpha-n1, interferon-beta-1a, interferon-beta-1b, interferon-lamda-1, interferon-lambda-2, and interferon-lambda-3. Examples of pegylated interferons include pegylated interferon-alpha-2a and pegylated interferon-alpha-2b.

In one embodiment the other therapeutic agent is a CTLA-4 pathway antagonist.

In one embodiment, the other therapeutic agent is an anti-4-1BB antibody. The term "4-1 BB antibody" as used herein means an antibody, as defined herein, capable of binding to human 4-1 BB receptor (also referred to herein as an "anti-4-1 BB antibody"). The terms "4-1 BB" and "4-1 BB receptor" are used interchangeably in the present application and refer to any form of 4-1 BB receptor, as well as variants, isoforms, and species homologs thereof that retain at least a part of the activity of 4-1 BB receptor. Accordingly, a binding molecule, as defined and disclosed herein, may also bind 4-1BB from species other than human. In other cases, a binding molecule may be completely specific for the human 4-1 BB and may not exhibit species or other types of cross-reactivity. Unless indicated differently, such as by specific reference to human 4-1 BB, 4-1BB includes all mammalian species of native sequence 4-1BB, e.g., human, canine, feline, equine and bovine. One exemplary human 4-1BB is a 255 amino acid protein (Accession No. NM_001561; NP_001552). 4-1BB comprises a signal sequence (amino acid residues 1-17), followed by an extracellular domain (169 amino acids), a transmembrane region (27 amino acids), and an intracellular domain (42 amino acids) (Cheuk ATC et al. 2004 Cancer Gene Therapy 11: 215-226). The receptor is expressed on the cell surface in monomer and dimer forms and likely trimerizes with 4-1 BB ligand to signal. "4-1 BB agonist" as used herein means, any chemical compound or biological molecule, as defined herein, which upon binding to 4-1 BB, (1) stimulates or activates 4-1 BB, (2) enhances, increases, promotes, induces, or prolongs an activity, function, or presence of 4-1 BB, or (3) enhances, increases, promotes, or induces the expression of 4-1 BB. 4-1 BB agonists useful in the any of the treatment method, medicaments and uses of the present invention include a monoclonal antibody (mAb), or antigen binding fragment thereof, which specifically binds to 4-1 BB. Alternative names or synonyms for 4-1 BB include CD137 and TNFRSF9. In any of the treatment method, medicaments and uses of the present invention in which a human individual is being treated, the 4-1 BB agonists increase a 4-1BB-mediated response. In some embodiments of the treatment method, medicaments and uses of the present invention, 4-1 BB agonists markedly enhance cytotoxic T-cell responses, resulting in anti-tumor activity in several models. Human 4-1BB comprises a signal sequence (amino acid residues 1-17), followed by an extracellular domain (169 amino acids), a transmembrane region (27 amino acids), and an intracellular domain (42 amino acids) (Cheuk ATC et al. 2004 Cancer Gene Therapy 11: 215-226). The receptor is expressed on the cell surface in monomer and dimer forms and likely trimerizes with 4-1 BB ligand to signal. Examples of mAbs that bind to human 4-1 BB, and useful in the treatment method, medicaments and uses of the present invention, are described in U.S. Pat. No. 8,337,850 and US20130078240. In some embodiments, the anti-4-1BB antibody has a VH as shown in SEQ ID NO: 17 and a VL as shown in SEQ ID NO: 18 of WO2017/130076.

In one embodiment the other therapeutic agent is a PD-1 pathway antagonist. In one embodiment, the other therapeutic agent is an anti-PD-1 antibody. In one embodiment, the other therapeutic agent is an anti-PD-L1 antibody. The programmed death 1 (PD-1) receptor and PD-1 ligands 1 and 2 (PD-L1 and PD-L2, respectively) play integral roles in immune regulation. Expressed on activated T cells, PD-1 is activated by PD-L1 (also known as B7-H1) and PD-L2 expressed by stromal cells, tumor cells, or both, initiating T-cell death and localized immune suppression (Dong et al., Nat Med 1999; 5:1365-69; Freeman et al. J Exp Med 2000; 192:1027-34), potentially providing an immune-tolerant environment for tumor development and growth. Conversely, inhibition of this interaction can enhance local T-cell responses and mediate antitumor activity in nonclinical animal models (Iwai Y, et al. Proc Natl Acad Sci USA 2002; 99:12293-97). Examples of anti-PD-1 antibodies that are useful in the treatment method, medicaments and uses of the present invention include BCD-100, camrelizumab, cemiplimab, genolimzumab (CBT-501), MED10680, nivolumab, pembrolizumab, RN888 (see WO2016/092419), sintilimab, spartalizumab, STI-A1110, tislelizumab, and TSR-042. In some embodiments, the anti-PD-1 antibody has a VH as shown in SEQ ID NO: 4 and a VL as shown in SEQ ID NO: 8 of U.S. Ser. No. 10/155,037. Examples of anti-PD-L1 antibodies that are useful in the treatment method, medicaments and uses of the present invention include atezolizumab, durvalumab, BMS-936559 (MDX-1105), and LY3300054.

The disclosed combination therapies may elicit a synergistic therapeutic effect, i.e., an effect greater than the sum of their individual effects or therapeutic outcomes. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of one or more therapeutic agents when they are used in combination.

Kit of Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

General Methods
Synthetic Experimental Procedures:

Experiments were generally carried out under inert atmosphere (nitrogen or argon), particularly in cases where oxygen- or moisture-sensitive reagents or intermediates were employed. Commercial solvents and reagents were generally used without further purification and dried over molecular sieves (generally Sure-Sea™ products from the Aldrich Chemical Company, Milwaukee, Wisconsin). Mass spectrometry data is reported from either liquid chromatography-mass spectrometry (LC-MS), atmospheric pressure chemical ionization (APCI), electrospray ionization (ESI) or liquid chromatography-Time of Flight (LC-TOF) methods. Chemical shifts for nuclear magnetic resonance (NMR) data are expressed in parts per million (ppm) referenced to residual peaks from the deuterated solvents employed.

For syntheses referencing procedures in other Examples or Methods, reaction Protocol (length of reaction and temperature) may vary. In general, reactions were followed by thin layer chromatography, LC-MS or HPLC, and subjected to work-up when appropriate. Purifications may vary between experiments: in general, solvents and the solvent ratios used for eluents/gradients were chosen to provide appropriate retention times. Unless otherwise specified, reverse phase HPLC fractions were concentrated via lyophilization/freeze-drying. Intermediate and final compounds were stored at (0° C.) or room temperature in closed vials or flasks under nitrogen. Compound names were generated with Chemdraw or ACD Labs software.

Abbreviations for solvents and/or reagents are based on American Chemical Society guidelines and are highlighted below:

Ac=Acetyl; AcOH=Acetic acid; Ac$_2$O=Acetic anhydride; Ad=Adamantyl; Bipy=2,2'-Bipyridine=2,2'-Dipyridine=2,2'-Dipyridyl; Bn=Benzyl; Bu=butyl; CataCXium A=Di-(1-adamantyl)-n-butylphosphine; CataXCium A-Pd-G3=[(Di(1-adamantyl)-butylphosphine)-2-(2'-amino-1,1'-biphenyl)]palladium(II) methanesulfonate; CO=carbon monoxide; DIAD=Diisopropyl azodicarboxylate; DBU=1,8-Diazabicyclo[5.4.0]undec-7-ene; DCE=1,2-Dichloroethane; DCM=Dichloromethane; DIPEA=N,N-Diisopropylethylamine; DMA=Dimethylacetamide; DMB=2,4-Dimethoxybenzyl; DMF=N,N-Dimethylformamide; DMF-DMA=N,N-Dimethylformamide dimethyl acetal; DMSO=Dimethyl sulfoxide; dppf=1,1'-Ferrocenediyl-bis(diphenylphosphine); dtbbpy=4,4'-Di-tert-butyl-2,2'-dipyridyl; Et=Ethyl; EtOAc=Ethyl acetate; h=hr=hour; HFIP=1,1,1,3,3,3-Hexafluoro-2-propanol; HPLC=High-performance Liquid Chromatography; [Ir(cod)OMe]2=Bis(1,5-cyclooctadiene)di-μ-methoxydiiridium(I)=[Ir(OMe)(1,5-cod)]2=(1,5-Cyclooctadiene)(methoxy)iridium(I) dimer; KOAc=Potassium acetate; LC=Liquid Chromatography; LCMS=Liquid Chromatography Mass Spectrometry; m-CPBA=3-Chloroperoxybenzoic acid=meta-Chloroperbenzoic acid=mCPBA; Me=Methyl; MeOH=Methanol; MeCN=ACN=Acetonitrile; MsOH=Methanesulfonic acid; n-Bu=n-Butyl; n-BuLi=n-Butyllithium; NCS=N-Chlorosuccinimide; Pin=Pinacol=2,3-Dimethyl-2,3-butanediol=Tetramethylethylene glycol; Pd(OAc)$_2$=Palladium (II) acetate; Pd(dppf)Cl$_2$=[1,1'-Bis(diphenylphosphino)ferrocene]-dichloropalladium (II); Phen=1,10-Phenanthroline; Ph=Phenyl; PMB=p-Methoxybenzyl; PhMe=Tol=Toluene; PivOH=Pivalic acid; rt=room temperature; TEA=Triethyl amine; TFA=Trifluoroacetic acid; Tf$_2$O=Triflic anhydride; THF=Tetrahydrofuran; TMS=Trimethylsilyl; Ts=Tosyl=Toluenesulfonyl; T3P=2,4,6-Tripropyl-1,3,5,2,4,6-trioxatriphosphorinane-2,4,6-trioxide; Xantphos=4,5-Bis(diphenylphosphino)-9,9-dimethylxanthene.

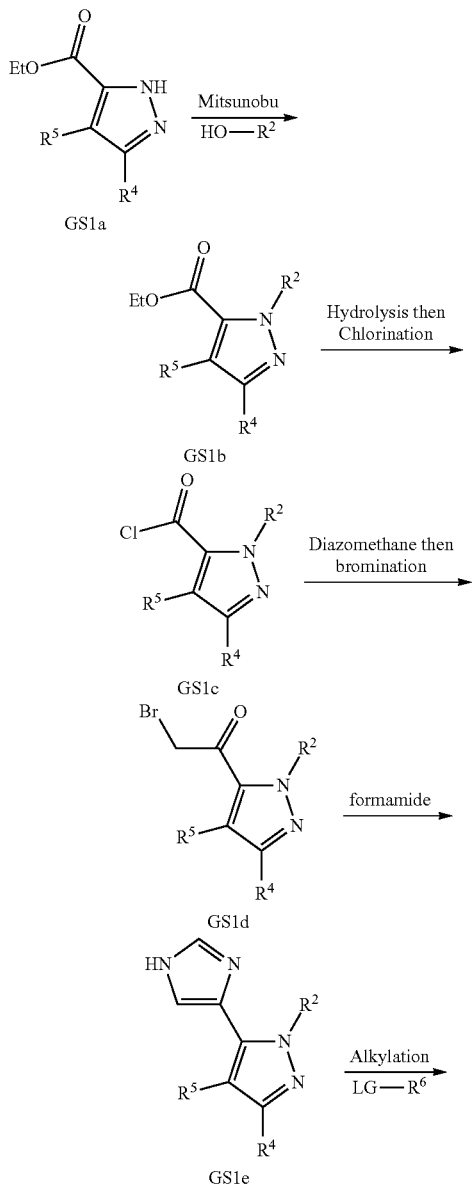

General Scheme I

-continued

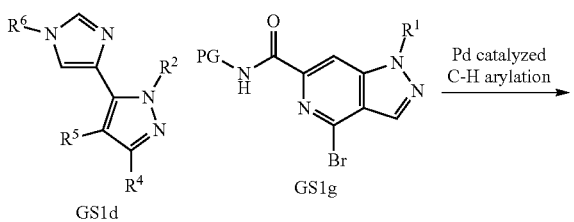

GS1d

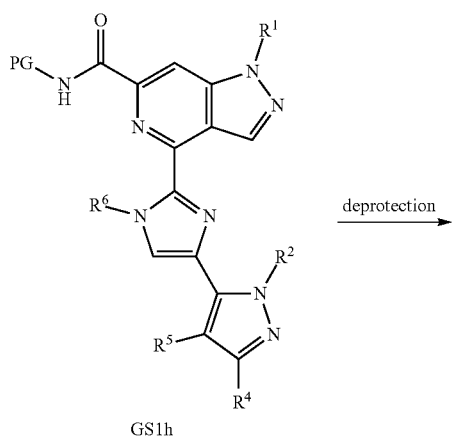

GS1h

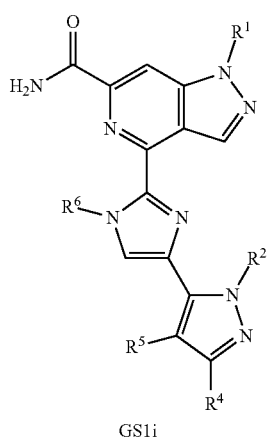

GS1i

As exemplified in General Scheme I, a compound of type GS1a can be alkylated with alcohols (HO—R²) under Mitsunobu alkylation conditions employing a suitable activating agent (such as di-isopropyl azodicarboxylate) and trialkyl/triaryl phosphine (such as tri-n-butyl phosphine or triphenylphosphine) in an appropriate solvent (such as THF, PhMe, or similar solvent) at temperatures ranging from −20° C. to rt to provide compounds such as GS1b. A compound such as GS1b can be hydrolyzed under alkaline conditions using an appropriate base (MOH where M=Li, Na, K, or Cs) in a suitable solvent (such as THF, MeOH, water or similar solvent) followed by chlorination with a suitable chlorinating agent (such as oxalyl dichloride or thionyl chloride) in a suitable solvent (such as THF, PhMe, DCM, DCE, or DMF) to provide compounds such as GS1c. A compound such as GS1c can be alkylated with diazomethane or an equivalent thereof (such as trimethylsilyl diazomethane) in a suitable solvent (such as diethyl ether, THF, MeCN, or similar solvent) followed by bromination with a suitable brominating agent (such as HBr, Ferric (III) bromide, or similar reagent) in a suitable solvent (such as AcOH, DCM, diethyl ether, MeCN, EtOAc, or similar solvent) to provide compounds such as GS1d. A compound such as GS1d can be condensed in neat formamide typically at temperatures >140° C. to provide compounds such as GS1e. A compound such as GS1e can be alkylated with an alkyl group (R⁶-LG) bearing a suitable leaving group (LG) (such as Cl, Br, OTs or similar leaving group) with an appropriate base (such as $Cs_2CO_3$, MH where M=Na, K or similar base) in an appropriate solvent (DMF, DMSO, THF or similar solvent) to provide compounds such as GS1f. A compound of type GS1f can be cross-coupled to a compound of type GS1 g via C—H activation (*SynLett.* 2020, 31, 1015-1021;) in the presence of a suitable catalyst system (such as Pd(dppf)Cl₂ or Pd(OAc)₂ or similar catalyst) sometimes in the presence of a copper co-catalyst (such as CuCl, CuBr, CuI, Cu(Xantphos)Cl, Cu(MeCN)₄PF₆, Cu(Phen)PPh₃Br or similar catalyst) sometimes in the presence of an additional phosphine ligand (such as PPh₃, cataCXium A, Xantphos, PCy₃·HBF₄, or similar phosphine ligand) with a suitable base (such as CsOPiv, CsOAc, K₂CO₃+PivOH, TMPMgCl·LiCl, or TMPZnCl·LiCl, DBU, n-BuLi+ZnCl₂, or similar base/combination) in an appropriate solvent (such as PhMe, Dioxane, MeCN, TFE, t-Amyl alcohol or similar solvent) at temperatures ranging from rt to 150° C. to provide compounds such as GS1h. Compounds such as GS1h can contain acid labile protecting groups which can be removed at this stage using conditions (such as TFA/DCM or MsOH/HFIP) known in the art (*Protective Groups in Organic Synthesis*, A. Wiley-Interscience Publication, 1981 or *Protecting Groups*, Georg Thieme Verlag, 1994) to afford compounds such as GS1i. Compounds at every step may be purified by standard techniques, such as column chromatography, crystallization, or reverse phase SFC or HPLC. If necessary, separation of regioisomers or stereoisomers of any product in the synthetic sequence can be carried out under standard methods known in the art such as chiral SFC or HPLC to afford single regio- or stereoisomers. Variables such as PG, LG, and R¹-R⁶ are as defined and/or depicted in the embodiments, schemes, examples, and claims herein.

Preparation of Head Group (HG) Intermediates

Preparation of 4-bromo-N-(2,4-dimethoxybenzyl)-1-methyl-1H-pyrazolo[4,3-c]pyridine-6-carboxamide (Int-HG-1) according to Scheme HG-1

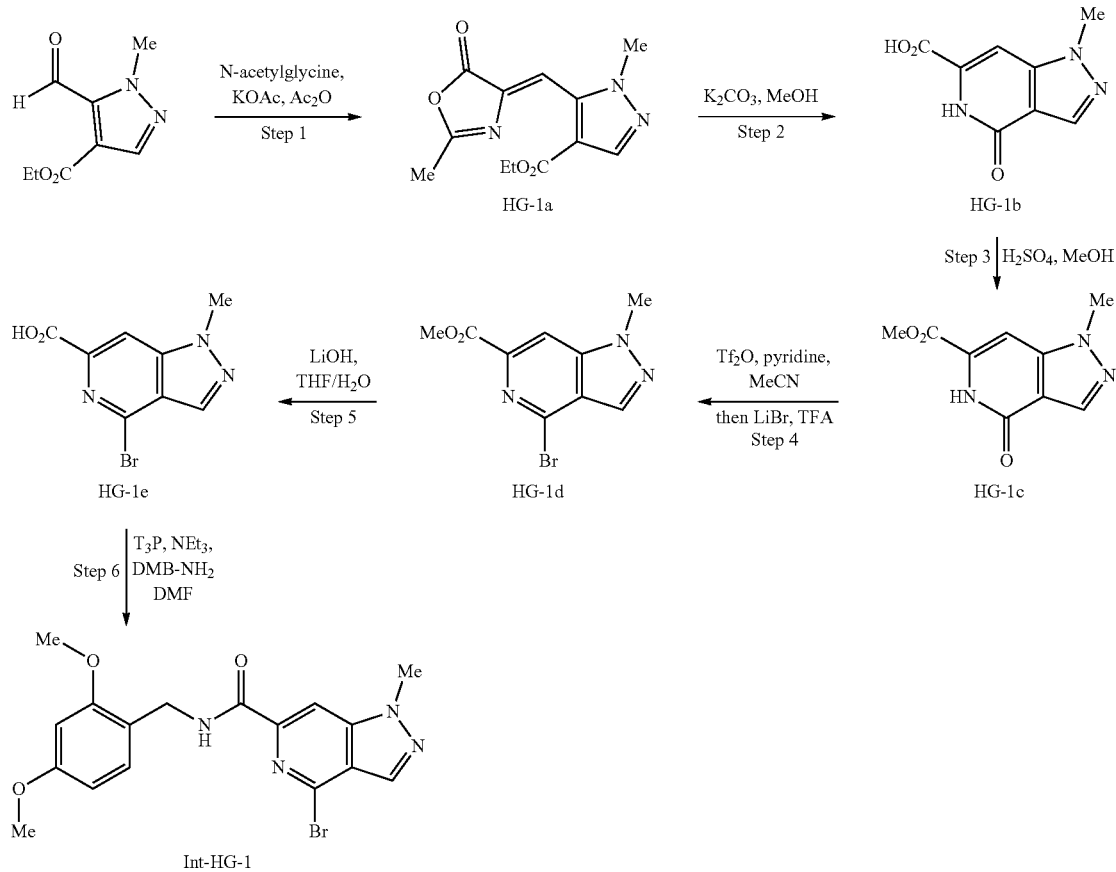

Step 1: Synthesis of Ethyl 1-methyl-5-{[(4Z)-2-methyl-5-oxo-1,3-oxazol-4-ylidene]methyl}pyrazole-4-carboxylate (HG-1a)

To a solution of ethyl 5-formyl-1-methyl-1H-pyrazole-4-carboxylate (10.7 g, 58.6 mmol) and N-acetylglycine (10.3 g, 88.0 mmol, 1.5 eq) in acetic anhydride (15 mL, 4 M) at room temperature was added potassium acetate (9.09 g, 88.0 mmol, 1.5 eq), and to this slurry was added an additional 5 mL Ac₂O to re-induce stirring. This was then topped with a Findenser and heated to 100° C. During heating, the white, turbid suspension became a clear yellow solution, and after 10 minutes, had become a brown solution. After 1 hr, the reaction was cooled to room temperature. TLC analysis (2:1 heptane/EtOAc, KMnO4 stain) showed consumption of starting material (Rf=0.61) concomitant with formation of product (Rf=0.29). The reaction was then transferred to 100 mL beaker, rinsing the reaction vial with DCM, and sat. aqueous sodium bicarbonate was added dropwise with magnetic stirring until effervescence ceased. After this, the contents of this beaker were transferred to a separatory funnel, where the organic layer was separated. Subsequently, the aqueous layer was extracted with 4×100 mL 3:1 DCM/iPrOH and 2×150 mL DCM. The combined organics were dried over MgSO4, filtered, and solvent removed under reduced pressure. The resultant dark brown residue was dissolved in about 5 mL DCM. To this was added MTBE dropwise (about 5 mL), and this mixture was subsequently poured into a flask containing 200 mL heptane. Upon sonication, a yellow solid precipitated from solution and was filtered off under reduced pressure. The mother liquor was then left to stand at 0° C. for 2 h, whereupon another crop of product crashed out and was again filtered under reduced pressure. These two batches were combined to give the title compound ethyl 1-methyl-5-{[(4Z)-2-methyl-5-oxo-1,3-oxazol-4-ylidene]methyl}pyrazole-4-carboxylate (HG-1a) as a light yellow solid (15.2 g, 98%). $^1$H NMR (400 MHz, Chloroform-d) δ 7.93 (s, 1H), 7.53 (s, 1H), 4.29 (q, J=7.1 Hz, 2H), 3.98 (s, 3H), 1.34 (t, J=7.1 Hz, 3H).

Step 2: Synthesis of 1-methyl-4-oxo-4,5-dihydro-1H-pyrazolo[4,3-c]pyridine-6-carboxylic Acid (HG-1b)

To ethyl 1-methyl-5-{[(4Z)-2-methyl-5-oxo-1,3-oxazol-4-ylidene]methyl}pyrazole-4-carboxylate (HG-1a) (15.2 g, 57.8 mmol) in methanol (57.8 mL, 1 M) was added potassium carbonate (16.8 g, 116 mmol, 2 eq) and the vessel was subsequently capped and heated to 70° C. After stirring for 16 h, the previously deep brown turbid solution had lightened to a tan-brown. Based on LCMS, all starting material was consumed, so the cooled mixture was filtered under reduced pressure and filter cake of washed with MeOH and MTBE. Addition of MTBE to the resultant filtrate led to precipitation of additional solid which was refiltered using the same apparatus. The solid filter cake was then suspended in $H_2O$ and conc. HCl was added to acidify to pH 1. A tan solid precipitated which was filtered off under reduced pressure, after which the filtrate was diluted with 1:1 MeOH/MTBE and filtered again under reduced pressure. These two batches were combined to afford the title compound 1-methyl-4-oxo-4,5-dihydro-1H-pyrazolo[4,3-c]pyridine-6-carboxylic acid (HG-1b) as a tan, solid (10.46 g, 94% yield). $^1$H NMR (400 MHz, DMSO-$d_6$) δ 10.56 (s, 1H), 8.11 (d, J=0.9 Hz, 1H), 7.40 (d, J=0.9 Hz, 1H), 4.03 (s, 3H).

Step 3: Synthesis of Methyl 1-methyl-4-oxo-4,5-dihydro-1H-pyrazolo[4,3-c]pyridine-6-carboxylate (HG-1c)

To 1-methyl-4-oxo-4,5-dihydro-1H-pyrazolo[4,3-c]pyridine-6-carboxylic acid (HG-1b) (10.46 g, 54.17 mmol) in methanol (40 mL, 1.4 M) was added conc. sulfuric acid (90 mmol, 5 mL, 2 eq) dropwise. This led to exotherm on the addition of each drop. The resultant yellow slurry was heated to 70° C. After 17 h, the reaction was cooled to room temperature, at which point starting material appeared to have been consumed and a white, microcrystalline solid began to precipitate from the solution. The reaction mixture was filtered under reduced pressure and the filter cake washed with water. This first batch was collected, after which the filtrate was diluted with 5 mL ACN, 5 mL MTBE and 10 mL EtOH before allowing to sit at 0° C. After 2 h, the white microcrystals which precipitated from solution were collected via vacuum filtration and combined with the previous batch to afford the title compound methyl 1-methyl-4-oxo-4,5-dihydro-1H-pyrazolo[4,3-c]pyridine-6-carboxylate (HG-1c) as a white solid (11.1 g, 99.0%). $^1$H NMR (400 MHz, Methanol-$d_4$) δ 8.20 (d, J=0.9 Hz, 1H), 7.56 (d, J=0.9 Hz, 1H), 4.12 (s, 3H), 4.04 (s, 3H).

Step 4: Synthesis of Methyl 4-bromo-1-methyl-1H-pyrazolo[4,3-c]pyridine-6-carboxylate (HG-1d)

To 1-methyl-4-oxo-4,5-dihydro-1H-pyrazolo[4,3-c]pyridine-6-carboxylate (HG-1c) (11.1 g) in acetonitrile (53.9 mL, 1.0 M) was added pyridine (6.51 mL, 80.8 mmol, 1.5 eq) in one portion, followed by $Tf_2O$ anhydride (13.6 mL, 80.8 mmol, 1.5 eq) portion wise in approximately 1 mL portions. After addition of 6 mL, the solution changed from yellow to red (though remaining turbid), and after addition of the remaining triflic anhydride, the reaction turned yellow again and began to clear. After 45 min, LCMS showed consumption of starting material along with clean formation of triflate. To the reaction mixture was then added lithium bromide (23.4 g, 269 mmol, 5 eq) and trifluoroacetic acid (5.23 mL, 59.3 mmol, 1.1 eq) to produce an orange suspension. After 1 hr from this point, LCM analysis showed disappearance of triflate and conversion to bromide. The reaction mixture was then poured slowly into an Erlenmeyer flask containing 200 mL sat. $NaHCO_3$ with magnetic stirring. Upon cessation of gas evolution, the biphasic was transferred to a separatory funnel containing 800 mL EtOAc, shaken, and aqueous layer discarded. The organic layer was then washed once with sodium thiosulfate to decolorize, and the two layers separated. The organics were dried over $MgSO_4$, filtered and solvent removed under reduced pressure. The resultant brown oil was dissolved in 10 mL DCM, and to this was added 10 mL MeCN and 10 mL acetone. This cloudy solution was left at 0° C. overnight, after which the product had precipitated and was collected via vacuum filtration to afford the title compound methyl 4-bromo-1-methyl-1H-pyrazolo[4,3-c]pyridine-6-carboxylate (HG-1d) as a tan solid (11.77 g, 81%). $^1$H NMR (400 MHz, Chloroform-d) δ 8.23 (1H, d, J=1 Hz), 8.14 (1H, d, J=1.0 Hz), 4.16 (3H, s), 4.05 (3H, s).

Step 5: Synthesis of 4-bromo-1-methyl-1H-pyrazolo[4,3-c]pyridine-6-carboxylic Acid (HG-1e)

4-bromo-1-methyl-1H-pyrazolo[4,3-c]pyridine-6-carboxylate (HG-1d) (1333 mg, 4.935 mmol) was added to a flask containing 5 mL tetrahydrofuran and 2 mL $H_2O$. To this solution was add lithium hydroxide (177 mg, 7.40 mmol, 1.5 eq) at room temperature and allowed to stir. After 2 h, LCMS analysis showed consumption of starting material concomitant with product formation. The reaction mixture was acidified to pH 1 with conc. HCl, at which point it became cloudy. The resultant acidic suspension was left at 0° C. for 1 hr, after which the product was observed to have precipitated. This solid was collected using vacuum filtration to afford the title compound 4-bromo-1-methyl-1H-pyrazolo[4,3-c]pyridine-6-carboxylic acid (HG-1e) as a white semi-crystalline solid (1.15 g, 90%). $^1$H NMR (400 MHz, DMSO-$d_6$) δ 13.43 (1H, br s), 8.49 (1H, d, J=0.8 Hz), 8.32 (1H, d, J=0.8 Hz), 4.18 (3H, s)

Step 6: Synthesis of 4-bromo-N-(2,4-dimethoxybenzyl)-1-methyl-1H-pyrazolo[4,3-c]pyridine-6-carboxamide (Int-HG-1)

To a suspension of 4-bromo-1-methyl-1H-pyrazolo[4,3-c]pyridine-6-carboxylic acid (HG-1e) (1.90 g, 9.79 mmol) in DMF (2 mL) was added first triethylamine (4.13 mL, 29.4 mmol), then dimethoxybenzylamine (1.64 g, 9.79 mmol), the latter of which led to a clear solution. To the solution was added T3P (8.60 mL, 50% in EtOAc, 14.7 mmol) after which the solution had turned yellow and warmed significantly. After 30 min, LCMS analysis of the turbid yellow suspension showed consumption of starting material and formation of product. This was diluted with 5 mL EtOAc with magnetic stirring, then filtered under reduced pressure. The solid was washed with EtOAc and dried to afford the title compound 4-bromo-N-(2,4-dimethoxybenzyl)-1-methyl-1H-pyrazolo[4,3-c]pyridine-6-carboxamide (Int-HG-1) as a white solid (3.18 g, 81%). $^1$H NMR (400 MHz, Chloroform-d) δ 8.53-8.38 (1H, m), 8.26 (1H, d, J=1 Hz), 8.09 (1H, d, J=1.0 Hz), 7.28 (1H, s), 6.50 (2H, dd, J=8.2, 2.4 Hz), 6.45 (2H, dd, J=8.2, 2.4 Hz), 4.63 (2H, d, J=6.1 Hz), 4.13 (3H, s), 3.90 (3H, s), 3.80 (3H, s).

Preparation of 4,6-dichloro-1-ethyl-1H-pyrazolo[4,3-c]pyridine (Int-HG-2) According to Scheme HG-2

Scheme HG-2

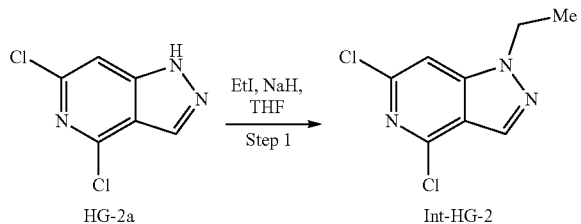

Step 1: Synthesis of 4,6-dichloro-1-ethyl-1H-pyrazolo[4,3-c]pyridine (Int-HG-2)

To a reaction flask containing 4,6-dichloro-1H-pyrazolo[4,3-c]pyridine (HG-2a) (1000 mg, 5.35 mmol) as a solution in THF (16 mL) was cooled in an ice water bath to 0° C. and charged with NaH (60 wt % in mineral oil, 428 mg, 10.7 mmol) in portions. The reaction mixture was stirred for 10 minutes at which point a brown solution was obtained. To the reaction mixture was added ethyl iodide (917 mg, 5.88 mmol) followed by stirring at 0° C. for an additional 30 minutes. At this stage, the ice bath was removed and the reaction allowed to warm gradually to room temperature and stirred for an additional 16h. LCMS analysis showed that starting material was still present thus the reaction was heated to 50° C. and stirred for an additional 2h. An additional aliquot of ethyl iodide was added (415 mg, 2.66 mmol) and the reaction was stirred at room temperature for 17h. The reaction was quenched with MeOH (5 mL) and the solution concentrated under vacuum to afford a yellow oil. The crude residue was purified via flash column chromatography (40 g SiO2, Isco, 0-20% EtOAc/Pet. Ether) to afford the title compound 4,6-dichloro-1-ethyl-1H-pyrazolo[4,3-c]pyridine (Int-HG-2) (482.3 mg, 42%) as a yellow solid. LCMS [M+H]=215.9 observed; $^1$H NMR (400 MHz, CHLOROFORM-d) δ=8.12 (d, J=0.8 Hz, 1H), 7.30 (d, J=0.9 Hz, 1H), 4.39 (q, J=7.3 Hz, 2H), 1.54 (t, J=7.3 Hz, 4H).

The intermediate in the table below was prepared according to the methods used in step 1 for the synthesis of 4,6-dichloro-1-ethyl-1H-pyrazolo[4,3-c]pyridine (Int-HG-2) according to Scheme HG-2 employing commercially available 4,6-dichloro-1H-pyrrolo[3,2-c]pyridine as the starting material with non-critical changes or substitutions to the exemplified procedure that one skilled in the art would be able to realize.

| Int-TG Number | Structure/IUPAC Name | Analytical Data |
|---|---|---|
| Int-HG-6 | ![structure] 4,6-dichloro-1-methyl-1H-pyrrolo[3,2-c]pyridine | LCMS [M + H] = 201.1 observed; $^1$H NMR (DMSO-$d_6$) δ: 7.76 (s, 1H), 7.60 (d, J = 3.3 Hz, 1H), 6.60 (d, J = 3.2 Hz, 1H), 3.83 (s, 3H). |

Preparation of 4-chloro-N-[(2,4-dimethoxyphenyl)methyl]-1-methyl-1H-pyrazolo[3,4-d]pyrimidine-6-carboxamide (Int-HG-3) According to Scheme HG-3

Scheme HG-3

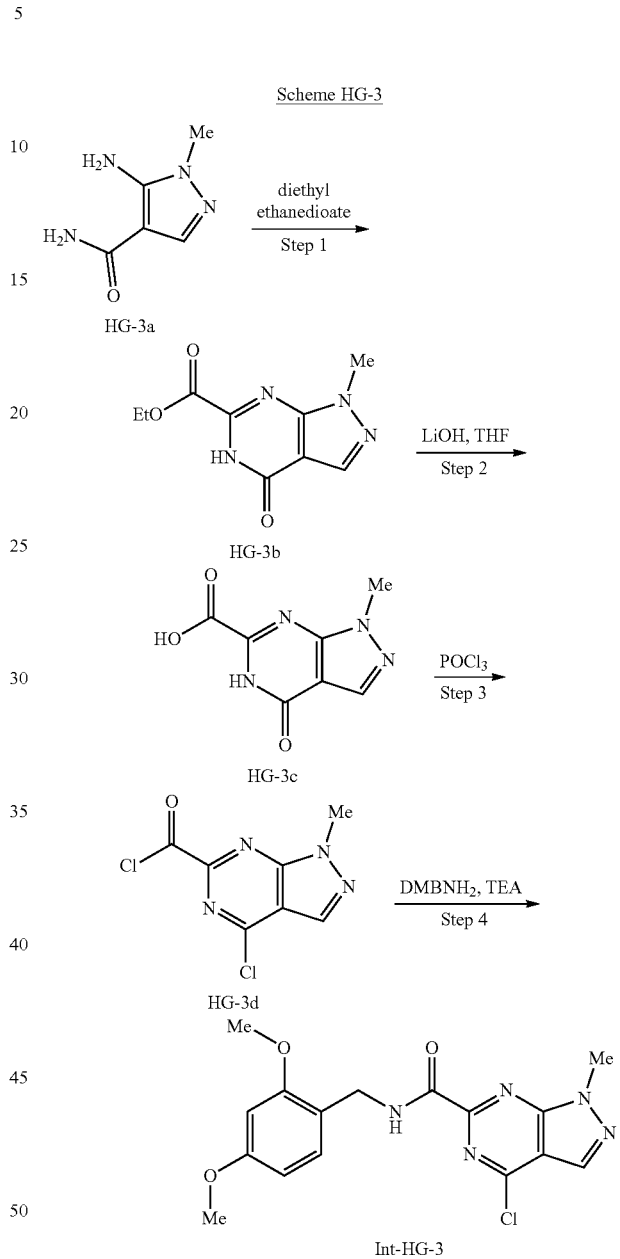

Step 1: Synthesis of Ethyl 1-methyl-4-oxo-4,5-dihydro-1H-pyrazolo[3,4-d]pyrimidine-6-carboxylate (HG-3b)

To a reaction flask containing 5-amino-1-methyl-1H-pyrazole-4-carboxamide (HG-3a) (1.5 g, 10.70 mmol) was added diethyl ethanedioate (25 mL). The reaction was heated at 185° C. overnight. The flask was removed from heating and allowed to cool gradually to room temperature which resulted in the precipitation of a grey solid. The grey solid was filtered and washed with petroleum ether. The solid was collected to afford the title compound Ethyl 1-methyl-4-oxo-4,5-dihydro-1H-pyrazolo[3,4-d] pyrimidine-6-carboxylate (HG-3b) (582 mg, 25%) as a grey solid. GC/MS m/z 222.1 [M]. $^1$H NMR (400 MHz, DMSO-d6) δ=12.68-12.41 (m, 1H), 8.27-7.99 (m, 1H), 4.52-4.27 (m, 2H), 4.03-3.82 (m, 3H), 1.44-1.18 (m, 3H).

Step 2: Synthesis of 4-hydroxy-1-methyl-1H-pyrazolo[3,4-d] pyrimidine-6-carboxylic Acid (HG-3c)

To a reaction flask containing ethyl 1-methyl-4-oxo-4,5-dihydro-1H-pyrazolo[3,4-d]pyrimidine-6-carboxylate (HG-3b) (300.0 mg, 1.35 mmol) was added THF (12 mL) and a solution of lithium hydroxide (80.8 mg, 3.38 mmol) in water (3 mL). The reaction was stirred at 25° C. overnight and then heated at 50° C. 2h. The reaction was removed from heating and allowed to cool gradually to room temperature. The solution was concentrated under reduced pressure. The aqueous solution thus obtained was acidified by the dropwise addition of HCl (1N) until pH=2-3 was reached. The solution was diluted with water and transferred to a separatory funnel. The aqueous phase was extracted with 2 portions DCM/IPA (3:1, 60 mL ea.). The combined organic extracts were dried (Na$_2$SO$_4$), filtered, and concentrated under reduced pressure. The residue thus obtained was further dried under high vacuum overnight to afford the title compound 4-hydroxy-1-methyl-1H-pyrazolo[3,4-d] pyrimidine-6-carboxylic acid (HG-3c) (240 mg, 91%) as a yellow solid. LC/MS m/z 195.1 [M+1]. $^1$H NMR (400 MHz, DMSO-d6) δ=12.37-12.16 (m, 1H), 8.23-8.03 (m, 1H), 4.09-3.83 (m, 3H).

Step 3: Synthesis of 4-chloro-1-methyl-1H-pyrazolo [3,4-d] pyrimidine-6-carbonyl Chloride (HG-3d)

To a reaction flask containing 4-hydroxy-1-methyl-1H-pyrazolo[3,4-d] pyrimidine-6-carboxylic acid (HG-3c) (300 mg, 1.55 mmol) was added phosphorus oxychloride (4.74 g, 30.9 mmol, 2.88 ml). The flask was fitted with a reflux condenser and the reaction heated at 90° C. for 4h. The reaction mixture was concentrated under reduced pressure and then azeotropically distilled with PhMe two times to afford the title compound 4-chloro-1-methyl-1H-pyrazolo[3,4-d] pyrimidine-6-carbonyl chloride (HG-3d) (357 mg, 98%) as a brown solid. LC/MS m/z 227 [M−1] (methyl ester)

Step 4: Synthesis of 4-chloro-N-(2,4-dimethoxybenzyl)-1-methyl-1H-pyrazolo[3,4-d] pyrimidine-6-carboxamide (Int-HG-3)

To a reaction flask containing 4-chloro-1-methyl-1H-pyrazolo[3,4-d] pyrimidine-6-carbonyl chloride (HG-3d) (357 mg, 1.55 mmol) was added DCM (8 mL). The solution was cooled to 0° C. followed by the addition of triethyl amine (938 mg, 9.27 mmol, 1.29 ml). To this mixture was added 1-(2,4-dimethoxyphenyl)methanamine (775 mg, 4.64 mmol, 0.696 ml). The reaction was stirred at 0° C. for 3h. The solution was concentrated under vacuum and the crude residue purified via flash column chromatography (12 g SiO$_2$, Isco, 3% MeOH/DCM) to afford the title compound 4-chloro-N-(2,4-dimethoxybenzyl)-1-methyl-1H-pyrazolo [3,4-d] pyrimidine-6-carboxamide (Int-HG-3) (224 mg, 40%) as a light yellow solid. LC/MS m/z 362 [M+1]. $^1$H NMR (400 MHz, DMSO-d6) δ=9.22-9.13 (m, 1H), 8.59-8.54 (m, 1H), 7.17-7.10 (m, 1H), 6.61-6.56 (m, 1H), 6.52-6.46 (m, 1H), 4.48-4.41 (m, 2H), 4.18-4.11 (m, 3H), 3.87-3.82 (m, 3H), 3.77-3.74 (m, 3H).

Preparation of Methyl 4,6-dichloro-1-methyl-1H-pyrazolo[4,3-c]pyridine (Int-HG-4) According to Scheme HG-4

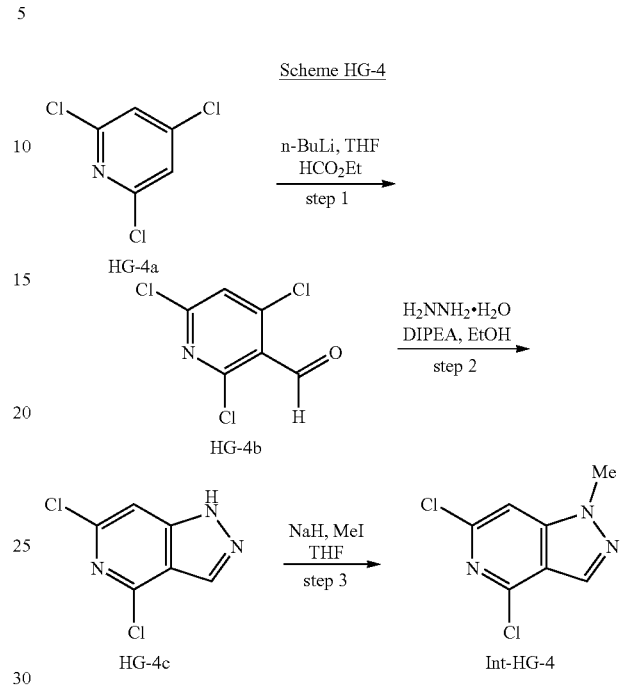

Step 1: Synthesis of 2,4,6-trichloropyridine-3-carbaldehyde (HG-4b)

A solution of 2,4,6-trichloropyridine (HG-4a) (9.00 g, 49.3 mmol) in anhydrous THF was cooled to −68° C. (internal temperature) under an atmosphere of N2 and n-BuLi (2.5 M in hexane, 20.7 mL, 51.8 mmol) was added dropwise, maintaining the reaction temperature below −63° C. (internal temperature). The mixture was stirred at −68° C. (internal temperature) for 30 min. Ethyl formate (4.75 g, 64.1 mmol) was added dropwise, maintaining the reaction temperature below −63° C. (internal temperature). The mixture was stirred at −68° C. (internal temperature) for 1 h. TLC analysis showed consumption of the starting material. The mixture was poured into a 1:1 mixture of ice and saturated aqueous NH$_4$Cl (100 mL). The mixture was stirred for 10 min and then extracted with EtOAc (2×200 mL). The combined organic layers were washed with brine (2×100 mL), dried over anhydrous Na$_2$SO$_4$, filtered, and concentrated to dryness. The residue was purified by flash chromatography (80 g SiO$_2$, 0-5% EtOAc/petroleum ether). The mixed fractions were re-purified by flash chromatography (20 g SiO$_2$, 0-5% EtOAc/petroleum ether). The product batches were combined to afford the title compound 2,4,6-trichloropyridine-3-carbaldehyde (HG-4b) (8.62 g, 83% yield) as a white solid. $^1$H NMR (400 MHz, CDCl$_3$) δ 10.42 (s, 1H), 7.46 (s, 1H).

Step 2: Synthesis of 4,6-dichloro-1H-pyrazolo[4,3-c]pyridine (HG-4c)

A solution of 2,4,6-trichloropyridine-3-carbaldehyde (HG-4b) (4.00 g, 19.0 mmol) and DIPEA (7.62 g, 58.9 mmol) in EtOH (100 mL) was cooled to −20° C. under an atmosphere of N$_2$ and hydrazine monohydrate (3.81 g, 76.0 mmol) was added dropwise. The mixture was stirred at −20° C. for 24 h and then 30° C. for 16 h. LCMS analysis showed formation of the desired product mass. The solution was concentrated to dryness. The resultant solids were slurried with 1:2 EtOAc/petroleum ether (300 mL) for 30 min. The solids were collected by filtration. The filter cake was purified by flash chromatography (40 g SiO$_2$, 8-50% EtOAc/petroleum ether) to afford the title compound 4,6-dichloro-1H-pyrazolo[4,3-c]pyridine (HG-4c) (1.6 g, 45% yield) as a white solid. $^1$H NMR (400 MHz, DMSO-d6) δ 14.06 (br s, 1H), 8.41 (s, 1H), 7.78 (d, J=1.0 Hz, 1H).

Step 3: Synthesis of 4,6-dichloro-1-methyl-1H-pyrazolo[4,3-c]pyridine (Int-HG-4)

To a solution of 4,6-dichloro-1H-pyrazolo[4,3-c]pyridine (HG-4c) (1.25 g, 6.65 mmol) in anhydrous THF at 0° C. was added NaH (60% dispersion in mineral oil, 500 mg, 12.5 mmol). The mixture was stirred at 0° C. for 10 min and then iodomethane (1.89 g, 13.3 mmol) was added dropwise at the same temperature. The mixture was stirred for 1 h at 0° C. and then 16 h at 25° C. TLC analysis (2:1 EtOAc/petroleum ether) showed complete consumption of the starting material. The reaction was quenched by addition of saturated aqueous NH$_4$Cl (20 mL) and then concentrated to remove the THF. The aqueous mixture was extracted with EtOAc (3×20 mL). The combined organic layers were dried over Na$_2$SO$_4$, filtered, and concentrated to dryness. The residue was purified by flash chromatography (40 g SiO$_2$, 5-30% EtOAc/petroleum ether) to afford the title compound 4,6-dichloro-1-methyl-1H-pyrazolo[4,3-c]pyridine (Int-HG-4) (510 mg, 38% yield) as an off-white solid. $^1$H NMR (400 MHz, DMSO-d$_6$) δ 8.42 (d, J=1.0 Hz, 1H), 8.05 (d, J=0.9 Hz, 1H), 4.12 (s, 3H).

Preparation of 4-(4-bromo-1-methyl-1H-imidazol-2-yl)-N-[(2,4-dimethoxyphenyl)methyl]-1-methyl-1H-pyrazolo[4,3-c]pyridine-6-carboxamide (Int-HG-5) According to Scheme HG-5

Scheme HG-5

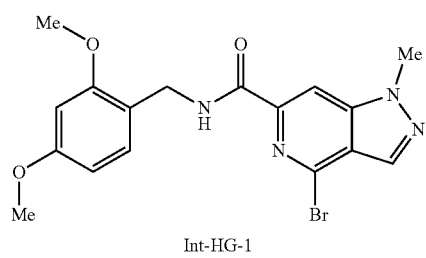

Int-HG-1

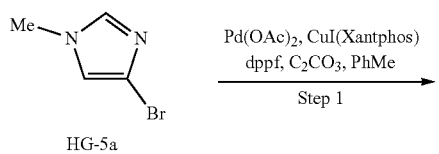

HG-5a

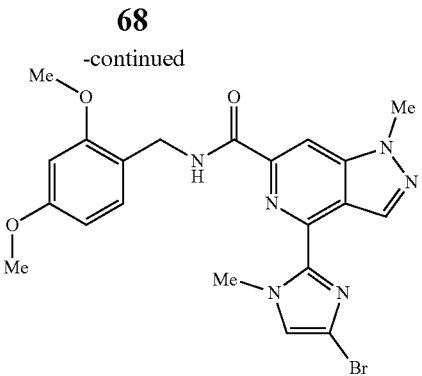

Int-HG-5

Step 1: Synthesis of 4-(4-bromo-1-methyl-1H-imidazol-2-yl)-N-[(2,4-dimethoxyphenyl)methyl]-1-methyl-1H-pyrazolo[4,3-c]pyridine-6-carboxamide (Int-HG-5)

A thick light brown suspension of 4-bromo-N-[(2,4-dimethoxyphenyl)methyl]-1-methyl-1H-pyrazolo[4,3-c]pyridine-6-carboxamide (Int-HG-1) (7.23 g, 17.8 mmol), bromo-1-methyl-imidazole (HG-5a) (2.34 g, 14.5 mmol), Pd(OAc)$_2$ (320 mg, 1.43 mmol), CuIXantphos (3.29 g, 4.27 mmol), dppf (397 mg, 0.717 mmol), and Cs$_2$CO$_3$ (14.0 g, 42.9 mmol) in PhMe (130 mL) was purged with N$_2$ for five cycles and heated to 125° C. with stirring for 17h. The reaction was removed from heating and allowed to cool gradually to room temperature. The suspension was filtered over a pad of Celite and the filter cake washed with DCM (100 mL) and EtOAc (100 mL). The filtrate was concentrated under vacuum and the crude residue purified via flash column chromatography (330 g SiO$_2$, Isco, 0-100% EtOAc/Pet. Ether) to afford the desired product contaminated with minor impurities. This material was further purified via prep-HPLC (YMC Triart C18 250×50 mm×7 um column, 36-76% MeCN/H$_2$O with 0.05% NH$_4$OH, 60 mL/min). The product containing fractions were concentrated under vacuum and triturated with MeOH for 1 h. The suspension was filtered and the solids were collected. The isolated material was further dried under vacuum to afford the title compound 4-(4-bromo-1-methyl-1H-imidazol-2-yl)-N-[(2,4-dimethoxyphenyl)methyl]-1-methyl-1H-pyrazolo[4,3-c]pyridine-6-carboxamide (Int-HG-5) (2.47 g, 31%) as a white solid. LCMS [M+H]=486.1 observed, $^1$H NMR (400 MHz, CHLOROFORM-d) δ=8.88 (d, J=1.0 Hz, 1H), 8.26 (d, J=1.0 Hz, 2H), 7.30 (d, J=8.2 Hz, 1H), 7.04 (s, 1H), 6.50 (d, J=2.2 Hz, 1H), 6.47 (dd, J=2.4, 8.3 Hz, 1H), 5.31 (s, 1H), 4.65 (d, J=6.0 Hz, 2H), 4.16 (s, 3H), 4.13 (s, 3H), 3.88 (s, 3H), 3.81 (s, 3H).

Preparation of 4,6-dichloro-1-cyclopropyl-1H-pyrazolo[4,3-c]pyridine (Int-HG-7) According to Scheme HG-7

Scheme HG-7

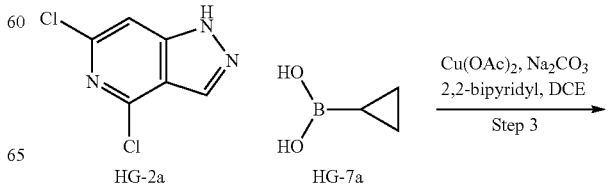

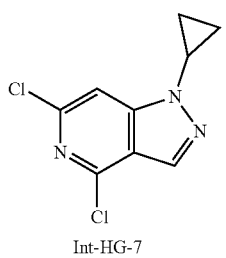

Int-HG-7

Step 1: Synthesis of 4,6-dichloro-1-cyclopropyl-1H-pyrazolo[4,3-c]pyridine (Int-HG-7)

A reaction vessel containing 4,6-dichloro-1H-pyrazolo[4,3-c]pyridine (HG-2a) (150 mg, 0.798 mmol), cyclopropylboronic acid (129 mg, 1.50 mmol), Na$_2$CO$_3$ (159 mg, 1.50 mmol), Cu(OAc)$_2$ (136 mg, 0.749 mmol), and 2,2'-bipyridine (117 mg, 0.749 mmol) in 1,2-dichloroethane (2.5 mL) was heated to 70° C. and stirred for 3 h. The mixture was then cooled to room temperature, diluted with water (20 mL), CH$_2$Cl$_2$ (20 mL), and filtered through a Celite pad. The phases were separated, and the aqueous phase was extracted with CH$_2$Cl$_2$ (10 mL×2). The combined organic extract was dried over anhydrous Na$_2$SO$_3$, filtered, and concentrated under vacuum. The crude residue was purified via flash column chromatography (12 g SiO$_2$, Combi-flash, 5-30% EtOAc/pet. ether) to afford the title compound to afford the title compound 4,6-dichloro-1-cyclopropyl-1H-pyrazolo[4,3-c]pyridine (Int-HG-7) (132 mg, 72%) as a yellow solid. LCMS [M+H]=227.9 observed; $^1$H NMR (CHLOROFORM-d) δ: 8.06 (s, 1H), 7.46 (s, 1H), 3.57-3.63 (m, 1H), 1.21-1.26 (m, 4H).

Preparation of 4,6-dichloro-1-(difluoromethyl)-1H-pyrazolo[4,3-c]pyridine (Int-HG-8) According to Scheme HG-8

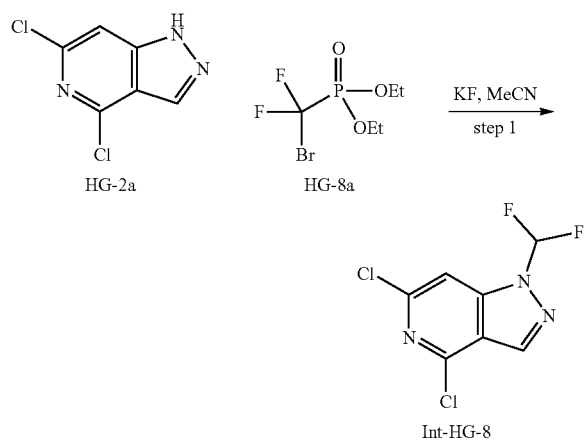

Step 1: Synthesis of 4,6-dichloro-1-(difluoromethyl)-1H-pyrazolo[4,3-c]pyridine (Int-HG-8)

To a solution of 4,6-dichloro-1H-pyrazolo[4,3-c]pyridine (HG-2a) (300 mg, 1.60 mmol) and KF (275 mg, 4.73 mmol) in MeCN (10 mL) was added diethyl (bromodifluoromethyl) phosphonate (HG-8a) (511 mg, 1.91 mmol) at room temperature (30° C.) and stirred 18 h. The reaction was then concentrated under vacuum then purified via flash column chromatography (40 g SiO$_2$, Combi-flash, 5-20% EtOAc/Pet. Ether) to afford the title compound 4,6-dichloro-1-(difluoromethyl)-1H-pyrazolo[4,3-c]pyridine (Int-HG-8) (120 mg, 32%) as a yellow solid. LCMS [M+H]=237.9 observed; $^1$H NMR (CHLOROFORM-d) δ: 8.24 (s, 1H), 7.67 (s, 1H), 7.46 (t, J=59.0 Hz, 1H).

Preparation of 4,6-dichloro-1-(fluoromethyl)-1H-pyrazolo[4,3-c]pyridine (Int-HG-9) According to Scheme HG-9

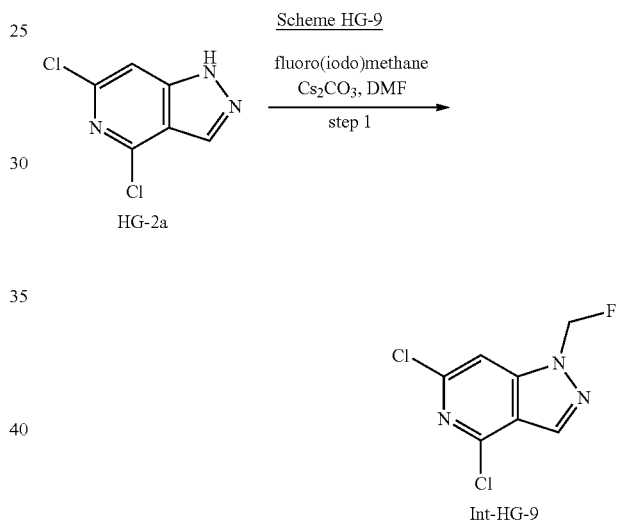

Step 1: Synthesis of 4,6-dichloro-1-(fluoromethyl)-1H-pyrazolo[4,3-c]pyridine (Int-HG-9)

To a yellow suspension of 4,6-dichloro-1H-pyrazolo[4,3-c]pyridine (HG-2a) (150 mg, 0.798 mmol) and Cs$_2$CO$_3$ (520 mg, 1.60 mmol) in anhydrous DMF (3 mL) was added fluoro(iodo)methane (162.3 mg, 1.015 mmol). The resulting dark gray mixture was stirred at room temperature (27° C.) for 1.5 hrs. TLC (Petroleum ether:EtOAc=2:1, UV and 12) showed the reaction was complete. The resulting mixture was diluted with water (10 mL) and extracted with EtOAc (10 mL*3). The combined organic extracts were washed with brine (10 mL*3), dried over anhydrous Na$_2$SO$_4$, filtered, and concentrated under vacuum. The crude residue was purified via flash column chromatography (EtOAc/Petroleum ether=0% to 12%, 12 g silica gel column) to afford the title compound 4,6-dichloro-1-(fluoromethyl)-1H-pyrazolo[4,3-c]pyridine (Int-HG-9) (131 mg, 74.6%) as a light yellow solid. $^1$H NMR (400 MHz, CHLOROFORM-d) δ=8.24 (s, 1H), 7.48 (s, 1H), 6.30 (d, J=53.8 Hz, 2H).

Preparation of Methyl 6-chloro-4-(methylamino)-5-nitropyridine-2-carboxylate (Int-HG-11) According to Scheme HG-11

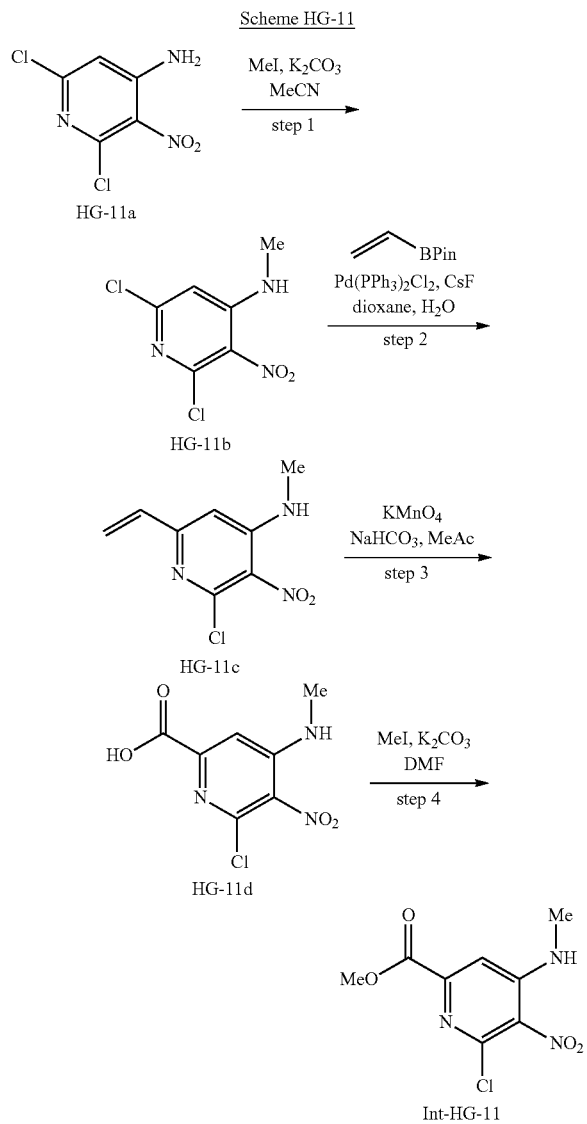

Step 1: Synthesis of 2,6-dichloro-N-methyl-3-nitropyridin-4-amine (HG-11b)

To a reaction vessel containing 2,6-dichloro-3-nitropyridin-4-amine (HG-11a) (2.00 g, 9.61 mmol) and $K_2CO_3$ (2.66 g, 19.2 mmol) in MeCN (30 mL) was added iodomethane (0.921 mL, 14.8 mmol) at room temperature. The mixture was heated to 90° C. for 5 h, then additional iodomethane (0.898 mL, 14.4 mmol) was added and stirred at 90° C. for 5 h. To the reaction was then added additional iodomethane (1.20 mL, 19.2 mmol), and the reaction was stirred at 90° C. for 8 h. The reaction was cooled to room temperature, filtered, and concentrated under vacuum. The crude residue was purified via flash column chromatography (80 g $SiO_2$, Combi-flash, 5-20% EtOAc/Pet. Ether) to afford the title compound 2,6-dichloro-N-methyl-3-nitropyridin-4-amine (HG-11b) (960 mg, 45%) as a yellow solid. LCMS [M+H]=221.8 observed; $^1$H NMR (CHLOROFORM-d) δ: 6.80 (br s, 1H), 6.68 (s, 1H), 3.02 (d, J=5.0 Hz, 3H).

Step 2: Synthesis of 2-chloro-6-ethenyl-N-methyl-3-nitropyridin-4-amine (HG-11c)

A solution of 2,6-dichloro-N-methyl-3-nitropyridin-4-amine (HG-11b) (1.06 g, 4.77 mmol), 4,4,5,5-tetramethyl-2-vinyl-1,3,2-dioxaborolane (882 mg, 5.73 mmol), CsF (2.18 g, 14.3 mmol), $Pd(PPh_3)_2Cl_2$ (335 mg, 0.477 mmol) in 1,4-dioxane (10.6 mL) and $H_2O$ (5.3 mL) was degassed with $N_2$ 3 times, heated to 90° C., and stirred for 16 h. The reaction was cooled to room temperature, diluted with EtOAc (20 mL), dried over $Na_2SO_4$, filtered through a Celite pad, and concentrated under vacuum. The crude residue was purified via flash column chromatography (80 g $SiO_2$, Combi-flash, 3-15% EtOAc/Pet. Ether) to afford the title compound 2-chloro-6-ethenyl-N-methyl-3-nitropyridin-4-amine (HG-11c) (385 mg, 38%) as a yellow solid. LCMS [M+H]=213.9 observed; $^1$H NMR (CHLOROFORM-d) δ: 6.96-7.08 (m, 2H), 6.60 (s, 1H), 6.53 (dd, J=16.6, 1.8 Hz, 1H), 5.68 (dd, J=10.5, 1.7 Hz, 1H), 2.99 (d, J=5.1 Hz, 3H).

Step 3: Synthesis of 6-chloro-4-(methylamino)-5-nitropyridine-2-carboxylic Acid (HG-11d)

To a reaction vessel containing 2-chloro-6-ethenyl-N-methyl-3-nitropyridin-4-amine (HG-11c) (340 mg, 1.59 mmol) in acetone (9 mL) at 27° C. was added $NaHCO_3$ (67 mg, 0.80 mmol) and KMnO4 (755 mg, 4.77 mmol, added in portions over 30 min). The solution was stirred for 4 h then diluted with MeOH (3 mL), $H_2O$ (3 mL), and basified to pH 10 with NaOH (2 N). The phases were separated, and the aqueous phase was extracted with EtOAc (10 mL×3). Then the resulting aqueous layer was acidified to pH 1-2 with HCl (2 N) and filtered to remove the precipitate. The filtered liquor was extracted with EtOAc (20 mL×3), the combined organic phases were dried over $Na_2CO_3$, filtered, and concentrated under vacuum to afford crude title compound 6-chloro-4-(methylamino)-5-nitropyridine-2-carboxylic acid (HG-11d) (208 mg, 56%) as a yellow solid, which was used without further purification.

Step 4: Synthesis of Methyl 6-chloro-4-(methylamino)-5-nitropyridine-2-carboxylate (Int-HG-11)

To a reaction vessel containing 6-chloro-4-(methylamino)-5-nitropyridine-2-carboxylic acid (HG-11d) (178 mg, 0.769 mmol) in DMF (1.8 mL) was added $K_2CO_3$ (212 mg, 1.54 mmol) and iodomethane (0.057 mL, 0.922 mmol). The reaction was stirred at room temperature for 2 h before dilution with $H_2O$ (5 mL). The phases were separated, the aqueous phase was extracted with EtOAc (10 mL×3), and the combined organic phases were washed with brine (15 mL×3). The organic phase was dried over $Na_2CO_3$, filtered, and concentrated under vacuum. The crude residue was purified via flash column chromatography (20 g $SiO_2$, Combi-flash, 5-30% EtOAc/Pet. Ether) to afford the title compound methyl 6-chloro-4-(methylamino)-5-nitropyridine-2-carboxylate (Int-HG-11) (108 mg, 43% for three combined batches) as a yellow solid. LCMS [M+H]=245.9 observed; $^1$H NMR (CHLOROFORM-d) δ: 8.07 (br s, 1H), 6.81 (s, 1H), 3.98 (s, 3H), 3.08 (d, J=5.0 Hz, 3H).

Preparation of Tail Group (TG) Intermediates

Preparation of 1-ethyl-5-(1H-imidazol-4-yl)-3-methyl-1H-pyrazole (Int-TG-1) According to Scheme TG-1

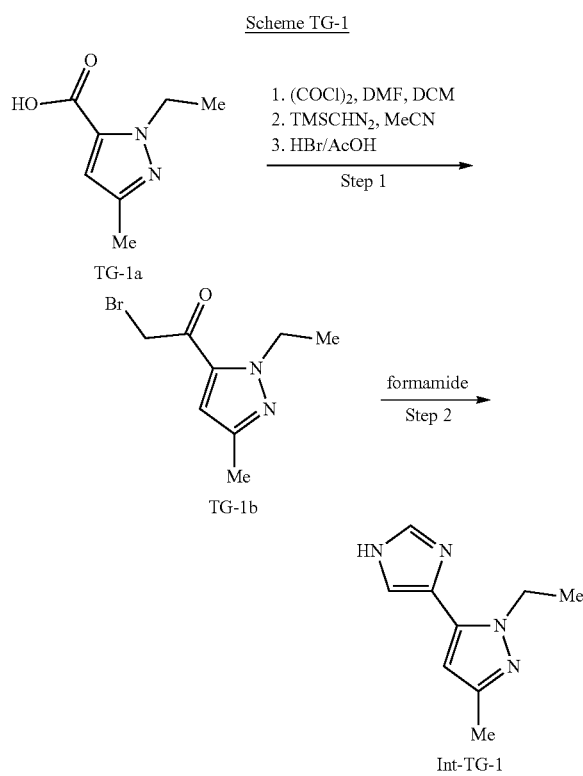

Step 1: Synthesis of 2-bromo-1-(1-ethyl-3-methyl-1H-pyrazol-5-yl)ethan-1-one (TG-1b)

To a yellow suspension of 1-ethyl-3-methyl-1H-pyrazole-5-carboxylic acid (TG-1a) (3 g, 19.4 mmol) in anhydrous DCM (100 mL) was added DMF (0.1 mL) followed by the slow addition of (COCl)$_2$ (3.0 mL, 35 mmol). The reaction was stirred for 0.5 h at room temperature. The solution was concentrated under vacuum and the crude residue was co-evaporated twice with DCM (50 mL ea.). The product was used in the next reaction without further purification. The product was dissolved in MeCN (100 mL), cooled in an ice water bath, and TMSCHN$_2$ (4890 mg, 42.8 mmol) was added at 0° C. The reaction was stirred at room temperature for 2h, then HBr (33% solution in AcOH, 8.3 mL, 50 mmol) was added to the solution at a rate which maintained internal temperature below 30° C. The reaction was stirred at room temperature for 2h. The reaction mixture was diluted with EtOAc (100 mL) and water (100 mL) and transferred to a separatory funnel. The phases were separated and the aqueous layer was extracted with EtOAc (100 mL). The combined organic extracts were washed with 3 portions brine (50 mL ea.), dried (Na$_2$SO$_4$), filtered, and concentrated under vacuum. The crude residue was purified via flash column chromatography (220 g SiO$_2$, Combi-flash, 85-100% EtOAc/Pet. Ether) to afford the title compound 2-bromo-1-(1-ethyl-3-methyl-1H-pyrazol-5-yl)ethan-1-one (TG-1b) (2.65 g, 59%) as a yellow oil. $^1$H NMR (400 MHz, CHLOROFORM-d) δ=6.68 (s, 1H), 4.52 (q, J=7.1 Hz, 2H), 4.29 (s, 2H), 2.31 (s, 3H), 1.39 (t, J=7.1 Hz, 3H).

Step 2: Synthesis of 1-ethyl-5-(1H-imidazol-4-yl)-3-methyl-1H-pyrazole (Int-TG-1)

A light yellow mixture of 2-bromo-1-(1-ethyl-3-methyl-1H-pyrazol-5-yl)ethan-1-one (TG-1b) (3.20 g 13.8 mmol) in formamide (14.0 mL) was heated to 140° C. and stirred for 16 hours. The reaction mixture was diluted with DCM (40 mL) and transferred to a separatory funnel. The phases were separated and the formamide phase was extracted with 3 portions DCM (30 mL ea.). The combined DCM extracts were concentrated under vacuum. The crude residue was purified via flash column chromatography (80 g SiO$_2$, Combi-flash, 0-100% EtOAc/Pet. Ether then 0-5% MeOH/EtOAc) to afford the desired product containing residual formamide. The mixture was dissolved in EtOAc, diluted with 1N HCl aq. (4 mL), and transferred to a separatory funnel. The phases were separated and the aqueous phase was extracted with 3 portions EtOAc (30 mL ea.). Then, the pH of the aqueous phase was adjusted with 2N NaOH aq. until pH=~10. The aqueous phase was extracted with 3 portions EtOAc (50 mL ea.). The combined organic extracts from this stage were dried (Na$_2$SO$_4$), filtered, and concentrated under vacuum. The crude residue was purified via flash column chromatography (80 g SiO$_2$, Combi-flash, 0-5% MeOH/EtOAc) to afford the title compound 1-ethyl-5-(1H-imidazol-4-yl)-3-methyl-1H-pyrazole (Int-TG-1) (790 mg, 32%) as a yellow solid contaminated with ~2 eq. of formamide. The material thus obtained was used without further purification. $^1$H NMR (400 MHz, CHLOROFORM-d) δ=7.71 (d, J=0.9 Hz, 1H), 7.18 (d, J=1.0 Hz, 1H), 6.16 (s, 1H), 4.39 (q, J=7.1 Hz, 2H), 2.28 (s, 3H), 1.41 (t, J=7.2 Hz, 3H).

The intermediate in the table below was prepared according to the methods used in steps 1-2 for the synthesis of 1-ethyl-5-(1H-imidazol-4-yl)-3-methyl-1H-pyrazole (Int-TG-1) employing commercially available 1-ethyl-3-(trifluoromethyl)-1H-pyrazole-5-carboxylic acid as the starting material with non-critical changes or substitutions to the exemplified procedures that one skilled in the art would be able to realize.

| Int-TG Number | Structure/IUPAC Name | Analytical Data |
|---|---|---|
| Int-TG-12 | 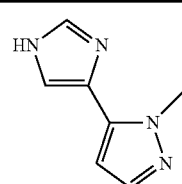<br>1-ethyl-5-(1H-imidazol-4-yl)-3-(trifluoromethyl)-1H-pyrazole | LCMS [M + H] = 231.0 observed; $^1$H NMR (CHLOROFORM-d) δ: 7.92-8.06 (m, 1H), 7.32 (s, 1H), 6.66 (s, 1H), 4.55 (q, J = 7.2 Hz, 2H), 3.79-3.95 (m, 1H), 1.48 (t, J = 7.3 Hz, 3H); $^{19}$F NMR (CHLOROFORM-d) δ: −61.99 (s, 1F). |

Preparation of 2-ethyl-1',4-dimethyl-1'H-1,4'-biimidazole (Int-TG-2) According to Scheme TG-2

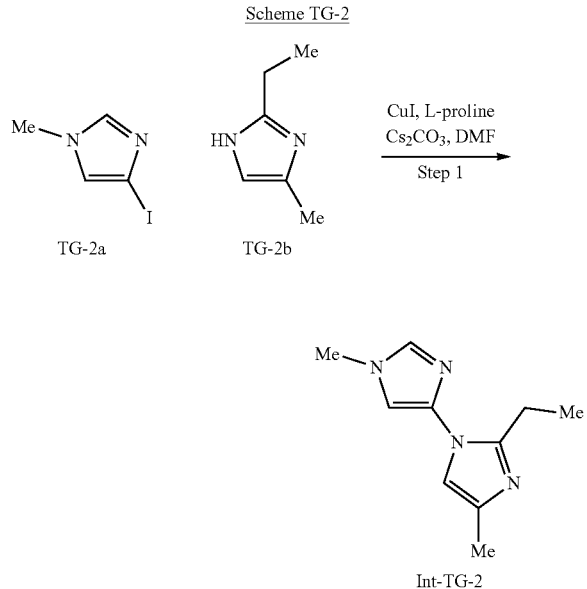 [SMILES: Cn1cnc(I)c1 ; CCc1nc(C)c[nH]1 ; CCc1nc(C)cn1-c1cn(C)cn1]

Step 1: Synthesis of 2-ethyl-1',4-dimethyl-1'H-1,4'-biimidazole (Int-TG-2)

To a mixture of 4-iodo-1-methylimidazole (TG-2a) (500 mg, 2.40 mmol) and 2-ethyl-5-methyl-1H-imidazole (TG-2b) (530 mg, 4.81 mmol) in anhydrous DMF (10 mL) was added $Cs_2CO_3$ (3.13 g 9.62 mmol), CuI (458 mg, 2.40 mmol), L-Proline (332 mg, 2.88 mmol). The resulting mixture was flushed with $N_2$ for 2 min, sealed, heated to 120° C. (heating block), and stirred for 40h. The reaction mixture was diluted with water (20 mL) and transferred to a separatory funnel with EtOAc. The phases were separated and the aqueous phase was extracted with 3 portions of EtOAc (20 mL ea.). The aqueous phase was saturated with brine and extracted with an additional 3 portions of EtOAc (20 mL ea.). The combined organic extracts were washed with 3 portions brine (15 mL ea.). The combined aqueous brine washes were back-extracted with 3 portions EtOAc (10 mL ea.). The organic extracts were again combined, dried ($Na_2SO_4$), filtered, and concentrated under vacuum. The crude residue was purified via flash column chromatography (20 g $SiO_2$, Combi-flash, 0-10% MeOH/DCM) to give the desired product as a yellow oil contaminated with residual DMF. The oil was diluted with DCM/MeOH (10:1, 20 mL) and transferred to a separatory funnel. The solution was washed with 3 portions brine (15 mL ea.). The organic phase was dried ($Na_2SO_4$), filtered, and concentrated under vacuum. The residue was purified via flash column chromatography (20 g $SiO_2$, Combi-flash, 0-10% MeOH/DCM) to afford the title compound 2-ethyl-1',4-dimethyl-1'H-1,4'-biimidazole (Int-TG-2) (140 mg, 30%) as a yellow oil. $^1$H NMR (400 MHz, CHLOROFORM-d) δ=7.36 (s, 1H), 6.83 (d, J=1.5 Hz, 1H), 6.80 (s, 1H), 3.74 (s, 3H), 2.77 (q, J=7.5 Hz, 2H), 2.24 (d, J=0.8 Hz, 3H), 1.28 (t, J=7.5 Hz, 3H).

Preparation of 1-[3-(benzyloxy)propyl]-5-(1H-imidazol-4-yl)-3-methyl-1H-pyrazole (Int-TG-3) According to Scheme TG-3

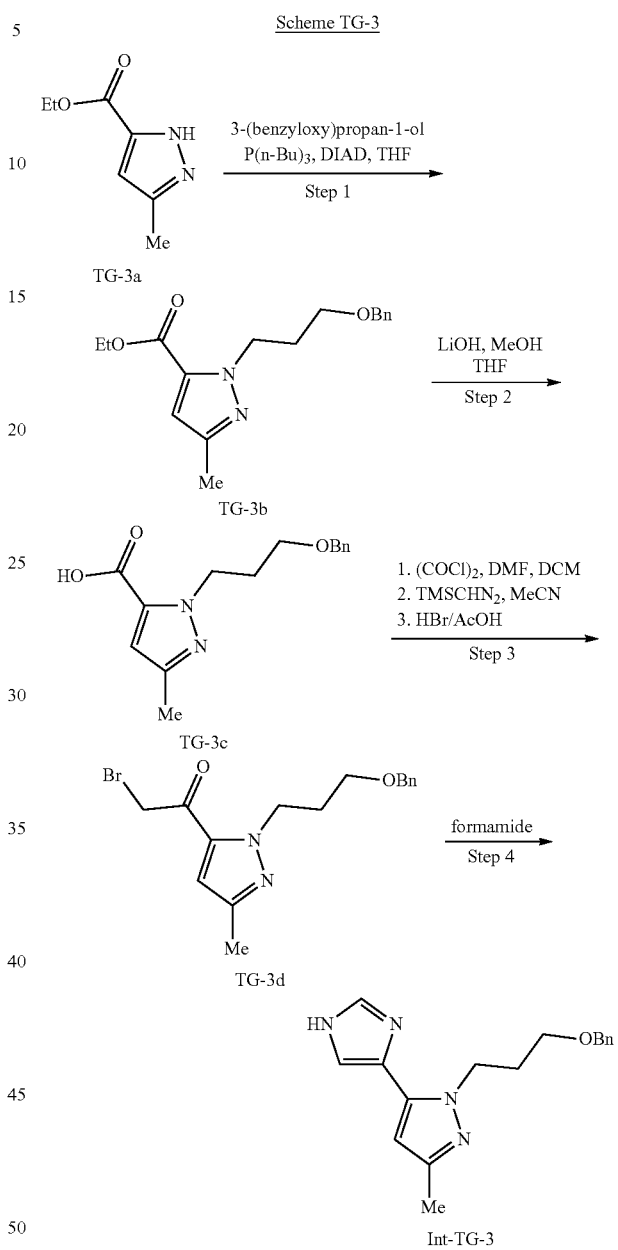

Step 1: Synthesis of Ethyl 1-[3-(benzyloxy)propyl]-3-methyl-1H-pyrazole-5-carboxylate (TG-3b)

A solution of ethyl 3-methyl-1H-pyrazole-5-carboxylate (TG-3a) (11.5 g, 74.6 mmol) and 3-(benzyloxy)propan-1-ol (13.0 g, 78.3 mmol) in THF (300 mL) was cooled in an ice water bath followed by the dropwise addition of P(n-Bu)$_3$ (33.2 g, 164 mmol) and DIAD (31.7 g, 157 mmol) while maintaining an internal reaction temperature below 10° C. The ice bath was removed and the colorless reaction solution was stirred at room temperature for 16 hours. The reaction mixture was concentrated under vacuum and the crude residue thus obtained was purified via flash column chromatography (330 g $SiO_2$, Combi-flash, 0-15% EtOAc/Pet.

Ether) to afford the title compound ethyl 1-[3-(benzyloxy)propyl]-3-methyl-1H-pyrazole-5-carboxylate (TG-3b) (21.4 g, 94%) as a colorless oil. LCMS [M+H]=302.8 observed; $^1$H NMR (400 MHz, DMSO-d6) δ=7.43-7.25 (m, 5H), 6.64 (s, 1H), 4.50 (t, J=7.1 Hz, 2H), 4.44 (s, 2H), 4.26 (q, J=7.1 Hz, 2H), 3.41 (t, J=6.1 Hz, 2H), 2.18 (s, 3H), 2.06-1.95 (m, 2H), 1.27 (t, J=7.1 Hz, 3H).

Step 2: Synthesis of 1-[3-(benzyloxy)propyl]-3-methyl-1H-pyrazole-5-carboxylic Acid (TG-3c)

To a solution of ethyl 1-[3-(benzyloxy)propyl]-3-methyl-1H-pyrazole-5-carboxylate (TG-3b) (21.4 g, 70.8 mmol) in MeOH (70 mL) was added THF (350 mL) and LiOH (4.45 g, 106 mmol) as 1N aqueous solution (106 mL). The reaction was stirred at room temperature for 24h. The reaction mixture was concentrated under vacuum to remove the volatile solvents. The aqueous suspension thus obtained was transferred to a separatory funnel with EtOAc. The phases were separated and the aqueous phase was extracted with EtOAc (50 mL). The pH of the aqueous phase was then adjusted with 1N HCl aq. to a pH=~1 and extracted with 2 portions of EtOAc (150 mL ea.). These organic extracts were combined, dried (Na$_2$SO$_4$), filtered, and concentrated under vacuum to afford the title compound 1-[3-(benzyloxy)propyl]-3-methyl-1H-pyrazole-5-carboxylic acid (TG-3c) (18.3 g, 94%) as a white solid. LCMS [M+H]=274.8 observed; $^1$H NMR (400 MHz, DMSO-d6) δ=13.20 (br s, 1H), 7.39-7.23 (m, 5H), 6.59 (s, 1H), 4.50 (t, J=7.2 Hz, 2H), 4.44 (s, 2H), 3.41 (t, J=6.3 Hz, 2H), 2.17 (s, 3H), 2.00 (quin, J=6.7 Hz, 2H).

Step 3: Synthesis of 1-{1-[3-(benzyloxy)propyl]-3-methyl-1H-pyrazol-5-yl}-2-bromoethan-1-one (TG-3d)

The reaction was performed as a set of two batches with 6.6 g of starting material each. To a colorless solution of 1-[3-(benzyloxy)propyl]-3-methyl-1H-pyrazole-5-carboxylic acid (TG-3c) (6.60 g, 24.1 mmol) in DCM (2000 mL) was added DMF (0.3 mL) followed by the dropwise addition of (COCl)$_2$ (3.66 mL, 43.3 mmol). The reaction was stirred at room temperature for 1 h and then concentrated under vacuum. The crude residue was co-evaporated 3 more times with DCM (100 mL ea.). The produce was used in the next step without further purification. The crude product was dissolved in MeCN (200 mL), the solution cooled in an ice water bath, followed by the dropwise addition of TMSCHN$_2$ (2M solution in hexane, 26.5 mL, 52.9 mmol) at 0° C. under inert atmosphere. The reaction was stirred at room temperature for 18h. At this stage, HBr (33% solution in AcOH, 10.3 mL, 62.6 mmol) was added a rate to maintain the internal temperature. The reaction was stirred at room temperature for 1.5h. The two reaction batches were combined, quenched with water (100 mL), and transferred to a separatory funnel with EtOAc (200 mL). The phases were separated and the aqueous phase was extracted with EtOAc (100 mL). The combined organic extracts were washed with 1 portion brine (200 mL), dried (Na$_2$SO$_4$), filtered, and concentrated under vacuum. The crude residue was purified via flash column chromatography (330 g SiO$_2$, Biotage, 0-19% EtOAc/Pet. Ether) to afford the title compound 1-{1-[3-(benzyloxy)propyl]-3-methyl-1H-pyrazol-5-yl}-2-bromoethan-1-one (TG-3d) (11.3 g, 66%) as a light-yellow oil. LCMS [M+H]=351.8 observed; $^1$H NMR (400 MHz, CHLOROFORM-d) δ=7.37-7.34 (m, 4H), 7.33-7.29 (m, 1H), 6.68 (s, 1H), 4.63 (t, J=7.2 Hz, 2H), 4.51 (s, 2H), 4.27 (s, 2H), 3.53 (t, J=6.1 Hz, 2H), 2.32 (s, 3H), 2.16-2.09 (m, 2H).

Step 4: Synthesis of 1-[3-(benzyloxy)propyl]-5-(1H-imidazol-4-yl)-3-methyl-1H-pyrazole (Int-TG-3)

The reaction was performed as a set of 10 batches with 1.13 g of starting material each. A solution of 1-{1-[3-(benzyloxy)propyl]-3-methyl-1H-pyrazol-5-yl}-2-bromoethan-1-one (TG-3d) in formamide (2.0 mL) was heated to 140° C. and stirred for 16h. All batches were allowed to cool to room temperature over 24h and then combined. The combined solution was diluted with DCM and transferred to a separatory funnel. The phases were separated and the formamide phase was extracted with DCM (30 mL). The combined DCM extracts were washed with water (50 mL), dried (Na$_2$SO$_4$), filtered, and concentrated under vacuum. The crude residue was purified via flash column chromatography [220 g SiO$_2$, Biotage, 0-7% MeOH/(EtOAc/DCM 1:1)] to afford the title compound 1-[3-(benzyloxy)propyl]-5-(1H-imidazol-4-yl)-3-methyl-1H-pyrazole (Int-TG-3) (5.4 g, 47%) as a brown solid upon standing. LCMS [M+H]=297.0 observed; $^1$H NMR (400 MHz, DMSO-d6) δ=12.31 (br s, 1H), 7.75 (s, 1H), 7.44 (s, 1H), 7.38-7.25 (m, 5H), 6.16 (s, 1H), 4.46 (br t, J=6.9 Hz, 2H), 4.41 (s, 2H), 3.42 (t, J=6.2 Hz, 2H), 2.14 (s, 3H), 2.04-1.95 (m, 2H).

The intermediates in the table below were prepared according to the methods used for the synthesis of 1-[3-(benzyloxy)propyl]-5-(1H-imidazol-4-yl)-3-methyl-1H-pyrazole (Int-TG-3) with non-critical changes or substitutions to the exemplified procedures that one skilled in the art would be able to realize.

| Int-TG Number | Reagents/Solvent used for step 1 | Structure/IUPAC Name | Analytical Data |
|---|---|---|---|
| Int-TG-4 | propan-1-ol (n-Bu)$_3$P, DIAD, THF | 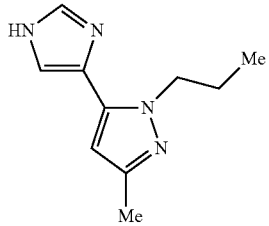 [SMILES: CCCn1nc(C)cc1-c1c[nH]cn1]<br>5-(1H-imidazol-4-yl)-3-methyl-1-propyl-1H-pyrazole | LCMS [M + H] = 190.8 observed; $^1$H NMR (400? MHz, METHANOL-d$_4$) δ = 7.82 (d, J = 0.9 Hz, 1H), 7.34 (d, J = 0.9 Hz, 1H), 6.24 (s, 1H), 4.23 (t, J = 7.3 Hz, 2H), 2.26 (s, 3H), 1.77 (qd, J = 7.4, 14.7 Hz, 2H), 0.84 (t, J = 7.4 Hz, 3H). |

| Int-TG Number | Reagents/Solvent used for step 1 | Structure/IUPAC Name | Analytical Data |
|---|---|---|---|
| Int-TG-5 | 2-methoxyethan-1-ol, (n-Bu)$_3$P, DIAD, THF | 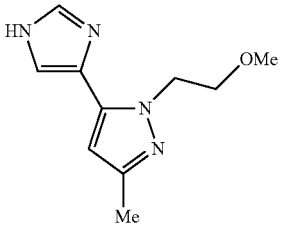 [SMILES: COCCn1nc(C)cc1-c1c[nH]cn1]<br>5-(1H-imidazol-4-yl)-1-(2-methoxyethyl)-3-methyl-1H-pyrazole | LCMS [M + H] = 207.1 observed; $^1$H NMR (400 MHz, METHANOL-d$_4$) δ = 7.80 (d, J = 0.9 Hz, 1H), 7.41 (d, J = 1.0 Hz, 1H), 6.23 (s, 1H), 4.38 (t, J = 5.6 Hz, 2H), 3.71 (t, J = 5.6 Hz, 2H), 3.24 (s, 3H), 2.25 (s, 3H). |
| Int-TG-6 | 3-methoxypropan-1-ol, (n-Bu)$_3$P, DIAD, THF | 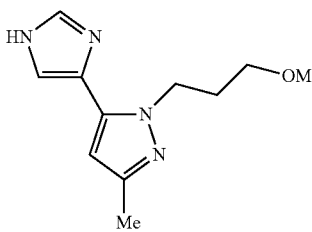<br>5-(1H-imidazol-4-yl)-1-(3-methoxypropyl)-3-methyl-1H-pyrazole | LCMS [M + H] = 221.1 observed; $^1$H NMR (400 MHz, METHANOL-d$_4$) δ = 7.81 (d, J = 1.0 Hz, 1H), 7.40 (d, J = 1.0 Hz, 1H), 6.25 (s, 1H), 4.34 (t, J = 7.1 Hz, 2H), 3.30-3.28 (m, 2H), 3.24 (s, 3H), 2.24 (s, 3H), 2.03-1.99 (m, 2H) |
| Int-TG-7 | Cyclopropylmethanol, (n-Bu)$_3$P, DIAD, THF | 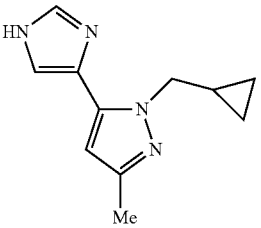 [SMILES: Cc1cc(-c2c[nH]cn2)n(CC2CC2)n1]<br>1-(cyclopropylmethyl)-5-(1H-imidazol-4-yl)-3-methyl-1H-pyrazole | LCMS [M + H] = 203.0 observed; $^1$H NMR (400 MHz. METHANOL-d$_4$) δ = 7.80 (d, J = 1.0 Hz, 1H), 7.35 (d, J = 1.1 Hz, 1H), 6.23 (s, 1H), 4.15 (d, J = 6.8 Hz, 2H), 2.25 (s, 3H), 1.22-1.13 (m, 1H), 0.47-0.40 (m, 2H), 0.25-0.18 (m, 2H). |
| Int-TG-8 | 3,3,3-trifluoropropan-1-ol, (n-Bu)$_3$P, DIAD, THF | 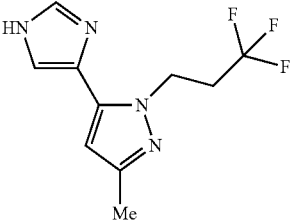 [SMILES: Cc1cc(-c2c[nH]cn2)n(CCC(F)(F)F)n1]<br>5-(1H-imidazol-4-yl)-3-methyl-1-(3,3,3-trifluoropropyl)-1H-pyrazole | LCMS [M + H] = 245.1 observed; $^1$H NMR (400 MHz, CHLOROFORM-d) δ = 8.05 (s, 1H), 7.25 (s, 1H), 6.20 (s, 1H), 4.68-4.59 (m, 2H), 2.87-2.66 (m, 2H), 2.28 (s, 3H) |

The intermediate in the table below was prepared according to the methods used in steps 2-4 for the synthesis of 1-[3-(benzyloxy)propyl]-5-(1H-imidazol-4-yl)-3-methyl-1H-pyrazole (Int-TG-3) employing ethyl 3-methyl-1-(2,2,2-trifluoroethyl)-1H-pyrazole-5-carboxylate (POT Int. Appl., 2017198341, 23 Nov. 2017) as the starting material with non-critical changes or substitutions to the exemplified procedures that one skilled in the art would be able to realize.

| Int-TG Number | Structure/IUPAC Name | Analytical Data |
|---|---|---|
| Int-TG-9 | 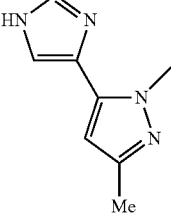<br>5-(1H-imidazol-4-yl)-3-methyl-1-(2,2,2-trifluoroethyl)-1H-pyrazole | LCMS [M + H] = 230.9 observed; ¹H NMR (400 MHz, DMSO-d₆) δ = 12.42 (br s, 1H), 7.80 (d, J = 1.0 Hz, 1H), 7.56 (s, 1H), 6.32 (s, 1H), 5.56 (q, J = 8.7 Hz, 2H), 2.16 (s, 3H). |

The intermediates in the table below were prepared according to the methods used for the synthesis of 1-[3-(benzyloxy)propyl]-5-(1H-imidazol-4-yl)-3-methyl-1H-pyrazole (Int-TG-3) with non-critical changes or substitutions to the exemplified procedures that one skilled in the art would be able to realize.

| Int-TG Number | Reagents/Solvent used for step 1 | Structure/IUPAC Name | Analytical Data |
|---|---|---|---|
| Int-TG-13 | 5-(benzyloxy)pentan-1-ol, (n-Bu)₃P, DIAD, THF | 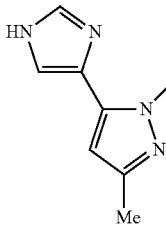<br>1-[5-(benzyloxy)pentyl]-5-(1H-imidazol-4-yl)-3-methyl-1H-pyrazole | LCMS [M + H] = 325.1 observed; ¹H NMR (CHLOROFORM-d) δ: 7.62 (s, 1H), 7.27 (s, 5H), 7.12 (s, 1H), 6.15 (s, 1H), 4.47 (s, 2H), 4.32 (t, J = 7.4 Hz, 2H), 3.45 (t, J = 6.4 Hz, 2H), 2.28 (s, 3H), 1.86 (quin, J = 7.5 Hz, 2H), 1.52-1.65 (m, 2H), 1.32-1.47 (m, 2H). |
| Int-TG-14 | 4-(benzyloxy)butan-1-ol, (n-Bu)₃P, DIAD, THF | 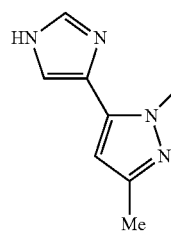<br>1-[4-(benzyloxy)butyl]-5-(1H-imidazol-4-yl)-3-methyl-1H-pyrazole | LCMS [M + H] = 311.1 observed; ¹H NMR (CHLOROFORM-d) δ: 7.71 (s, 1H), 7.27 (s, 5H), 7.15 (s, 1H), 6.17 (s, 1H), 4.46 (s, 2H), 4.33 (t, J = 7.3 Hz, 2H), 3.47 (t, J = 6.4 Hz, 2H), 2.26 (s, 3H), 1.92 (quin, J = 7.4 Hz, 2H), 1.56-1.66 (m, 2H). |

The intermediates in the table below were prepared according to the methods used for the synthesis of 1-[3-(benzyloxy)propyl]-5-(1H-imidazol-4-yl)-3-methyl-1H-pyrazole (Int-TG-3) with non-critical changes or substitutions to the exemplified procedures that one skilled in the art would be able to realize.

| Int-TG Number | Reagents/Solvent used for step 1 | Structure/IUPAC Name | Analytical Data |
|---|---|---|---|
| Int-TG-22 | 4,4-difluorobutan-1-ol, (n-Bu)$_3$P, DIAD, THF | 1-(4,4-difluorobutyl)-5-(1H-imidazol-4-yl)-3-methyl-1H-pyrazole | LCMS [M + H] = 241.0 observed; $^1$H NMR (400 MHz, DMSO-d$_6$) δ = 12.36 (br s, 1H), 7.76 (s, 1H), 7.45 (s, 1H), 6.17 (s, 1H), 5.96 (td, J = 0.5, 56.2 Hz, 1H), 4.46 (t, J = 6.7 Hz, 2H), 2.13 (s, 3H), 1.90-1.73 (m, 4H); $^{19}$F NMR (376 MHz, DMSO-d$_6$) δ = −15.43 (br s, 1F). |
| Int-TG-26 | 4-bromobutanenitrile K$_2$CO$_3$, DMF | 4-[5-(1H-imidazol-4-yl)-3-methyl-1H-pyrazol-1-yl]butanenitrile | LCMS [M + H] = 215.9 observed; $^1$H NMR (400 MHz, CHLOROFORM-d) δ = 7.72 (d, J = 1.0 Hz, 1H), 7.24 (d, J = 1.1 Hz, 1H), 6.17 (s, 1H), 4.57 (t, J = 6.5 Hz, 2H), 2.40-2.35 (m, 2H), 2.28 (s, 3H), 2.26-2.20 (m, 2H). |

Preparation of 1-ethyl-4-[(4-methoxyphenyl)methoxy]-3-methyl-5-(1-methyl-1H-imidazol-4-yl)-1H-pyrazole (Int-TG-10) According to Scheme TG-10

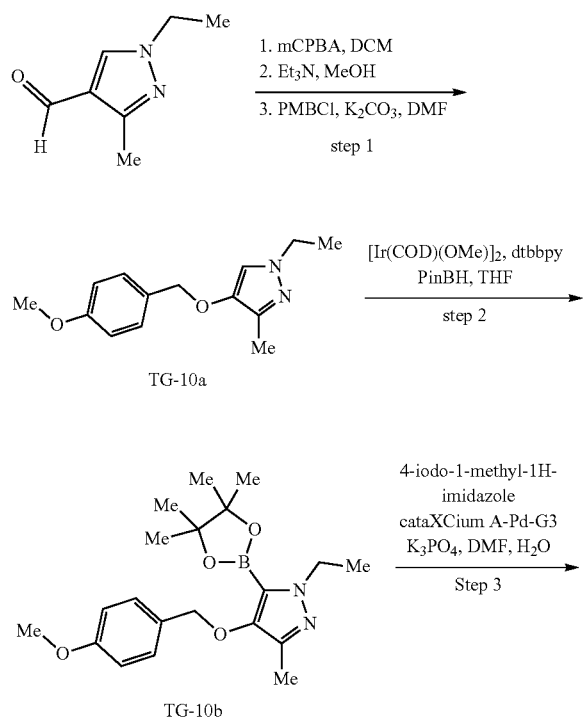

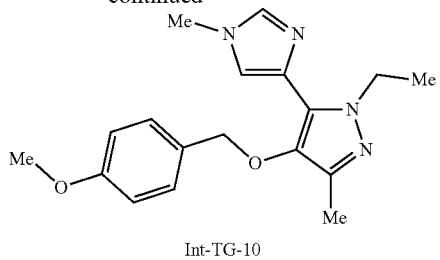

Step 1: Synthesis of 1-ethyl-4-[(4-methoxyphenyl)methoxy]-3-methyl-1H-pyrazole (TG-10a)

To a 100 mL flask containing 1-ethyl-3-methyl-1H-pyrazole-4-carbaldehyde (1.0 g, 7.24 mmol) was added DCM and m-chloroperoxybenzoic acid (mCPBA) (3.24 g, 77% purity, 14.5 mmol). The solution was heated to 40° C. for 1 h. The reaction was cooled to room temperature, diluted with DCM, washed with mixture of sat Na$_2$SO$_3$ aq., 2 portions sat. Na$_2$CO$_3$ aq., brine, dried (Na$_2$SO$_4$), filtered and concentrated under vacuum to afford 1-ethyl-3-methyl-1H-pyrazol-4-yl formate (1 g) which was used in the without further purification. To a 100 mL flask containing 1-ethyl-3-methyl-1H-pyrazol-4-yl formate (1 g, 6.49 mmol) was added MeOH and Et$_3$N (0.9 mL, 6.48 mmol). The solution was stirred at room temperature for 30 min. The solution was concentrated in vacuo to afford 1-ethyl-3-methyl-1H-pyrazol-4-ol as a pink oil which was used without further purification. To a solution of 1-ethyl-3-methyl-1H-pyrazol-4-ol (546 mg, 4.33 mmol) and PMBCl (749 mg, 4.78 mmol) in DMF (8.5 mL) was added K$_2$CO$_3$ (660 mg, 4.77 mmol). The reaction was stirred at 25° C. for 16h. The reaction was quenched with H$_2$O (25 mL) and transferred to a separatory funnel with EtOAc. The phases were separated and the aqueous phase was extracted with 3 portions EtOAc (20 mL ea.). The combined organic extracts were dried (Na₂SO₄), filtered, and concentrated under vacuum. The crude residue was purified via flash column chromatography (20 g SiO₂, Combi-flash, 60-100% EtOAc/Pet. Ether) to afford the title compound 1-ethyl-4-[(4-methoxyphenyl)methoxy]-3-methyl-1H-pyrazole (TG-10a) (903 mg, 84%) as a white solid. LCMS [M+H]=247.0 observed; ¹H NMR (400 MHz, CHLOROFORM-d) δ=7.33 (d, J=8.8 Hz, 2H), 6.96 (s, 1H), 6.91 (d, J=8.8 Hz, 2H), 4.81 (s, 2H), 4.00 (q, J=7.3 Hz, 2H), 3.83 (s, 3H), 2.19 (s, 3H), 1.41 (t, J=7.4 Hz, 3H).

Step 2: Synthesis of 1-ethyl-4-[(4-methoxyphenyl) methoxy]-3-methyl-5-(4,4,5,5-tetramethyl-1,3,2-dioxaborolan-2-yl)-1H-pyrazole (TG-10b)

To a colorless solution of 1-ethyl-4-[(4-methoxyphenyl) methoxy]-3-methyl-1H-pyrazole (TG-10a) (186 mg, 0.756 mmol) in anhydrous THF (3.7 mL) was added (1,5-cyclooctadiene)(methoxy)iridium(I) dimer (18.0 mg, 0.027 mmol), 4,4'-di-tert-butyl-2,2'-bipyridine (203 mg, 0.756 mmol) and 4,4,5,5-tetramethyl-[1,3,2]-dioxaboralane (246 mg, 1.92 mmol) under N₂ atmosphere. The reaction mixture was heated to 60° C. and stirred under inert atmosphere for 18h. The reaction was removed from heating and allowed to cool gradually to room temperature. The solution was concentrated under vacuum and the crude residue purified via flash column chromatography (20 g SiO₂, Combi-flash, 5-30% EtOAc/Pet. Ether) to afford the title compound 1-ethyl-4-[(4-methoxyphenyl)methoxy]-3-methyl-5-(4,4,5,5-tetramethyl-1,3,2-dioxaborolan-2-yl)-1H-pyrazole (TG-10b) (108 mg, 38%) as a colorless oil. LCMS [M+H]=373.2 observed.

Step 3: Synthesis of 1-ethyl-4-[(4-methoxyphenyl) methoxy]-3-methyl-5-(1-methyl-1H-imidazol-4-yl)-1H-pyrazole (Int-TG-10)

To a mixture of 1-ethyl-4-[(4-methoxyphenyl)methoxy]-3-methyl-5-(4,4,5,5-tetramethyl-1,3,2-dioxaborolan-2-yl)-1H-pyrazole (TG-10b) (108 mg, 0.291 mmol) and 4-iodo-1-methyl-1H-imidazole (89.3 mg, 0.429 mmol) in DMF (2.0 mL)/H₂O (0.50 mL) was added K₃PO₄ (185 mg, 0.874 mmol) and cataCXium A-Pd-G3 (10.6 mg, 0.015 mmol). The reaction was flushed with N₂ for 2 min., sealed, heated to 80° C., and stirred under inert atmosphere for 16h. The reaction was removed from heating and allowed to cool gradually to room temperature. The solution was diluted with H₂O (5 mL) and transferred to a separatory funnel with EtOAc. The phases were separated and the aqueous phase was extracted with 3 portions EtOAc (10 mL ea.). The combined organic extracts were washed with 3 portions brine (15 mL ea.), dried (Na₂SO₄), filtered, and concentrated under vacuum. The crude residue was purified via flash column chromatography (20 g SiO₂, Combi-flash, 0-7.5% MeOH/DCM) to afford the title compound 1-ethyl-4-[(4-methoxyphenyl)methoxy]-3-methyl-5-(1-methyl-1H-imidazol-4-yl)-1H-pyrazole (Int-TG-10) (45.6 mg, 48%) as a light-yellow gum. LCMS [M+H]=327.2 observed; ¹H NMR (400 MHz, CHLOROFORM-d) δ=7.58 (br s, 1H), 7.26 (d, J=8.8 Hz, 2H), 7.17 (d, J=0.8 Hz, 1H), 6.87 (d, J=8.5 Hz, 2H), 4.75 (s, 2H), 4.51 (q, J=7.0 Hz, 2H), 3.82 (s, 3H), 3.72 (s, 3H), 2.14 (s, 3H), 1.39 (t, J=7.2 Hz, 3H).

Preparation of 4-chloro-1-ethyl-3-methyl-5-(1-methyl-1H-imidazol-4-yl)-1H-pyrazole (Int-TG-11) According to Scheme TG-11

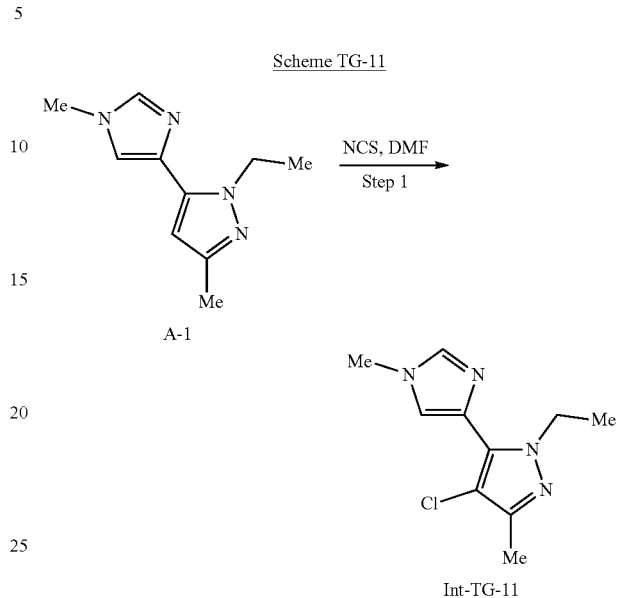

Step 1: Synthesis of 4-chloro-1-ethyl-3-methyl-5-(1-methyl-1H-imidazol-4-yl)-1H-pyrazole (Int-TG-11)

The yellow suspension of 1-ethyl-3-methyl-5-(1-methyl-1H-imidazol-4-yl)-1H-pyrazole (A-1) (100 mg, 0.526 mmol) in anhydrous DMF (3.5 mL) was added NCS (105 mg, 0.788 mmol). The reaction was stirred at room temperature for 10h. The reaction was quenched with H₂O (5 mL) and transferred to a separatory funnel with EtOAc. The phases were separated and the aqueous phase was extracted with 3 portions EtOAc (10 mL ea.). The combined organic extracts were concentrated under vacuum and the crude residue was purified via preparatory thin-layer chromatography (SiO₂, 10% MeOH/DCM) to afford the title compound 4-chloro-1-ethyl-3-methyl-5-(1-methyl-1H-imidazol-4-yl)-1H-pyrazole (Int-TG-11) (101 mg, 85%) as an orange oil. LCMS [M+H]=225.0 observed; ¹H NMR (400 MHz, METHANOL-d₄) δ=8.31 (s, 1H), 7.69 (d, J=1.0 Hz, 1H), 4.25 (q, J=7.3 Hz, 2H), 3.90 (s, 3H), 2.24 (s, 3H), 1.32 (t, J=7.2 Hz, 3H).

Preparation of 5-(1-ethyl-1H-imidazol-4-yl)-1-(3-methoxypropyl)-3-methyl-1H-pyrazole (Int-TG-15) According to Scheme TG-15

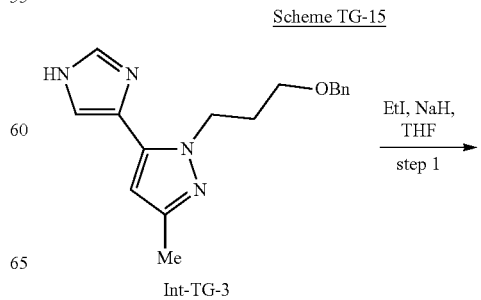

-continued

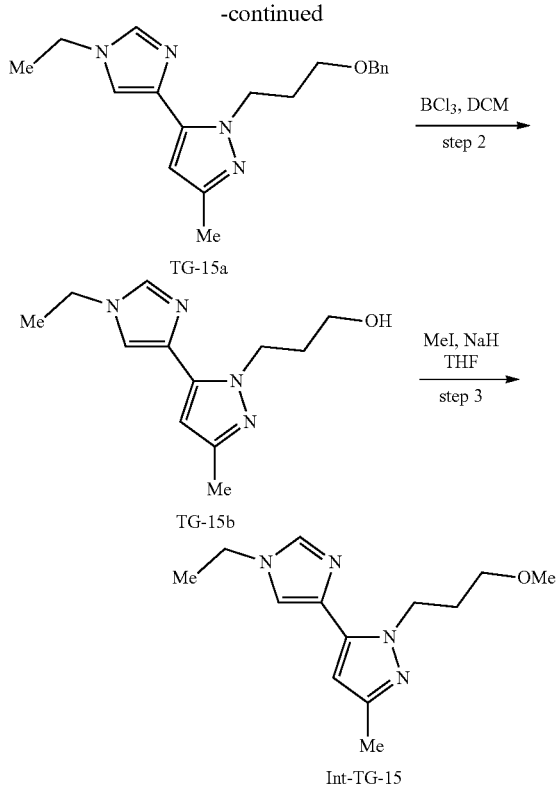

Step 1: Synthesis of 1-[3-(benzyloxy)propyl]-5-(1-ethyl-1H-imidazol-4-yl)-3-methyl-1H-pyrazole (TG-15a)

To a dark yellow partially dissolved solution of 1-[3-(benzyloxy)propyl]-5-(1H-imidazol-4-yl)-3-methyl-1H-pyrazole (Int-TG-3) (900 mg, 3.04 mmol) in THF (25 mL) was added NaH (60 wt % mineral oil) (364 mg, 9.11 mmol) at 0° C. under $N_2$. The reaction was stirred at 0° C. for 15 min during which time gas evolution was observed and a dark yellow suspension formed. At this stage, a solution of iodoethane (616 mg, 3.95 mmol) in THF (2 mL) was added. The reaction was stirred at 0° C. for 30 min at which point the ice bath was removed. The reaction was warmed to 25° C. and stirred for 16 h. The reaction was cooled in an ice water bath (0° C.) and quenched by the dropwise addition of $H_2O$ (20 mL). The reaction mixture was transferred to a separatory funnel with EtOAc and the phases separated. The aqueous phase was extracted with 3 portions EtOAc (20 mL). The combined organic extracts were washed with 1 portion brine (20 mL), dried ($Na_2SO_4$), filtered, and concentrated under vacuum. The crude residue was purified via flash column chromatography (40 g $SiO_2$, 0-10% MeOH/DCM) to afford the title compound 1-[3-(benzyloxy)propyl]-5-(1-ethyl-1H-imidazol-4-yl)-3-methyl-1H-pyrazole (TG-15a) (858 mg, 87%) as a yellow oil. LCMS [M+H]=325.1 observed; $^1H$ NMR (400 MHz, CHLOROFORM-d) δ=7.50 (s, 1H), 7.38-7.30 (m, 5H), 7.18 (s, 1H), 6.24 (s, 1H), 4.54-4.46 (m, 4H), 3.89-3.80 (m, 2H), 3.55 (t, J=6.0 Hz, 2H), 2.30 (s, 3H), 2.24-2.16 (m, 2H), 1.39 (t, J=7.3 Hz, 3H).

Step 2: Synthesis of 3-[5-(1-ethyl-1H-imidazol-4-yl)-3-methyl-1H-pyrazol-1-yl]propan-1-ol (TG-15b)

To a yellow solution of 1-[3-(benzyloxy)propyl]-5-(1-ethyl-1H-imidazol-4-yl)-3-methyl-1H-pyrazole (TG-15a) (859 mg, 2.65 mmol) in DCM (25 mL) was added $BCl_3$ (931 mg, 7.94 mmol) drop-wise at 0° C. under $N_2$. The resulting yellow suspension was warmed to room temperature (22° C.) and stirred for 16 h. The reaction was cooled in an ice water bath (0° C.) and quenched with MeOH (5 mL). The solution was neutralized to pH ~7 by the addition of $NH_3$/MeOH (7 M). The solution was removed from the ice bath and warmed gradually to room temperature with stirring over 30 min. The suspension was filtered and the filtrated was concentrated under vacuum. The crude residue was purified via flash column chromatography (20 g S102, 0-10% MeOH/DCM) to afford the title compound 3-[5-(1-ethyl-1H-imidazol-4-yl)-3-methyl-1H-pyrazol-1-yl]propan-1-ol (TG-15b) (180 mg, 29%) as a yellow solid. LCMS [M+H]=235.2 observed.

Step 3: Synthesis of 5-(1-ethyl-1H-imidazol-4-yl)-1-(3-methoxypropyl)-3-methyl-1H-pyrazole (Int-TG-15)

To a solution of 3-[5-(1-ethyl-1H-imidazol-4-yl)-3-methyl-1H-pyrazol-1-yl]propan-1-ol (TG-15b) (180 mg, 0.768 mmol) in THF (2 mL) was added NaH (60 wt % mineral oil) (76.8 mg, 1.92 mmol) at 0° C. under $N_2$. The reaction was stirred at 0° C. for 15 min during which time gas evolution was observed and a dark yellow suspension formed. At this stage, a solution of iodomethane (164 mg, 1.15 mmol) in THF (1 mL) was added. The reaction was stirred at 0° C. for 30 min. at which point the ice bath was removed. The reaction was warmed to 25° C. and stirred for 1 h. The reaction was cooled in an ice water bath (0° C.) and quenched by the dropwise addition of $H_2O$ (15 mL). The reaction mixture was transferred to a separatory funnel with EtOAc and the phases separated. The aqueous phase was extracted with 3 portions EtOAc (20 mL). The combined organic extracts were washed with 1 portion brine (20 mL), dried ($Na_2SO_4$), filtered, and concentrated under vacuum. The crude residue was purified via flash column chromatography (4 g $SiO_2$, 0-10% MeOH/DCM) to afford the title compound 5-(1-ethyl-1H-imidazol-4-yl)-1-(3-methoxypropyl)-3-methyl-1H-pyrazole (Int-TG-15) (148 mg, 77%) as a brown oil. LCMS [M+H]=249.0 observed; $^1H$ NMR (400 MHz, CHLOROFORM-d) δ=7.65 (s, 1H), 7.23 (s, 1H), 6.27 (s, 1H), 4.47 (t, J=7.1 Hz, 2H), 4.07 (q, J=7.3 Hz, 2H), 3.41 (t, J=6.1 Hz, 2H), 3.31 (s, 3H), 2.30 (s, 3H), 2.14 (quin, J=6.6 Hz, 2H), 1.54 (t, J=7.4 Hz, 3H).

Preparation of 4-(benzyloxy)-1-(3-methoxypropyl)-3-methyl-5-(1-methyl-1H-imidazol-4-yl)-1H-pyrazole (Int-TG-16) According to Scheme TG-16

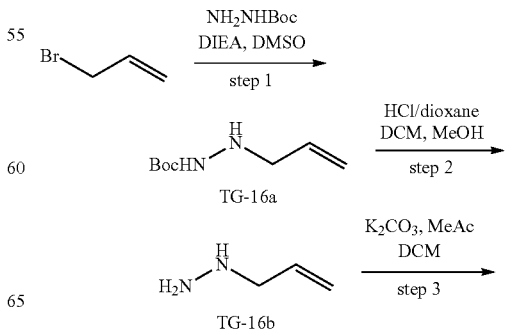

-continued

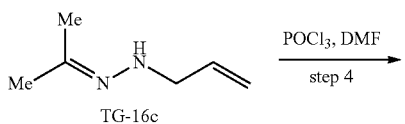
TG-16c

POCl₃, DMF
step 4 →

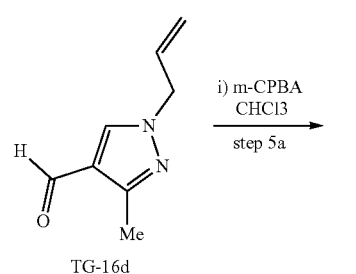
TG-16d i) m-CPBA
CHCl₃
step 5a →

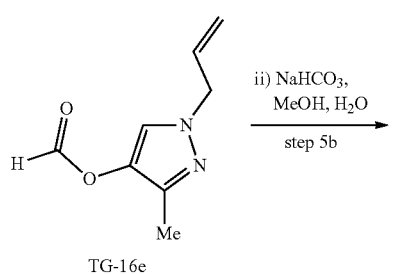
TG-16e ii) NaHCO₃,
MeOH, H₂O
step 5b →

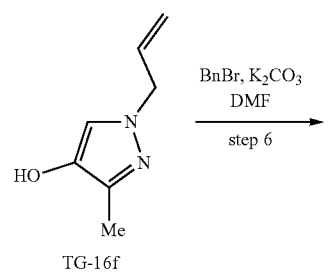
TG-16f

BnBr, K₂CO₃
DMF
step 6 →

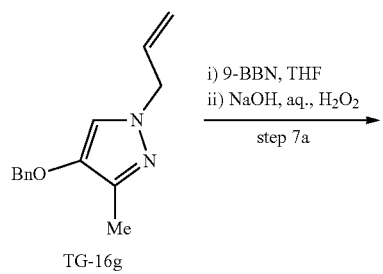
TG-16g i) 9-BBN, THF
ii) NaOH, aq., H₂O₂
step 7a →

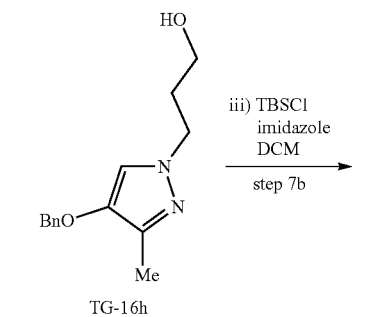
TG-16h iii) TBSCl
imidazole
DCM
step 7b →

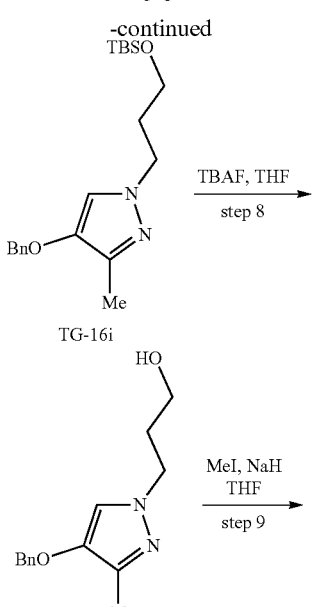
TG-16i

TBAF, THF
step 8 →

TG-16j

MeI, NaH
THF
step 9 →

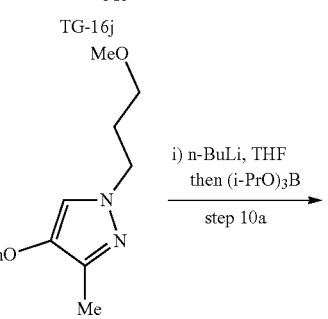
TG-16k i) n-BuLi, THF
then (i-PrO)₃B
step 10a →

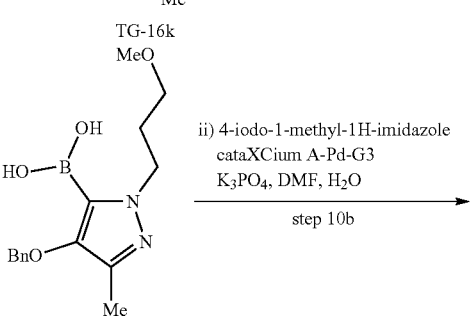
TG-16l ii) 4-iodo-1-methyl-1H-imidazole
cataXCium A-Pd-G3
K₃PO₄, DMF, H₂O
step 10b →

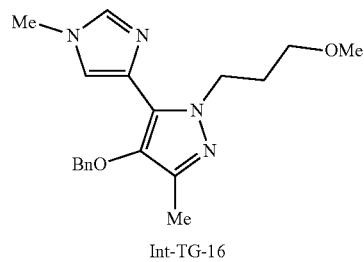
Int-TG-16

Step 1: Synthesis of tert-butyl 2-allylhydrazine-1-carboxylate (TG-16a)

To a solution of allyl bromide (35.8 mL, 413 mmol) and tert-butyl hydrazinecarboxylate (65.5 g, 496 mmol) in DMSO (150 mL) at room temperature (15° C.) was added NEt₃ (72.0 mL, 413 mmol). The mixture was heated to 50°

C. and stirred for 15 h. The reaction was then diluted with EtOAc (400 mL) and basified to pH 8-9 with aqueous NaHCO$_3$. The phases were separated, and the aqueous phase was extracted with EtOAc (400 mL). The organic extract was washed with brine (100 mL×2), water (100 mL), and concentrated under vacuum. The crude residue was purified via flash column chromatography (220 g×2 and 80 g SiO$_2$ columns, Combi-flash, 0-30% EtOAc/Pet. Ether) to afford the title compound tert-butyl 2-allylhydrazine-1-carboxylate (TG-16a) (31 g, 44%) as a colorless oil, which solidified upon standing. $^1$H NMR (DMSO-d$_6$) δ: 8.16 (br s, 1H), 5.71-5.83 (m, 1H), 5.14 (dq, J=17.3, 1.7 Hz, 1H), 5.01-5.08 (m, 1H), 4.41-4.49 (m, J=4.8 Hz, 1H), 3.27-3.32 (m, 2H), 1.38 (s, 9H).

Step 2: Synthesis of Allylhydrazine (TG-16b)

To a solution of tert-butyl 2-allylhydrazine-1-carboxylate (TG-16a) (28 g, 163 mmol) in CH$_2$Cl$_2$ (100 mL) at 15° C. was added HCl in dioxane (224 mL, 894 mmol, 4 M) and stirred for 20 h at 25-30° C. To the mixture was then added MeOH (100 mL) and stirred at 25° C. for 4 h. The reaction was concentrated to three quarters of the volume, and additional MeOH (50 mL) was added followed by HCl in MeOH (200 mL, 800 mmol, 4 M) and HCl in dioxane (100 mL, 400 mmol, 4 M). The mixture was stirred at 25-30° C. for an additional 20 h before concentrated under vacuum to afford the title compound allylhydrazine (TG-16b) (24 g, 100%) as a white solid. $^1$H NMR (DMSO-d$_6$) δ: 5.79-5.93 (m, 1H), 5.25-5.39 (m, 2H), 3.49-3.56 (m, 2H).

Step 3: Synthesis of 1-allyl-2-(propan-2-ylidene)hydrazine (TG-16c)

To a solution of allylhydrazine (TG-16b) (24.0 g, 165 mmol) in CH$_2$Cl$_2$ (331 mL) at 15° C. was added acetone (14.0 mL, 190 mmol) and K$_2$CO$_3$ (80.0 g, 579 mmol). The reaction was stirred at 20° C. for 20 h before the mixture was filtered, washed with CH$_2$Cl$_2$ (300 mL×2), and filtrate concentrated under vacuum to afford the title compound 1-allyl-2-(propan-2-ylidene)hydrazine (TG-16c) (16.8 g, 90%) as a yellow oil. $^1$H NMR (CHLOROFORM-d) δ: 5.92-6.04 (m, 1H), 5.09-5.24 (m, 2H), 4.45 (br s, 1H), 3.75-3.82 (m, 2H), 1.94 (s, 3H), 1.76 (s, 3H).

Step 4: Synthesis of 1-allyl-3-methyl-1H-pyrazole-4-carbaldehyde (TG-16d)

To a reaction vessel containing DMF (100 mL) at 0° C. was added POCl$_3$ (37.1 mL, 406 mmol) dropwise and stirred for 1 h. The mixture was cooled to −20 to −30° C. and a solution of 1-allyl-2-(propan-2-ylidene)hydrazine (TG-16c) (17.9 g, 159 mmol) in DMF (100 mL) was added dropwise. The reaction was stirred at −15° C. for 1.5 h, warmed to rt, then heated to 80° C. for 5 h. The reaction was then cooled to room temperature, poured slowly into ice water (200 mL), and basified to pH 9-10 with 30% aqueous NaOH (~70 g of solid NaOH). The phases were then separated, and the aqueous phase was extracted with CH$_2$Cl$_2$ (500 mL×1, 200 mL×2), washed with brine (300 mL×3), and concentrated under vacuum. The crude residue was purified via flash column chromatography (120 g SiO$_2$, Combi-flash, 4-45% EtOAc/Pet. Ether) to afford the title compound 1-allyl-3-methyl-1H-pyrazole-4-carbaldehyde (TG-16d) (19 g, 79%) as a yellow oil. $^1$H NMR (DMSO-d$_6$): 9.81 (s, 1H), 8.35 (s, 1H), 5.95-6.06 (m, 1H), 5.13-5.26 (m, 2H), 4.74 (dt, J=5.9, 1.4 Hz, 2H), 2.35 (s, 3H).

Step 5: Synthesis of 1-allyl-3-methyl-1H-pyrazol-4-ol (TG-16f)

To a solution of 1-allyl-3-methyl-1H-pyrazole-4-carbaldehyde (TG-16d) (19.0 g, 126 mmol) in CHCl$_3$ (316 mL) at 10° C. was added 3-chlorobenzoperoxoic acid (25.7 g, 127 mmol) and stirred at 25-30° C. for 40 h. The reaction was then filtered and the filtrate concentrated under vacuum. The crude residue was purified via flash column chromatography (120 g SiO$_2$, Combi-flash, 0-20% EtOAc/Pet. Ether) to afford the compound 1-allyl-3-methyl-1H-pyrazol-4-yl formate (TG-16e) (21 g) as a yellow semi-solid, which was used without further purification. LCMS [M+H]=167.0 observed. To a solution of 1-allyl-3-methyl-1H-pyrazol-4-yl formate (TG-16e) (21 g) in MeOH (150 mL) and H$_2$O (20 mL) at 15° C. was added NaHCO$_3$ (12.7 g, 152 mmol) and stirred for 5 h. The reaction mixture was filtered, washed with MeOH, and concentrated under vacuum. The crude residue was purified via flash column chromatography (80 g SiO$_2$, Combi-flash, 10-100% EtOAc/Pet. Ether) to afford the title compound 1-allyl-3-methyl-1H-pyrazol-4-ol (TG-16f) (11 g, 63% over two steps) as a yellow oil. LCMS [M+H]=138.9 observed; $^1$H NMR (CHLOROFORM-d) δ: 7.02 (s, 1H), 5.90-6.01 (m, 1H), 5.14-5.26 (m, 2H), 4.51-4.59 (m, 2H), 2.19 (s, 3H).

Step 6: Synthesis of 1-allyl-4-(benzyloxy)-3-methyl-1H-pyrazole (TG-16 g)

To a solution of 1-allyl-3-methyl-1H-pyrazol-4-ol (TG-16f) (11.1 g, 80.2 mmol) and K$_2$CO$_3$ (16.6 g, 120 mmol) in DMF (186 mL) at 15° C. was added benzyl bromide (10.5 mL, 88.2 mmol). The mixture was heated to 50° C. and stirred for 20 h. The reaction was then cooled to room temperature, poured slowly into ice water (400 mL), and diluted with EtOAc (300 mL). The phases were then separated, and the aqueous phase was extracted with EtOAc (200 mL×2), washed with water (200 mL×2), brine (200 mL×2), and concentrated under vacuum. The crude residue was purified via flash column chromatography (120 g SiO$_2$, Combi-flash, 0-40% EtOAc/Pet. Ether) to afford the title compound 1-allyl-4-(benzyloxy)-3-methyl-1H-pyrazole (TG-16 g) (14.6 g, 80%) as a yellow oil. LCMS [M+H]=229.0 observed; $^1$H NMR (CHLOROFORM-d) δ: 7.30-7.43 (m, 5H), 6.97 (s, 1H), 5.91-6.03 (m, 1H), 5.14-5.26 (m, 2H), 4.89 (s, 2H), 4.54-4.59 (m, 2H), 2.21 (s, 3H).

Step 7: Synthesis of 4-(benzyloxy)-1-(3-((tert-butyldimethylsilyl)oxy)propyl)-3-methyl-1H-pyrazole (TG-16i)

To a solution of 1-allyl-4-(benzyloxy)-3-methyl-1H-pyrazole (TG-16 g) (4.40 g, 19.3 mmol) in THF (110 mL) at 0° C. under N$_2$ was added 9-borabicyclo[3.3.1]nonane (77.1 mL, 38.5 mmol, 0.5 M in THF) dropwise. The mixture was heated to 20-30° C. and stirred for 3 h. The reaction was then cooled to 0° C. and aqueous NaOH (4.75 mL, 71.3 mmol, 6 M) was added dropwise, followed by H$_2$O$_2$ (7.28 mL, 71.3 mmol). The mixture was stirred at 0-15° C. for 30 min. The reaction cooled to 0-5° C., quenched with aqueous Na$_2$SO$_3$ (30 g, 150 mL H$_2$O), and stirred for 15 min. The phases were then separated, and the aqueous phase was extracted with MTBE/EtOAc (100 mL×2, 1:1 v/v), the combined organic phase was washed with brine (100 mL), and concentrated under vacuum. The crude residue was purified via flash column chromatography (40 g SiO$_2$, Combi-flash, 10-100% EtOAc/Pet. Ether) to afford the compound 3-(4-(benzyloxy)-3-methyl-1H-pyrazol-1-yl)propan-1-ol (TG-16h) (5.30 g) as a yellow oil. $^1$H NMR (CHLOROFORM-d) δ: 7.31-7.44 (m, 5H), 6.96 (s, 1H), 4.89 (s, 2H), 4.07-4.11 (m, 2H), 3.60 (q, J=5.5 Hz, 2H), 2.91 (t, J=5.8 Hz, 1H), 2.19 (s, 3H), 1.97 (quin, J=6.0 Hz, 2H). To a solution of 3-(4-(benzyloxy)-3-methyl-1H-pyrazol-1-yl)propan-1-ol (TG-16h) (5.30 g) in CH$_2$Cl$_2$ (100 mL) at 0° C. were added imidazole (2.20 g, 32.3 mmol) and tert-butylchlorodimethylsilane (3.57 g, 32.7 mmol). The mixture was warmed to room temperature (15-25° C.) and stirred for 15 h. The reaction was then quenched with H$_2$O (100 mL) and diluted with CH$_2$Cl$_2$ (50 mL). The phases were then separated, and the aqueous phase was extracted with CH$_2$Cl$_2$ (50 mL). The combined organic phase was washed with brine (50 mL) and concentrated under vacuum. The crude residue was purified via flash column chromatography (80 g SiO$_2$, Combi-flash, 0-15% EtOAc/Pet. Ether) to afford the title compound 4-(benzyloxy)-1-(3-((tert-butyldimethylsilyl)oxy)propyl)-3-methyl-1H-pyrazole (TG-16i) (5.2 g, 75%) as a colorless oil.

Step 8: Synthesis of 3-(4-(benzyloxy)-3-methyl-1H-pyrazol-1-yl)propan-1-ol (TG-16j)

To a solution of 4-(benzyloxy)-1-(3-((tert-butyldimethylsilyl)oxy)propyl)-3-methyl-1H-pyrazole (TG-16i) (1.49 g, 4.13 mmol) in THF (15 mL) at room temperature was added Tetrabutylammonium fluoride (4.2 mL, 4.2 mmol, 1.0 M in THF). The mixture was then concentrated under vacuum, and the crude residue was purified via flash column chromatography (20 g SiO$_2$, Combi-flash, 0-5% MeOH in 1:1 EtOAc:CH$_2$Cl$_2$) to afford the title compound 3-(4-(benzyloxy)-3-methyl-1H-pyrazol-1-yl)propan-1-ol (TG-16j) (974 mg, 96%) as a yellow oil, which solidified upon standing. $^1$H NMR (CHLOROFORM-d) δ: 7.30-7.44 (m, 5H), 6.96 (s, 1H), 4.89 (s, 2H), 4.06-4.14 (m, 2H), 3.60 (t, J=5.7 Hz, 2H), 2.20 (s, 3H), 1.97 (quin, J=6.0 Hz, 2H).

Step 9: Synthesis of 4-(benzyloxy)-1-(3-methoxypropyl)-3-methyl-1H-pyrazole (TG-16k)

To a solution of 3-(4-(benzyloxy)-3-methyl-1H-pyrazol-1-yl)propan-1-ol (TG-16j) (971 mg, 3.94 mmol) in THF (13 mL) at 0° C. was added NaH (190 mg, 4.70 mmol). The mixture was warmed to 20° C. and stirred for 15 min. To the reaction was then added a solution of iodomethane (655 mg, 4.62 mmol) in THF (2 mL) was added dropwise and stirred at 20° C. for 1 h. The reaction was quenched with H$_2$O (5 mL) and the phases were separated. The aqueous phase was extracted with EtOAc (5 mL×3), the organic layer was washed with brine (20 mL), dried over Na$_2$SO$_4$, filtered, and concentrated in vacuum to afford the title compound 4-(benzyloxy)-1-(3-methoxypropyl)-3-methyl-1H-pyrazole (TG-16k) (1.03 mg, 101%) as a yellow oil. $^1$H NMR (CHLOROFORM-d) δ: 7.30-7.45 (m, 5H), 6.95 (s, 1H), 4.90 (s, 2H), 4.04 (t, J=6.8 Hz, 2H), 3.26-3.31 (m, 5H), 2.22 (s, 3H), 1.98-2.08 (m, 2H).

Step 10: Synthesis of 4-(benzyloxy)-1-(3-methoxypropyl)-3-methyl-5-(1-methyl-1H-imidazol-4-yl)-1H-pyrazole (Int-TG-16)

To a solution of 4-(benzyloxy)-1-(3-methoxypropyl)-3-methyl-1H-pyrazole (TG-16k) (373 mg, 1.43 mmol) in anhydrous THF (7.2 mL) at −65° C. (internal temperature) was added n-BuLi (1.5 mL, 3.8 mmol, 2.5 M in hexane) dropwise to maintain internal temperature below −60° C., and the mixture was stirred for 1.5 h. To the reaction was then added triisopropyl borate (3.3 mL, 14 mmol), the reaction was removed from the cold bath, gradually warmed to room temperature, and stirred for 16 h. The reaction was quenched with a saturated aqueous solution of NH$_4$Cl (3 mL) followed by H$_2$O. The phases were separated, the aqueous phase was extracted with EtOAc (8 mL×3), the organic layer was washed with brine (10 mL), dried over Na$_2$SO$_4$, filtered, and concentrated in vacuum to afford the compound (4-(benzyloxy)-1-(3-methoxypropyl)-3-methyl-1H-pyrazol-5-yl)boronic acid (TG-16I) (529 mg) as a yellow gum, which was used without further purification. LCMS [M+H]=305.1 observed. A reaction vessel containing (4-(benzyloxy)-1-(3-methoxypropyl)-3-methyl-1H-pyrazol-5-yl)boronic acid (TG-16I) (529 mg), 4-iodo-1-methyl-1H-imidazole (325 mg, 1.56 mmol), K$_3$PO$_4$ (885 mg, 4.17 mmol), cataCXium A Pd G3 (56 mg, 0.077 mmol), in DMF (8 mL) and H$_2$O (2 mL) was backfilled N$_2$ and heated to 80° C. and stirred for 22 h. The reaction was then diluted with H$_2$O (20 mL), the phases were separated, the aqueous phase was extracted with EtOAc (20 mL×4). The combined organic phase was washed with brine (20 mL×2), dried over Na$_2$SO$_4$, filtered, and concentrated in vacuum. The crude residue was purified via flash column chromatography (20 g SiO$_2$, Combi-flash, 0-21% EtOAc/Pet. Ether then 20% MeOH/EtOAc) and repurified by preparative thin layer chromatography (EtOAc/MeOH 10:1) to afford the title compound 4-(benzyloxy)-1-(3-methoxypropyl)-3-methyl-5-(1-methyl-1H-imidazol-4-yl)-1H-pyrazole (Int-TG-16) (31 mg, 6.4% over two steps) as a yellow gum. LCMS [M+H]=341.1 observed. $^1$H NMR (CHLOROFORM-d) δ: 7.47 (s, 1H), 7.30-7.39 (m, 5H), 7.15 (s, 1H), 4.82 (s, 2H), 4.53 (t, J=7.0 Hz, 2H), 3.69 (s, 3H), 3.36 (t, J=6.4 Hz, 2H), 3.27 (s, 3H), 2.15 (s, 3H), 2.03-2.11 (m, 2H).

Preparation of 4-[(4-methoxyphenyl)methoxy]-3-methyl-5-(1-methyl-1H-imidazol-4-yl)-1-propyl-1H-pyrazole (Int-TG-17) According to Scheme TG-17

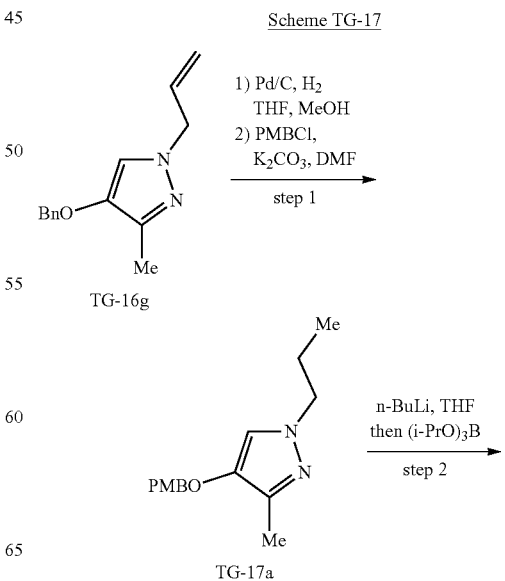

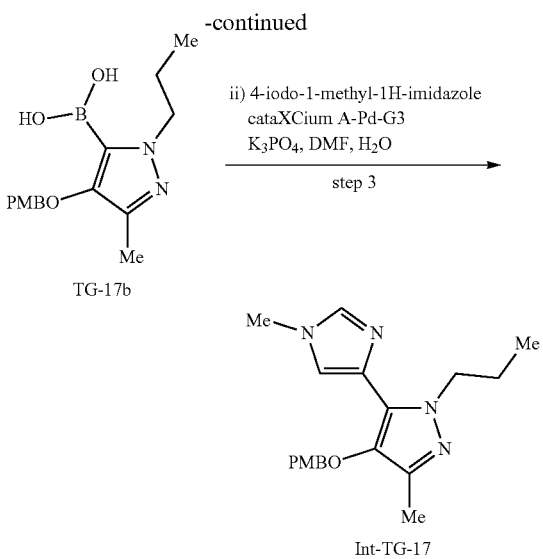

TG-17b

Int-TG-17

Step 1: Synthesis of 4-[(4-methoxyphenyl)methoxy]-3-methyl-1-propyl-1H-pyrazole (TG-17a)

A reaction vessel containing 4-(benzyloxy)-3-methyl-1-(prop-2-en-1-yl)-1H-pyrazole (TG-16 g) (505 mg, 2.21 mmol), wet Pd/C (10%, 230 mg, 0.22 mmol), NEt₃ (1.0 mL, 7.2 mmol) in MeOH (10 mL) and THF (10 mL) was stirred under H₂ (15 psi, balloon) at 20° C. for 2 h. The reaction was then filtered through a Celite pad and the filtrate concentrated under vacuum to afford 3-methyl-1-(prop-2-en-1-yl)-1H-pyrazol-4-ol as a grey oil (378 mg) which was used without further purification. LCMS [M+H]=140.8 observed; $^1$H NMR (CHLOROFORM-d) δ: 6.99 (s, 1H), 3.88 (t, J=7.1 Hz, 2H), 2.18 (s, 3H), 1.79 (sxt, J=7.3 Hz, 2H), 0.88 (t, J=7.4 Hz, 3H). To a solution of 3-methyl-1-(prop-2-en-1-yl)-1H-pyrazol-4-ol (378 mg) and 1-(chloromethyl)-4-methoxybenzene (390 mg, 2.49 mmol) in DMF (5 mL) was added K₂CO₃ (342 mg, 2.48 mmol) and stirred at 20° C. for 17 h. The reaction was then heated to 50° C. for 30 min before diluting with H₂O (20 mL). The phases were separated, and the aqueous phase was extracted with EtOAc (20 mL×4). The organic extract was washed with brine (20 mL×3), dried over Na₂SO₃, filtered, and concentrated under vacuum. The crude residue was purified via flash column chromatography (12 g SiO₂, Combi-flash, 0-80% EtOAc/Pet. Ether) and repurified via flash column chromatography (12 g SiO₂, Combi-flash, 0-60% EtOAc/Pet. Ether) to afford the title compound 4-[(4-methoxyphenyl)methoxy]-3-methyl-1-propyl-1H-pyrazole (TG-17a) (419 mg, 73% over two steps) as a yellow oil. LCMS [M+H]=260.9 observed; $^1$H NMR (CHLOROFORM-d) δ: 7.29-7.35 (m, 2H), 6.88-6.96 (m, 3H), 4.81 (s, 2H), 3.89 (t, J=7.1 Hz, 2H), 3.82 (s, 3H), 2.18 (s, 3H), 1.80 (sxt, J=7.3 Hz, 2H), 0.89 (t, J=7.4 Hz, 3H).

Step 2: Synthesis of {4-[(4-methoxyphenyl)methoxy]-3-methyl-1-propyl-1H-pyrazol-5-yl}boronic Acid (TG-17b)

To a solution of 4-[(4-methoxyphenyl)methoxy]-3-methyl-1-propyl-1H-pyrazole (TG-17a) (337 mg, 1.29 mmol) in anhydrous THF (6.0 mL) at −65° C. (internal temperature) was added n-BuLi (1.4 mL, 3.5 mmol, 2.5 M in hexane) dropwise to maintain internal temperature below −60° C., and the mixture was stirred for 1.5 h. To the reaction was then added triisopropyl borate (3.0 mL, 13 mmol), the reaction was removed from the cold bath, gradually warmed to room temperature, and stirred for 16 h. The reaction was quenched with H₂O (5 mL), the phases were separated, and the aqueous phase was extracted with EtOAc (5 mL×3). The combined organic phase was dried over Na₂SO₄, filtered, and concentrated in vacuum to afford {4-[(4-methoxyphenyl)methoxy]-3-methyl-1-propyl-1H-pyrazol-5-yl}boronic acid (TG-17b) (564 mg) as an off-white oily solid, which was used without further purification. LCMS [M+H]=305.0 observed.

Step 3: Synthesis of 4-[(4-methoxyphenyl)methoxy]-3-methyl-5-(1-methyl-1H-imidazol-4-yl)-1-propyl-1H-pyrazole (Int-TG-17)

A reaction vessel containing {4-[(4-methoxyphenyl)methoxy]-3-methyl-1-propyl-1H-pyrazol-5-yl}boronic acid (TG-17b) (564 mg), 4-iodo-1-methyl-1H-imidazole (299 mg, 1.44 mmol), K₃PO₄ (834 mg, 3.93 mmol), cataCXium A Pd G3 (95 mg, 0.13 mmol), in 1,4-dioxane (8.8 mL) and H₂O (2.2 mL) was backfilled with N₂ and heated to 80° C. and stirred for 22 h. The reaction was then diluted with H₂O (20 mL), the phases were separated, the aqueous phase was extracted with EtOAc (20 mL×4). The combined organic phase was washed with brine (20 mL×2), dried over Na₂SO₄, filtered, and concentrated in vacuum. The crude residue was purified via preparative thin layer chromatography (SiO₂, EtOAc:MeOH 20:1) to afford the impure compound 4-[(4-methoxyphenyl)methoxy]-3-methyl-5-(1-methyl-1H-imidazol-4-yl)-1-propyl-1H-pyrazole (Int-TG-17) (268 mg) as a yellow gum, which was used without further purification. LCMS [M+H]=341.1 observed; $^1$H NMR (CHLOROFORM-d) δ: 7.48 (s, 1H), 7.23-7.26 (m, 2H), 7.12-7.16 (m, 1H), 6.85-6.89 (m, 2H), 4.74 (s, 2H), 4.39-4.43 (m, 2H), 3.82 (s, 3H), 3.70 (s, 3H), 2.13 (s, 3H), 1.77-1.85 (m, 2H), 0.86 (t, J=7.4 Hz, 3H).

Preparation of Ethyl 1-ethyl-4-fluoro-3-methyl-1H-pyrazole-5-carboxylate (Int-TG-18) According to Scheme TG-18

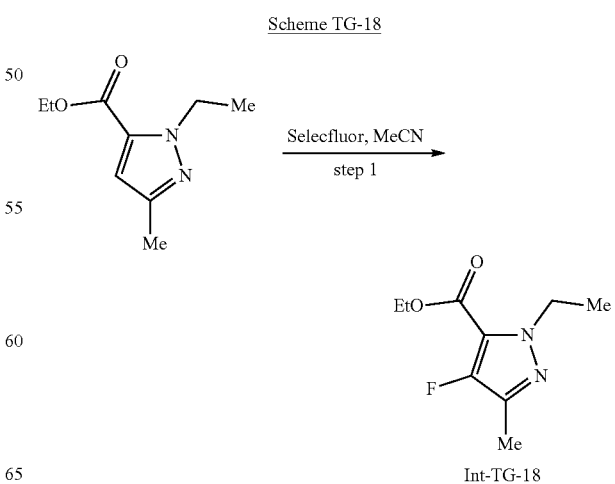

Int-TG-18

Step 1: Synthesis of Ethyl 1-ethyl-4-fluoro-3-methyl-1H-pyrazole-5-carboxylate (Int-TG-18)

To a solution of ethyl 1-ethyl-3-methyl-1H-pyrazole-5-carboxylate (13.0 g, 71.3 mmol) in MeCN (150 mL) was added Selectfluor (75.8 g, 214 mmol), heated to 90° C., and stirred for 14 h. The reaction was then cooled to room temperature, filtered, and concentrated under vacuum. The crude residue was purified via flash column chromatography (0-5% EtOAc/Pet. Ether) and repurified via flash column chromatography (0-5% EtOAc/Pet. Ether) to afford ethyl 1-ethyl-4-fluoro-3-methyl-1H-pyrazole-5-carboxylate (Int-TG-18) (11.5 g, 80%) as a colorless oil, which was used without further purification. LCMS [M+H]=201.0 observed. $^1$H NMR (CHLOROFORM-d) δ: 4.35-4.50 (m, 4H), 2.24 (s, 3H), 1.37-1.43 (m, 6H).

The intermediate in the table below was prepared according to the methods used in steps 2-4 of Scheme TG-3 for the synthesis of 1-[3-(benzyloxy)propyl]-5-(1H-imidazol-4-yl)-3-methyl-1H-pyrazole (Int-TG-3) with non-critical changes or substitutions to the exemplified procedures that one skilled in the art would be able to realize.

| Int-TG Number | Starting materials used for step 1 | Structure/IUPAC Name | Analytical Data |
|---|---|---|---|
| Int-TG-19 | Int-TG-18 | ![structure] 1-ethyl-4-fluoro-5-(1H-imidazol-4-yl)-3-methyl-1H-pyrazole | LCMS [M + H] = 195.0 observed; $^1$H NMR (METHANOL-$d_4$) δ: 7.83 (s, 1H), 7.39 (s, 1H), 4.21-4.40 (m, 2H), 2.21 (s, 3H), 1.30 (t, J = 7.2 Hz, 3H). |

Preparation of 1-ethyl-4-iodo-1H-imidazole (Int-TG-20) According to Scheme TG-20

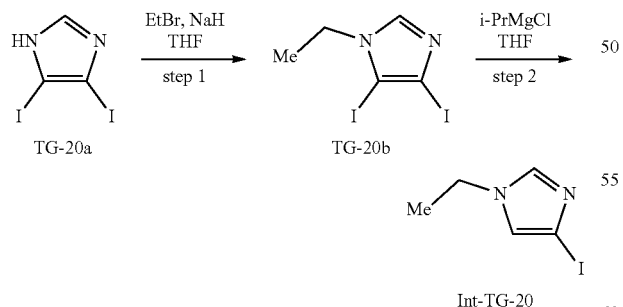

Scheme TG-20

Step 1: Synthesis of 1-ethyl-4,5-diiodo-1H-imidazole (TG-20b)

To a solution of 4,5-diiodo-1H-imidazole (TG-20a) (1.00 g, 3.13 mmol) in THF (8.0 mL) at 0° C. was added NaH (138 mg, 3.44 mmol, 60% in mineral oil) in small portions. The mixture was warmed to 20° C. and stirred for 1 h. To the reaction was then added ethyl bromide (1.56 mL, 20.9 mmol) and stirred for 18 h. The mixture was concentrated under vacuum, the residue taken up in EtOAc (10 mL), filtered, and concentrated under vacuum. The residue was then triturated in EtOAc:pet. ether (1:1, 10 mL) at room temperature for 15 min, filtered, and concentrated under vacuum to afford the title compound 1-ethyl-4,5-diiodo-1H-imidazole (TG-20b) (690 mg, 63%) as a colorless solid. LCMS [M+H]=348.8 observed; $^1$H NMR (CHLOROFORM-d) δ: 7.65 (s, 1H), 4.03 (q, J=7.3 Hz, 2H), 1.42 (t, J=7.3 Hz, 3H).

Step 2: Synthesis of 1-ethyl-4-iodo-1H-imidazole (Int-TG-20)

To a solution of 1-ethyl-4,5-diiodo-1H-imidazole (TG-20b) (690 mg, 1.98 mmol) in THF (7.0 mL) at 0° C. was added isopropylmagnesium chloride (0.992 mL, 1.98 mmol, 2.0 M in THF) dropwise. The mixture was stirred at 0° C. and stirred for 20 min. To the reaction was then added H$_2$O (0.5 mL), warmed to 20° C. and stirred for 1 h. The mixture was concentrated under vacuum, and the residue taken up in EtOAc (5 mL) and filtered. The filtrate was washed with brine (10 mL), dried over Na$_2$SO$_3$, and concentrated under vacuum. The crude residue was purified via flash column chromatography (12 g SiO$_2$, Combi-flash, 0-30% MeOH/CH$_2$Cl$_2$) to afford the title compound 1-ethyl-4-iodo-1H-imidazole (Int-TG-20) (300 mg, 68%) as a colorless oil. LCMS [M+H]=222.9 observed; $^1$H NMR (CHLOROFORM-d) δ: 7.55 (s, 1H), 7.04 (d, J=1.3 Hz, 1H), 4.02 (q, J=7.3 Hz, 2H), 1.47 (t, J=7.4 Hz, 3H).

The intermediate in the table below was prepared according to the methods used in step 3 of Scheme TG-10 for the synthesis of 1-ethyl-4-[(4-methoxyphenyl)methoxy]-3-methyl-5-(1-methyl-1H-imidazol-4-yl)-1H-pyrazole (Int-TG-10) with non-critical changes or substitutions to the exemplified procedures that one skilled in the art would be able to realize.

| Int-TG Number | Starting materials used | Structure/IUPAC Name | Analytical Data |
|---|---|---|---|
| Int-TG-21 | Int-TG-20, TG-10b | ![structure] 1-ethyl-5-(1-ethyl-1H-imidazol-4-yl)-4-[(4-methoxyphenyl)methoxy]-3-methyl-1H-pyrazole | LCMS [M + H] = 341.1 observed; $^1$H NMR (CHLOROFORM-d) δ: 7.53 (s, 1H), 7.22 7.30 (m, 3H), 6.87 (d, J = 8.5 Hz, 2H), 4.74 (s, 2H), 4.51 (q, J = 7.0 Hz, 2H), 4.00 (q, J = 7.4 Hz, 2H), 3.82 (s, 3H), 2.16 (s, 3H), 1.47 (t, J = 7.4 Hz, 3H), 1.40 (t, J = 7.2 Hz, 3H). |

Preparation of 3-methyl-5-(1-methyl-1H-imidazol-4-yl)-1-[(oxetan-3-yl)methyl]-1H-pyrazole (Int-TG-23) According to Scheme TG-23

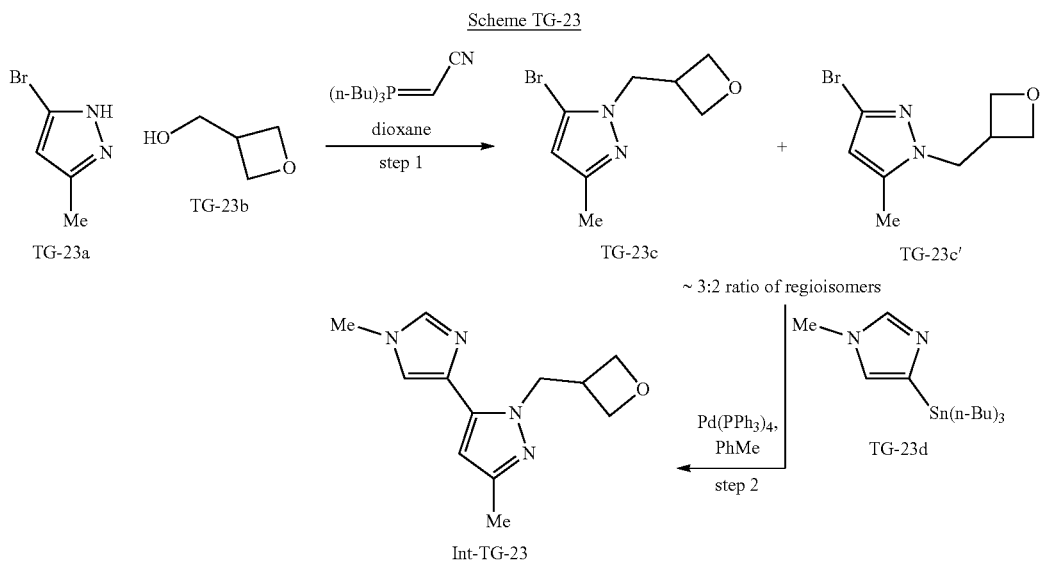

Scheme TG-23

Step 1: Synthesis of 5-bromo-3-methyl-1-[(oxetan-3-yl)methyl]-1H-pyrazole (TG-23c) and 3-bromo-5-methyl-1-[(oxetan-3-yl)methyl]-1H-pyrazole (TG-23c′)

To a solution of 5-bromo-3-methyl-1H-pyrazole (TG-23a) (1500 mg, 9.317 mmol) and (oxetan-3-yl)methanol (TG-23b) (1.5 mL, 19 mmol) in dioxane (37.5 mL) was added (cyanomethylene)tributylphosphorane (4500 mg, 18.6 mmol) at room temperature (19° C.). The brown solution was stirred at room temperature (19° C.) for 16 h. LCMS analysis showed starting material still remained. At this stage, an additional aliquot of (cyanomethylene) tributylphosphorane (1000 mg, 4.143 mmol) and (oxetan-3-yl)methanol (TG-23b) (334 µL, 4.15 mmol) were added and the reaction was stirred at room temperature (20° C.) for 19 h. The reaction mixture was diluted with EtOAc (50 mL) and transferred to a separatory funnel. The solution was washed with 3 portions brine (20 mL), dried ($Na_2SO_4$), filtered, and concentrated under vacuum. The crude residue was purified by reverse phase prep-HPLC (YMC Triart C18 250*50 mm*7 um column, 11-51% MeCN/water (0.05% $NH_4OH$ v/v), 60 mL/min). The product containing fractions were collected and extracted with 2 portions EtOAc (100 mL). The combined organic extracts were dried ($Na_2SO_4$), filtered, and concentrated under vacuum to afford the title compounds 5-bromo-3-methyl-1-[(oxetan-3-yl)methyl]-1H-pyrazole (TG-23c) and 3-bromo-5-methyl-1-[(oxetan-3-yl)methyl]-1H-pyrazole (TG-23c′) (1.71 g, ~3:2 r.r., 79%) as a yellow oil. TG-23c (major product) $^1$H NMR (400 MHz, CHLOROFORM-d) δ=6.06 (s, 1H), 4.82 (br d, J=4.9 Hz, 2H), 4.57 (t, J=6.2 Hz, 2H), 4.39 (d, J=7.3 Hz, 2H), 3.60-3.46 (m, 1H), 2.23 (s, 3H). TG-23c′ (minor product) $^1$H NMR (400 MHz, CHLOROFORM-d) δ=6.02 (s, 1H), 4.87-4.77 (m, 2H), 4.49 (t, J=6.1 Hz, 2H), 4.29 (d, J=7.5 Hz, 2H), 3.61-3.43 (m, 1H), 2.29 (s, 3H). The mixture of regioisomeric products (1588 mg) was further purified by prep-SFC to afford the desired major regioisomer 5-bromo-3-methyl-1-[(oxetan-3-yl)methyl]-1H-pyrazole (TG-23c) (950 mg) as a yellow oil. $^1$H NMR (400 MHz, CHLOROFORM-d) δ=6.07 (s, 1H), 4.81 (d, J=6.4 Hz, 1H), 4.79 (d, J=6.5 Hz, 1H), 4.57 (t, J=6.2 Hz, 2H), 4.39 (d, J=7.4 Hz, 2H), 3.62-3.43 (m, 1H), 2.23 (s, 3H).

Step 2: Synthesis of 3-methyl-5-(1-methyl-1H-imidazol-4-yl)-1-[(oxetan-3-yl)methyl]-1H-pyrazole (Int-TG-23)

To a solution of 5-bromo-3-methyl-1-[(oxetan-3-yl)methyl]-1H-pyrazole (TG-23c) (325 mg, 1.41 mmol) in toluene (9 mL) was added 1-methyl-4-(tributylstannyl)-1H-imidazole (TG-23d) (650 mg, 1.4 mmol) and Pd(PPh$_3$)$_4$ (325 mg, 0.281 mmol) at room temperature (20° C.). After the addition, the reaction mixture was stirred at 100° C. under $N_2$ for 16 h. The reaction mixture was filtered and the filtrate concentrated under vacuum. The crude residue was purified via flash column chromatography (20 g $SiO_2$, Isco, 0-5% MeOH/DCM) to afford the title compound 3-methyl-5-(1-methyl-1H-imidazol-4-yl)-1-[(oxetan-3-yl)methyl]-1H-pyrazole (Int-TG-23) (199 mg, 61%) as a yellow oil. LCMS [M+H]=233.2 observed; $^1$H NMR (400 MHz, CHLOROFORM-d) δ=7.50 (s, 1H), 7.05 (s, 1H), 6.09 (s, 1H), 4.83-4.69 (m, 4H), 4.55 (t, J=6.2 Hz, 2H), 3.74 (s, 3H), 3.65-3.51 (m, 1H), 2.25 (s, 3H).

The intermediate in the table below was prepared according to the methods used for the synthesis of 3-methyl-5-(1-methyl-1H-imidazol-4-yl)-1-[(oxetan-3-yl)methyl]-1H-pyrazole (Int-TG-23) with non-critical changes or substitutions to the exemplified procedures that one skilled in the art would be able to realize.

| Int-TG Number | Reagents/Solvent used for step 1 | Structure/IUPAC Name | Analytical Data |
|---|---|---|---|
| Int-TG-24 | (Rac)-(oxetan-2-yl)methanol, (n-Bu)$_3$P = CHCN, dioxane | (Rac)-3-methyl-5-(1-methyl-1H-imidazol-4-yl)-1-[(oxetan-2-yl)methyl]-1H-pyrazole | LCMS [M + H] = 233.1 observed; $^1$H NMR (400 MHz, CHLOROFORM-d) δ = 7.52 (s, 1H), 7.15 (d, J = 1.3 Hz, 1H), 6.19 (s, 1H), 5.24-5.15 (m, 1H), 4.68 (t, J = 5.3 Hz, 2H), 4.66-4.58 (m, 1H), 4.51-4.44 (m, 1H), 3.74 (s, 3H), 2.74-2.60 (m, 2H), 2.28 (s, 3H). |

Preparation of 1-(3-methoxypropyl)-3-methyl-5-(1-methyl-1H-imidazol-4-yl)-1H-pyrazole (Int-TG-25) According to Scheme TG-25

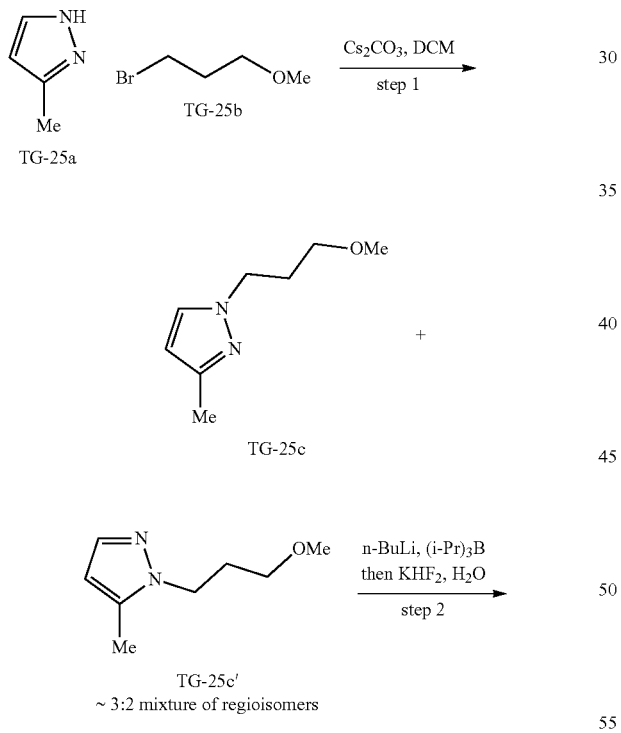

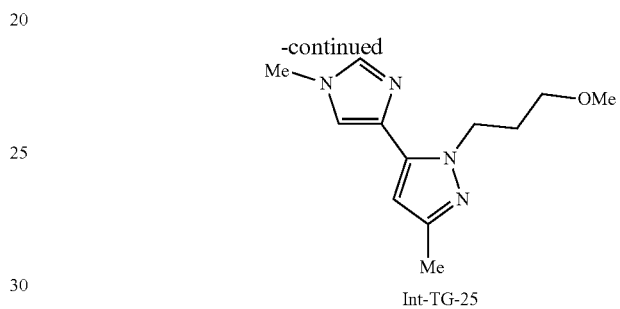

Int-TG-25

Step 1: Synthesis of 1-(3-methoxypropyl)-3-methyl-1H-pyrazole (TG-25c)

To a solution of 3-methyl-1H-pyrazole (TG-25a) (5.00 g, 60.9 mmol) and 1-bromo-3-methoxypropane (TG-25b) (18.6 g, 122 mmol) in CH$_2$Cl$_2$ (40 mL) was added Cs$_2$CO$_3$ (29.3 g, 89.9 mmol). The reaction was heated to reflux and stirred for 14 h. The mixture was then filtered, the filter cake was washed with CH$_2$Cl$_2$ (60 mL), and the filtrate concentrated under vacuum. Residual 1-bromo-3-methoxypropane (TG-25b) was removed via distillation (~0.1 MPa, 33-36° C.), and the remaining crude 1-(3-methoxypropyl)-3-methyl-1H-pyrazole (TG-25c) and 1-(3-methoxypropyl)-5-methyl-1H-pyrazole (TG-25c') (7.50 g) were isolated as a ~3:2 regioisomeric mixture which was used in the next step without further purification. LCMS [M+H]=155.1 observed.

Step 2: Synthesis of Potassium trifluoro[1-(3-methoxypropyl)-3-methyl-1H-pyrazol-5-yl]borate (TG-25d)

To a solution of 1-(3-methoxypropyl)-3-methyl-1H-pyrazole (TG-25c) and 1-(3-methoxypropyl)-5-methyl-1H-pyrazole (TG-25c') (1.65 g) in THF (43 mL) at 0° C. was added n-BuLi (7.4 mL, 18 mmol, 2.5 M in hexane) dropwise. The reaction was stirred for 10 min before warming to room temperature for 2 h. The reaction was then cooled to 0° C. and triisopropyl borate (9.9 mL, 43 mmol) was added dropwise. Following completion of the addition, the reaction was warmed to room temperature and stirred for 2 h. The reaction was then cooled to 0° C. followed by addition of KHF$_2$ (3.35 g, 42.9 mmol) and H$_2$O (3 mL). The reaction was warmed to 60° C. (internal temperature=45° C.) and stirred for 2 h. Additional KHF$_2$ (2.51 g, 32.1 mmol) and H₂O (3 mL) were then added, and the reaction was stirred at 80° C. (internal temperature=60° C.) for 1 h. The crude was then decanted and concentrated under vacuum to afford compound potassium trifluoro[1-(3-methoxypropyl)-3-methyl-1H-pyrazol-5-yl]borate (TG-25d) (2.20 g) as a brown oil, which was used without further purification.

Step 3: Synthesis of 1-(3-methoxypropyl)-3-methyl-5-(1-methyl-1H-imidazol-4-yl)-1H-pyrazole (Int-TG-25)

A reaction vessel containing potassium trifluoro[1-(3-methoxypropyl)-3-methyl-1H-pyrazol-5-yl]borate (TG-25d) (2.20 g), 4-iodo-1-methyl-1H-imidazole (1.35 g, 6.49 mmol), K₃PO₄ (4.09 g, 19.3 mmol), cataCXium A-Pd-G3 (237 mg, 0.326 mmol), H₂O (6.0 mL), and 1,4-dioxane (30 mL) was backfilled with N₂ and stirred at 80° C. (internal temperature) for 13 h. The reaction was filtered, the phases were separated, and the aqueous phase was extracted with EtOAc (6 mL×3). To the combined organic phase was added brine (20 mL) and water (20 mL), the phases separated, and the aqueous phase extracted with EtOAc (15 mL×3). The combined organic phase was dried over Na₂SO₄, filtered, and concentrated under vacuum. The crude residue was purified via flash column chromatography (40 g SiO₂, Combi-flash, 0-100% EtOAc/pet. ether then 0-20% MeOH/EtOAc) to afford the title compound 1-(3-methoxypropyl)-3-methyl-5-(1-methyl-1H-imidazol-4-yl)-1H-pyrazole (Int-TG-25) (498 mg, 26% over three steps) as a brown oil. LCMS [M+H]=235.4 observed; ¹H NMR (METHANOL-d₄) δ: 7.73 (s, 1H), 7.41 (d, J=1.2 Hz, 1H), 6.25 (s, 1H), 4.37 (t, J=7.1 Hz, 2H), 3.81 (s, 3H), 3.32-3.36 (m, 2H), 3.26 (s, 3H), 2.26 (s, 3H), 1.97-2.05 (m, 2H).

Preparation of [5-(1H-imidazol-4-yl)-3-methyl-1H-pyrazol-1-yl]acetonitrile (Int-TG-27) According to Scheme TG-27

Scheme TG-27

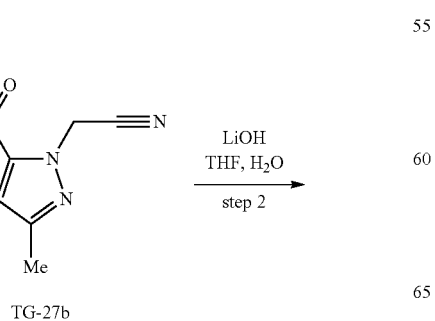

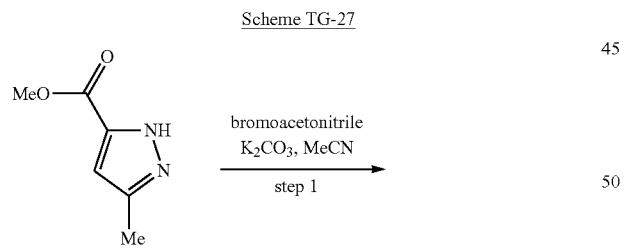

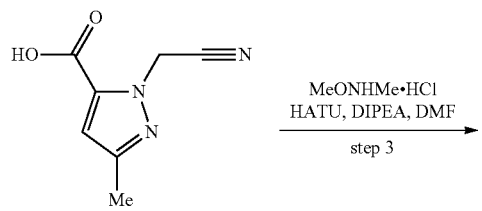

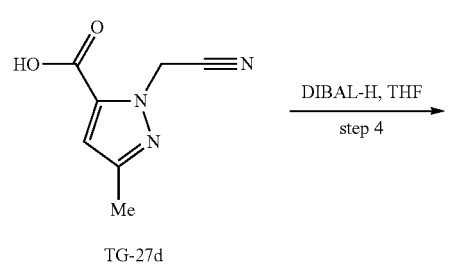

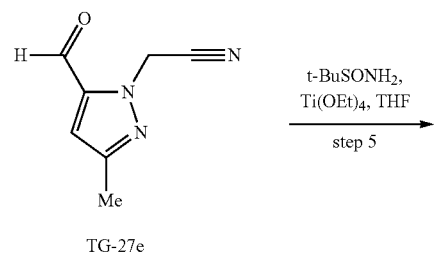

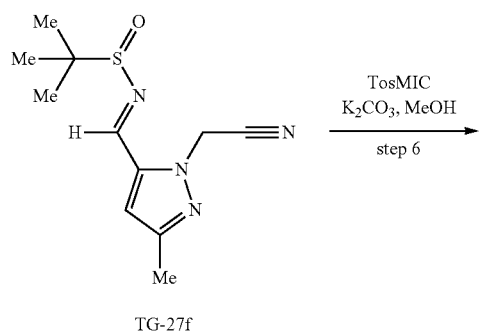

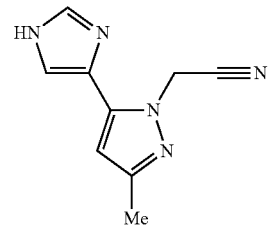

Step 1: Synthesis of Methyl 1-(cyanomethyl)-3-methyl-1H-pyrazole-5-carboxylate (TG-27b)

To a solution of ethyl 3-methyl-1H-pyrazole-5-carboxylate (TG-3a) (3.00 g, 19.5 mmol) and 2-bromoacetonitrile (2.80 g, 2.34 mmol) in MeCN (30 mL) was added $K_2CO_3$ (5.38 g, 38.9 mmol) and heated to 85° C. and stirred for 5 h. The mixture was then filtered, and the filtrate concentrated under vacuum. The crude residue was purified via flash column chromatography (40 g $SiO_2$, Combi-flash, 0-30% EtOAc/Pet. Ether) to afford the title compound methyl 1-(cyanomethyl)-3-methyl-1H-pyrazole-5-carboxylate (TG-27b) (1.75 g, 46%) as an off-white solid. $^1$H NMR (CHLOROFORM-d) δ: 6.71 (s, 1H), 5.45 (s, 2H), 4.38 (q, J=7.3 Hz, 2H), 2.30 (s, 3H), 1.39 (t, J=7.0 Hz, 3H).

Step 2: Synthesis of 1-(cyanomethyl)-3-methyl-1H-pyrazole-5-carboxylic Acid (TG-27c)

To a solution of methyl 1-(cyanomethyl)-3-methyl-1H-pyrazole-5-carboxylate (TG-27b) (1.85 g, 9.57 mmol) in THF (37 mL) and $H_2O$ (9.25 mL) at 0° C. was added lithium hydroxide monohydrate (442 mg, 10.5 mmol) and stirred for 4 h. The mixture was then acidified to pH 1 with aqueous HCl (1 N), the phases separated, and the aqueous phase was extracted with EtOAc (20 mL×3). The combined organic extract was dried over $Na_2SO_3$, filtered, and concentrated under vacuum to afford the title compound 1-(cyanomethyl)-3-methyl-1H-pyrazole-5-carboxylic acid (TG-27c) (1.55 g, 98%) as a yellow solid. LCMS [M+H]=166.0 observed; $^1$H NMR (DMSO-$d_6$) δ: 6.73 (s, 1H), 5.60 (s, 2H), 2.20 (s, 4H).

Step 3: Synthesis of 1-(cyanomethyl)-3-methyl-1H-pyrazole-5-carboxylic Acid (TG-27d)

To a solution of 1-(cyanomethyl)-3-methyl-1H-pyrazole-5-carboxylic acid (TG-27c) (1.38 g, 8.36 mmol) and O-methylhydroxylamine hydrochloride (978 mg, 10.0 mmol) in anhydrous DMF (23 mL) was added HATU (4.77 g, 12.5 mmol) and stirred for 10 min. To the reaction was then added N—N-diisopropylethylamine (2.98 mL, 16.7 mmol), and the reaction was stirred for 16 h. The reaction was diluted with $H_2O$ (20 mL), the phases were separated, and the aqueous phase was extracted with $CH_2Cl_2$ (20 mL×3). The combined organic phase was washed with a saturated aqueous solution of $NH_4Cl$ (20 mL×3), a saturated aqueous solution of $Na_2CO_3$ (20 mL×3), brine (20 mL×3), dried over $Na_2SO_4$, filtered, and concentrated in vacuum. The crude residue was purified via flash column chromatography (40 g $SiO_2$, Combi-flash, 12.5-75% EtOAc/Pet. Ether) to afford 1-(cyanomethyl)-3-methyl-1H-pyrazole-5-carboxylic acid (TG-27d) (1.91 g, 94% over three combined batches) as a yellow solid, containing some impurities. This material was used without further purification. LCMS [M+H]=209.1 observed. $^1$H NMR (CHLOROFORM-d) δ: 6.70 (s, 1H), 5.47 (s, 2H), 3.71 (s, 3H), 2.31 (s, 3H).

Step 4: Synthesis of (5-formyl-3-methyl-1H-pyrazol-1-yl)acetonitrile (TG-27e)

To a solution of 1-(cyanomethyl)-3-methyl-1H-pyrazole-5-carboxylic acid (TG-27d) (1.60 g, 7.68 mmol) in anhydrous THF (76.8 mL) at −10° C. under $N_2$ was added dibutylaluminum hydride (15.4 mL, 15.4 mmol, 1 M) dropwise to maintain the internal temperature below −5° C. The reaction was stirred at −5° C. for 2 h before being quenched with saturated aqueous solution of $NH_4Cl$ (50 mL), treated with Celite, and stirred at room temperature for 15 min. The mixture was filtered, and the filtered cake was washed with EtOAc (20 mL×5). The phases were separated, and the aqueous phase was extracted with EtOAc (20 mL×3). The combined organic phase was dried over anhydrous $Na_2SO_4$, filtered, and concentrated under vacuum. The crude residue was purified via flash column chromatography (40 g $SiO_2$, Combi-flash, 5-30% EtOAc/Pet. Ether) to afford the title compound (5-formyl-3-methyl-1H-pyrazol-1-yl)acetonitrile (TG-27e) (465 mg, 41%) as a yellow solid. $^1$H NMR (CHLOROFORM-d) δ: 9.81 (s, 1H), 6.78 (s, 1H), 5.43 (s, 2H), 2.34 (s, 3H).

Step 5: Synthesis of N-{(E)-[1-(cyanomethyl)-3-methyl-1H-pyrazol-5-yl]methylidene}-2-methylpropane-2-sulfinamide (TG-27f)

To a solution of (5-formyl-3-methyl-1H-pyrazol-1-yl)acetonitrile (TG-27e) (385 mg, 2.58 mmol) in anhydrous THF (7.7 mL) was added 2-methylpropane-2-sulfinamide (375 mg, 3.10 mmol) and tetraethoxytitanium (1.18 g, 5.16 mmol). The reaction was stirred at room temperature for 2 h before being concentrated under vacuum. The crude residue was purified via flash column chromatography (20 g $SiO_2$, Combi-flash, 10-50% EtOAc/Pet. Ether) to afford the title compound N-{(E)-[1-(cyanomethyl)-3-methyl-1H-pyrazol-5-yl]methylidene}-2-methylpropane-2-sulfinamide (TG-27f) (607 mg, 93%) as an off-white solid. LCMS [M+H]=253.8 observed; $^1$H NMR (CHLOROFORM-d) δ: 8.52 (s, 1H), 6.60 (s, 1H), 5.62 (d, J=17.1 Hz, 1H), 5.33 (d, J=17.3 Hz, 1H), 2.33 (s, 3H), 1.31 (s, 9H).

Step 6: Synthesis of [5-(1H-imidazol-4-yl)-3-methyl-1H-pyrazol-1-yl]acetonitrile (Int-TG-27)

To a solution of N-{(E)-[1-(cyanomethyl)-3-methyl-1H-pyrazol-5-yl]methylidene}-2-methylpropane-2-sulfinamide (TG-27f) (540 mg, 2.14 mmol) in MeOH (6.8 mL) at −5° C. was added 1-((isocyanomethyl)sulfonyl)-4-methylbenzene (460 mg, 2.35 mmol) and $K_2CO_3$ (355 mg, 2.57 mmol) and stirred for 30 min. The reaction was quenched with a saturated aqueous solution of $NH_4Cl$ (10 mL), the phases were separated, and the aqueous phase was extracted with EtOAc (15 mL×3). The combined organic phase was dried over $Na_2SO_4$, filtered, and concentrated under vacuum. The crude residue was purified via flash column chromatography (40 g $SiO_2$, Combi-flash, 0-7% MeOH/EtOAc) to afford the title compound [5-(1H-imidazol-4-yl)-3-methyl-1H-pyrazol-1-yl]acetonitrile (Int-TG-27) (78 mg, 19%) as an off-white solid. LCMS [M+H]=188.0 observed; $^1$H NMR (METHANOL-$d_4$) δ: 7.81 (s, 1H), 7.48 (s, 1H), 6.33 (s, 1H), 5.55 (s, 2H), 2.26 (s, 3H).

Preparation of Examples

Preparation of 4-[4-(1-ethyl-3-methyl-1H-pyrazol-5-yl)-1-methyl-1H-imidazol-2-yl]-1-methyl-1H-pyrazolo[4,3-c]pyridine-6-carboxamide (Example AIA01) According to Scheme A

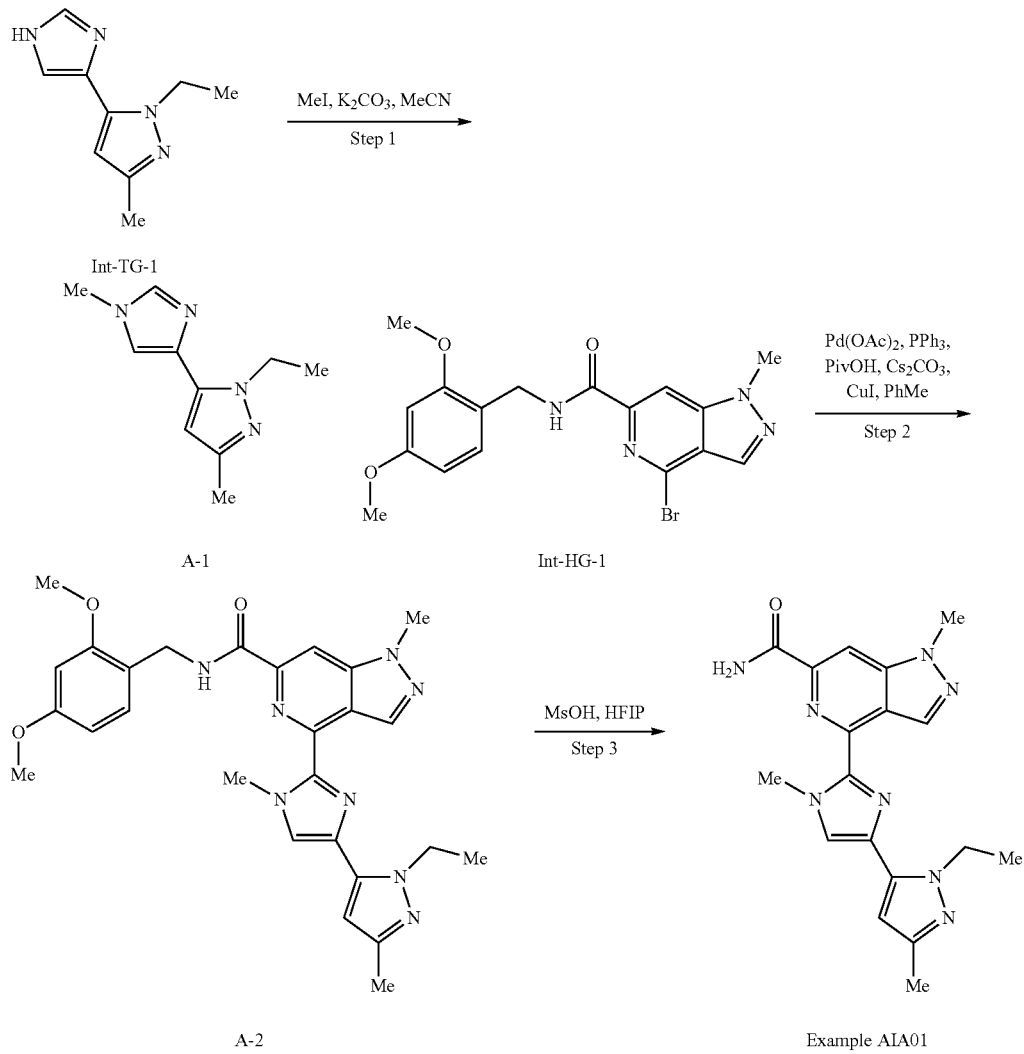

Step 1: Synthesis of 1-ethyl-3-methyl-5-(1-methyl-1H-imidazol-4-yl)-1H-pyrazole (A-1)

To a yellow mixture of 1-ethyl-5-(1H-imidazol-4-yl)-3-methyl-1H-pyrazole (Int-TG-1) (790 mg, 2.9 mmol) and K$_2$CO$_3$ (1.21 g, 8.74 mmol) in anhydrous MeCN (8.0 mL) was added MeI (455 mg, 3.21 mmol) drop-wise. The reaction was stirred at room temperature for 3h. The reaction was filtered and the filtrate was concentrated under vacuum. The crude residue was purified via flash column chromatography (40 g SiO$_2$, Combi-flash, 50% EtOAc/DCM) to give the desired product contaminated with formamide. The product was re-purified by preparatory thin-layer chromatography (10% MeOH/DCM) to afford the title compound 1-ethyl-3-methyl-5-(1-methyl-1H-imidazol-4-yl)-1H-pyrazole (A-1) (869 mg, 55%) as a yellow oil. LCMS [M+H]=191.3 observed; $^1$H NMR (400 MHz, CHLOROFORM-d) δ=7.49 (d, J=0.7 Hz, 1H), 7.04 (d, J=1.3 Hz, 1H), 6.13 (s, 1H), 4.45 (q, J=7.2 Hz, 2H), 3.74 (s, 3H), 2.29 (s, 3H), 1.43 (t, J=7.2 Hz, 3H).

Step 2: Synthesis of N-[(2,4-dimethoxyphenyl)methyl]-4-[4-(1-ethyl-3-methyl-1H-pyrazol-5-yl)-1-methyl-1H-imidazol-2-yl]-1-methyl-1H-pyrazolo[4,3-c]pyridine-6-carboxamide (A-2)

A reaction vessel was charged with 1-ethyl-3-methyl-5-(1-methyl-1H-imidazol-4-yl)-1H-pyrazole (A-1) (660 mg, 3.47 mmol), 4-bromo-N-(2,4-dimethoxybenzyl)-1-methyl-1H-pyrazolo[4,3-c]pyridine-6-carboxamide (Int-HG-1)

(2.10 g, 5.17 mmol), Pd(OAc)$_2$ (236 mg, 1.09 mmol), CuI (200 mg, 1.05 mmol), PPh$_3$ (273 mg, 1.04 mmol), Cs$_2$CO$_3$ (3401.7 mg, 10.440 mmol), PivOH (385 mg, 3.77 mmol), and PhMe (26 mL). The solution was flushed with N$_2$ for 2 min, sealed, and heated to 110° C. for 27h. LCMS analysis indicated incomplete conversion of starting material so additional aliquots of Pd(OAc)$_2$ (124 mg, 0.551 mmol), CuI (101 mg, 0.529 mmol), PPh$_3$ (139 mg, 0.529 mmol), Cs$_2$CO$_3$ (1.14 g, 3.51 mmol), and PivOH (184 mg, 1.80 mmol) were added. The reaction mixture was again flushed with N$_2$ for 2 min, sealed, and heated to 110° C. for 19h. The reaction was filtered through a pad of Celite and the filter cake washed with DCM (20 mL) and then 3 portions of DCM/MeOH (10:1, 10 mL ea.). The combined filtrates were concentrated under vacuum. The crude residue was purified via flash column chromatography (40 g SiO$_2$, Isco, 0-100% EtOAc/Pet. Ether then 10% MeOH/EtOAc) to afford the title compound N-[(2,4-dimethoxyphenyl)methyl]-4-[4-(1-ethyl-3-methyl-1H-pyrazol-5-yl)-1-methyl-1H-imidazol-2-yl]-1-methyl-1H-pyrazolo[4,3-c]pyridine-6-carboxamide (A-2) (1.15 g, 65%) as a yellow gum containing some residual (A-1) starting material. The material was used in the next step without further purification. LCMS [M+H]=515.1 observed.

Step 3: Synthesis of 4-[4-(1-ethyl-3-methyl-1H-pyrazol-5-yl)-1-methyl-1H-imidazol-2-yl]-1-methyl-1H-pyrazolo[4,3-c]pyridine-6-carboxamide (Example AIA01)

To a reaction vessel containing N-[(2,4-dimethoxyphenyl)methyl]-4-[4-(1-ethyl-3-methyl-1H-pyrazol-5-yl)-1-methyl-1H-imidazol-2-yl]-1-methyl-1H-pyrazolo[4,3-c]pyridine-6-carboxamide (A-2) (1.15 g, 1.60 mmol) was added HFIP (10 mL) followed by the dropwise addition of MsOH (1.50 g, 15.6 mmol). The reaction was stirred at room temperature for 1 h which was accompanied by gradual formation of a dark red solution. The reaction was concentrated under vacuum and the residue dissolved in DCM (8 mL). The solution was neutralized with 7M NH$_3$/MeOH to adjust the pH to ~8 which led to the precipitation of solids. The suspension was concentrated under vacuum and the crude residue diluted with DCM (20 mL) and water (20 mL). The solids that did not dissolve were filtered off at this stage. The filtrate was transferred to a separatory funnel and the phases were separated. The aqueous phase was extracted with 3 portions DCM (10 mL ea.). The combined organic extracts were dried (Na$_2$SO$_4$), filtered, and concentrated under vacuum. The crude residue was purified via preparatory thin-layer chromatography (EtOAc/MeOH/NH$_4$OH, 20:1:0.1) to afford the desired product contaminated with some residual (A-1). The material thus obtained was subject to further purification by flash column chromatography (SiO$_2$, Isco, DCM/MeOH, 10:1) to afford the desired product which still contained residual (A-1). The beige solid thus obtained was diluted with DMSO and filtered. The filtrate was further purified by preparatory HPLC (Boston Prime C18 150×30 mm×5 um column, 27-57% MeCN/H$_2$O with 0.05% NH$_4$OH, 25 mL/min) to afford the title compound 4-[4-(i-ethyl-3-methyl-1H-pyrazol-5-yl)-1-methyl-1H-imidazol-2-yl]-1-methyl-1H-pyrazolo[4,3-c]pyridine-6-carboxamide (Example AIA01) (114 mg, 20%) as a fluffy white solid. LCMS [M+H]=365.3 observed; $^1$H NMR (400 MHz, DMSO-d$_6$) δ=8.73 (d, J=0.9 Hz, 1H), 8.35 (d, J=0.6 Hz, 1H), 7.94 (br s, 1H), 7.90 (br s, 1H), 7.86 (s, 1H), 6.32 (N, 1H), 4.55 (q, J=7.1 Hz, 2H), 4.24 (8, 3H), 4.19 (s, 3H), 2.18 (s, 3H), 1.40 (t, J=7.1 Hz, 3H).

The examples in the table below were prepared according to the methods used for the synthesis of 4-[4-(1-ethyl-3-methyl-1H-pyrazol-5-yl)-1-methyl-1H-imidazol-2-yl]-1-methyl-1H-pyrazolo[4,3-c]pyridine-6-carboxamide (Example AIA1) with non-critical changes or substitutions to the exemplified procedures that one skilled in the art would be able to realize.

| Example Number | Reagents/Solvent used for step 1 | Structure/IUPAC Name | Analytical Data |
|---|---|---|---|
| AIA02 | iodoethane, K$_2$CO$_3$, MeCN | 4-[1-ethyl-4-(1-ethyl-3-methyl-1H-pyrazol-5-yl)-1H-imidazol-2-yl]-1-methyl-1H-pyrazolo[4,3-c]pyridine-6-carboxamide | LCMS [M + H] = 379.2 observed; $^1$H NMR (400 MHz, DMSO-d$_6$) δ = 8.74 (d, J = 0.6 Hz, 1H), 8.36 (s, 1H), 7.92 (s, 2H), 7.75 (br d, J = 1.5 Hz, 1H), 6.33 (s, 1H), 4.76 (q, J = 7.1 Hz, 2H), 4.56 (q, J = 7.1 Hz, 2H), 4.19 (s, 3H), 2.18 (s, 3H), 1.45 (t, J = 7.2 Hz, 3H), 1.40 (t, J = 7.1 Hz, 3H). |

-continued

| Example Number | Reagents/Solvent used for step 1 | Structure/IUPAC Name | Analytical Data |
|---|---|---|---|
| AIA03 | 2-iodopropane, C₂CO₃, MeCN | 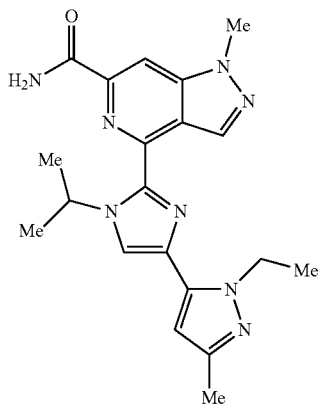 [SMILES: CCn1nc(C)cc1-c1cn(C(C)C)c(-c2nc(C(N)=O)cc3c2cnn3C)n1]<br>4-[4-(1-ethyl-3-methyl-1H-pyrazol-5-yl)-1-(propan-2-yl)-1H-imidazol-2-yl]-1-methyl-1H-pyrazolo[4,3-c]pyridine-6-carboxamide | LCMS [M + H] = 393.1 observed; ¹H NMR (400 MHz, DMSO-d₆) δ = 8.69 (s, 1H), 8.37 (s, 1H), 8.07 (s, 1H), 7.93 (br s, 1H), 7.68 (br s, 1H), 6.36 (s, 1H), 5.82 (spt, J = 6.6 Hz, 1H), 4.57 (q, J = 7.1 Hz, 2H), 4.19 (s, 3H), 2.18 (s, 3H), 1.55 (d, J = 6.6 Hz, 6H), 1.40 (t, J = 7.1 Hz, 3H). |
| AIA04 | 1,1-difluoro-2-iodoethane, Cs₂CO₃, DMF | 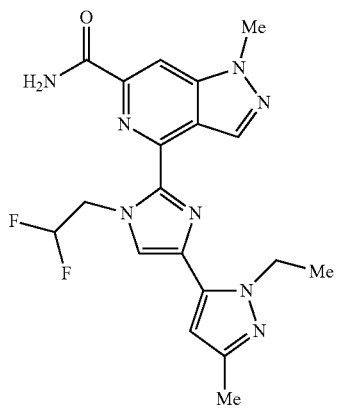 [SMILES: CCn1nc(C)cc1-c1cn(CC(F)F)c(-c2nc(C(N)=O)cc3c2cnn3C)n1]<br>4-[1-(2,2-difluoroethyl)-4-(1-ethyl-3-methyl-1H-pyrazol-5-yl)-1H-imidazol-2-yl]-1-methyl-1H-pyrazolo[4,3-c]pyridine-6-carboxamide | LCMS [M + H] = 415.2 observed; ¹H NMR (400 MHz, DMSO-d₆) δ = 8.72 (s, 1H), 8.37 (s, 1H), 7.98-7.80 (m, 3H), 6.55 (tt, J = 3.5, 55.3 Hz, 1H), 6.36 (s, 1H), 5.32 (dt, J = 3.2, 14.9 Hz, 2H), 4.54 (q, J = 7.1 Hz, 2H), 4.19 (s, 3H), 2.19 (s, 3H), 1.40 (t, J = 7.1 Hz, 3H); ¹⁹F NMR (376 MHz, DMSO-d₆) δ = −122.51 (s, 2F). |

Preparation of 4-[1-cyclopropyl-4-(1-ethyl-3-methyl-1H-pyrazol-5-yl)-1H-imidazol-2-yl]-1-methyl-1H-pyrazolo[4,3-c]pyridine-6-carboxamide (Example AIB01) According to Scheme B

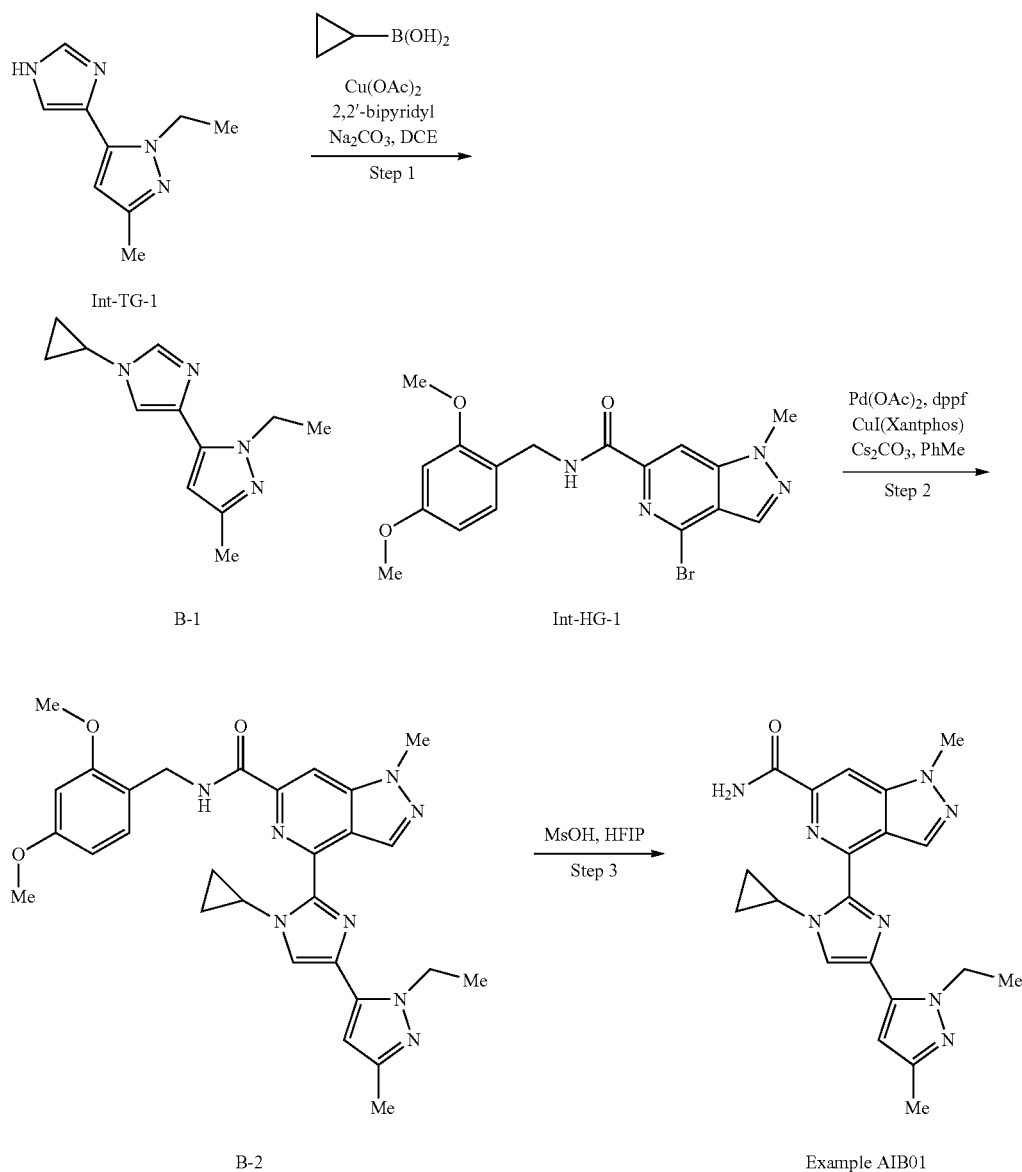

Step 1: Synthesis of 5-(1-cyclopropyl-1H-imidazol-4-yl)-1-ethyl-3-methyl-1H-pyrazole (B-1)

To a reaction vessel containing 1-ethyl-5-(1H-imidazol-4-yl)-3-methyl-1H-pyrazole (Int-TG-1) (106 mg, 0.430 mmol) was added 2,2'-bipyridyl (64.3 mg, 0.412 mmol), Cu(OAc)$_2$ (73.3 mg, 0.404 mmol), cyclopropylboronic acid (103.6 mg, 1.21 mmol), Na$_2$CO$_3$ (134.3 mg, 1.27 mmol) and DCE (1.2 mL). The reaction was heated to 70° C. and stirred for 3h. The reaction was removed from heating and allowed to cool to rt. The solution was diluted with water (10 mL) and transferred to a separatory funnel with DCM (10 mL). The phases were separated and the aqueous phase was extracted with 3 portions of DCM (10 mL ea.). The combined organic extracts were washed with 2 portions sat. NH$_4$Cl aq. (10 mL ea.), 1 portion brine (15 mL), dried (Na$_2$SO$_4$), filtered, and concentrated under vacuum. The crude residue was purified via preparatory thin-layer chromatography (SiO$_2$, DCM/MeOH 10:1) to afford the title compound 5-(1-cyclopropyl-1H-imidazol-4-yl)-1-ethyl-3-methyl-1H-pyrazole (B-1) (45.3 mg) as a dark brown oil containing minor impurities. The material was used in the next without further purification. LCMS [M+H]=216.8 observed.

Step 2: Synthesis of 4-[1-cyclopropyl-4-(1-ethyl-3-methyl-1H-pyrazol-5-yl)-1H-imidazol-2-yl]-N-[(2,4-dimethoxyphenyl)methyl]-1-methyl-1H-pyrazolo[4,3-c]pyridine-6-carboxamide (B-2)

To a reaction vessel containing 5-(1-cyclopropyl-1H-imidazol-4-yl)-1-ethyl-3-methyl-1H-pyrazole (B-1) (111 mg, 0.293 mmol) was added 4-bromo-N-(2,4-dimethoxybenzyl)-1-methyl-1H-pyrazolo[4,3-c]pyridine-6-carboxamide (Int-HG-1) (175.4 mg, 0.433 mmol), Pd(OAc)$_2$ (6.6 mg, 0.029 mmol), CuI(Xantphos) (67.1 mg, 0.087 mmol), dppf (8.8 mg, 0.016 mmol), Cs$_2$CO$_3$ (285 mg, 0.876 mmol) and PhMe (2.7 mL). The vessel was purged with N$_2$ for five cycles. The reaction mixture was heated to 110° C. and stirred for 15h. LCMS analysis at this stage showed that the starting material had not been consumed. Additional aliquots of Pd(OAc)$_2$ (7.8 mg, 0.035 mmol), 4-bromo-N-(2,4-dimethoxybenzyl)-1-methyl-1H-pyrazolo[4,3-c]pyridine-6-carboxamide (Int-HG-1) (60.5 mg, 0.149 mmol), dppf (10.2 mg, 0.018 mmol) were added and the reaction heated to 110° C. for 8 h. The reaction was removed from heating and allowed to cool gradually to rt. The solution was diluted with DCM (10 mL) and filtered through a pad of Celite. The filter cake was washed with 3 portions DCM (5 mL ea.) and the filtrate concentrated under vacuum. The crude residue was purified via preparatory thin-layer chromatography (SiO$_2$, 100% EtOAc) to afford the desired product contaminated with minor impurities. The material was re-purified by preparatory thin-layer chromatography (EtOAc/MeOH 10:1) to afford the title compound 4-[1-cyclopropyl-4-(1-ethyl-3-methyl-1H-pyrazol-5-yl)-1H-imidazol-2-yl]-N-[(2,4-dimethoxyphenyl)methyl]-1-methyl-1H-pyrazolo[4,3-c]pyridine-6-carboxamide (B-2) (109 mg) which contained a minor amount of residual (B-1). The material was used in the next step without further purification. LCMS [M+H]=541.2 observed.

Step 3: Synthesis of 4-[1-cyclopropyl-4-(1-ethyl-3-methyl-1H-pyrazol-5-yl)-1H-imidazol-2-yl]-1-methyl-1H-pyrazolo[4,3-c]pyridine-6-carboxamide (AIB01)

To a yellow solution of 4-[1-cyclopropyl-4-(1-ethyl-3-methyl-1H-pyrazol-5-yl)-1H-imidazol-2-yl]-N-[(2,4-dimethoxyphenyl)methyl]-1-methyl-1H-pyrazolo[4,3-c]pyridine-6-carboxamide (B-2) (109 mg, 0.12 mmol) in HFIP (2.0 mL) was added MsOH (118 mg, 1.23 mmol). The reaction was stirred at room temperature for 2h which was accompanied by gradual formation of a dark purple solution. The solution was concentrated under vacuum and co-evaporated with DCM (5 mL ea.) 3 times. The crude residue was suspended in DMSO and MeOH followed by filtration. The filtrate was purified via preparatory HPLC (Boston Prime C18 150×30 mm×5 um column, 28-58% MeCN/H$_2$O with 0.05% NH$_4$OH, 25 mL/min) to afford the title compound 4-[1-cyclopropyl-4-(1-ethyl-3-methyl-1H-pyrazol-5-yl)-1H-imidazol-2-yl]-1-methyl-1H-pyrazolo[4,3-c]pyridine-6-carboxamide (AIB01) (10 mg, 22%) as a white solid. LCMS [M+H]=391.2 observed; $^1$H NMR (400 MHz, DMSO-d$_6$) δ=8.67 (d, J=0.6 Hz, 1H), 8.38 (s, 1H), 7.98 (br s, 1H), 7.87 (s, 1H), 7.84 (br d, J=1.8 Hz, 1H), 6.35 (s, 1H), 4.55 (q, J=7.1 Hz, 2H), 4.48-4.40 (m, 1H), 4.19 (s, 3H), 2.17 (s, 3H), 1.39 (t, J=7.1 Hz, 3H), 1.08-1.00 (m, 2H), 1.00-0.93 (m, 2H).

Preparation of 1-ethyl-4-[4-(1-ethyl-3-methyl-1H-pyrazol-5-yl)-1-methyl-1H-imidazol-2-yl]-1H-pyrazolo[4,3-c]pyridine-6-carboxamide (Example AIC01) According to Scheme C

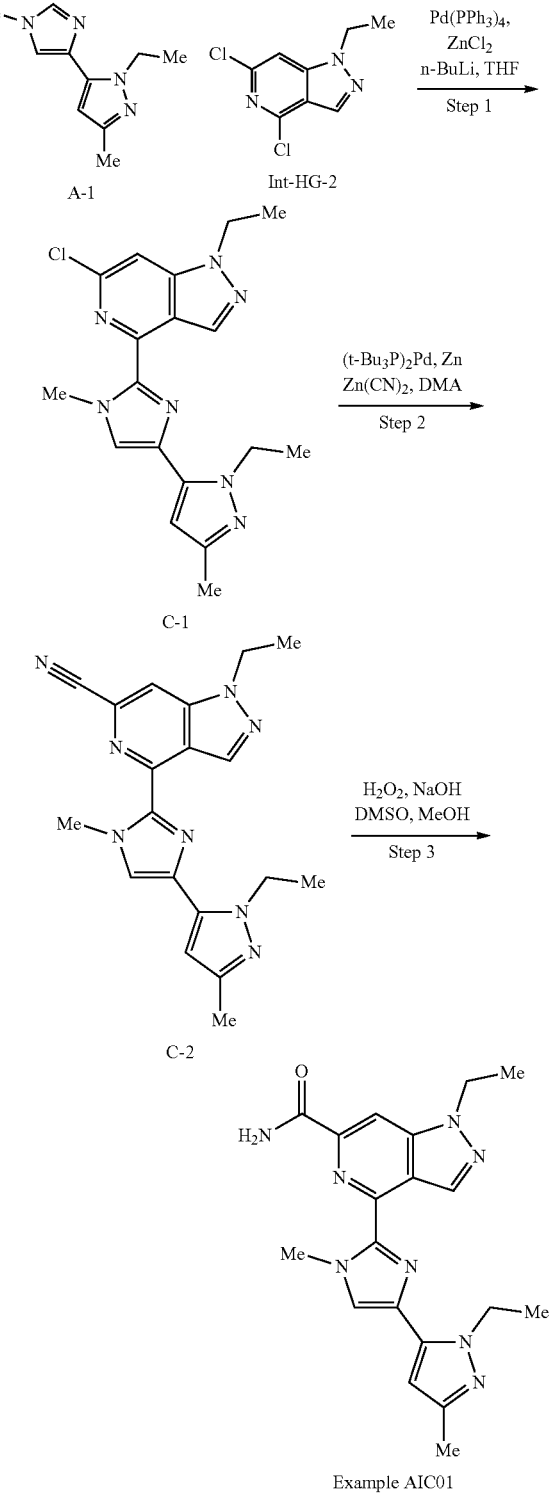

Scheme C

Example AIC01

Step 1: Synthesis of 6-chloro-1-ethyl-4-[4-(1-ethyl-3-methyl-1H-pyrazol-5-yl)-1-methyl-1H-imidazol-2-yl]-1H-pyrazolo[4,3-c]pyridine (C-1)

To a reaction vessel containing 1-ethyl-3-methyl-5-(1-methyl-1H-imidazol-4-yl)-1H-pyrazole (A-1) (196 mg, 1.03 mmol) was added THF (5 mL). The solution was cooled to −78° C. in a dry-ice/AcMe bath. To the solution was added n-BuLi (505 µL, 1.26 mmol) dropwise under inert atmosphere. After the addition, the reaction mixture was stirred at −78° C. for 1 h. Then, $ZnCl_2$ (1.4 mL, 380 mg, 2.8 mmol) was added at −78° C. and then the ice bath was removed to allow the reaction to warm gradually to room temperature. At this stage, 4,6-dichloro-1-ethyl-1H-pyrazolo[4,3-c]pyridine (Int-HG-2) (235 mg, 1.09 mmol) and $Pd(PPh_3)_4$ (255 mg, 0.221 mmol) were added and the mixture was heated to 60° C. and stirred under inert atmosphere for 14h. The solution was concentrated under vacuum and the crude residue purified via flash column chromatography (40 g $SiO_2$, Isco, 100% DCM to 1% MeOH/DCM) to afford the title compound 6-chloro-1-ethyl-4-[4-(1-ethyl-3-methyl-1H-pyrazol-5-yl)-1-methyl-1H-imidazol-2-yl]-1H-pyrazolo[4,3-c]pyridine (C-1) (115 mg, 30%) as a yellow solid. LCMS [M+H]=370.1 observed; $^1$H NMR (400 MHz, CHLOROFORM-d) δ=8.86 (s, 1H), 7.29 (s, 1H), 7.24 (s, 1H), 6.22 (s, 1H), 4.67 (q, J=7.2 Hz, 2H), 4.41 (q, J=7.3 Hz, 2H), 4.28 (s, 3H), 2.32 (s, 3H), 1.55 (t, J=7.2 Hz, 6H).

Step 2: Synthesis of 1-ethyl-4-[4-(1-ethyl-3-methyl-1H-pyrazol-5-yl)-1-methyl-1H-imidazol-2-yl]-1H-pyrazolo[4,3-c]pyridine-6-carbonitrile (C-2)

To a reaction vessel containing 6-chloro-1-ethyl-4-[4-(1-ethyl-3-methyl-1H-pyrazol-5-yl)-1-methyl-1H-imidazol-2-yl]-1H-pyrazolo[4,3-c]pyridine (C-1) (115 mg, 0.310 mmol) was added DMA (5 mL), $Zn(CN)_2$ (50.0 mg, 0.426 mmol), Zn powder (14.4 mg, 0.220 mmol) and $(t-Bu_3P)_2Pd$ (32.7 mg, 0.064 mmol). The reaction solution was flushed with $N_2$ for 2 minutes, sealed, heated to 120° C. and stirred for 16 h. The reaction mixture was removed from heating and allowed to cool gradually to room temperature. The solution was filtered over a pad of Celite and the filter cake was washed with 2 portions EtOAc (5 mL ea.) and 2 portions $H_2O$ (3 mL ea.). The filtrate was transferred to a separatory funnel and the phases were separated. The aqueous phase was extracted with 3 portions EtOAc (5 mL). The combined organic extracts were washed with 3 portions brine (10 mL ea.), dried ($Na_2SO_4$), filtered, and concentrated under vacuum to afford the title compound 1-ethyl-4-[4-(1-ethyl-3-methyl-1H-pyrazol-5-yl)-1-methyl-1H-imidazol-2-yl]-1H-pyrazolo[4,3-c]pyridine-6-carbonitrile (C-2) (143 mg) which was used in the next step without further purification. LCMS [M+H]=361.1 observed.

Step 3: Synthesis of 1-ethyl-4-[4-(1-ethyl-3-methyl-1H-pyrazol-5-yl)-1-methyl-1H-imidazol-2-yl]-1H-pyrazolo[4,3-c]pyridine-6-carboxamide (Example AIC01)

To a reaction vessel containing 1-ethyl-4-[4-(1-ethyl-3-methyl-1H-pyrazol-5-yl)-1-methyl-1H-imidazol-2-yl]-1H-pyrazolo[4,3-c]pyridine-6-carbonitrile (C-2) (143 mg, 0.311 mmol) was added DMSO (2.7 mL), MeOH (5.5 mL), $H_2O_2$ (243 µL, 3.11 mmol) and NaOH (2M in $H_2O$, 777 µL, 1.55 mmol). The reaction was stirred at 25° C. for 16h and then quenched with sat. $Na_2SO_3$ aq. (2 mL). The solution was concentrated under vacuum and the DMSO suspension filtered. The filtrate was purified via preparatory HPLC (Waters Xbridge BEH C18 100×25 mm×5 um column, 21-61% MeCN/$H_2O$, 25 mL/min) to afford the desired product containing minor impurities. The material was further purified by trituration with MTBE (2 mL) and stirred at room temperature for 10 minutes. The suspension was filtered and the filter cake was washed with MTBE (1 mL). The solid was collected and dried under vacuum to afford the title compound 1-ethyl-4-[4-(1-ethyl-3-methyl-1H-pyrazol-5-yl)-1-methyl-1H-imidazol-2-yl]-1H-pyrazolo[4,3-c]pyridine-6-carboxamide (Example AIC01) (37 mg, 31%) as a pale yellow solid. LCMS [M+H]=379.4 observed; $^1$H NMR (400 MHz, DMSO-$d_6$) δ=8.75 (s, 1H), 8.37 (s, 1H), 7.94 (br s, 1H), 7.89 (br p, 1H), 7.85 (s, 1H), 6.30 (s, 1H), 4.60 (q, J=7.3 Hz, 2H), 4.55 (q, J=7.0 Hz, 2H), 4.24 (s, 3H), 2.18 (s, 3H), 1.45 (t, J=7.1 Hz, 3H), 1.40 (t, J=7.1 Hz, 3H).

The examples in the table below were prepared according to the methods used for the synthesis of 1-ethyl-4-[4-(1-ethyl-3-methyl-1H-pyrazol-5-yl)-1-methyl H-imidazol-2-yl]-1H-pyrazolo[4,3-c]pyridine-6-carboxamide (Example AIC) with non-critical changes or substitutions to the exemplified procedures that one skilled in the art would be able to realize.

| Example Number | Starting materials used for step 1 | Structure/IUPAC Name | Analytical Data |
|---|---|---|---|
| AIC02 | Int-HG-6, A-1 | 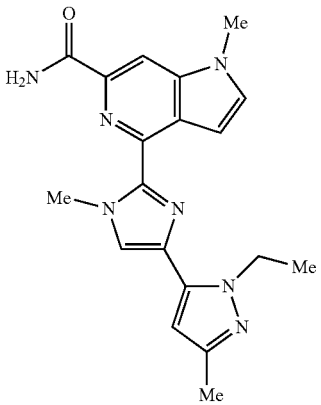 [SMILES: CCn1nc(C)cc1-c1cn(C)c(-c2nc(C(N)=O)cc3c2ccn3C)n1]<br>4-[4-(1-ethyl-3-methyl-1H-pyrazol-5-yl)-1-methyl-1H-imidazol-2-yl]-1-methyl-1H-pyrrolo[3,2-c]pyridine-6-carboxamide | LCMS [M + H] = 364.2 observed; $^1$H NMR (400 MHz, DMSO-$d_6$) δ ppm 8.23 (s, 1 H) 7.89 (br s, 1 H) 7.76 (s, 1 H) 7.69 (d, J = 3.01 Hz, 1 H) 7.66 (br s, 1 H) 7.27 (d, J = 2.51 Hz, 1 H) 6.27 (s, 1H) 4.55 (q, J = 7.19 Hz, 2 H) 4.18 (s, 3 H) 3.95 (s, 3 H) 2.18 (s, 3 H) 1.39 (t, J = 7.15 Hz, 3H) |

-continued

| Example Number | Starting materials used for step 1 | Structure/IUPAC Name | Analytical Data |
|---|---|---|---|
| AIC03 | Int-HG-2, Int-TF-G-25 | 1-ethyl-4-{4-[1-(3-methoxypropyl)-3-methyl-1H-pyrazol-5-yl]-1-methyl-1H-imidazol-2-yl}-1H-pyrazolo[4,3-c]pyridine-6-carboxamide | LCMS [M + H] = 423.3 observed; $^1$H NMR (DMSO-$d_6$) δ: 8.81 (d, J = 0.9 Hz, 1H), 8.36 (d, J = 0.9 Hz, 1H), 7.81-7.98 (m, 3H), 6.30 (s, 1H), 4.56-4.64 (m, 4H), 4.22 (s, 3H), 3.36 (t, J = 6.1 Hz, 2H), 3.19 (s, 3H), 2.17 (s, 3H), 2.01-2.08 (m, 2H), 1.44 (t, 7.2 Hz, 3H). |
| AIC04 | Int-HG-4, Int-TF-G-23 | 1-methyl-4-(1-methyl-4-{3-methyl-1-[(oxetan-3-yl)methyl]-1H-pyrazol-5-yl}-1H-imidazol-2-yl)-1H-pyrazolo[4,3-c]pyridine-6-carboxamide | LCMS [M + H] = 407.1 observed; $^1$H NMR (METHANOL-$d_4$) δ: 8.86 (s, 1H), 8.38 (s, 1H), 8.10 (s, 1H), 6.95 (s, 1H), 5.02-5.10 (m, 1H), 4.56-4.64 (m, 2H), 4.32-4.39 (m, 4H), 4.22 (s, 3H), 3.83-3.87 (m, 2H), 3.59-3.69 (m, 1H), 2.52 (s, 3H). |

Preparation of 4-(2-ethyl-1,4-dimethyl-1H-[1,4'-biimidazol]-2'-yl)-1-methyl-1H-pyrazolo[4,3-c]pyridine-6-carboxamide (Example AID01) According to Scheme D Scheme D

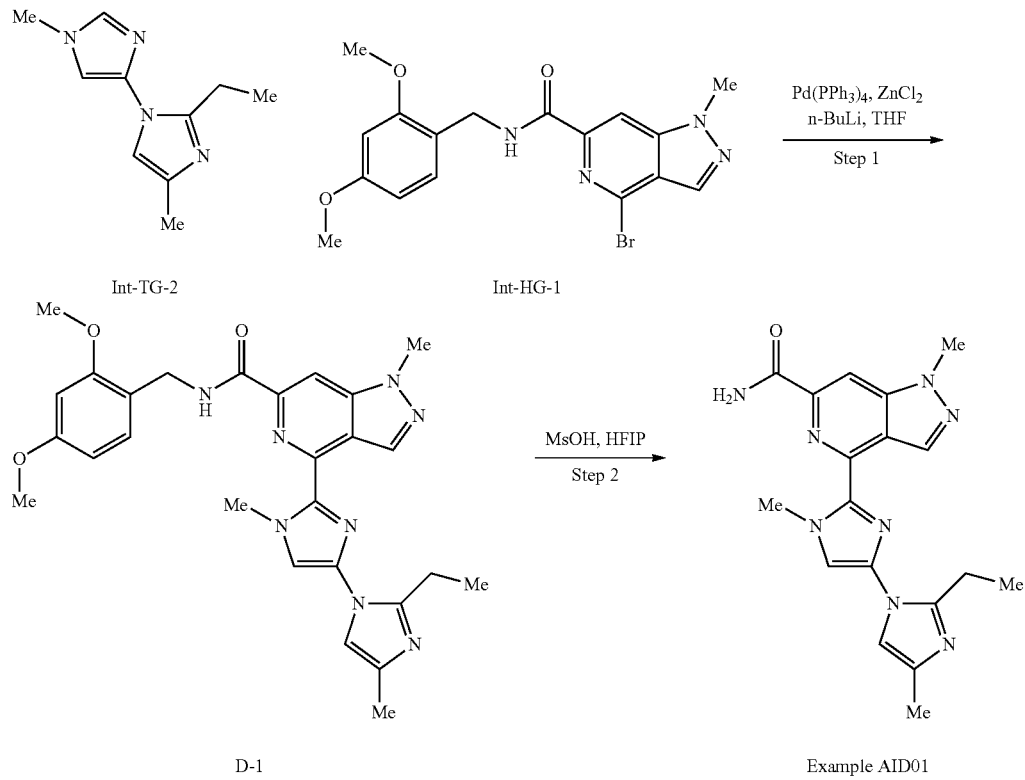

Step 1: Synthesis of N-[(2,4-dimethoxyphenyl)methyl]-4-(2-ethyl-1',4-dimethyl-1'H-[1,4'-biimidazol]-2'-yl)-1-methyl-1H-pyrazolo[4,3-c]pyridine-6-carboxamide (D-1)

To a reaction vessel containing 2-ethyl-1',4-dimethyl-1'H-1,4'-biimidazole (Int-TG-2) (135 mg, 0.710 mmol) was added anhydrous THF (5.0 mL) and the solution cooled to −78° C. in a dry ice/AcMe bath. To the solution was added n-BuLi (0.6 mL, 1.50 mmol) drop-wise at −78° C. under inert atmosphere. The resulting mixture was stirred at −78° C. for 2h. At this stage, $ZnCl_2$ (2M in Me-THF, 0.88 mL, 1.8 mmol) was added drop-wise at −78° C. and the reaction stirred for 10 min at which point the dry ice/AcMe bath was removed allowing the solution to gradually warm to room temperature over 30 min. The vessel was then charged with 4-bromo-N-[(2,4-dimethoxyphenyl)methyl]-1-methyl-1H-pyrazolo[4,3-c]pyridine-6-carboxamide (Int-HG-1) (317 mg, 0.782 mmol) and $Pd(PPh_3)_4$ (82.0 mg, 0.071 mmol). The resulting brown suspension was flushed with $N_2$ for 2 min, sealed, and heated at 80° C. with stirring for 18h. The reaction vessel was removed from heating and allowed to cool gradually to room temperature. The solution was diluted with DCM/MeOH (10:1) and filtered through a pad of Celite. The filtrate was concentrated under vacuum and the crude residue purified via flash column chromatography (40 g $SiO_2$, Combi-flash, 2.5-15% MeOH/DCM) to afford the desired product contaminated with minor impurities. This material was re-purified via flash column chromatography (20 g $SiO_2$, Combi-flash, 50-100% EtOAc/Pet. Ether) to afford the title compound N-[(2,4-dimethoxyphenyl)methyl]-4-(2-ethyl-1',4-dimethyl-1'H-[1,4'-biimidazol]-2'-yl)-1-methyl-1H-pyrazolo[4,3-c]pyridine-6-carboxamide (D-1) (162 mg, 44%) as a yellow solid containing minor impurities. The material was used in the next step without further purification. LCMS [M+H]=515.4 observed.

Step 2: Synthesis of 4-(2-ethyl-1',4-dimethyl-1'H-[1,4'-biimidazol]-2'-yl)-1-methyl-1H-pyrazolo[4,3-c]pyridine-6-carboxamide (Example AID01)

To a reaction vessel containing N-[(2,4-dimethoxyphenyl)methyl]-4-(2-ethyl-1',4-dimethyl-1'H-[1,4'-biimidazol]-2'-yl)-1-methyl-1H-pyrazolo[4,3-c]pyridine-6-carboxamide (D-1) (160 mg, 0.311 mmol) was added HFIP (3 mL) and MsOH (299 mg, 3.11 mmol). The resulting brown-red solution was stirred at room temperature for 2h which resulted in the gradual formation of a purple solution. The solution was diluted with DCM (20 mL) and the pH adjusted by the addition of $NH_3$ (7M solution in MeOH) to achieve pH=~8 followed by concentration under vacuum. The crude solid was triturated with DCM/MeOH (10:1, 5 mL) with stirring for 5 min, filtered, and the solids washed with 3 portions DCM/MeOH (10:1, 2 mL ea.). The filtrate was concentrated under vacuum and the crude residue purified via prep-HPLC (YMC Triart C18 250×50 mm×7 um column, 16-56% MeCN/H$_2$O with 0.05% NH$_4$OH, 60 mL/min) to afford the title compound 4-(2-ethyl-1',4-dimethyl-1'H-[1,4'-biimidazol]-2'-yl)-1-methyl-1H-pyrazolo[4,3-c]pyridine-6-carboxamide (Example AID01) (68 mg, 61%) as a white solid. LCMS [M+H]=365.1 observed; $^1$H NMR (400 MHz, DMSO-d$_6$) δ=8.71 (s, 1H), 8.36 (s, 1H), 7.94 (br s, 1H), 7.88 (br s, 1H), 7.68 (s, 1H), 7.16 (s, 1H), 4.24 (s, 3H), 4.18 (s, 3H), 2.84 (q, J=7.5 Hz, 2H), 2.13 (s, 3H), 1.24 (t, J=7.5 Hz, 3H).

Preparation of 4-{4-[1-(3-hydroxypropyl)-3-methyl-1H-pyrazol-5-yl]-1-methyl-1H-imidazol-2-yl}-1-methyl-1H-pyrazolo[4,3-c]pyridine-6-carboxamide (Example AIE01) According to Scheme E Scheme E

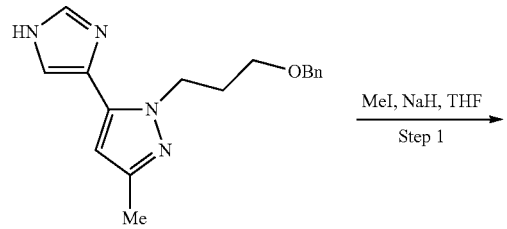

Int-TG-3

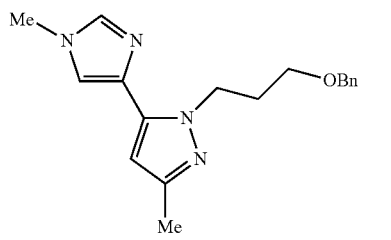 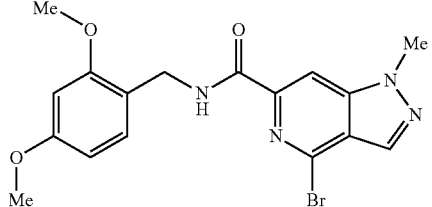

E-1  Int-HG-1

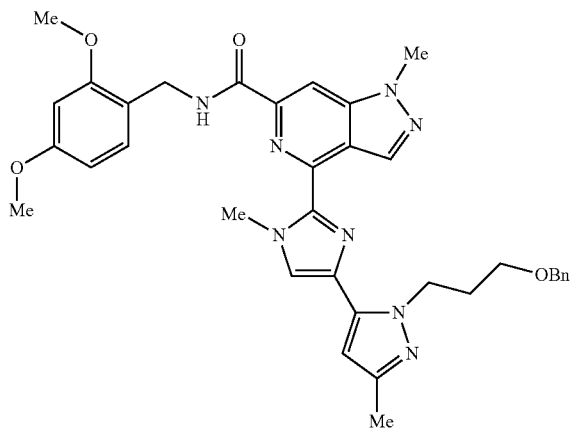

E-2

125

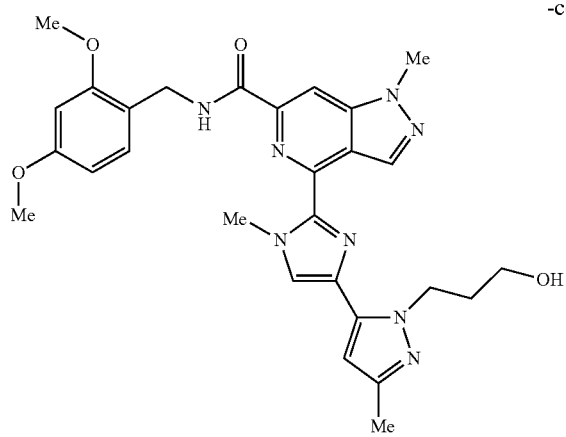

E-3

126

-continued

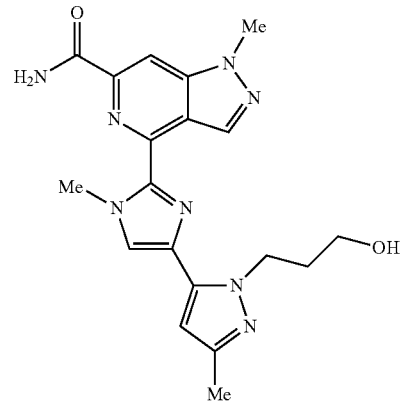

Example AIE01

MsOH, HFIP
Step 4

Step 1: Synthesis of 1-[3-(benzyloxy)propyl]-3-methyl-5-(1-methyl-1H-imidazol-4-yl)-1H-pyrazole (E-1)

To a reaction vessel containing 1-[3-(benzyloxy)propyl]-5-(1H-imidazol-4-yl)-3-methyl-1H-pyrazole (Int-TG-3) (4.40 g, 14.9 mmol) was added THF (140 mL). The solution was cooled to 0° C. in an ice water bath followed by the portion wise addition of NaH (60 wt % mineral oil, 831 mg, 20.8 mmol). The reaction was stirred at 0° C. for 15 min. which resulted in formation of a dark yellow suspension. To the solution, was added MeI (3.08 g, 21.7 mmol) and the reaction stirred at 0° C. for 30 min. at which point the ice bath was removed. The reaction was warmed gradually to room temperature over the course of 1 h. The reaction was quenched by the careful addition of water (50 mL) and transferred to a separatory funnel with EtOAc. The phases were separated and the aqueous phase was extracted with 3 portions EtOAc (100 mL ea.). The combined organic extracts were washed with brine (100 mL), dried (Na$_2$SO$_4$), filtered, and concentrated under vacuum. The crude residue (3.5 g) was combined with the crude material from another batch (1.16 g) and purified via flash column chromatography (120 g SiO$_2$, Biotage, 0-10% MeOH/EtOAc) to afford the desired product contaminated with minor impurities. The material was re-purified via flash column chromatography (120 g SiO$_2$, Combi-flash, 0-10% MeOH/EtOAc) to afford the title compound 1-[3-(benzyloxy)propyl]-3-methyl-5-(1-methyl-1H-imidazol-4-yl)-1H-pyrazole (E-1) (2.82 g, 52%) as a brown oil. LCMS [M+H]=311.0 observed; $^1$H NMR (400 MHz, DMSO-d$_6$) δ=7.66 (s, 1H), 7.42 (s, 1H), 7.37-7.24 (m, 6H), 6.12 (s, 1H), 4.43 (t, J=7.2 Hz, 2H), 4.40 (s, 2H), 3.63 (s, 3H), 3.41 (t, J=6.2 Hz, 2H), 2.13 (s, 3H), 2.03-1.95 (m, 2H).

Step 2: Synthesis of 4-(4-{1-[3-(benzyloxy)propyl]-3-methyl-1H-pyrazol-5-yl}-1-methyl-1H-imidazol-2-yl)-N-[(2,4-dimethoxyphenyl)methyl]-1-methyl-1H-pyrazolo[4,3-c]pyridine-6-carboxamide (E-2)

To a reaction vessel containing 1-[3-(benzyloxy)propyl]-3-methyl-5-(1-methyl-1H-imidazol-4-yl)-1H-pyrazole (E-1) (1.08 g, 3.48 mmol) was added 4-bromo-N-[(2,4-dimethoxyphenyl)methyl]-1-methyl-1H-pyrazolo[4,3-c]pyridine-6-carboxamide (Int-HG-1) (2.82 g, 6.96 mmol), PhMe (36 mL), Cs$_2$CO$_3$ (3.40 g, 10.4 mmol), Pd(OAc)$_2$ (391 mg, 1.74 mmol), PPh$_3$ (456 mg, 1.74 mmol), CuI (331 mg, 1.74 mmol) and PivOH (711 mg, 6.96 mmol). The resulting mixture was degassed with N$_2$ for 3 cycles, sealed, and heated to 130° C. with stirring for 18h. The reaction was removed from heating and allowed to cool gradually to room temperature. The solution was diluted with DCM/MeOH (10:1, 30 mL), filtered through Celite, and the filtrate concentrated under vacuum. The crude residue was purified via flash column chromatography (120 g SiO$_2$, Combi-flash, 20-100% EtOAc/Pet. Ether) to afford the title compound 4-(4-{1-[3-(benzyloxy)propyl]-3-methyl-1H-pyrazol-5-yl}-1-methyl-1H-imidazol-2-yl)-N-[(2,4-dimethoxyphenyl)methyl]-1-methyl-1H-pyrazolo[4,3-c]pyridine-6-carboxamide (E-2) (1.10 g, 49%) as a light yellow solid contaminated with some minor impurities. This material was used in the next step without further purification. LCMS [M+H]=635.5 observed.

Step 3: Synthesis of N-[(2,4-dimethoxyphenyl)methyl]-4-{4-[1-(3-hydroxypropyl)-3-methyl-1H-pyrazol-5-yl]-1-methyl-1H-imidazol-2-yl}-1-methyl-1H-pyrazolo[4,3-c]pyridine-6-carboxamide (E-3)

To a reaction vessel containing 4-(4-{1-[3-(benzyloxy)propyl]-3-methyl-1H-pyrazol-5-yl}-1-methyl-1H-imidazol-2-yl)-N-[(2,4-dimethoxyphenyl)methyl]-1-methyl-1H-pyrazolo[4,3-c]pyridine-6-carboxamide (E-2) (1.10 g, 1.73 mmol) was added DCM (26 mL) and the solution was cooled to 0° C. in an ice water bath. To the solution, was added BCl$_3$ (1 M in DCM, 5.2 mL, 5.20 mmol) dropwise at 0° C. The ice bath was removed and the reaction warmed gradually to room temperature with stirring for 21 h. The solution was cooled to 0° C. in an ice water bath and carefully quenched with MeOH (12 mL). The pH of the solution was adjusted with NH$_3$ (7M solution in MeOH) to pH=~8 and stirred for 30 min. resulting in formation of a light-yellow suspension. The suspension was filtered and the filtrate concentrated under vacuum. The crude residue was purified via flash column chromatography (40 g SiO$_2$, Combi-flash, 0-10% MeOH/DCM) to afford the title compound N-[(2,4-dimethoxyphenyl)methyl]-4-{4-[1-(3-hydroxypropyl)-3-methyl-1H-pyrazol-5-yl]-1-methyl-1H-imidazol-2-yl}-1-methyl-1H-pyrazolo[4,3-c]pyridine-6-carboxamide (E-3) (680 mg, 72%) as an off-white solid. LCMS [M+H]=545.4 observed.

Step 4: Synthesis of 4-{4-[1-(3-hydroxypropyl)-3-methyl-1H-pyrazol-5-yl]-1-methyl-1H-imidazol-2-yl}-1-methyl-1H-pyrazolo[4,3-c]pyridine-6-carboxamide (Example AIE01)

To a reaction vessel containing N-[(2,4-dimethoxyphenyl)methyl]-4-{4-[1-(3-hydroxypropyl)-3-methyl-1H-pyrazol-5-yl]-1-methyl-1H-imidazol-2-yl}-1-methyl-1H-pyrazolo[4,3-c]pyridine-6-carboxamide (E-3) (680 mg, 1.25 mmol) was added HFIP (12.5 mL) and MsOH (1.20 g, 12.5 mmol). The reaction was stirred at room temperature for 2.5h at which point a dark purple solution had been formed. The solution was concentrated under vacuum and diluted with DCM/MeOH (10:1, 30 mL). The pH of the solution was then adjusted with NH$_3$ (7M solution in MeOH) to pH=~8 which lead to the precipitation of solids. The suspension was filtered and the filter cake washed with 4 portions DCM/MeOH (10:1, 5 mL ea.). The filtrate was concentrated under vacuum and the crude residue purified via flash column chromatography (40 g SiO$_2$, Combi-flash, 0-10% MeOH/DCM). Fractions containing the desired product were collected, concentrated, and further lyophilized to afford the title compound 4-{4-[1-(3-hydroxypropyl)-3-methyl-1H-pyrazol-5-yl]-1-methyl-1H-imidazol-2-yl}-1-methyl-1H-pyrazolo[4,3-c]pyridine-6-carboxamide (Example AIE01) (400 mg, 82%) as a light-yellow solid. LCMS [M+H]=395.3 observed; $^1$H NMR (400 MHz, DMSO-d$_6$) δ=8.77 (d, J=1.0 Hz, 1H), 8.35 (d, J=0.9 Hz, 1H), 7.94 (br s, 1H), 7.87 (br s, 1H), 7.85 (s, 1H), 6.32 (s, 1H), 4.65-4.53 (m, 3H), 4.23 (s, 3H), 4.19 (s, 3H), 3.45 (q, J=6.1 Hz, 2H), 2.18 (s, 3H), 1.97 (quin, J=6.7 Hz, 2H).

The examples in the table below were prepared according to the methods used for the synthesis of 4-{4-[1-(3-hydroxypropyl)-3-methyl-1H-pyrazol-5-yl]-1-methyl-1H-imidazol-2-yl}-1-methyl-1H-pyrazolo[4,3-c]pyridine-6-carboxamide (Example AIE01) according to Scheme E with non-critical changes or substitutions to the exemplified procedures that one skilled in the art would be able to realize.

| Example Number | Reagents used for step 1 | Structure/IUPAC Name | Analytical Data |
|---|---|---|---|
| AIE02 | Int-TG-3, EtI, NaH, THF | 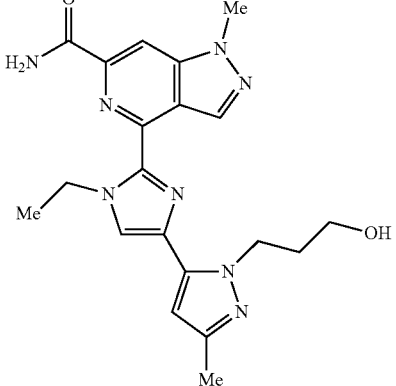<br>4-{1-ethyl-4-[1-(3-hydroxypropyl)-3-methyl-1H-pyrazol-5-yl]-1H-imidazol-2-yl}-1-methyl-1H-pyrazolo[4,3-c]pyridine-6-carboxamide | LCMS [M + H] = 409.4 observed; $^1$H NMR (DMSO-d$_6$) δ: 8.77 (d, J = 1.0 Hz, 1H), 8.36 (d, J = 1.0 Hz, 1H), 7.87-7.95 (m, 2H), 7.75 (br s, 1H), 6.34 (s, 1H), 4.74 (q, J = 7.1 Hz, 2H), 4.55-4.62 (m, 3H), 4.19 (s, 3H), 3.42-3.49 (m, 2H), 2.18 (s, 3H), 1.93-2.01 (m, 2H), 1.45 (t, J = 7.2 Hz. 3H). |
| AIE03 | Int-TG-13, MeI, NaH, THF | 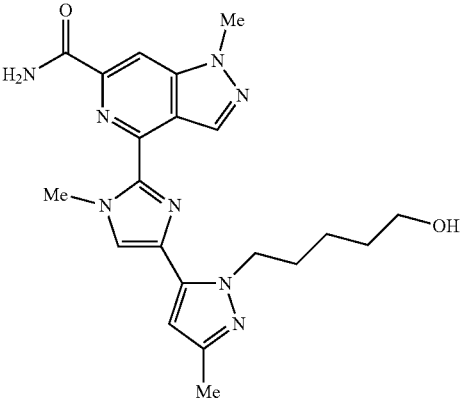 [SMILES: Cc1cc(-c2cn(C)c(-c3nc(C(N)=O)cc4c3cnn4C)n2)n(CCCCCO)n1]<br>4-{4-[1-(5-hydroxypentyl)-3-methyl-1H-pyrazol-5-yl]-1-methyl-1H-imidazol-2-yl}-1-methyl-1H-pyrazolo[4,3-c]pyridine-6-carboxamide | LCMS [M + H] = 423.2 observed; $^1$H NMR (DMSO-d$_6$) δ: 8.73 (s, 1H), 8.35 (s, 1H), 7.81-7.99 (m, 3H), 6.30 (s, 1H), 4.52 (t, J = 7.0 Hz, 2H), 4.31 (t, J = 5.0 Hz, 1H), 4.24 (s, 3H), 4.19 (s, 3H), 2.18 (s, 3H), 1.77-1.88 (m, 2H), 1.27-1.46 (m, 4H) (24H out of 26H observed). |

| Example Number | Reagents used for step 1 | Structure/IUPAC Name | Analytical Data |
|---|---|---|---|
| AIE04 | Int-TG-14, MeI, NaH, THF | 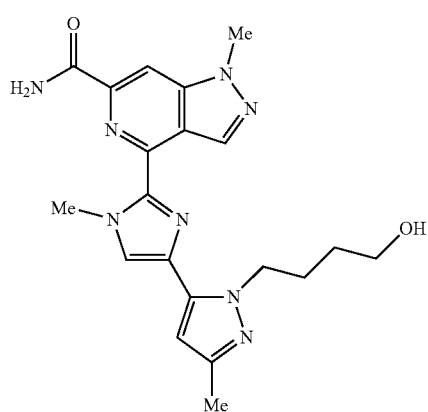 [SMILES: Cc1cc(-c2cn(C)c(-c3nc(C(N)=O)cc4c3cnn4C)n2)n(CCCCO)n1]<br>4-{4-[1-(4-hydroxybutyl)-3-methyl-1H-pyrazol-5-yl]-1-methyl-1H-imidazol-2-yl}-1-methyl-1H-pyrazolo[4,3-c]pyridine-6-carboxamide | LCMS [M + H] = 409.1 observed; $^1$H NMR (DMSO-$d_6$) δ 8.74 (s, 1H), 8.36 (s, 1H), 7.94 (br s, 1H), 7.89 (br s, 1H), 7.85 (s, 1H), 6.32 (s, 1H), 4.56 (t, J = 7.3 Hz, 2H), 4.39 (t, J = 5.1 Hz, 1H), 4.25 (s, 3H), 4.20 (s, 3H), 3.40-3.35 (m, 2H), 2.18 (s, 3H), 1.84 (br t, J = 7.3 Hz, 2H), 1.48-1.40 (m, 2H). |

Preparation of 1-methyl-4-[1-methyl-4-(3-methyl-1-propyl-1H-pyrazol-5-yl)-1H-imidazol-2-yl]-1H-pyrazolo[4,3-c]pyridine-6-carboxamide (Example AIF01) According to Scheme F Scheme F

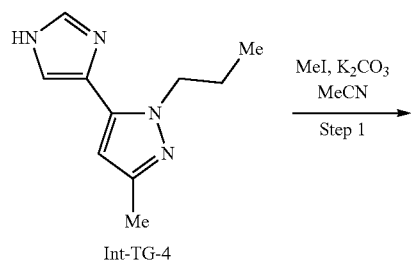

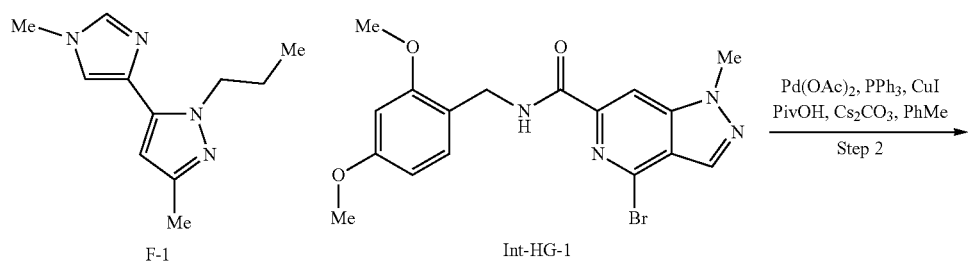

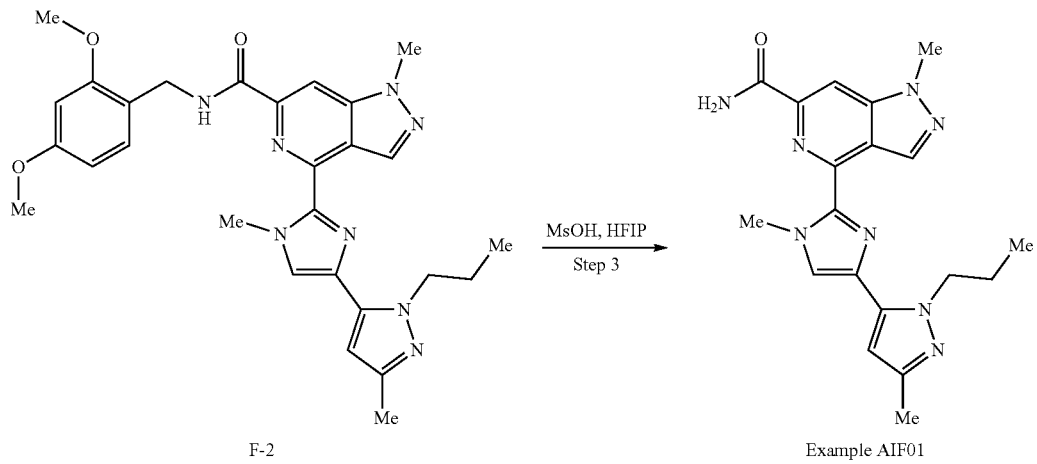

F-2            Example AIF01

Step 1: Synthesis of 3-methyl-5-(1-methyl-1H-imidazol-4-yl)-1-propyl-1H-pyrazole (F-1)

To reaction vessel containing 5-(1H-imidazol-4-yl)-3-methyl-1-propyl-1H-pyrazole (Int-TG-4) (417 mg, 1.33 mmol) was added $K_2CO_3$ (461 mg, 3.34 mmol), MeCN (10 mL). To the solution, was added MeI (91.4 µL, 1.47 mmol) drop-wise and the resulting yellow suspension stirred at 25° C. for 16 h. The solution was diluted with $H_2O$ (10 mL) and transferred to a separatory funnel with EtOAc. The phases were separated and the aqueous phase was extracted with 2 portions EtOAc (10 mL ea.). The combined organic extracts were concentrated under vacuum and the crude residue purified via preparatory TLC ($SiO_2$, 10% MeOH/DCM) to afford the title compound 3-methyl-5-(1-methyl-1H-imidazol-4-yl)-1-propyl-1H-pyrazole (F-1) (233 mg, 63%) as a yellow oil contaminated with minor impurities. This material was used in the next step without further purification. LCMS [M+H]=205.0 observed

Step 2: Synthesis of N-[(2,4-dimethoxyphenyl)methyl]-1-methyl-4-[1-methyl-4-(3-methyl-1-propyl-1H-pyrazol-5-yl)-1H-imidazol-2-yl]-1H-pyrazolo[4,3-c]pyridine-6-carboxamide (F-2)

To a reaction vessel containing 4-bromo-N-[(2,4-dimethoxyphenyl)methyl]-1-methyl-1H-pyrazolo[4,3-c]pyridine-6-carboxamide (Int-HG-1) (553 mg, 1.36 mmol) was added 3-methyl-5-(1-methyl-1H-imidazol-4-yl)-1-propyl-1H-pyrazole (F-1) (233 mg, 0.91 mmol), in PhMe (7 mL), was $Cs_2CO_3$ (874 mg, 2.68 mmol), PivOH (94.3 mg, 0.923 mmol), $PPh_3$ (59.2 mg, 0.226 mmol), CuI (34.3 mg, 0.180 mmol), and $Pd(OAc)_2$ (53.1 mg, 0.237 mmol). The resulting mixture was flushed with $N_2$ for 0.5 min, sealed, heated to 110° C., and stirred for 16h. The reaction was removed from heating and allowed to cool gradually to rt. The suspension was filtered and the filter cake washed with 2 portions DCM (10 mL ea.). The filtrate was concentrated under vacuum and the crude residue was purified via flash column chromatography ($SiO_2$, Isco, 0-3% MeOH/DCM) to afford the title compound N-[(2,4-dimethoxyphenyl)methyl]-1-methyl-4-[1-methyl-4-(3-methyl-1-propyl-1H-pyrazol-5-yl)-1H-imidazol-2-yl]-1H-pyrazolo[4,3-c]pyridine-6-carboxamide (F-2) (435 mg, 90%) as a yellow oil contaminated with minor impurities. This material was used in the next step without further purification. LCMS [M+H]=529.3 observed.

Step 3: Synthesis of 1-methyl-4-[1-methyl-4-(3-methyl-1-propyl-1H-pyrazol-5-yl)-1H-imidazol-2-yl]-1H-pyrazolo[4,3-c]pyridine-6-carboxamide (Example AIF01)

To a reaction vessel containing N-[(2,4-dimethoxyphenyl)methyl]-1-methyl-4-[1-methyl-4-(3-methyl-1-propyl-1H-pyrazol-5-yl)-1H-imidazol-2-yl]-1H-pyrazolo[4,3-c]pyridine-6-carboxamide (F-2) (435 mg, 0.51 mmol) was added HFIP (6 mL) and MsOH (490 mg, 5.10 mmol). The reaction was stirred at 25° C. for 1h during which the solution gradually turned purple. The solution was concentrated under vacuum and purified via prep-HPLC (Phenomenex Gemini-NX 80×40 mm×3 um column, 22-62% MeCN/$H_2O$ with 0.05% $NH_4OH$, 25 mL/min). Product containing fractions were lyophilized to afford the title compound 1-methyl-4-[1-methyl-4-(3-methyl-1-propyl-1H-pyrazol-5-yl)-1H-imidazol-2-yl]-1H-pyrazolo[4,3-c]pyridine-6-carboxamide (Example AIF01) (86 mg, 38%) as a white solid. LCMS [M+H]=379.0 observed; $^1$H NMR (400 MHz, DMSO-$d_6$) δ=8.73 (s, 1H), 8.35 (s, 1H), 7.93 (br s, 1H), 7.88 (br s, 1H), 7.84 (s, 1H), 6.31 (s, 1H), 4.50 (t, J=7.3 Hz, 2H), 4.24 (s, 3H), 4.19 (s, 3H), 2.18 (s, 3H), 1.84 (sxt, J=7.3 Hz, 2H), 0.89 (t, J=7.4 Hz, 3H).

The examples in the table below were prepared according to the methods used for the synthesis of 1-methyl-4-[1i-methyl-4-(3-methyl-1-propyl-1H-pyrazol-5-yl)-1H-imidazol-2-yl]-1H-pyrazolo[4,3-c]pyridine-6-carboxamide (Example AIF01) with non-critical changes or substitutions to the exemplified procedures that one skilled in the art would be able to realize.

| Example Number | Reagents used for step 1 | Structure/IUPAC Name | Analytical Data |
|---|---|---|---|
| AIF02 | Int-TG-5, MeI, K₂CO₃, MeCN | 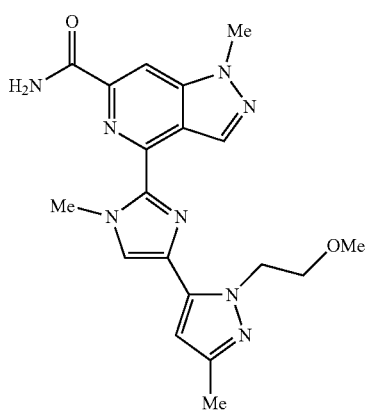 [SMILES: COCCn1nc(C)cc1-c1cn(C)c(-c2nc(C(N)=O)cc3c2cnn3C)n1]<br>4-{4-[1-(2-methoxyethyl)-3-methyl-1H-pyrazol-5-yl]-1-methyl-1H-imidazol-2-yl}-1-methyl-1H-pyrazolo[4,3-c]pyridine-6-carboxamide | LCMS [M + H] = 395.3 observed; $^1$H NMR (400 MHz, DMSO-d$_6$) δ = 8.79 (d, J = 0.8 Hz, 1H), 8.35 (d, J = 0.8 Hz, 1H), 7.93 (br s, 1H), 7.88 (br s, 1H), 7.86 (s, 1H), 6.32 (s, 1H), 4.73 (t, J = 6.3 Hz, 2H), 4.24 (s, 3H), 4.19 (s, 3H), 3.77 (t, J = 6.3 Hz, 2H), 3.23 (s, 3H), 2.18 (s, 3H). |
| AIF03 | Int-TG-6, MeI, K₂CO₃, MeCN | 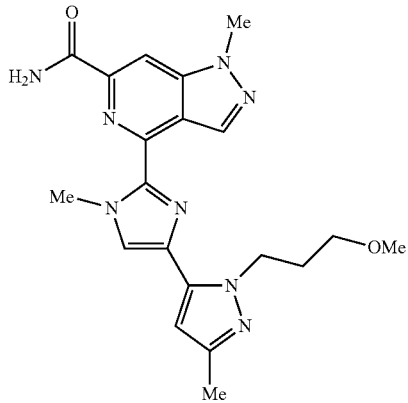 [SMILES: COCCCn1nc(C)cc1-c1cn(C)c(-c2nc(C(N)=O)cc3c2cnn3C)n1]<br>4-{4-[1-(3-methoxypropyl)-3-methyl-1H-pyrazol-5-yl]-1-methyl-1H-imidazol-2-yl}-1-methyl-1H-pyrazolo[4,3-c]pyridine-6-carboxamide | LCMS [M + H] = 409.3 observed; $^1$H NMR (400 MHz, DMSO-d$_6$ + D$_2$O) δ = 8.78 (s, 1H), 8.30 (s, 1H), 7.81 (s, 1H), 6.32 (s, 1H), 4.61 (br t, J = 7.2 Hz, 2H), 4.21 (s, 3H), 4.16 (s, 3H), 3.35 (t, J = 6.1 Hz, 2H), 3.18 (s, 3H), 2.17 (s, 3H), 2.03 (quin, J = 6.3 Hz, 2H). |

| Example Number | Reagents used for step 1 | Structure/IUPAC Name | Analytical Data |
|---|---|---|---|
| AIF04 | Int-TG-7, MeI, K₂CO₃, MeCN | 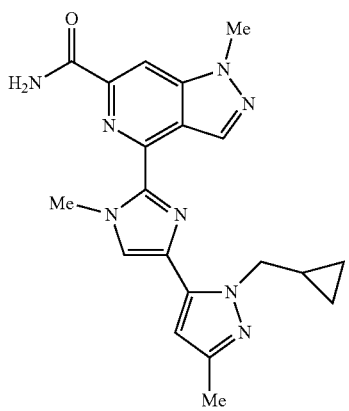 [SMILES: Cc1cc(-c2cn(C)c(-c3nc(C(N)=O)cc4c3cnn4C)n2)n(CC2CC2)n1]<br>4-{4-[1-(cyclopropylmethyl)-3-methyl-1H-pyrazol-5-yl]-1-methyl-1H-imidazol-2-yl}-1-methyl-1H-pyrazolo[4,3-c]pyridine-6-carboxamide | LCMS [M + H] = 391.2 observed: $^1$H NMR (400 MHz, DMSO-$d_6$) δ = 8.76 (s, 1H), 8.35 (s, 1H), 7.93 (brs, 1H), 7.90-7.84 (m, 2H), 6.32 (s, 1H), 4.46 (br d, J = 6.8 Hz, 2H), 4.24 (s, 3H), 4.19 (s, 3H), 2.18 (s, 3H), 1.44-1.31 (m, 1H), 0.53-0.42 (m, 2H), 0.41-0.33 (m, 2H). |
| AIF05 | Int-TG-8, MeI, K₂CO₃, MeCN | 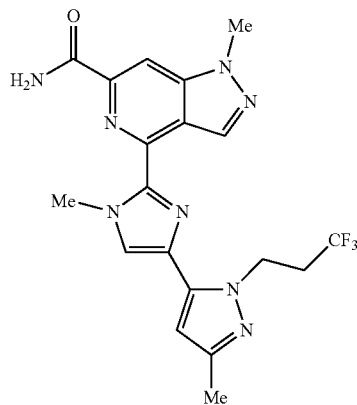 [SMILES: Cc1cc(-c2cn(C)c(-c3nc(C(N)=O)cc4c3cnn4C)n2)n(CCC(F)(F)F)n1]<br>1-methyl-4-{1-methyl-4-[3-methyl-1-(3,3,3-trifluoropropyl)-1H-pyrazol-5-yl]-1H-imidazol-2-yl}-1H-pyrazolo[4,3-c]pyridine-6-carboxamide | LCMS [M + H] = 433.2 observed; $^1$H NMR (400 MHz, DMSO-$d_6$) δ = 8.69 (s, 1H), 8.36 (s, 1H), 7.95 (brs, 1H), 7.90 (s, 1H), 7.88 (br s, 1H), 6.34 (s, 1H), 4.90 (t, J = 7.3 Hz, 2H), 4.23 (s, 3H), 4.19 (s, 3H), 2.99-2.83 (m, 2H), 2.19 (s, 3H). |

| Example Number | Reagents used for step 1 | Structure/IUPAC Name | Analytical Data |
|---|---|---|---|
| AIF06 | Int-TG-9, MeI, $K_2CO_3$, MeCN | 1-methyl-4-{1-methyl-4-[3-methyl-1-(2,2,2-trifluoroethyl)-1H-pyrazol-5-yl]-1H-imidazol-2-yl}-1H-pyrazolo[4,3-c]pyridine-6-carboxamide | LCMS [M + H] = 419.1 observed; $^1$H NMR (400 MHz, DMSO-$d_6$) δ = 8.65 (d, J = 0.9 Hz, 1H), 8.37 (d, J = 0.8 Hz, 1H), 7.98 (s, 1H), 7.96 (br s, 1H), 7.88 (br s, 1H), 6.47 (s, 1H), 5.65 (q, J = 9.1 Hz, 2H), 4.23 (s, 3H), 4.19 (s, 3H), 2.21 (s, 3H); $^{19}$F NMR (376 MHz, DMSO-$d_6$) δ = −68.99 (s, 3F). |

The examples in the table below were prepared according to the methods used in steps 2-3 for the synthesis of 1-methyl-4-[1-methyl-4-(3-methyl-1-propyl-1H-pyrazol-5-yl)-1H-imidazol-2-yl]-1H-pyrazolo[4,3-c]pyridine-6-carboxamide (Example AIF01) employing 1-ethyl-4-[(4-methoxyphenyl)methoxy]-3-methyl-5-(1-methyl-1H-imidazol-4-yl)-1H-pyrazole (Int-TG-10) as starting material with non-critical changes or substitutions to the exemplified procedures that one skilled in the art would be able to realize.

| Example Number | Structure/IUPAC Name | Analytical Data |
|---|---|---|
| AIF07 | 4-[4-(1-ethyl-4-hydroxy-3-methyl-1H-pyrazol-5-yl)-1-methyl-1H-imidazol-2-yl]-1-methyl-1H-pyrazolo[4,3-c]pyridine-6-carboxamide | LCMS [M + H] = 381.1 observed; $^1$H NMR (400 MHz, DMSO-$d_6$) δ = 8.70 (s, 1H), 8.34 (s, 1H), 8.09 (s, 1H), 7.93 (brs, 1H), 7.88 (br s, 1H), 7.78 (s, 1H), 4.54 (q, J = 6.9 Hz, 2H), 4.27 (s, 3H), 4.18 (s, 3H), 2.11 (s, 3H), 1.35 (t, J = 7.0 Hz, 3H). |

The examples in the table below were prepared according to the methods used in steps 2-3 for the synthesis of 1-methyl-4-[1-methyl-4-(3-methyl-1-propyl-1H-pyrazol-5-yl)-1H-imidazol-2-yl]-1H-pyrazolo[4,3-c]pyridine-6-carboxamide (Example AIF01) employing 4-chloro-1-ethyl-3-methyl-5-(1-methyl-1H-imidazol-4-yl)-1H-pyrazole (Int-TG-11) as starting material with non-critical changes or substitutions to the exemplified procedures that one skilled in the art would be able to realize.

| Example Number | Structure/IUPAC Name | Analytical Data |
|---|---|---|
| AIF08 | 4-[4-(4-chloro-1-ethyl-3-methyl-1H-pyrazol-5-yl)-1-methyl-1H-imidazol-2-yl]-1-methyl-1H-pyrazolo[4,3-c]pyridine-6-carboxamide | LCMS [M + H] = 399.1 observed; $^1$H NMR (400 MHz, DMSO-$d_6$) δ = 8.70 (s, 1H), 8.38 (s, 1H), 8.03 (s, 1H), 7.96 (br s, 1H), 7.89 (br s, 1H), 4.58 (q, J = 7.1 Hz, 2H), 4.29 (s, 3H), 4.19 (s, 3H), 2.19 (s, 3H), 1.40 (t, J = 7.1 Hz, 3H). |

The examples in the table below were prepared according to the methods used for the synthesis of 1-methyl-4-[1-methyl-4-(3-methyl-1-propyl-1H-pyrazol-5-yl)-1H-imidazol-2-yl]-1H-pyrazolo[4,3-c]pyridine-6-carboxamide (Example AIF01) with non-critical changes or substitutions to the exemplified procedures that one skilled in the art would be able to realize.

| Example Number | Reagents used for step 1 | Structure/IUPAC Name | Analytical Data |
|---|---|---|---|
| AIF09 | Int-TG-12, MeI, K₂CO₃, MeCN | 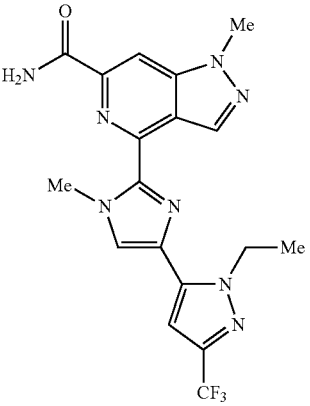 [SMILES: CCn1nc(C(F)(F)F)cc1-c1cn(C)c(-c2nc(C(N)=O)cc3c2cnn3C)n1]<br>4-{4-[1-ethyl-3-(trifluoromethyl)-1H-pyrazol-5-yl]-1-methyl-1H-imidazol-2-yl}-1-methyl-1H-pyrazolo[4,3-c]pyridine-6-carboxamide | LCMS [M + H] = 419.2 observed; ¹H NMR (DMSO-d₆) δ: 8.75 (d, J = 1.0 Hz, 1H), 8.38 (d, J = 1.0 Hz, 1H), 8.05 (s, 1H), 7.94 (br s, 1H), 7.89 (br s, 1H), 7.05 (s, 1H), 4.73 (q, J = 7.2 Hz, 2H), 4.26 (s, 3H), 4.19 (s, 3H), 1.47 (t, J = 7.2 Hz, 3H). |

The examples in the table below were prepared according to the methods used in steps 2-3 for the synthesis of 1-methyl-4-[1-methyl-4-(3-methyl-1-propyl-1H-pyrazol-5-yl)-1H-imidazol-2-yl]-1H-pyrazolo[4,3-c]pyridine-6-carboxamide (Example AIF01) with non-critical changes or substitutions to the exemplified procedures that one skilled in the art would be able to realize.

| Example Number | Starting Materials | Structure/IUPAC Name | Analytical Data |
|---|---|---|---|
| AIF10 | Int-TG-16, Int-HG-1 | 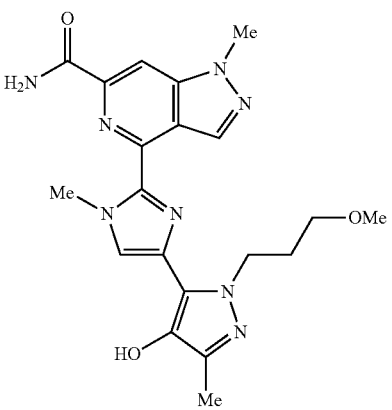 [SMILES: COCCCn1nc(C)c(O)c1-c1cn(C)c(-c2nc(C(N)=O)cc3c2cnn3C)n1]<br>4-{4-[4-hydroxy-1-(3-methoxypropyl)-3-methyl-1H-pyrazol-5-yl]-1-methyl-1H-imidazol-2-yl}-1-methyl-1H-pyrazolo[4,3-c]pyridine-6-carboxamide | LCMS [M + H] = 425.3 observed; ¹H NMR (DMSO-d₆) δ: 8.78 (d, J = 1.0 Hz, 1H), 8.34 (d, J = 0.9 Hz, 1H), 8.11 (s, 1H), 7.94 (br s, 1H), 7.87 (br s, 1H), 7.79 (s, 1H), 4.61 (t, J = 7.2 Hz, 2H), 4.27 (s, 3H), 4.19 (s, 3H), 3.20 (s, 3H), 2.12 (s, 3H), 1.96-2.05 (m, 2H) (22H out of 24H observed). |

| Example Number | Starting Materials | Structure/IUPAC Name | Analytical Data |
|---|---|---|---|
| AIF11 | Int-TG-17, Int-HG-1 | 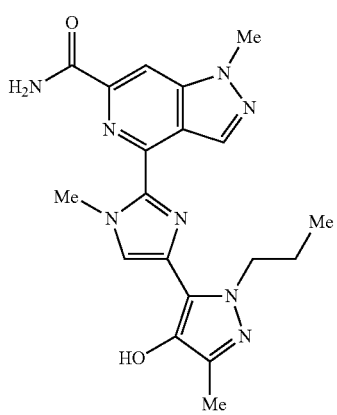 [SMILES: CCCn1nc(C)c(O)c1-c1cn(C)c(-c2nc(C(N)=O)cc3c2cnn3C)n1]<br>4-[4-(4-hydroxy-3-methyl-1-propyl-1H-pyrazol-5-yl)-1-methyl-1H-imidazol-2-yl]-1-methyl-1H-pyrazolo[4,3-c]pyridine-6-carboxamide | LCMS [M + H] = 395.4 observed; $^1$H NMR (DMSO-$d_6$) δ: 8.71 (d, J = 0.9 Hz, 1H), 8.34 (d, J = 1.0 Hz, 1H), 8.09 (s, 1H), 7.93 (br s, 1H), 7.86 (br s, 1H), 7.78 (s, 1H), 4.44-4.53 (m, 2H), 4.26 (s, 3H), 4.18 (s, 3H), 2.11 (s, 3H), 1.74-1.85 (m, 2H), 0.86 (t, J = 7.3 Hz, 3H). |

The examples in the table below were prepared according to the methods used for the synthesis of 1-methyl-4-[1i-methyl-4-(3-methyl-1-propyl-1H-pyrazol-5-yl)-1H-imidazol-2-yl]-1H-pyrazolo[4,3-c]pyridine-6-carboxamide (Example AIF01) with non-critical changes or substitutions to the exemplified procedures that one skilled in the art would be able to realize.

The examples in the table below were prepared according to the methods used in steps 2-3 for the synthesis of 1-methyl-4-[1-methyl-4-(3-methyl-1-propyl-1H-pyrazol-5-yl)-1H-imidazol-2-yl]-1H-pyrazolo[4,3-c]pyridine-6-carboxamide (Example AIF01) with non-critical changes or substitutions to the exemplified procedures that one skilled in the art would be able to realize.

| Example Number | Reagents used for step 1 | Structure/IUPAC Name | Analytical Data |
|---|---|---|---|
| AIF12 | Int-TG-19, MeI, K$_2$CO$_3$, MeCN | 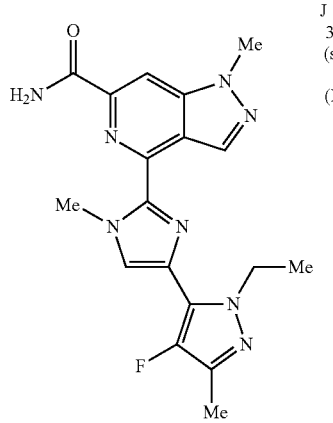<br>4-[4-(1-ethyl-4-fluoro-3-methyl-1H-pyrazol-5-yl)-1-methyl-1H-imidazol-2-yl]-1-methyl-1H-pyrazolo[4,3-c]pyridine-6-carboxamide | LCMS [M + H] = 383.3 observed; $^1$H NMR (DMSO-$d_6$) δ: 8.70 (s, 1H), 8.37 (s, 1H), 7.82-7.98 (m, 3H), 4.55 (q, J = 7.1 Hz, 2H), 4.28 (s, 3H), 4.19 (s, 3H), 2.18 (s, 3H), 1.39 (t, J = 7.1 Hz, 3H); $^{19}$F NMR (DMSO-$d_6$) δ: −176.15 (s, 1F). |

| Example Number | Starting Materials | Structure/IUPAC Name | Analytical Data |
|---|---|---|---|
| AIF13 | Int-TG-21, Int-HG-1 | 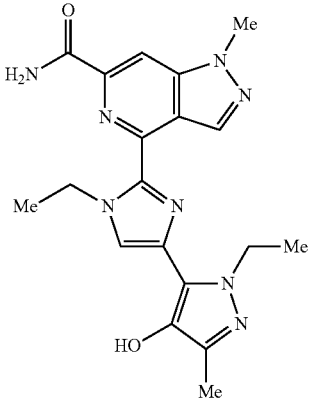 [SMILES: CCn1cc(-c2c(O)c(C)nn2CC)nc1-c1nc(C(N)=O)cc2c1cnn2C]<br>4-[1-ethyl-4-(1-ethyl-4-hydroxy-3-methyl-1H-pyrazol-5-yl)-1H-imidazol-2-yl]-1-methyl-1H-pyrazolo[4,3-c]pyridine-6-carboxamide | LCMS [M + H] = 395.2 observed; $^1$H NMR (DMSO-$d_6$) δ: 8.72 (s, 1H), 8.35 (s, 1H), 8.09 (s, 1H), 7.91 (br s, 1H), 7.83 (s, 1H), 7.74 (br s, 1H), 4.79 (q, J = 7.3 Hz, 2H), 4.54 (q, J = 7.0 Hz, 2H), 4.19 (s, 3H), 2.11 (s, 3H), 1.44 (t, J = 7.0 Hz, 3H), 1.36 (t, J = 7.3 Hz, 3H). |

The examples in the table below were prepared according to the methods used for the synthesis of 1-methyl-4-[1-methyl-4-(3-methyl-1-propyl-1H-pyrazol-5-yl)-1H-imidazol-2-yl]-1H-pyrazolo[4,3-c]pyridine-6-carboxamide (Example AIF01) with non-critical changes or substitutions to the exemplified procedures that one skilled in the art would be able to realize.

| Example Number | Reagents used for step 1 | Structure/IUPAC Name | Analytical Data |
|---|---|---|---|
| AIF14 | Int-TG-22, MeI, NaH, THF | 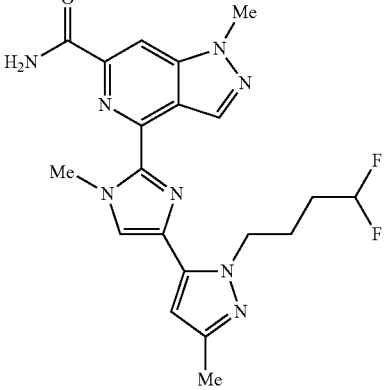<br>4-{4-[1-(4,4-difluorobutyl)-3-methyl-1H-pyrazol-5-yl]-1-methyl-1H-imidazol-2-yl}-1-methyl-1H-pyrazolo[4,3-c]pyridine-6-carboxamide | LCMS [M + H] = 429.3 observed; $^1$H NMR (CHLOROFORM-d) δ: 8.84 (s, 1H), 8.31 (s, 1H), 7.74 (br s, 1H), 7.29 (s, 1H), 6.23 (s, 1H), 5.88 (br s, 1H), 5.77 (tt, J = 57.0, 4.3 Hz, 1H), 4.72 (t, J = 6.9 Hz, 2H), 4.27 (s, 3H), 4.20 (s, 3H), 2.32 (s, 3H), 2.06-2.17 (m, 2H), 1.81-1.96 (m, 2H); $^{19}$F NMR (CHLOROFORM-d) δ: −115.83 (s, 1F). |

| Example Number | Reagents used for step 1 | Structure/IUPAC Name | Analytical Data |
|---|---|---|---|
| AIF15 | Int-TG-26, MeI, NaH, THF | (structure shown)<br><br>4-{4-[1-(3-cyanopropyl)-3-methyl-1H-pyrazol-5-yl]-1-methyl-1H-imidazol-2-yl}-1-methyl-1H-pyrazolo[4,3-c]pyridine-6-carboxamide | LCMS [M + H] = 404.2 observed; $^1$H NMR (DMSO-$d_6$) δ: 8.71 (d, J = 0.9 Hz, 1H), 8.34-8.37 (m, 1H), 7.93 (br s, 1H), 7.84-7.88 (m, 2H), 6.35 (s, 1H), 4.59 (t, J = 6.7 Hz, 2H), 4.23 (s, 3H), 4.17-4.21 (m, 3H), 2.09-2.22 (m, 5H) (19H out of 21H observed). |

Preparation of 4-[4-(1-ethyl-3-methyl-1H-pyrazol-5-yl)-1-methyl-1H-imidazol-2-yl]-1-methyl-1H-pyrazolo[3,4-d]pyrimidine-6-carboxamide (Example AIG01) According to Scheme G

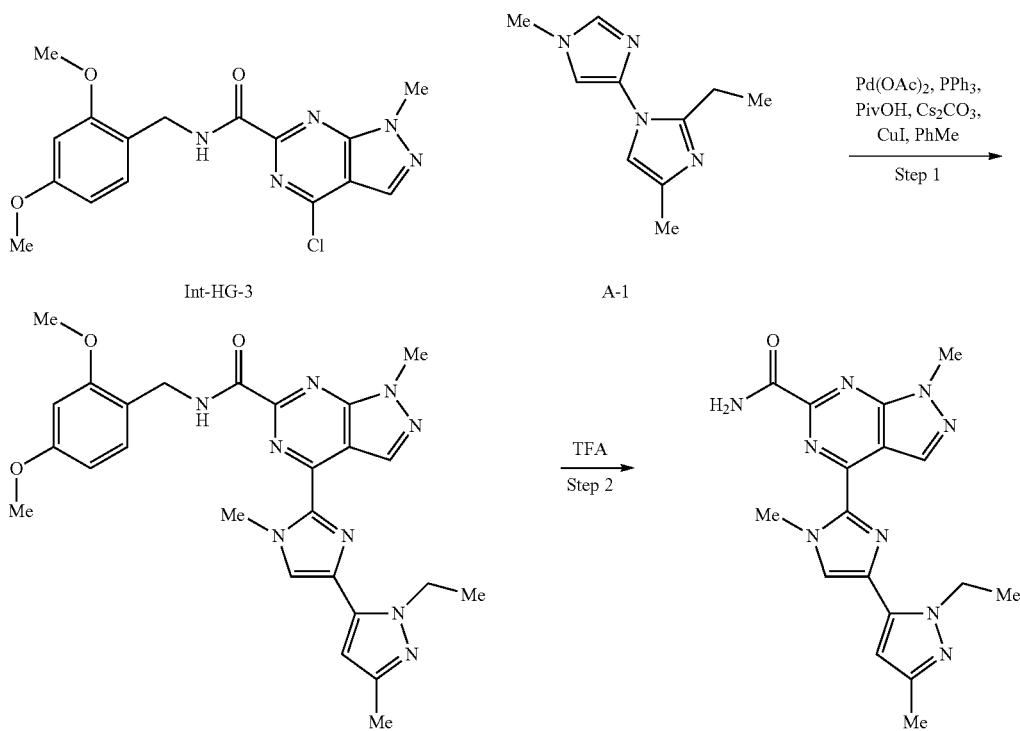

Scheme G

Step 1: Synthesis of N-[(2,4-dimethoxyphenyl)methyl]-4-[4-(1-ethyl-3-methyl-1H-pyrazol-5-yl)-1-methyl-1H-imidazol-2-yl]-1-methyl-1H-pyrazolo[3,4-d]pyrimidine-6-carboxamide (G-1)

To a solution of 4-chloro-N-[(2,4-dimethoxyphenyl)methyl]-1-methyl-1H-pyrazolo[3,4-d]pyrimidine-6-carboxamide (Int-HG-3) (173 mg, 0.478 mmol) and 1-ethyl-3-methyl-5-(1-methyl-1H-imidazol-4-yl)-1H-pyrazole (A-1) (70 mg, 0.37 mmol) in PhMe (3.8 mL), was added $Cs_2CO_3$ (360 mg, 1.10 mmol), $Pd(OAc)_2$ (25 mg, 0.110 mmol), $PPh_3$ (29 mg, 0.110 mmol), CuI (21 mg, 0.110 mmol), and PivOH (78 mg, 0.736 mmol). The reaction mixture was heated at 110° C. for 2h. The reaction was removed from heating and allowed to cool to room temperature. The solution was diluted with DCM (30 mL), filtered over Celite, and the Celite cake washed with 10% MeOH in DCM (30 mL). The filtrate was concentrated under reduced pressure and the crude residue purified by column chromatography (12 g $SiO_2$, MeOH/DCM 1:10) to afford the title compound N-[(2,4-dimethoxyphenyl)methyl]-4-[4-(1-ethyl-3-methyl-1H-pyrazol-5-yl)-1-methyl-1H-imidazol-2-yl]-1-methyl-1H-pyrazolo[3,4-d]pyrimidine-6-carboxamide (G-1) (22 mg, 12%) as yellow oil. LC/MS m/z 516 [M+1].

Step 2: Synthesis of 4-[4-(1-ethyl-3-methyl-1H-pyrazol-5-yl)-1-methyl-1H-imidazol-2-yl]-1-methyl-1H-pyrazolo[3,4-d]pyrimidine-6-carboxamide (AIG01)

To a reaction flask containing N-(2,4-dimethoxybenzyl)-4-(4-(1-ethyl-3-methyl-1H-pyrazol-5-yl)-1-methyl-1H-imidazol-2-yl)-1-methyl-1H-pyrazolo[3,4-d] pyrimidine-6-carboxamide (G-1) (22 mg, 0.041 mmol) was added TFA (1.0 mL). The reaction was heated at 35° C. overnight. The reaction mixture was concentrated under reduced pressure and then azeotropically distilled with PhMe. The crude residue was dissolved in DMSO (0.7 mL) purified via reversed phase chromatography to afford the title compound 4-[4-(1-ethyl-3-methyl-1H-pyrazol-5-yl)-1-methyl-1H-imidazol-2-yl]-1-methyl-1H-pyrazolo[3,4-d]pyrimidine-6-carboxamide (AIG01) (2.6 mg, 17%) as a white solid. LC/MS m/z 366 [M+1].

Preparation of Examples AIH01-AIH19 According to Scheme H

Scheme H

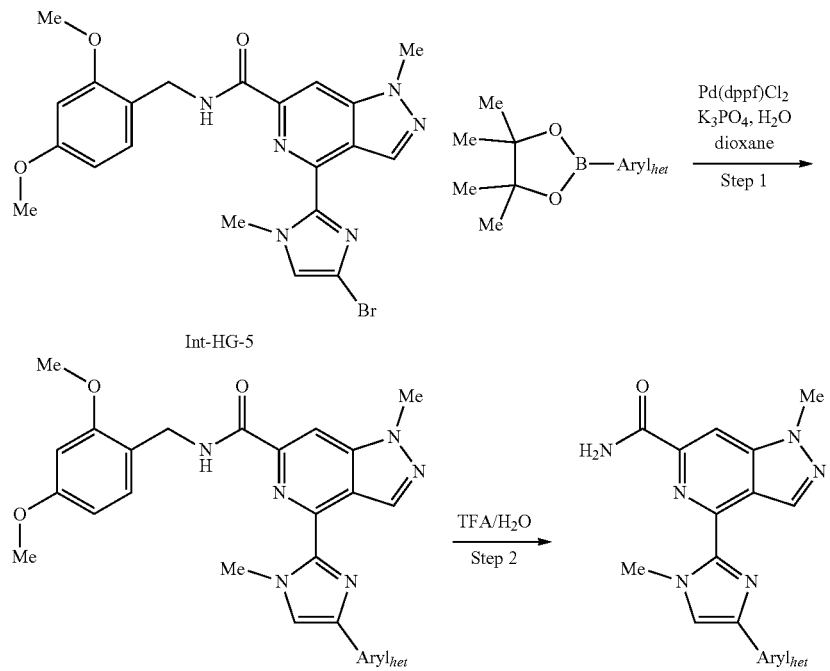

Step 1: Suzuki Cross-Coupling General Procedure

To each reaction vial was added the appropriate commercially available heteroaryl boronate ester (120 μM, 1.2 eq.) followed by addition of 4-(4-bromo-1-methyl-1H-imidazol-2-yl)-N-[(2,4-dimethoxyphenyl)methyl]-1-methyl-1H-pyrazolo[4,3-c]pyridine-6-carboxamide (Int-HG-5) (100 μmol of a 0.125 M solution in dioxane, 1.0 eq.), $K_3PO_4$ (300 μmol of a 1.5 M solution in water, 3.0 eq.) and $Pd(dppf)Cl_2$ (5 μmol, 0.05 eq.) under inert atmosphere. The vials were capped, heated to 100° C., and agitated for 16h. The reaction solutions were concentrated by Speedvac and the vials diluted with $H_2O$ (1 mL ea.). The aqueous solutions were extracted with 3 portions of EtOAc (1 mL ea.). The combined organic extracts were collected and concentrated by Speedvac.

Step 2: Amide Deprotection General Procedure

To each reaction vial containing a unique intermediate from step 1 was added a solution of TFA/$H_2O$ (10:1). The vials were capped, heated to 80° C., and agitated for 16h. The reaction solutions were concentrated by Speedvac and the crude residues purified via prep-HPLC to afford examples AIH01-AIH19.

| Example Number | Structure | IUPAC Name | Analytical Data |
|---|---|---|---|
| AIH01 | 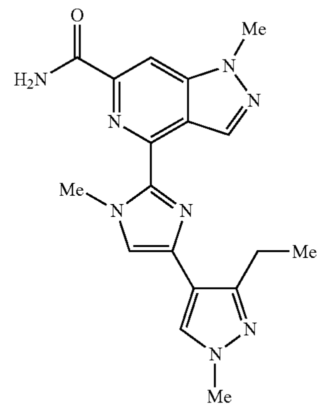 [SMILES: CCc1nn(C)cc1-c1cn(C)c(-c2nc(C(N)=O)cc3c2cnn3C)n1] | 4-[4-(3-ethyl-1-methyl-1H-pyrazol-4-yl)-1-methyl-1H-imidazol-2-yl]-1-methyl-1H-pyrazolo[4,3-c]pyridine-6-carboxamide | LCMS [M + H] = 365 observed |
| AIH02 | 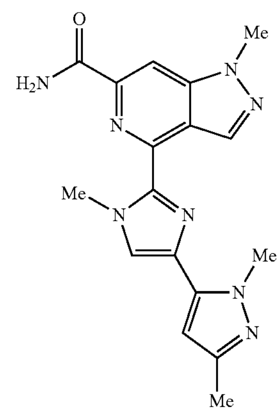 [SMILES: Cc1cc(-c2cn(C)c(-c3nc(C(N)=O)cc4c3cnn4C)n2)n(C)n1] | 4-[4-(1,3-dimethyl-1H-pyrazol-5-yl)-1-methyl-1H-imidazol-2-yl]-1-methyl-1H-pyrazolo[4,3-c]pyridine-6-carboxamide | LCMS [M + H] = 351 observed |
| AIH03 | 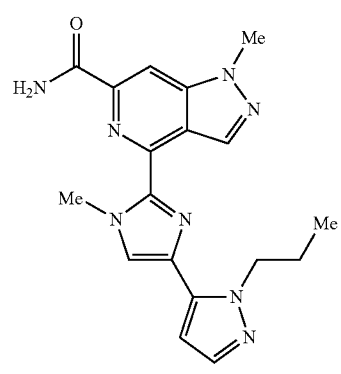 [SMILES: CCCn1nccc1-c1cn(C)c(-c2nc(C(N)=O)cc3c2cnn3C)n1] | 1-methyl-4-[1-methyl-4-(1-propyl-1H-pyrazol-5-yl)-1H-imidazol-2-yl]-1H-pyrazolo[4,3-c]pyridine-6-carboxamide | LCMS [M + H] = 365 observed |

-continued

| Example Number | Structure | IUPAC Name | Analytical Data |
|---|---|---|---|
| AIH04 | 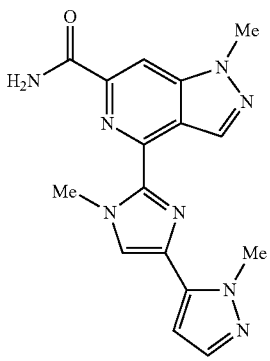 [SMILES: Cn1cc(-c2ccnn2C)nc1-c1nc(C(N)=O)cc2c1cnn2C] | 1-methyl-4-[1-methyl-4-(1-methyl-1H-pyrazol-5-yl)-1H-imidazol-2-yl]-1H-pyrazolo[4,3-c]pyridine-6-carboxamide | LCMS [M + H] = 337 observed |
| AIH05 | 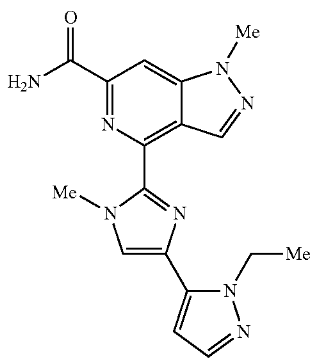 [SMILES: CCn1nccc1-c1cn(C)c(-c2nc(C(N)=O)cc3c2cnn3C)n1] | 4-[4-(1-ethyl-1H-pyrazol-5-yl)-1-methyl-1H-imidazol-2-yl]-1-methyl-1H-pyrazolo[4,3-c]pyridine-6-carboxamide | LCMS [M + H] = 351 observed |
| AIH06 | 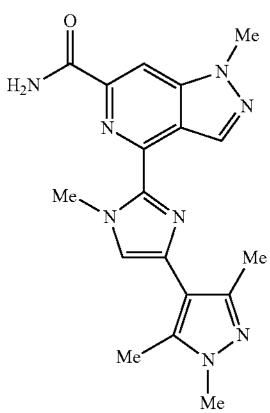 [SMILES: Cc1nn(C)c(C)c1-c1cn(C)c(-c2nc(C(N)=O)cc3c2cnn3C)n1] | 1-methyl-4-[1-methyl-4-(1,3,5-trimethyl-1H-pyrazol-4-yl)-1H-imidazol-2-yl]-1H-pyrazolo[4,3-c]pyridine-6-carboxamide | LCMS [M + H] = 365 observed |
| AIH07 | 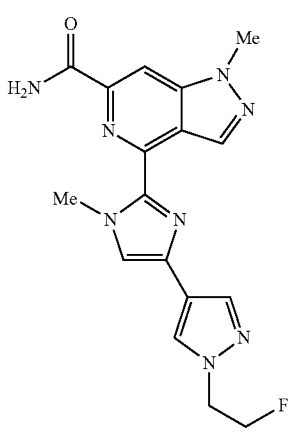 [SMILES: Cn1cc(-c2cnn(CCF)c2)nc1-c1nc(C(N)=O)cc2c1cnn2C] | 4-{4-[1-(2-fluoroethyl)-1H-pyrazol-4-yl]-1-methyl-1H-imidazol-2-yl}-1-methyl-1H-pyrazolo[4,3-c]pyridine-6-carboxamide | LCMS [M + H] = 369 observed |

-continued

| Example Number | Structure | IUPAC Name | Analytical Data |
|---|---|---|---|
| AIH08 | 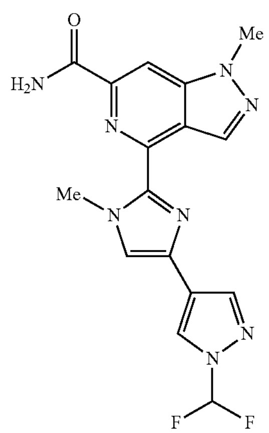 [SMILES: Cn1cc(-c2cnn(C(F)F)c2)nc1-c1nc(C(N)=O)cc2c1cnn2C] | 4-{4-[1-(difluoromethyl)-1H-pyrazol-4-yl]-1-methyl-1H-imidazol-2-yl}-1-methyl-1H-pyrazolo[4,3-c]pyridine-6-carboxamide | LCMS [M + H] = 373 observed |
| AIH09 | 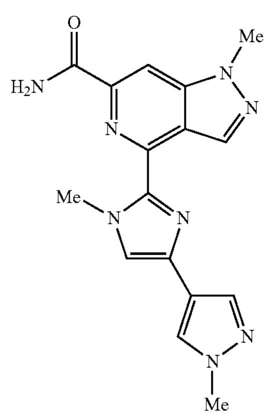 [SMILES: Cn1cc(-c2cn(C)c(-c3nc(C(N)=O)cc4c3cnn4C)n2)cn1] | 1-methyl-4-[1-methyl-4-(1-methyl-1H-pyrazol-4-yl)-1H-imidazol-2-yl]-1H-pyrazolo[4,3-c]pyridine-6-carboxamide | LCMS [M + H] = 337 observed |
| AIH10 | 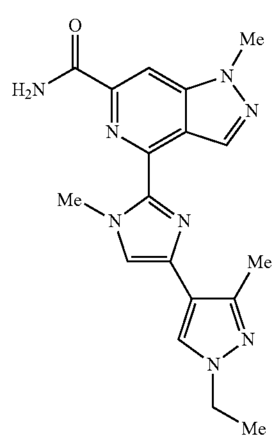 [SMILES: CCn1cc(-c2cn(C)c(-c3nc(C(N)=O)cc4c3cnn4C)n2)c(C)n1] | 4-[4-(1-ethyl-3-methyl-1H-pyrazol-4-yl)-1-methyl-1H-imidazol-2-yl]-1-methyl-1H-pyrazolo[4,3-c]pyridine-6-carboxamide | LCMS [M + H] = 365 observed |

| Example Number | Structure | IUPAC Name | Analytical Data |
|---|---|---|---|
| AIH11 | 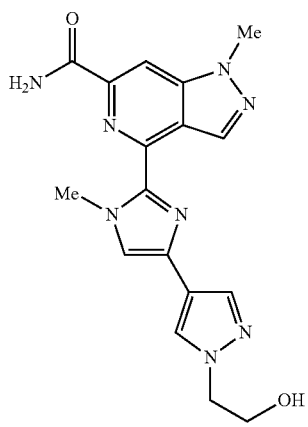 [SMILES: Cn1cc(-c2cnn(CCO)c2)nc1-c1nc(C(N)=O)cc2c1cnn2C] | 4-{4-[1-(2-hydroxyethyl)-1H-pyrazol-4-yl]-1-methyl-1H-imidazol-2-yl}-1-methyl-1H-pyrazolo[4,3-c]pyridine-6-carboxamide | LCMS [M + H] = 368 observed |
| AIH12 | 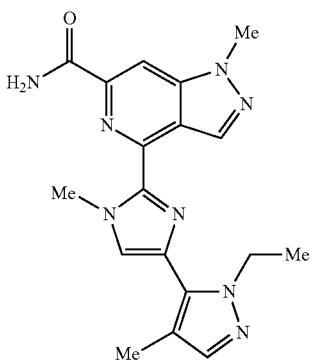 [SMILES: CCn1ncc(C)c1-c1cn(C)c(-c2nc(C(N)=O)cc3c2cnn3C)n1] | 4-[4-(1-ethyl-4-methyl-1H-pyrazol-5-yl)-1-methyl-1H-imidazol-2-yl]-1-methyl-1H-pyrazolo[4,3-c]pyridine-6-carboxamide | LCMS [M + H] = 365 observed |
| AIH13 | 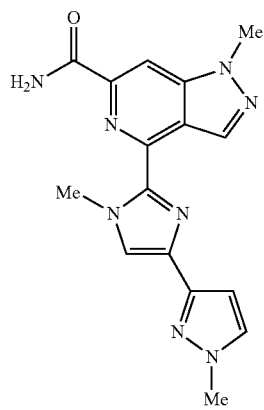 | 1-methyl-4-[1-methyl-4-(1-methyl-1H-pyrazol-3-yl)-1H-imidazol-2-yl]-1H-pyrazolo[4,3-c]pyridine-6-carboxamide | LCMS [M + H] = 337 observed |

-continued

| Example Number | Structure | IUPAC Name | Analytical Data |
|---|---|---|---|
| AIH14 | 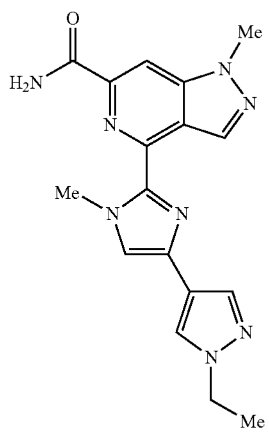 [SMILES: CCn1cc(-c2cn(C)c(-c3nc(C(N)=O)cc4c3cnn4C)n2)cn1] | 4-[4-(1-ethyl-1H-pyrazol-4-yl)-1-methyl-1H-imidazol-2-yl]-1-methyl-1H-pyrazolo[4,3-c]pyridine-6-carboxamide | LCMS [M + H] = 351 observed |
| AIH15 | 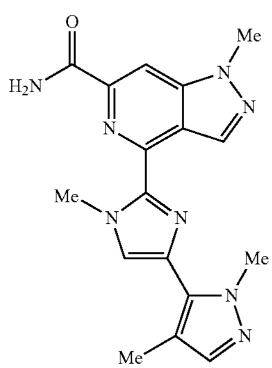 [SMILES: Cc1cnn(C)c1-c1cn(C)c(-c2nc(C(N)=O)cc3c2cnn3C)n1] | 4-[4-(1,4-dimethyl-1H-pyrazol-5-yl)-1-methyl-1H-imidazol-2-yl]-1-methyl-1H-pyrazolo[4,3-c]pyridine-6-carboxamide | LCMS [M + H] = 351 observed |
| AIH16 | 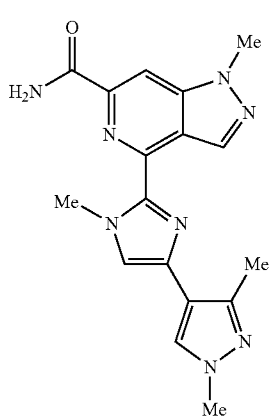 [SMILES: Cc1nn(C)cc1-c1cn(C)c(-c2nc(C(N)=O)cc3c2cnn3C)n1] | 4-[4-(1,3-dimethyl-1H-pyrazol-4-yl)-1-methyl-1H-imidazol-2-yl]-1-methyl-1H-pyrazolo[4,3-c]pyridine-6-carboxamide | LCMS [M + H] = 351 observed |

-continued
| Example Number | Structure | IUPAC Name | Analytical Data |
|---|---|---|---|
| AIH17 | 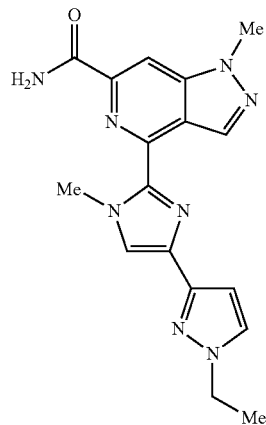 [SMILES: CCn1ccc(-c2cn(C)c(-c3nc(C(N)=O)cc4c3cnn4C)n2)n1] | 4-[4-(1-ethyl-1H-pyrazol-3-yl)-1-methyl-1H-imidazol-2-yl]-1-methyl-1H-pyrazolo[4,3-c]pyridine-6-carboxamide | LCMS [M + H] = 351 observed |
| AIH18 | 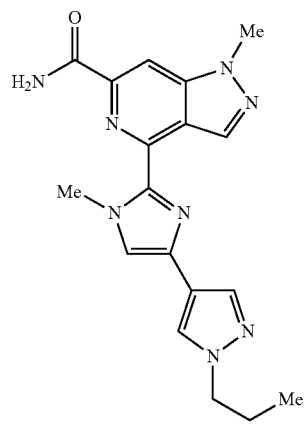 [SMILES: CCCn1cc(-c2cn(C)c(-c3nc(C(N)=O)cc4c3cnn4C)n2)cn1] | 1-methyl-4-[1-methyl-4-(1-propyl-1H-pyrazol-4-yl)-1H-imidazol-2-yl]-1H-pyrazolo[4,3-c]pyridine-6-carboxamide | LCMS [M + H] = 365 observed |

| Example Number | Structure | IUPAC Name | Analytical Data |
|---|---|---|---|
| AIH19 | 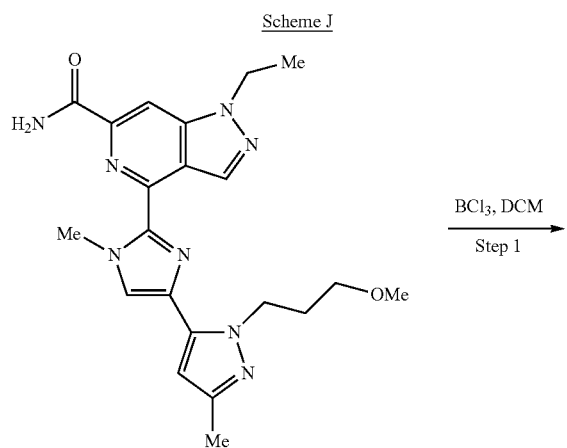 | 1-methyl-4-{1-methyl-4-[1-(propan-2-yl)-1H-pyrazol-5-yl]-1H-imidazol-2-yl}-1H-pyrazolo[4,3-c]pyridine-6-carboxamide | LCMS [M + H] = 365 observed |

Preparation of 1-ethyl-4-{4-[1-(3-hydroxypropyl)-3-methyl-1H-pyrazol-5-yl]-1-methyl-1H-imidazol-2-yl}-1H-pyrazolo[4,3-c]pyridine-6-carboxamide (Example AIJ01) According to Scheme J

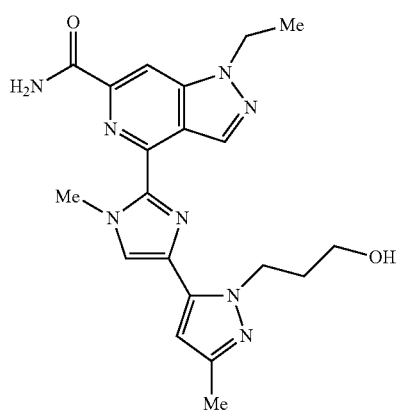

Step 1: Synthesis of 1-ethyl-4-{4-[1-(3-hydroxypropyl)-3-methyl-1H-pyrazol-5-yl]-1-methyl-1H-imidazol-2-yl}-1H-pyrazolo[4,3-c]pyridine-6-carboxamide (Example AIJ01)

To a yellow solution of 1-ethyl-4-{4-[1-(3-methoxypropyl)-3-methyl-1H-pyrazol-5-yl]-1-methyl-1H-imidazol-2-yl}-1H-pyrazolo[4,3-c]pyridine-6-carboxamide (AIC03) (120 mg, 0.284 mmol) in DCM (6 mL), cooled with an ice water bath, was added $BCl_3$ (99.8 mg, 0.852 mmol) drop-wise under $N_2$. The resulting yellow suspension was allowed to warm gradually to room temperature (20° C.) with stirring for 48h. LCMS analysis indicated the reaction was not complete thus the solution was cooled in an ice-water batch and an additional aliquot of $BCl_3$ (99.8 mg, 0.852 mmol) was added drop-wise under $N_2$. The ice-bath was removed and the resulting yellow suspension was allowed to warm gradually to room temperature (20° C.) with stirring for 21 h. LCMS analysis indicated the reaction was not complete thus the solution was cooled in an ice-water batch and an additional aliquot of $BCl_3$ (166 mg, 1.42 mmol) was added drop-wise under $N_2$. The ice-bath was removed and the resulting yellow suspension was allowed to warm gradually to room temperature (20° C.) with stirring for 21h. The reaction mixture was cooled to 0° C., quenched with MeOH (2 mL), basified with $NH_3$/MeOH (7 M) to pH 7-8, then warmed to room temperature and stirred for 30 mins. The resulting solution was concentrated under vacuum. The crude residue was diluted with water (5 mL) and transferred to a separatory funnel. The solution was extracted with 2 portions DCM/MeOH (10:1, 5 mL). The combined organic extracts were washed with brine (5 mL), dried over anhydrous $Na_2SO_4$, filtered, and concentrated under vacuum to afford the crude product as a yellow solid. The crude residue was purified by Prep.TLC (silica gel, DCM:MeOH=10:1, Rf~0.3) to furnish a light yellow solid which was further lyophilized for 16h to afford the title compound 1-ethyl-4-{4-[1-(3-hydroxypropyl)-3-methyl-1H-pyrazol-5-yl]-1-methyl-1H-imidazol-2-yl}-1H-pyrazolo[4,3-c]pyridine-6-carboxamide (Example AIJ01) (15.78 mg, 14%) as a light yellow solid. LCMS [M+H]=409.2 observed; $^1$H NMR (DMSO-$d_6$) δ: 8.80 (s, 1H), 8.38 (s, 1H), 7.84-8.01 (m, 3H), 6.32 (s, 1H), 4.55-4.68 (m, 4H), 4.23 (s, 3H), 3.46 (q, J=5.3 Hz, 2H), 2.19 (s, 3H), 1.93-2.03 (i, 2H), 1.45 (t, J=7.3 Hz, 3H).

The example in the table below was prepared according to the methods used in steps 1-3 of scheme C followed by the procedure used in scheme J for the synthesis of 1-ethyl-4-{4-[E-(3-hydroxypropyl)-3-methyl-1H-pyrazol-5-yl]-1-methyl-1H-imidazol-2-yl}-H-pyrazolo[4,3-c]pyridine-6-carboxamide (Example AIJ01) with non-critical changes or substitutions to the exemplified procedures that one skilled in the art would be able to realize.

| Example Number | Starting materials used for step 1 | Structure/IUPAC Name | Analytical Data |
|---|---|---|---|
| AIJ02 | Int-HG-6, E-1 | 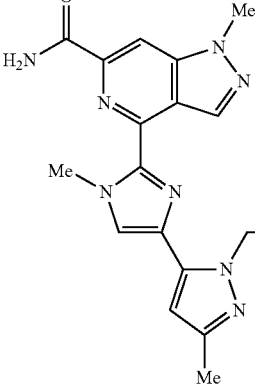<br>4-{4-[1-(3-hydroxypropyl)-3-methyl-1H-pyrazol-5-yl]-1-methyl-1H-imidazol-2-yl}-1-methyl-1H-pyrrolo[3,2-c]pyridine-6-carboxamide | LCMS [M + H] = 394.2 observed; $^1$H NMR (DMSO-$d_6$) δ: 8.23 (s, 1H), 7.90 (br s, 1 H), 7.77 (s, 1H), 7.68 (d, J = 3.3 Hz, 1H), 7.66 (br s, 1H), 7.27 (d, J = 3.0 Hz, 1H), 6.28 (s, 1H), 4.55-4.64 (m, 3H), 4.17 (s, 3H), 3.95 (s, 3H), 3.44 (q, J = 6.2 Hz, 2H), 2.18 (s, 3H), 1.96 (quin, J = 6.8 Hz, 2H). |

Preparation of 4-{1-ethyl-4-[1-(3-methoxypropyl)-3-methyl-1H-pyrazol-5-yl]-1H-imidazol-2-yl}-1-methyl-1H-pyrazolo[4,3-c]pyridine-6-carboxamide (Example AIK01) According to Scheme K

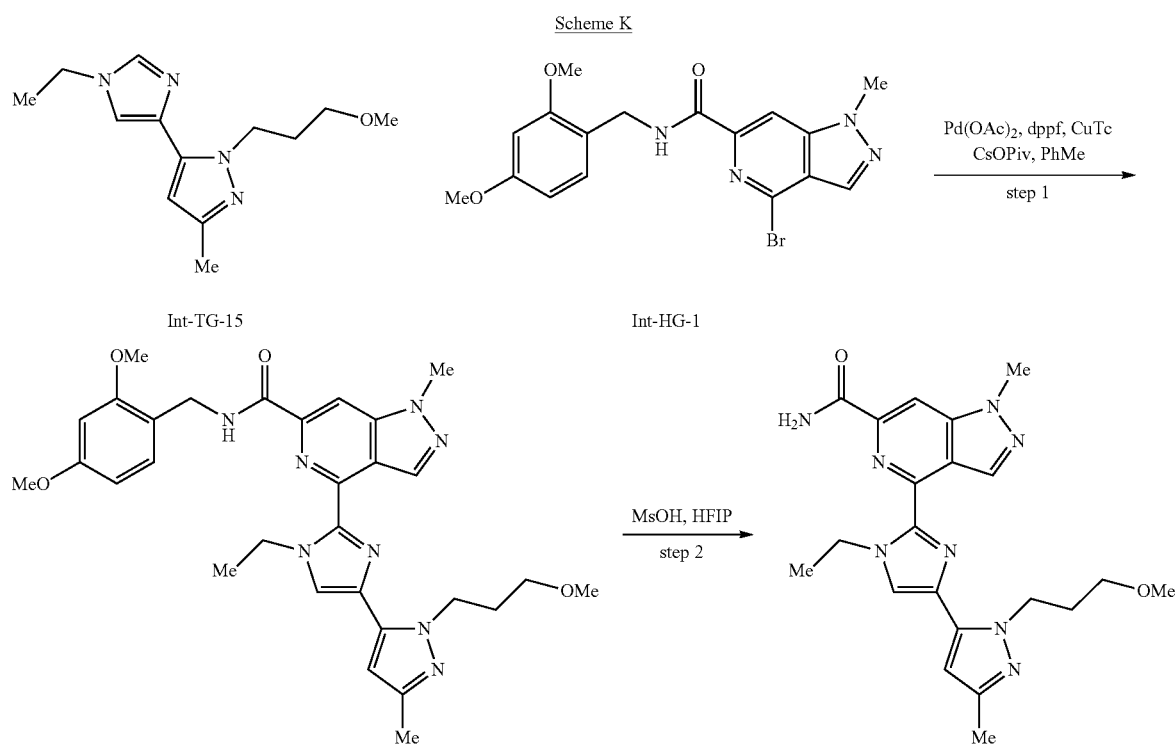

Step 1: Synthesis of N-[(2,4-dimethoxyphenyl)methyl]-4-{1-ethyl-4-[1-(3-methoxypropyl)-3-methyl-1H-pyrazol-5-yl]-1H-imidazol-2-yl}-1-methyl-1H-pyrazolo[4,3-c]pyridine-6-carboxamide (K-1)

To a solution of 5-(1-ethyl-1H-imidazol-4-yl)-1-(3-methoxypropyl)-3-methyl-1H-pyrazole (Int-TG-15) (510 mg, 2.05 mmol) and 4-bromo-N-[(2,4-dimethoxyphenyl)methyl]-1-methyl-1H-pyrazolo[4,3-c]pyridine-6-carboxamide (Int-HG-1) (916 mg, 2.26 mmol) in anhydrous toluene (16 mL) was added Pd(OAc)$_2$ (46 mg, 0.205 mmol), dppf (228 mg, 0.411 mmol), ((thiophene-2-carbonyl)oxy)copper (157 mg, 0.823 mmol), and cesium pivalate (961 mg, 4.11 mmol). The mixture was flushed with N$_2$ for 2 min, sealed, heated to 100° C., and stirred for 16 h. The reaction was then filtered, concentrated under vacuum, diluted with CH$_2$Cl$_2$, filtered, and concentrated under vacuum. The crude residue was purified via flash column chromatography (20 g SiO$_2$, Combi-flash, 20-80% CH$_2$Cl$_2$/EtOAc) to afford the title compound N-[(2,4-dimethoxyphenyl)methyl]-4-{1-ethyl-4-[1-(3-methoxypropyl)-3-methyl-1H-pyrazol-5-yl]-1H-imidazol-2-yl}-1-methyl-1H-pyrazolo[4,3-c]pyridine-6-carboxamide (K-1) (1.067 g, 91%) as a brown gum. LCMS [M+H]=573.2 observed; $^1$H NMR (CHLOROFORM-d) δ: 8.92 (s, 1H), 8.24 (s, 1H), 8.09 (br t, J=5.7 Hz, 1H), 7.29 (s, 1H), 7.23 (s, 1H), 6.42-6.48 (m, 2H), 6.22 (s, 1H), 4.54-4.68 (m, 6H), 4.13 (s, 3H), 3.82 (s, 3H), 3.78 (s, 3H), 3.40 (t, J=6.1 Hz, 2H), 3.25 (s, 3H), 2.28 (s, 3H), 2.11-2.23 (m, 2H), 1.40 (t, J=7.2 Hz, 3H).

Step 2: Synthesis of 4-{1-ethyl-4-[1-(3-methoxypropyl)-3-methyl-1H-pyrazol-5-yl]-1H-imidazol-2-yl}-1-methyl-1H-pyrazolo[4,3-c]pyridine-6-carboxamide (Example AIK01)

To a solution of N-[(2,4-dimethoxyphenyl)methyl]-4-{1-ethyl-4-[1-(3-methoxypropyl)-3-methyl-1H-pyrazol-5-yl]-1H-imidazol-2-yl}-1-methyl-1H-pyrazolo[4,3-c]pyridine-6-carboxamide (K-1) (1.067 g, 1.86 mmol) in HFIP (15 mL) was added methanesulfonic acid (895 mg, 9.32 mmol) at room temperature and stirred for 1 h. The reaction was then basified to pH=8 with NH$_3$/MeOH, concentrated under vacuum, diluted with CH$_2$Cl$_2$, filtered, and concentrated under vacuum. The crude residue was purified via flash column chromatography (40 g SiO$_2$, Combi-flash, 97-100% CH$_2$Cl$_2$/MeOH), then repurified via flash column chromatography (40 g SiO$_2$, Combi-flash, 97-100% CH$_2$Cl$_2$/MeOH). The material was then dried by lyophilization, triturated with MTBE (50 mL) for 3 h, and the solid collected via filtration. The material was again purified via flash column chromatography (40 g SiO$_2$, Combi-flash, 99-100% EtOAc/MeOH) to afford compound 4-{1-ethyl-4-[1-(3-methoxypropyl)-3-methyl-1H-pyrazol-5-yl]-1H-imidazol-2-yl}-1-methyl-1H-pyrazolo[4,3-c]pyridine-6-carboxamide (Example AIK01) (559 mg, 56%)) as a gray solid. LCMS [M+H]=423.3 observed. $^1$H NMR (DMSO-d$_6$) δ: 8.80 (d, J=0.8 Hz, 1H), 8.36 (d, J=0.9 Hz, 1H), 7.89-7.93 (m, 2H), 7.75 (br s, 1H), 6.33 (s, 1H), 4.75 (q, J=7.3 Hz, 2H), 4.62 (t, J=7.3 Hz, 2H), 4.19 (s, 3H), 3.36 (t, J=6.1 Hz, 2H), 3.19 (s, 3H), 2.18 (s, 3H), 2.01-2.09 (m, 2H), 1.45 (t, J=7.2 Hz, 3H).

Preparation of 4-(4-{1-[3-(difluoromethoxy)propyl]-3-methyl-1H-pyrazol-5-yl}-1-methyl-1H-imidazol-2-yl)-1-methyl-1H-pyrazolo[4,3-c]pyridine-6-carboxamide (Example AIL01) According to Scheme L

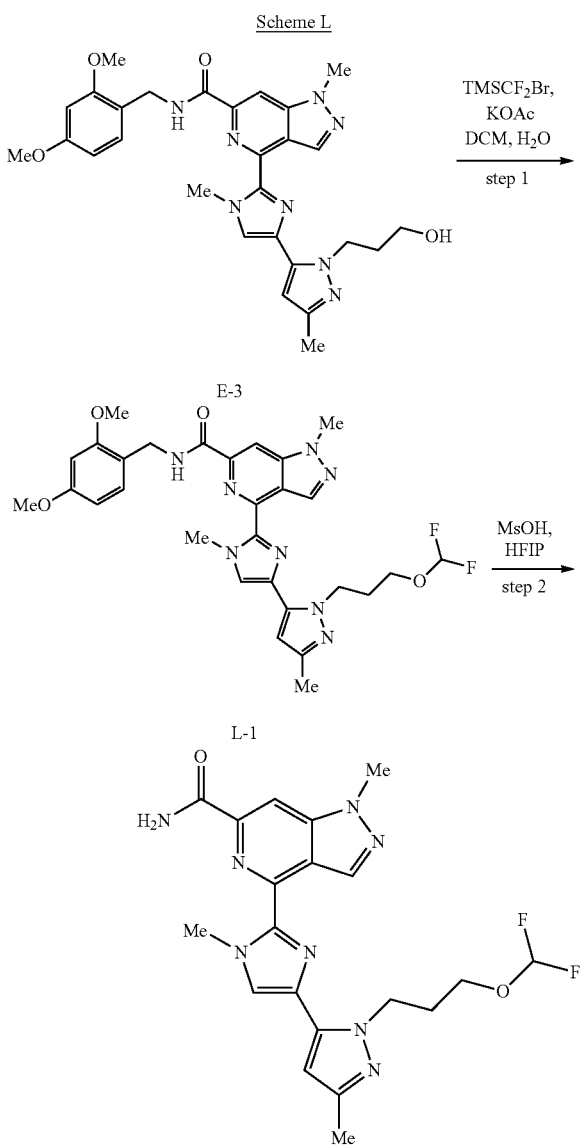

Scheme L

Example AIL01

Step 1: Synthesis of 4-(4-{1-[3-(difluoromethoxy)propyl]-3-methyl-1H-pyrazol-5-yl}-1-methyl-1H-imidazol-2-yl)-N-[(2,4-dimethoxyphenyl)methyl]-1-methyl-1H-pyrazolo[4,3-c]pyridine-6-carboxamide (L-1)

To a solution of N-[(2,4-dimethoxyphenyl)methyl]-4-{4-[1-(3-hydroxypropyl)-3-methyl-1H-pyrazol-5-yl]-1-methyl-1H-imidazol-2-yl}-1-methyl-1H-pyrazolo[4,3-c]pyridine-6-carboxamide (E-3) (195 mg, 0.358 mmol) in CH$_2$Cl$_2$ (0.4 mL) was added (bromodifluoromethyl)trimethylsilane (73 mg, 0.36 mmol) and KOAc (70 mg, 0.72 mmol) in H$_2$O (0.4 mL) and stirred at 18° C. for 16 h. To the reaction was then added MeOH and concentrated under vacuum. The residue was taken up in CH₂Cl₂ (15 mL) and H₂O (25 mL) and the phases were separated. The aqueous phase was collected and concentrated under vacuum to give 4-(4-{1-[3-(difluoromethoxy)propyl]-3-methyl-1H-pyrazol-5-yl}-1-methyl-1H-imidazol-2-yl)-N-[(2,4-dimethoxyphenyl)methyl]-1-methyl-1H-pyrazolo[4,3-c]pyridine-6-carboxamide (L-1) (170 mg) as a brown solid, which was used without further purification. LCMS [M+H]=595.4 observed.

Step 2: Synthesis of 4-(4-{1-[3-(difluoromethoxy)propyl]-3-methyl-1H-pyrazol-5-yl}-1-methyl-1H-imidazol-2-yl)-1-methyl-1H-pyrazolo[4,3-c]pyridine-6-carboxamide Formic Acid Salt (Example AIL01)

To a solution of 4-(4-{1-[3-(difluoromethoxy)propyl]-3-methyl-1H-pyrazol-5-yl}-1-methyl-1H-imidazol-2-yl)-N-[(2,4-dimethoxyphenyl)methyl]-1-methyl-1H-pyrazolo[4,3-c]pyridine-6-carboxamide (L-1) (250 mg) in HFIP (2.5 mL) was added methanesulfonic acid (402 mg, 4.18 mmol) at room temperature (18° C.) and stirred for 1.5 h. The crude mixture was purified via prep-HPLC (Boston Prime C18 150×30 mm×5 um column, 2-42% MeCN/H₂O with formic acid (0.225%), 25 mL/min) to afford 4-(4-{1-[3-(difluoromethoxy)propyl]-3-methyl-1H-pyrazol-5-yl}-1-methyl-1H-imidazol-2-yl)-1-methyl-1H-pyrazolo[4,3-c]pyridine-6-carboxamide formic acid salt (AIL01) (38 mg, 17% over two batches) as a white solid. LCMS [M+H]=445.4 observed. $^1$H NMR (METHANOL-d₄) δ: 8.80 (s, 1H), 8.52 (s, 1H), 8.42 (br s, 2H), 8.22 (t, J=54.0 Hz, 1H), 7.26 (s, 1H), 5.48 (t, J=7.5 Hz, 2H), 4.37 (s, 3H), 4.23 (s, 3H), 3.66 (t, J=5.8 Hz, 2H), 2.74 (s, 3H), 2.14-2.26 (m, 2H); $^{19}$F NMR (METHANOL-d₄) δ: −97.73 (s, 1F).

Preparation of 1-methyl-4-[1-methyl-4-(3-methyl-1-{[(2R)-oxetan-2-yl]methyl}-1H-pyrazol-5-yl)-1H-imidazol-2-yl]-1H-pyrazolo[4,3-c]pyridine-6-carboxamide (Example AIM01) According to Scheme M

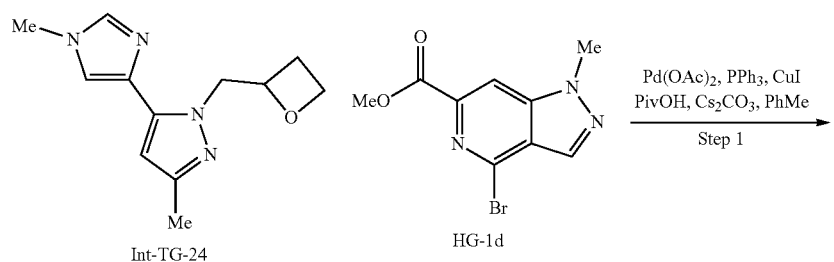

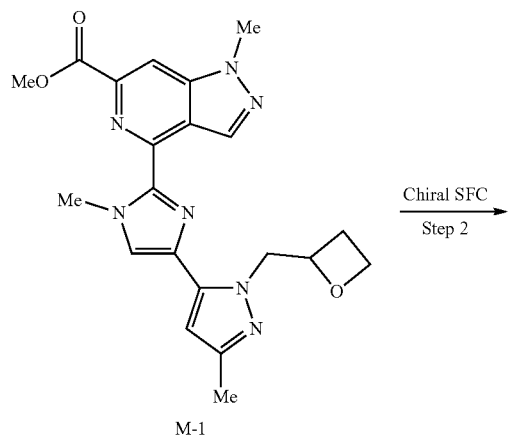

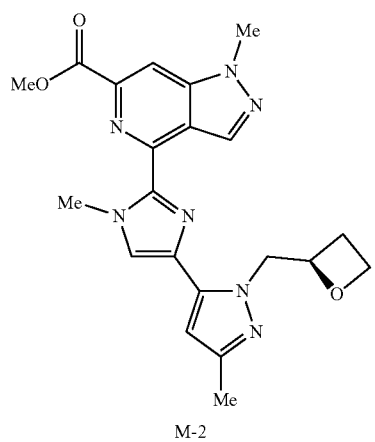

M-2

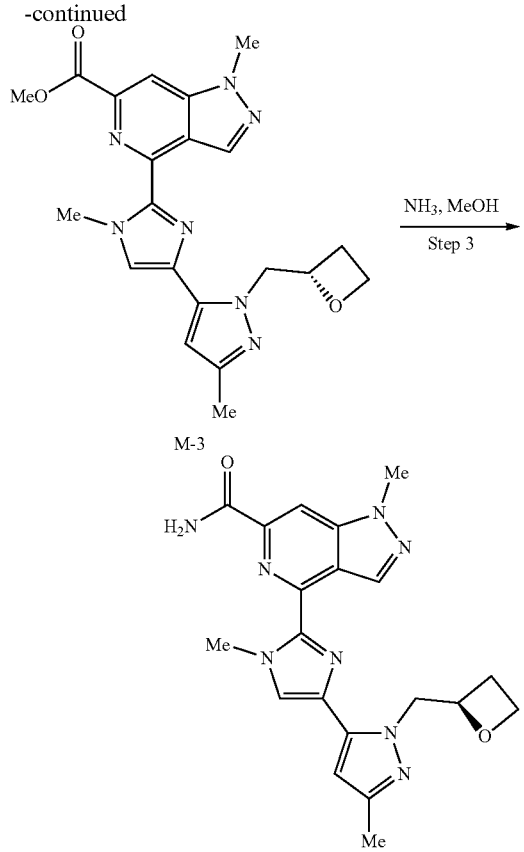

Example AIM01

Step 1: Synthesis of (Rac)-methyl 1-methyl-4-(1-methyl-4-{3-methyl-1-[(oxetan-2-yl)methyl]-1H-pyrazol-5-yl}-1H-imidazol-2-yl)-1H-pyrazolo[4,3-c]pyridine-6-carboxylate (M-1)

A reaction vessel was charged with (Rac)-3-methyl-5-(1-methyl-1H-imidazol-4-yl)-1-[(oxetan-2-yl)methyl]-1H-pyrazole (Int-TG-24) (297.8 mg, 1.28 mmol), methyl 4-bromo-1-methyl-1H-pyrazolo[4,3-c]pyridine-6-carboxylate (HG-1d) (519 mg, 1.92 mmol), Pd(OAc)$_2$ (57.6 mg, 0.256 mmol), CuI (48.8 mg, 0.256 mmol), PPh$_3$ (67.3 mg, 0.256 mmol), Cs$_2$CO$_3$ (1250 mg, 3.85 mmol), PivOH (157 mg, 1.54 mmol), and PhMe (8 mL). The solution was flushed with N$_2$ for 2 min, sealed, and heated to 110° C. for 20h. The reaction was removed from heating and gradually cooled to room temperature. The suspension was filtered and the filtrate concentrated under vacuum. The crude residue was purified via prep-HPLC (Boston Prime C18150×30 mm×5 μm column, 20-60% MeCN/H$_2$O (0.05% NH$_4$OH v/v), 25 mL/min) to afford the title compound (Rac)-methyl 1-methyl-4-(1-methyl-4-{3-methyl-1-[(oxetan-2-yl)methyl]-1H-pyrazol-5-yl}-1H-imidazol-2-yl)-1H-pyrazolo[4,3-c]pyridine-6-carboxylate (M-1) (80 mg, 15%) as a white solid. LCMS [M+H]=422.3 observed; $^1$H NMR (400 MHz, METHANOL-d$_4$) δ=8.76 (s, 1H), 8.27 (s, 1H), 7.61 (s, 1H), 6.36 (s, 1H), 5.27 (quin, J=6.4 Hz, 1H), 5.00 (dd, J=6.2, 14.1 Hz, 1H), 4.83-4.80 (m, 1H), 4.68-4.62 (m, 1H), 4.55-4.48 (m, 1H), 4.30 (s, 3H), 4.15 (s, 3H), 4.01 (s, 3H), 2.77-2.60 (m, 2H), 2.27 (s, 3H).

Step 2: Synthesis of methyl 1-methyl-4-[1-methyl-4-(3-methyl-1-{[(2R)-oxetan-2-yl]methyl}-1H-pyrazol-5-yl)-1H-imidazol-2-yl]-1H-pyrazolo[4,3-c]pyridine-6-carboxylate (M-2) and methyl 1-methyl-4-[1-methyl-4-(3-methyl-1-{[(2S)-oxetan-2-yl]methyl}-1H-pyrazol-5-yl)-1H-imidazol-2-yl]-1H-pyrazolo[4,3-c]pyridine-6-carboxylate (M-3)

A racemic mixture of (Rac)-methyl 1-methyl-4-(1-methyl-4-{3-methyl-1-[(oxetan-2-yl)methyl]-1H-pyrazol-5-yl}-1H-imidazol-2-yl)-1H-pyrazolo[4,3-c]pyridine-6-carboxylate (M-1) (90 mg, 0.214 mmol) was purified by chiral prep-SFC (Daicel Chiralpak IC 250 mm*30 mm, 10 μm column, 50% EtOH (0.1% NH$_4$OH)/CO$_2$, 80 mL/min) to afford the title compounds methyl 1-methyl-4-[1-methyl-4-(3-methyl-1-{[(2R)-oxetan-2-yl]methyl}-1H-pyrazol-5-yl)-1H-imidazol-2-yl]-1H-pyrazolo[4,3-c]pyridine-6-carboxylate (M-2) (40 mg, 44%) LCMS [M+H]=422.3 observed and methyl 1-methyl-4-[1-methyl-4-(3-methyl-1-{[(2S)-oxetan-2-yl]methyl}-1H-pyrazol-5-yl)-1H-imidazol-2-yl]-1H-pyrazolo[4,3-c]pyridine-6-carboxylate (M-3) (50 mg, 56%) LCMS [M+H]=422.3 observed as white solids respectively. The absolute stereochemistry of the enantiomers was arbitrarily assigned (1$^{st}$ eluting peak (R) and 2$^{nd}$ eluting peak (S)).

Step 3: Synthesis of 1-methyl-4-[1-methyl-4-(3-methyl-1-{[(2R)-oxetan-2-yl]methyl}-1H-pyrazol-5-yl)-1H-imidazol-2-yl]-1H-pyrazolo[4,3-c]pyridine-6-carboxamide (Example AIM01)

The reaction vessel containing methyl 1-methyl-4-[1-methyl-4-(3-methyl-1-{[(2R)-oxetan-2-yl]methyl}-1H- pyrazol-5-yl)-1H-imidazol-2-yl]-1H-pyrazolo[4,3-c]pyridine-6-carboxylate (M-2) (40.0 mg, 0.0949 mmol) was added in NH₃ (7 M solution in MeOH) (5 mL, 30 mmol). The reaction was stirred at 20° C. for 18 h and then concentrated under vacuum. The crude residue was purified via prep-HPLC (Phenomenex Gemini-NX 80*40 mm*3 μm column, 13-53% MeCN/H₂O (0.05% NH₄OH v/v), 25 mL/min) to afford the title compound 1-methyl-4-[1-methyl-4-(3-methyl-1-{[(2R)-oxetan-2-yl]methyl}-1H-pyrazol-5-yl)-1H-imidazol-2-yl]-1H-pyrazolo[4,3-c]pyridine-6-carboxamide (Example AIM01) (28 mg, 73%) as a white solid. LCMS [M+H]=407.4 observed; ¹H NMR (400 MHz, METHANOL-d₄) δ=8.80 (d, J=1.0 Hz, 1H), 8.31 (d, J=1.0 Hz, 1H), 7.68 (s, 1H), 6.38 (s, 1H), 5.28 (quin, J=6.3 Hz, 1H), 5.00 (dd, J=6.3, 14.3 Hz, 1H), 4.85-4.79 (m, 1H), 4.68-4.62 (m, 1H), 4.50 (td, J=6.0, 9.0 Hz, 1H), 4.27 (s, 3H), 4.19 (s, 3H), 2.78-2.58 (m, 2H), 2.28 (s, 3H).

The example in the table below was prepared according to the methods used in step 3 of scheme M for the synthesis of 1-methyl-4-[1-methyl-4-(3-methyl-1-{[(2R)-oxetan-2-yl]methyl}-1H-pyrazol-5-yl)-1H-imidazol-2-yl]-1H-pyrazolo[4,3-c]pyridine-6-carboxamide (Example AIM01) with non-critical changes or substitutions to the exemplified procedures that one skilled in the art would be able to realize.

| Example Number | Starting materials used | Structure/IUPAC Name | Analytical Data |
|---|---|---|---|
| AIM02 | M-3 | 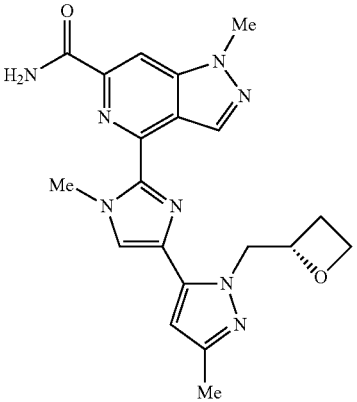 [SMILES: Cc1cc(-c2cn(C)c(-c3nc(C(N)=O)cc4c3cnn4C)n2)n(C[C@@H]2CCO2)n1]<br>1-methyl-4-[1-methyl-4-(3-methyl-1-{[(2S)-oxetan-2-yl]methyl}-1H-pyrazol-5-yl)-1H-imidazol-2-yl]-1H-pyrazolo[4,3-c]pyridine-6-carboxamide | LCMS [M + H] = 407.4 observed; ¹H NMR (METHANOL-d₄) δ: 8.81 (s, 1H), 8.31 (s, 1H), 7.68 (s, 1H), 6.38 (s, 1H), 5.23-5.32 (m, 1H), 4.96-5.04 (m, 1H), 4.81-4.85 (m, 1H), 4.62-4.67 (m, 1H), 4.47-4.54 (m, 1H), 4.27 (s, 3H), 4.19 (s, 3H), 2.59-2.77 (m, 2H), 2.28 (s, 3H). |

Preparation of 1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine-6-carboxamide (Example AIN01) According to Scheme N

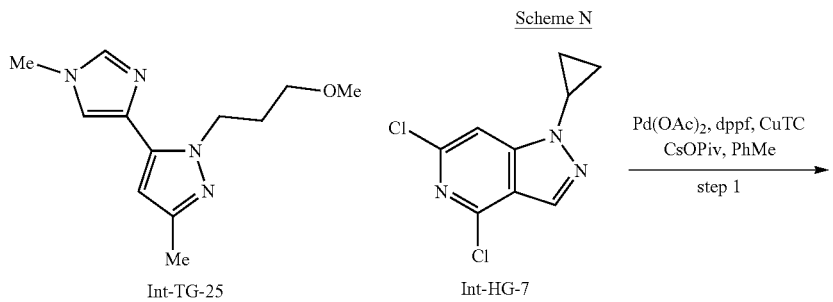

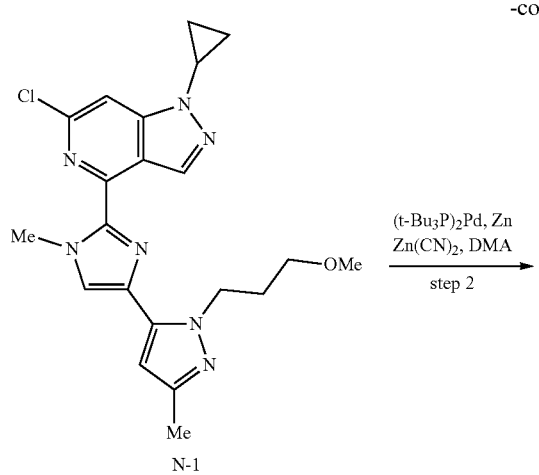

N-1

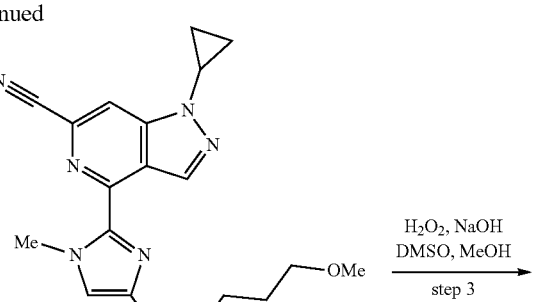

N-2

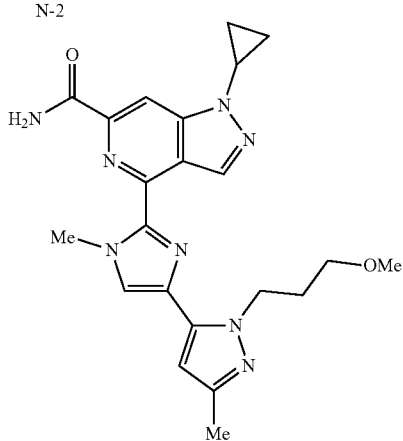

Example AIN01

Step 1: Synthesis of 6-chloro-1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine (N-1)

To a yellow solution of 4,6-dichloro-1-cyclopropyl-1H-pyrazolo[4,3-c]pyridine (Int-HG-7) (129.4 mg, 0.567 mmol) and 1-(3-methoxypropyl)-3-methyl-5-(1-methyl-1H-imidazol-4-yl)-1H-pyrazole (Int-TG-25) (160 mg, 0.681 mmol) in anhydrous toluene (3 mL) was added Pd(OAc)$_2$ (25.5 mg, 0.113 mmol), dppf (62.9 mg, 0.113 mmol), Copper(I) thiophene-2-carboxylate (CuTC) (43.3 mg, 0.227 mmol) and CsOPiv (266 mg, 1.13 mmol). The resulting mixture was flushed with N$_2$ for 2 min, sealed, and heated to 100° C. (heating block) for 16 h. The reaction was removed from the heating block and cooled gradually to room temperature. The solution was diluted with 10% MeOH/DCM, filtered through a pad of Celite, and the filtrate concentrated under vacuum. The crude residue was purified via flash column chromatography (20 g SiO$_2$, 12-75% EtOAc/Pet Ether) to afford the title compound 6-chloro-1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine (N-1) (160 mg, 66%) as a yellow gum. $^1$H NMR (400 MHz, CHLOROFORM-d) δ=8.84 (s, 1H), 7.44 (d, J=0.8 Hz, 1H), 7.28 (s, 1H), 6.24 (s, 1H), 4.69 (t, J=7.2 Hz, 2H), 4.25 (s, 3H), 3.64-3.55 (m, 1H), 3.43 (t, J=6.1 Hz, 2H), 3.29 (s, 3H), 2.31 (s, 3H), 2.24-2.15 (m, 2H), 1.25-1.21 (m, 4H).

Step 2: Synthesis of 1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine-6-carbonitrile (N-2)

To a solution of 6-chloro-1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine (N-1) (160 mg, 0.376 mmol) and Zn powder (21.1 mg, 0.323 mmol), (t-Bu$_3$P)$_2$Pd (38.4 mg, 0.0751 mmol) in DMA (2 mL) was added Zn(CN)$_2$ (90.0 mg, 0.766 mmol). The resulting mixture was flushed with N$_2$ for 2 min, sealed, heated to 120° C., and stirred for 18 h. The reaction was removed from the heating block and cooled to room temperature gradually. The solution was diluted with EtOAc (5 mL) and filtered through a pad of Celite. The filtrate was transferred to a separatory funnel with EtOAc and diluted with H$_2$O (5 mL). The phases were separated and the aqueous phase was extracted with 3 portions EtOAc (5 mL). The combined organic extracts were washed with 3 portions brine (10 mL), dried (Na$_2$SO$_4$), filtered, and concentrated under vacuum to afford crude 1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine-6-carbonitrile (N-2) (150 mg) as a yellow solid which was used in the next step without further purification. LCMS [M+H]=417.3 observed.

Step 3: Synthesis of 1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine-6-carboxamide (Example AIN01)

To a light yellow suspension of crude 1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine-6-carbonitrile (N-2) (150 mg, 0.360 mmol) in DMSO (1.2 mL)/MeOH (3.6 mL) was added NaOH (72 mg, 1.80 mmol, 2M in $H_2O$) drop-wise at 5° C. to maintain the inner temperature below 10° C. Upon complete addition, $H_2O_2$ (408 mg, 3.60 mmol, 30% solution). At this stage, the ice bath was removed and the reaction warmed gradually to room temperature (27° C.) with stirring for 3h. The reaction was reverse-quenched into a flask containing ice-cold sat. $Na_2SO_3$ (10 mL). The solution was transferred to a separatory funnel with EtOAc and the phases were separated. The aqueous phase was extracted with 3 portions EtOAc (10 mL). The combined organic extracts were washed with 3 portions brine (10 mL), dried ($Na_2SO_4$), filtered, and concentrated under vacuum. The crude residue was purified via prep-HPLC (YMC-Triart Prep C18 150*40 mm*7 μm column, 21-61 MeCN/$H_2O$ (0.05% $NH_4OH$ v/v), 60 mL/min) to afford the title compound 1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine-6-carboxamide (Example AIN01) (85 mg, 52% over 2 steps) as a white solid. LCMS [M+H]=435.2 observed; 1H NMR (DMSO-$d_6$) δ: 8.75 (s, 1H), 8.31 (s, 1H), 7.89-7.99 (m, 2H), 7.84 (s, 1H), 6.30 (s, 1H), 4.61 (t, J=7.3 Hz, 2H), 4.22 (s, 3H), 3.95-4.00 (m, 1H), 3.34-3.37 (m, 2H), 3.19 (s, 3H), 2.18 (s, 3H), 2.00-2.08 (m, 2H), 1.16-1.24 (in, 4H).

The example in the table below was prepared according to the methods used in steps 1-3 of scheme N for the synthesis of 1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine-6-carboxamide (Example AIN01) with non-critical changes or substitutions to the exemplified procedures that one skilled in the art would be able to realize.

| Example Number | Starting materials used in step 1 | Structure/IUPAC Name | Analytical Data |
|---|---|---|---|
| AIN02 | Int-HG-8, Int-TG-25 | 1-(difluoromethyl)-4-{4-[1-(3-methoxypropyl)-3-methyl-1H-pyrazol-5-yl]-1-methyl-1H-imidazol-2-yl}-1H-pyrazolo[4,3-c]pyridine-6-carboxamide | 1H NMR (DMSO-$d_6$) δ: 9.10 (s, 1H), 8.51 (s, 1H), 8.46 (t, J = 57.3 Hz, 1H), 8.01 (br s, 2H), 7.89 (s, 1H), 6.33 (s, 1H), 4.58-4.65 (m, 2H), 4.24 (s, 3H), 3.35-3.38 (m, 2H), 3.20 (s, 3H), 2.18 (s, 3H), 2.01-2.09 (m, 2H); 19F NMR (DMSO-$d_6$) δ: −95.95 (s, 2F). |
| AIN03 | Int-HG-9, Int-TG-25 | 1-(fluoromethyl)-4-{4-[1-(3-methoxypropyl)-3-methyl-1H-pyrazol-5-yl]-1-methyl-1H-imidazol-2-yl}-1H-pyrazolo[4,3-c]pyridine-6-carboxamide | LCMS [M + H] = 427.4 observed; 1H NMR (DMSO-$d_6$) δ: 9.00 (s, 1H), 8.59 (s, 1H), 7.92-8.04 (m, 2H), 7.87 (s, 1H), 6.72 (d, J = 53.2 Hz, 2H), 6.32 (s, 1H), 4.62 (t, J = 7.3 Hz, 2H), 4.24 (s, 3H), 3.37 (t, J = 6.0 Hz, 2H), 3.20 (s, 3H), 2.18 (s, 3H), 2.01-2.09 (m, 2H); 19F NMR (DMSO-$d_6$) δ: −164.40 (s, 1F). |

The example in the table below was prepared according to the methods used for steps 1-3 of scheme N for the synthesis of 1-cyclopropyl-4-{4-[1-(3-methoxypropyl)-3-methyl-1H-pyrazol-5-yl]-1-methyl-1H-imidazol-2-yl}-1H-pyrazolo[4,3-c]pyridine-6-carboxamide (Example AIN01), followed by the procedure used in step 3 of scheme B with non-critical changes or substitutions to the exemplified procedures that one skilled in the art would be able to realize.

| Example Number | Starting materials used for step 1 | Structure/IUPAC Name | Analytical Data |
| --- | --- | --- | --- |
| AIN04 | Int-HG-2, Int-TG-10 | 1-ethyl-4-[4-(1-ethyl-4-hydroxy-3-methyl-1H-pyrazol-5-yl)-1-methyl-1H-imidazol-2-yl]-1H-pyrazolo[4,3-c]pyridine-6-carboxamide | LCMS [M + H] = 395.3 observed; $^1$H NMR (DMSO-$d_6$) δ: 8.73 (s, 1H), 8.35 (s, 1H), 8.10 (s, 1H), 7.80-7.99 (m, 2H), 7.78 (s, 1H), 4.49-4.65 (m, 4H), 4.26 (s, 3H), 2.11 (s, 3H), 1.44 (t, J = 7.2 Hz, 3H), 1.36 (t, J = 7.2 Hz, 3H). |

Preparation of 4-{4-[1-(cyanomethyl)-3-methyl-1H-pyrazol-5-yl]-1-methyl-1H-imidazol-2-yl}-1-methyl-1H-pyrazolo[4,3-c]pyridine-6-carboxamide (Example AIP01) and 4-{4-[1-(2-amino-2-oxoethyl)-3-methyl-1H-pyrazol-5-yl]-1-methyl-1H-imidazol-2-yl}-1-methyl-1H-pyrazolo[4,3-c]pyridine-6-carboxamide (Example AIP02) According to Scheme P Scheme P

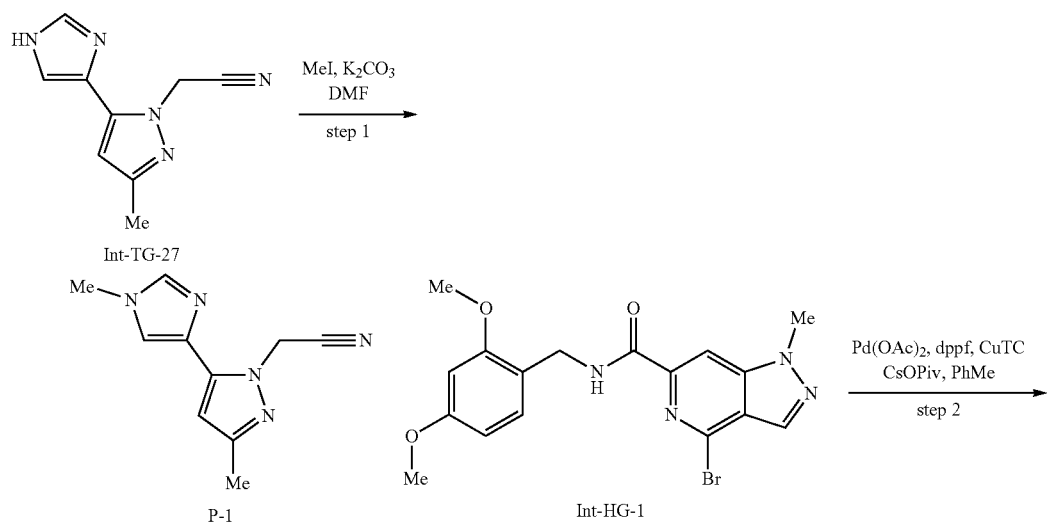

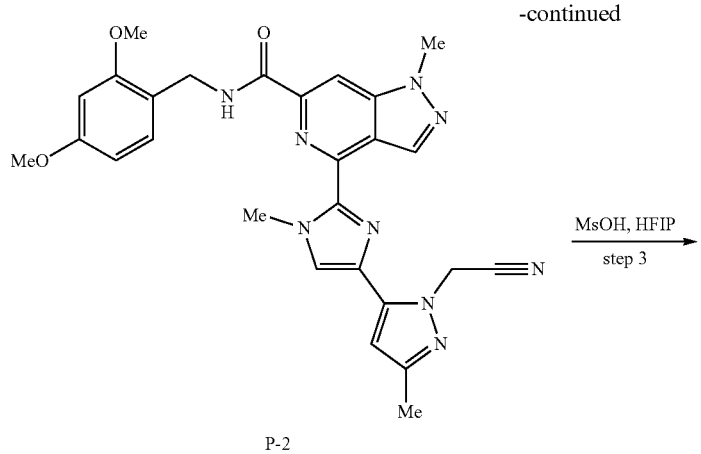

P-2

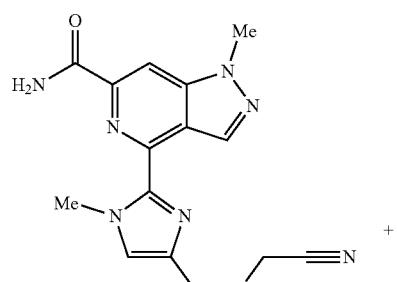

Example AIP01

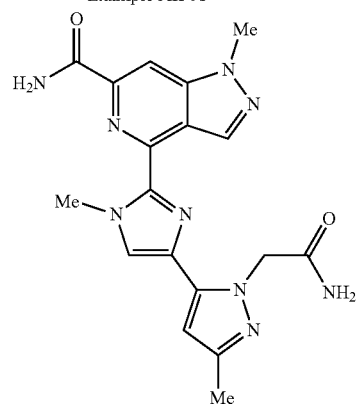

Example AIP02

Step 1: Synthesis of [3-methyl-5-(1-methyl-1H-imidazol-4-yl)-1H-pyrazol-1-yl]acetonitrile (P-1)

To a solution of [5-(1H-imidazol-4-yl)-3-methyl-1H-pyrazol-1-yl]acetonitrile (Int-TG-27) (70 mg, 0.37 mmol) in anhydrous DMF (2.0 mL) was added $K_2CO_3$ (129 mg, 0.935 mmol) followed by iodomethane (66 mg, 0.47 mmol) dropwise. The reaction was stirred at room temperature for 16 h. The mixture was then diluted with brine (5 mL), the phases separated, and the aqueous phase was extracted with EtOAc (5 mL×3). The combined organic extract was washed with brine (5 mL×3), dried over anhydrous $Na_2SO_3$, filtered, and concentrated under vacuum to afford the title compound [3-methyl-5-(1-methyl-1H-imidazol-4-yl)-1H-pyrazol-1-yl]acetonitrile (P-1) (68 mg, 91%) as a yellow solid. LCMS [M+H]=202.1 observed; $^1$H NMR (CHLOROFORM-d) δ: 7.51 (s, 1H), 7.14 (d, J=1.0 Hz, 1H), 6.16 (s, 1H), 5.65 (s, 2H), 3.76 (s, 3H), 2.28 (s, 3H).

Step 2: Synthesis of 4-{4-[1-(cyanomethyl)-3-methyl-1H-pyrazol-5-yl]-1-methyl-1H-imidazol-2-yl}-N-[(2,4-dimethoxyphenyl)methyl]-1-methyl-1H-pyrazolo[4,3-c]pyridine-6-carboxamide (P-2)

To a solution of [3-methyl-5-(1-methyl-1H-imidazol-4-yl)-1H-pyrazol-1-yl]acetonitrile (P-1) (65 mg, 0.32 mmol) and 4-bromo-N-(2,4-dimethoxybenzyl)-1-methyl-1H-pyrazolo[4,3-c]pyridine-6-carboxamide (Int-HG-1) (144 mg, 0.355 mmol) in anhydrous toluene (5.0 mL) was added Pd(OAc)$_2$ (27 mg, 0.12 mmol), dppf (36 mg, 0.065 mmol), ((thiophene-2-carbonyl)oxy)copper (25 mg, 0.129 mmol), and cesium pivalate (151 mg, 0.646 mmol). The mixture was flushed with $N_2$ for 2 min, sealed, heated to 100° C., and stirred for 40 h. The reaction was then filtered through a Celite pad and concentrated under vacuum. The crude residue was purified via flash column chromatography (20 g SiO$_2$, Combi-flash, 20-100% EtOAc/pet. ether) to afford the title compound 4-{4-[1-(cyanomethyl)-3-methyl-1H-pyrazol-5-yl]-1-methyl-1H-imidazol-2-yl}-N-[(2,4-dimethoxyphenyl)methyl]-1-methyl-1H-pyrazolo[4,3-c]pyridine-6-carboxamide (P-2) (30 mg, 18%) as a yellow solid. LCMS [M+H]=526.4 observed; $^1$H NMR (CHLOROFORM-d) δ: 8.85 (s, 1H), 8.26-8.34 (m, 2H), 7.28-7.35 (m, 2H), 6.43-6.53 (m, 2H), 6.26 (s, 1H), 5.72 (s, 2H), 4.62-4.71 (m, 2H), 4.17-4.22 (m, 6H), 3.89 (s, 3H), 3.81 (s, 3H), 2.32 (s, 3H).

Step 3: Synthesis of 4-{4-[1-(cyanomethyl)-3-methyl-1H-pyrazol-5-yl]-1-methyl-1H-imidazol-2-yl}-1-methyl-1H-pyrazolo[4,3-c]pyridine-6-carboxamide (Example AIP01) and 4-{4-[1-(2-amino-2-oxoethyl)-3-methyl-1H-pyrazol-5-yl]-1-methyl-1H-imidazol-2-yl}-1-methyl-1H-pyrazolo[4,3-c]pyridine-6-carboxamide (Example AIP02)

To a solution of 4-{4-[1-(cyanomethyl)-3-methyl-1H-pyrazol-5-yl]-1-methyl-1H-imidazol-2-yl}-N-[(2,4-dimethoxyphenyl)methyl]-1-methyl-1H-pyrazolo[4,3-c]pyridine-6-carboxamide (P-2) (32 mg, 0.061 mmol) in HFIP (1.0 mL) was added methanesulfonic acid (58 mg, 0.61 mmol) and stirred for 2 h. The reaction was then concentrated under vacuum, diluted with CH$_2$Cl$_2$/MeOH (10:1 v:v, 5 mL), basified to pH 7-8 with NH$_3$ in MeOH (7 M), filtered, the filter cake washed with CH$_2$Cl$_2$/MeOH (10:1 v:v, 1 mL×3), and the filtrate was concentrated under vacuum. The crude mixture was purified via preparative thin layer chromatography (CH$_2$Cl$_2$/MeOH, 10:1 v:v) to afford the title compound 4-{4-[1-(cyanomethyl)-3-methyl-1H-pyrazol-5-yl]-1-methyl-1H-imidazol-2-yl}-1-methyl-1H-pyrazolo[4,3-c]pyridine-6-carboxamide (Example AIP01) (9 mg, 39%) as a white solid. LCMS [M+H]=376.2 observed; $^1$H NMR (DMSO-d$_6$) δ: 8.84 (s, 1H), 8.38 (s, 1H), 7.85-8.02 (m, 3H), 6.46 (s, 1H), 5.81 (s, 2H), 4.17-4.29 (m, 6H), 2.22 (s, 3H). Additionally, title compound 4-{4-[1-(2-amino-2-oxoethyl)-3-methyl-1H-pyrazol-5-yl]-1-methyl-1H-imidazol-2-yl}-1-methyl-1H-pyrazolo[4,3-c]pyridine-6-carboxamide (Example AIP02) (4 mg, 17%) was isolated as a white solid. LCMS [M+H]=394.4 observed; $^1$H NMR (DMSO-d$_6$) δ: 8.76 (d, J=1.0 Hz, 1H), 8.35 (d, J=1.0 Hz, 1H), 7.95 (br s, 1H), 7.83-7.90 (m, 2H), 7.27 (s, 11H), 7.18 (br s, 11H), 6.37 (s, 11H), 5.24 (s, 2H), 4.22 (s, 3H), 4.19 (s, 3H), 2.19 (s, 3H).

The examples in the table below were prepared according to the methods used for steps 1-3 of scheme P for the synthesis of 4-{4-[1-(cyanomethyl)-3-methyl-1H-pyrazol-5-yl]-1-methyl-1H-imidazol-2-yl}-1-methyl-1H-pyrazolo[4,3-c]pyridine-6-carboxamide (Example AIP01) with non-critical changes or substitutions to the exemplified procedures that one skilled in the art would be able to realize.

| Example Number | Reagents used for step 1 | Structure/IUPAC Name | Analytical Data |
|---|---|---|---|
| AIP03 | Int-TG-1, BnBr, K$_2$CO$_3$, MeCN | 4-[1-benzyl-4-(3-methyl-1-propyl-1H-pyrazol-5-yl)-1H-imidazol-2-yl]-1-methyl-1H-pyrazolo[4,3-c]pyridine-6-carboxamide | LCMS [M + H] = 441 observed |
| AIP04 | Int-TG-1, 1-bromo-2-methoxyethane, K$_2$CO$_3$, MeCN | 4-[4-(1-ethyl-3-methyl-1H-pyrazol-5-yl)-1-(2-methoxyethyl)-1H-imidazol-2-yl]-1-methyl-1H-pyrazolo[4,3-c]pyridine-6-carboxamide | LCMS [M + H] = 409 observed |

| Example Number | Reagents used for step 1 | Structure/IUPAC Name | Analytical Data |
|---|---|---|---|
| AIP05 | Int-TG-1, (Rac)-1-bromopropan-2-ol-, K₂CO₃, MeCN | 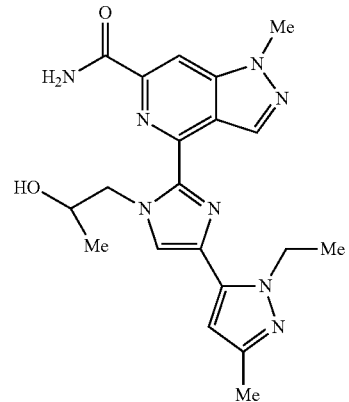 [SMILES: CCn1nc(C)cc1-c1cn(CC(C)O)c(-c2nc(C(N)=O)cc3c2cnn3C)n1]<br>(Rac)-4-[4-(1-ethyl-3-methyl-1H-pyrazol-5-yl)-1-(2-hydroxypropyl)-1H-imidazol-2-yl]-1-methyl-1H-pyrazolo[4,3-c]pyridine-6-carboxamide | LCMS [M + H] = 409 observed |

Preparation of 4-{4-[1-(2-cyanoethyl)-3-methyl-1H-pyrazol-5-yl]-1-methyl-1H-imidazol-2-yl}-1-methyl-1H-pyrazolo[4,3-c]pyridine-6-carboxamide (Example AIQ01) According to Scheme Q Scheme Q

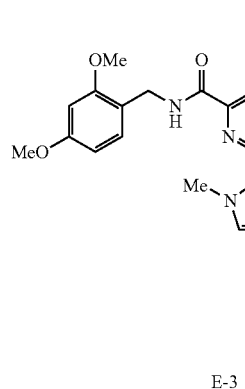

E-3

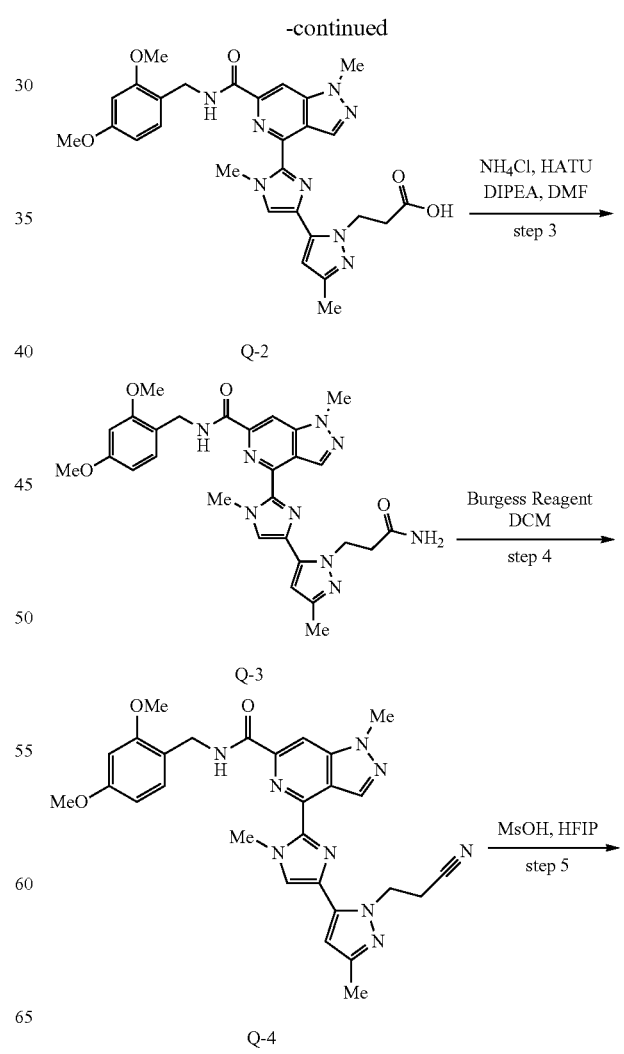

-continued

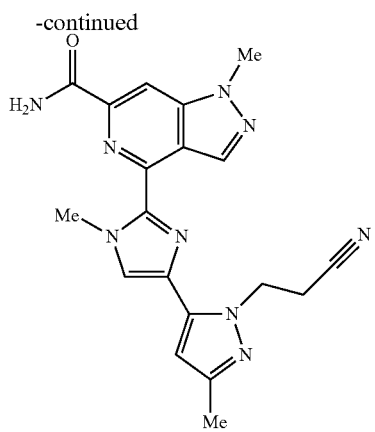

Example AIQ01

Step 1: Synthesis of N-[(2,4-dimethoxyphenyl)methyl]-1-methyl-4-{1-methyl-4-[3-methyl-1-(3-oxopropyl)-1H-pyrazol-5-yl]-1H-imidazol-2-yl}-1H-pyrazolo[4,3-c]pyridine-6-carboxamide (Q-1)

To an orange solution of N-[(2,4-dimethoxyphenyl)methyl]-4-{4-[1-(3-hydroxypropyl)-3-methyl-1H-pyrazol-5-yl]-1-methyl-1H-imidazol-2-yl}-1-methyl-1H-pyrazolo[4,3-c]pyridine-6-carboxamide (E-3) (600 mg, 0.83 mmol) in DCM (20 mL) was added Dess-Martin periodinane (526 mg, 1.24 mmol). The resulting mixture was stirred at 20° C. for 16 h. The resulting yellow suspension was diluted with DCM (20 mL), filtered over a pad of Celite, and concentrated under vacuum. The crude residue was purified via flash column chromatography (40 g SiO$_2$, 0-10% MeOH/DCM) to afford the title compound N-[(2,4-dimethoxyphenyl)methyl]-1-methyl-4-{1-methyl-4-[3-methyl-1-(3-oxopropyl)-1H-pyrazol-5-yl]-1H-imidazol-2-yl}-1H-pyrazolo[4,3-c]pyridine-6-carboxamide (Q-1) (500 mg, 83%) as a yellow solid. LCMS [M+H]=543.1 observed; $^1$H NMR (400 MHz, CHLOROFORM-d) δ=9.86 (t, J=1.2 Hz, 1H), 8.80 (d, J=1.0 Hz, 1H), 8.31 (br t, J=6.4 Hz, 1H), 8.28 (d, J=0.9 Hz, 1H), 7.31 (d, J=8.3 Hz, 1H), 7.27 (br s, 1H), 6.51 (d, J=2.3 Hz, 1H), 6.48 (dd, J=2.4, 8.3 Hz, 1H), 6.21 (s, 1H), 4.98 (t, J=7.0 Hz, 2H), 4.67 (d, J=6.0 Hz, 2H), 4.20 (s, 3H), 4.17 (s, 3H), 3.89 (s, 3H), 3.82 (s, 3H), 3.14 (dt, J=1.3, 7.0 Hz, 2H), 2.30 (s, 3H).

Step 2: Synthesis of 3-{5-[2-(6-{[(2,4-dimethoxyphenyl)methyl]carbamoyl}-1-methyl-1H-pyrazolo[4,3-c]pyridin-4-yl)-1-methyl-1H-imidazol-4-yl]-3-methyl-1H-pyrazol-1-yl}propanoic Acid (Q-2)

To a colorless mixture of N-[(2,4-dimethoxyphenyl)methyl]-1-methyl-4-{1-methyl-4-[3-methyl-1-(3-oxopropyl)-1H-pyrazol-5-yl]-1H-imidazol-2-yl}-1H-pyrazolo[4,3-c]pyridine-6-carboxamide (Q-1) (420 mg, 0.774 mmol) in THF (10 mL) was added t-BuOH (5 mL) and 2-methyl-2-butene (1630 mg, 23.2 mmol). The resulting solution was cooled in an ice-water bath (0° C.) followed by the slow addition of NaClO$_2$ (700 mg, 7.74 mmol) and NaH$_2$PO$_4$ (929 mg, 7.74 mmol) as a solution in H$_2$O (5 mL). After the addition was complete, the ice bath was removed, and the reaction was stirred at room temperature (20° C.) for 16h. The reaction was quenched with Na$_2$S$_2$O$_3$ aq. (3 mL), the pH adjusted to ~3-4 via the addition of sat. NaHSO$_4$ aq., and the solution transferred to a separatory funnel with EtOAc. The phases were separated and the aqueous phase was extracted with 3 portions EtOAc (15 mL). The combined organic extracts were washed with brine, dried (Na$_2$SO$_4$), filtered, and concentrated under vacuum. The crude residue was purified via flash column chromatography (SiO$_2$, Isco, 0-10% MeOH/DCM) to afford the title compound 3-{5-[2-(6-{[(2,4-dimethoxyphenyl)methyl]carbamoyl}-1-methyl-1H-pyrazolo[4,3-c]pyridin-4-yl)-1-methyl-1H-imidazol-4-yl]-3-methyl-1H-pyrazol-1-yl}propanoic acid (Q-2) (355 mg, 82%) as a white solid. LCMS [M+H]=559.1 observed.

Step 3: Synthesis of 4-{4-[1-(3-amino-3-oxopropyl)-3-methyl-1H-pyrazol-5-yl]-1-methyl-1H-imidazol-2-yl}-N-[(2,4-dimethoxyphenyl)methyl]-1-methyl-1H-pyrazolo[4,3-c]pyridine-6-carboxamide (Q-3)

A solution of 3-{5-[2-(6-{[(2,4-dimethoxyphenyl)methyl]carbamoyl}-1-methyl-1H-pyrazolo[4,3-c]pyridin-4-yl)-1-methyl-1H-imidazol-4-yl]-3-methyl-1H-pyrazol-1-yl}propanoic acid (Q-2) (355 mg, 0.636 mmol) in DMF (10 mL) was cooled to 0° C. in an ice water bath. To the solution was added DIPEA (246 mg, 1.91 mmol), HATU (290 mg, 0.763 mmol), and the reaction was stirred for 15 min. at 0° C. At this stage, NH$_4$Cl (170 mg, 3.18 mmol) was added and the reaction was stirred at 20° C. for 16 h. The reaction was reverse quenched into a flask containing ice water (5 mL) and the solution transferred to a separatory funnel with EtOAc. The phases were separated and the aqueous phase was extracted with 3 portions EtOAc (10 mL). The combined organic extracts were washed with 1 portion NH$_4$Cl aq., 1 portion brine, dried (Na$_2$SO$_4$), filtered, and concentrated under vacuum. The crude residue was purified via prep-TLC (SiO$_2$, 10% MeOH/DCM) to afford the title compound 4-{4-[1-(3-amino-3-oxopropyl)-3-methyl-1H-pyrazol-5-yl]-1-methyl-1H-imidazol-2-yl}-N-[(2,4-dimethoxyphenyl)methyl]-1-methyl-1H-pyrazolo[4,3-c]pyridine-6-carboxamide (Q-3) (280 mg, 79%) as a yellow solid. LCMS [M+H]=558.1 observed.

Step 4: Synthesis of 4-{4-[1-(2-cyanoethyl)-3-methyl-1H-pyrazol-5-yl]-1-methyl-1H-imidazol-2-yl}-N-[(2,4-dimethoxyphenyl)methyl]-1-methyl-1H-pyrazolo[4,3-c]pyridine-6-carboxamide (Q-4)

To a stirred suspension of 4-{4-[1-(3-amino-3-oxopropyl)-3-methyl-1H-pyrazol-5-yl]-1-methyl-1H-imidazol-2-yl}-N-[(2,4-dimethoxyphenyl)methyl]-1-methyl-1H-pyrazolo[4,3-c]pyridine-6-carboxamide (Q-3) (280 mg, 0.502 mmol) in DCM (20 mL) was added Methyl N-(triethylammoniosulfonyl)carbamate (Burgess Reagent) (359 mg, 1.51 mmol) and the reaction stirred under N$_2$ at 25° C. for 16 h. The reaction was diluted with H$_2$O (10 mL) and transferred to a separatory funnel with DCM. The phases were separated and the aqueous phase was extracted with 3 portions DCM (10 mL). The combined organic extracts were dried (Na$_2$SO$_4$), filtered, and concentrated under vacuum. The crude residue was purified via prep-TLC (SiO$_2$, 10% MeOH/DCM) to afford the title compound 4-{4-[1-(2-cyanoethyl)-3-methyl-1H-pyrazol-5-yl]-1-methyl-1H-imidazol-2-yl}-N-[(2,4-dimethoxyphenyl)methyl]-1-methyl-1H-pyrazolo[4,3-c]pyridine-6-carboxamide (Q-4) (160 mg, 59%) as a yellow solid. LCMS [M+H]=540.1 observed.

Step 5: Synthesis of 4-{4-[1-(2-cyanoethyl)-3-methyl-1H-pyrazol-5-yl]-1-methyl-1H-imidazol-2-yl}-1-methyl-1H-pyrazolo[4,3-c]pyridine-6-carboxamide (Example AIQ01)

To a light yellow solution of 4-{4-[1-(2-cyanoethyl)-3-methyl-1H-pyrazol-5-yl]-1-methyl-1H-imidazol-2-yl}-N-

[(2,4-dimethoxyphenyl)methyl]-1-methyl-1H-pyrazolo[4,3-c]pyridine-6-carboxamide (Q-4) (160 mg, 0.297 mmol) in HFIP (5 mL) was added MeSO$_3$H (214 mg, 2.22 mmol). The reaction color changed to purple and was stirred at room temperature (20° C.) for 1 h. The solution was concentrated under vacuum and the crude residue purified via prep-HPLC (Boston Prime C18 150*30 mm*5 μm column, 15-45 MeCN/H$_2$O (0.05% NH$_4$OH v/v), 30 mL/min). Product containing fractions were collected and lyophilized to afford the title compound 4-{4-[1-(2-cyanoethyl)-3-methyl-1H-pyrazol-5-yl]-1-methyl-1H-imidazol-2-yl}-1-methyl-1H-pyrazolo[4,3-c]pyridine-6-carboxamide (Example AIQ01) (18 mg, 31%) as a white solid. LCMS [M+H]=390.3 observed; $^1$H NMR (DMSO-d$_6$) δ: 8.74 (s, 1H), 8.37 (s, 1H), 7.85-8.00 (m, 3H), 6.37 (s, 1H), 4.86 (t, J=6.6 Hz, 2H), 4.16-4.28 (m, J=15.4 Hz, 6H), 3.12 (t, J=6.5 Hz, 2H), 2.20 (s, 3H).

BIOLOGICAL EXAMPLES

Biochemical Assay Methods
Scintillation Proximity Assay (SPA) Competitive Binding A radioligand binding assay was developed to determine whether compound interactions were competitive with a tritium-labeled version of the native STING ligand, $^3$H-cyclic guanine (2',5') monophosphate adenine (3,5') monophosphate ($^3$H-cGAMP). The STING constructs (WT and H232R) were comprised of residues 155-341 with both N- and C-terminal truncations; the N-terminal transmembrane domains were removed (1-154), as well as the C-terminal tail (342-379). A highly specific N-terminal biotinylation was achieved enzymatically with the E. coli biotin ligase (BirA) and inclusion of the high-affinity biotinylation peptide AviTag™. 100 nM STING protein was immobilized on 20 μg streptavidin polyvinyl toluene (SA-PVT) beads in 150 mM NaCl, 25 mM Hepes (pH 7.5), 0.1 mM EDTA, 1 mM DTT, 0.005% (v/v) Tween-20, 1% (v/v) DMSO. 100 nM $^3$H-cGAMP and compounds were added and allowed to come to equilibrium at room temperature (20 min). Compounds were tested in three-fold dilution series from a 100 μM starting concentration and normalized to a positive control compound that completely blocked $^3$H-cGAMP binding and the negative control DMSO. The K$_I$ for competitive binding was determined from the IC$_{50}$ with the Cheng-Prusoff equation (Cheng & Prusoff, Biochemical Pharmacology, 22 (1973), pp. 3099-3108). The K$_D$ values for $^3$H-cGAMP used in the Cheng-Prusoff equation were determined empirically to be 1 nM for WT STING, and 750 nM for R232H STING. SPA competitive binding data is provided in Table 1.

TABLE 1

| Example Number | R232-STING SPA-IC50 Ki (μM) |
|---|---|
| AIA01 | 0.0107 |
| AIA02 | 0.0180 |
| AIA03 | 0.0714 |
| AIA04 | 0.0338 |
| AIB01 | 0.2572 |
| AIC01 | 0.0121 |
| AIC02 | 0.1130 |
| AIC03 | 0.0078 |
| AID01 | 0.0875 |
| AIE01 | 0.0036 |
| AIE02 | 0.0127 |
| AIE03 | 0.0107 |

TABLE 1-continued

| Example Number | R232-STING SPA-IC50 Ki (μM) |
|---|---|
| AIE04 | 0.0137 |
| AIF01 | 0.0098 |
| AIF02 | 0.0546 |
| AIF03 | 0.0057 |
| AIF04 | 0.0236 |
| AIF05 | >0.9901 |
| AIF06 | 0.0182 |
| AIF07 | 0.0020 |
| AIF08 | >0.9901 |
| AIF09 | >0.9901 |
| AIF10 | 0.0013 |
| AIF11 | 0.0003 |
| AIF12 | 0.0024 |
| AIF13 | 0.0029 |
| AIF14 | 0.0282 |
| AIF15 | 0.0466 |
| AIG01 | 0.0818 |
| AIH01 | 0.3519 |
| AIH02 | 0.0227 |
| AIH03 | 0.1483 |
| AIH04 | 0.1510 |
| AIH05 | 0.0933 |
| AIJ01 | 0.0102 |
| AIJ02 | 0.0397 |
| AIK01 | 0.0152 |
| AIL01 | 0.0246 |
| AIM01 | 0.1749 |
| AIM02 | 0.1351 |
| AIN01 | 0.0046 |
| AIN02 | 0.0209 |
| AIN03 | 0.0128 |
| AIN04 | 0.0029 |
| AIP01 | 0.0431 |
| AIP02 | 0.1609 |
| AIP03 | >0.9901 |
| AIP04 | 0.0352 |
| AIP05 | 0.0271 |
| AIQ01 | 0.0626 |

Phosphorylation of IRF3: THP-1 cell ELISA

STING activation results in recruitment of TBK1 and phosphorylation of IRF3 transcription factor before induction of type I interferons. THP-1 cells (InvivoGen) were grown in RPMI media plus 2 mM L-glutamine, 10% fetal bovine serum, and 0.5% Pen-Strep. 10$^4$ cells were seeded in 96-well plates and incubated overnight 37N, 5% 002. Compounds serial diluted compounds in media (final 0.5% DMSO) were added to the cells and incubated for an additional 3 hours. After incubation, the plates were centrifuged at 2000 rpm for 5 min. The cells were then lysed in 100 μl RIPA buffer and vortexed for 30 minutes at room temperature. 25 μl of lysate was then transferred to clear polystyrene High Bind plates that had been previously coated with mouse anti-human IRF-3 capture antibody (BD Pharmigen), and allowed to incubate at 4° C. for 16 hours. The plates were then washed and incubated with rabbit anti-phospho-IRF3 detection antibody (Cell Signaling Technologies) for 1.5 hours at room temperature. Finally, an HRP-linked secondary antibody (Cell Signaling Technologies) was added for 30 min before the Glo Substrate Reagent (R&D Systems) was used generate the luminescent signal. The signal was measured using a Perkin-Elmer Envision microplate reader. Data were normalized to "% effect" with a positive control STING agonist that was known to maximize the phosphorylated IRF3 signal and the negative control was DMSO. IRF3 Phosphorylation data is provided in Table 2.

TABLE 2

| Example Number | THP-1 CELL P-IRF3 EC50 ($\mu$M) |
|---|---|
| AIA01 | 0.67 |
| AIA02 | 0.80 |
| AIA03 | 4.89 |
| AIA04 | 1.26 |
| AIC01 | 1.26 |
| AIC02 | >10.0 |
| AIC03 | 0.65 |
| AID01 | 6.42 |
| AIE01 | 0.20 |
| AIE02 | 0.20 |
| AIE03 | 0.31 |
| AIE04 | 0.69 |
| AIF01 | 0.50 |
| AIF02 | 2.09 |
| AIF03 | 0.14 |
| AIF04 | 2.12 |
| AIF06 | 2.61 |
| AIF07 | 0.31 |
| AIF10 | 0.07 |
| AIF11 | 0.01 |
| AIF12 | 0.31 |
| AIF13 | 0.25 |
| AIF14 | 1.37 |
| AIF15 | 1.35 |
| AIG01 | >10.0 |
| AIH02 | 4.30 |
| AIH03 | 6.58 |
| AIH04 | >10.0 |
| AIH05 | >10.0 |
| AIJ01 | 0.40 |
| AIJ02 | 1.51 |
| AIK01 | 0.33 |
| AIL01 | 0.53 |
| AIM01 | >10.0 |
| AIM02 | >10.0 |
| AIN01 | 0.73 |
| AIN02 | 0.99 |
| AIN03 | 0.68 |
| AIN04 | 0.37 |
| AIP01 | >10.0 |
| AIP02 | >10.0 |
| AIP04 | 1.14 |
| AIP05 | 1.23 |
| AIQ01 | 2.24 |

Interferon-$\beta$ Induction: THP-1 ISG Reporter Cell Line

THP-1 Lucia™ ISG cells (InvivoGen) express the secreted luciferase "Lucia" reporter gene under the control of an IRF-inducible composite promotor comprised of five interferon response elements. THP-1 Lucia™ ISG cells were grown in RPMI media plus 2 mM L-glutamine, 10% fetal bovine serum, and 0.5% Pen-Strep. Hygromycin B and Zeocin were present to maintain stable transfection. $10^4$ cells were seeded in 96-well plates and incubated overnight 37° C., 5% $CO_2$. 50 $\mu$L of serial diluted compounds in media (final 0.5% DMSO) was and incubated for an additional 24 hours. After incubation, the plates were centrifuged at 2000 rpm for 10 min. 50 $\mu$l of cell culture supernatant of each well was transferred to a white, opaque 96-well plate. One pouch of QUANTI-Luc™ (InvivoGen) powder was prepared in 25 mL of endotoxin-free water and 100 $\mu$L of prepared warm QUANTI-Luc solution were added to each well containing the supernatant. The luminescence signal was measured using a Perkin-Elmer Envision microplate reader. Data were normalized to "% effect" with a positive control STING agonist that was known to maximize the luciferase signal and the negative control DMSO.

Interferon-$\beta$ Induction Data is Provided in Table 3.

TABLE 3

| Example Number | THP-1 Lucia ISG Cells IFN-$\beta$ EC50 ($\mu$M) |
|---|---|
| AIA01 | 0.82 |
| AIA02 | 0.77 |
| AIA03 | 4.53 |
| AIA04 | 1.31 |
| AIC01 | 1.17 |
| AIC02 | >10.0 |
| AIC03 | 0.70 |
| AID01 | 6.31 |
| AIE01 | 0.22 |
| AIE02 | 0.27 |
| AIE03 | 0.31 |
| AIE04 | 0.74 |
| AIF01 | 0.54 |
| AIF02 | 2.16 |
| AIF03 | 0.16 |
| AIF04 | 2.38 |
| AIF06 | 2.57 |
| AIF07 | 0.20 |
| AIF10 | 0.03 |
| AIF11 | <0.01 |
| AIF12 | 0.37 |
| AIF13 | 0.16 |
| AIF14 | 1.32 |
| AIF15 | 1.83 |
| AIG01 | >10.0 |
| AIH02 | 2.56 |
| AIH03 | 6.26 |
| AIH04 | >10.0 |
| AIH05 | >10.0 |
| AIJ01 | 0.45 |
| AIJ02 | 1.92 |
| AIK01 | 0.43 |
| AIL01 | 0.53 |
| AIM01 | >10.0 |
| AIM02 | 8.96 |
| AIN01 | 0.80 |
| AIN02 | 1.20 |
| AIN03 | 0.85 |
| AIN04 | 0.31 |
| AIP01 | >10.0 |
| AIP02 | >10.0 |
| AIP04 | 1.24 |
| AIP05 | 1.25 |
| AIQ01 | 2.26 |

These examples are provided for illustrative purposes only and not to limit the scope of the claims provided herein. It will be apparent to those of ordinary skill in the art that certain changes and modifications may be made thereto without departing from the spirit or scope of the claims.

All publications and patent applications cited in the specification are herein incorporated by reference in their entirety.

We claim:
1. A compound having the structure:
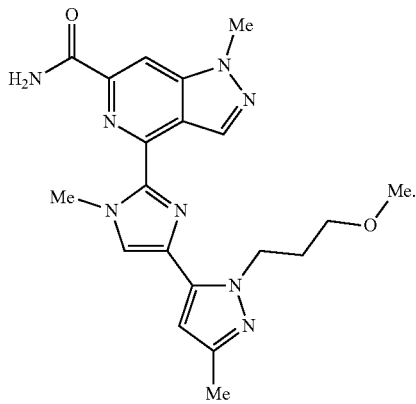 [SMILES: COCCCn1nc(C)cc1-c1cn(C)c(-c2nc(C(N)=O)cc3c2cnn3C)n1]
2. A compound having the structure:
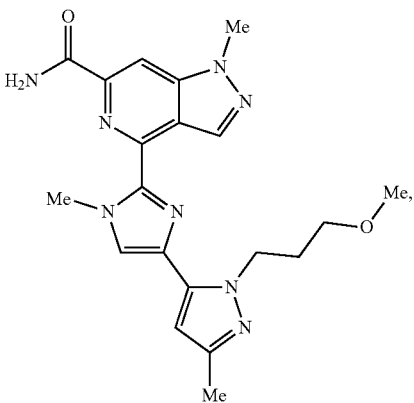 [SMILES: COCCCn1nc(C)cc1-c1cn(C)c(-c2nc(C(N)=O)cc3c2cnn3C)n1]
or a pharmaceutically acceptable salt thereof.
3. A pharmaceutical composition comprising a compound of claim 1 and a pharmaceutically acceptable carrier.
4. A pharmaceutical composition comprising a compound of claim 2 and a pharmaceutically acceptable carrier.
* * * * *